US011130783B2

(12) United States Patent
Hering et al.

(10) Patent No.: US 11,130,783 B2
(45) Date of Patent: Sep. 28, 2021

(54) CD40 TARGETED PEPTIDES AND USES THEREOF

(71) Applicants: Regents of the University of Minnesota, Minneapolis, MN (US); Diabetes-Free, Inc., Wilmington, DE (US)

(72) Inventors: Bernhard J. Hering, Minnetonka, MN (US); Sabarinathan Ramachandran, Dayton, MN (US); Prashant Girinath, Chelsea, MA (US)

(73) Assignees: Regents of the University of Minnesota, Minneapolis, MN (US); Diabetes-Free, Inc., Wilmington, DE (US)

( * ) Notice: Subject to any disclaimer, the term of this patent is extended or adjusted under 35 U.S.C. 154(b) by 0 days.

(21) Appl. No.: 17/089,463

(22) Filed: Nov. 4, 2020

(65) Prior Publication Data

US 2021/0070805 A1 Mar. 11, 2021

Related U.S. Application Data

(63) Continuation of application No. PCT/US2019/061325, filed on Nov. 13, 2019.

(60) Provisional application No. 62/760,796, filed on Nov. 13, 2018.

(51) Int. Cl.
| | |
|---|---|
| *C07K 7/08* | (2006.01) |
| *A61K 9/127* | (2006.01) |
| *A61K 9/51* | (2006.01) |
| *A61K 35/15* | (2015.01) |
| *A61K 38/00* | (2006.01) |
| *A61P 37/06* | (2006.01) |
| *A61K 47/69* | (2017.01) |

(52) U.S. Cl.
CPC .............. *C07K 7/08* (2013.01); *A61K 9/127* (2013.01); *A61K 9/51* (2013.01); *A61K 35/15* (2013.01); *A61K 47/6901* (2017.08); *A61P 37/06* (2018.01); *A61K 38/00* (2013.01)

(58) Field of Classification Search
None
See application file for complete search history.

(56) References Cited

U.S. PATENT DOCUMENTS

| | | | |
|---|---|---|---|
| 3,536,809 | A | 10/1970 | Applezweig et al. |
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 4,716,149 | A | 12/1987 | Bonelli et al. |
| 4,723,958 | A | 2/1988 | Pope et al. |
| 4,747,825 | A | 5/1988 | Linkie et al. |
| 4,880,078 | A | 11/1989 | Inoue et al. |
| 4,897,268 | A | 1/1990 | Tice et al. |
| 4,948,592 | A | 8/1990 | Ayer et al. |
| 4,965,251 | A | 10/1990 | Stamatoyannopoulos |
| 5,059,595 | A | 10/1991 | Le Grazie |
| 5,073,543 | A | 12/1991 | Marshall et al. |
| 5,075,109 | A | 12/1991 | Tice et al. |
| 5,120,548 | A | 6/1992 | McClelland et al. |
| 5,223,409 | A | 6/1993 | Ladner et al. |
| 5,290,540 | A | 3/1994 | Prince et al. |
| 5,350,674 | A | 9/1994 | Boenisch et al. |
| 5,354,556 | A | 10/1994 | Sparks et al. |
| 5,399,346 | A | 3/1995 | Anderson et al. |
| 5,403,590 | A | 4/1995 | Forse |
| 5,580,859 | A | 12/1996 | Felgner et al. |
| 5,585,362 | A | 12/1996 | Wilson et al. |
| 5,589,466 | A | 12/1996 | Felgner et al. |
| 5,591,767 | A | 1/1997 | Mohr et al. |
| 5,639,476 | A | 6/1997 | Oshlack et al. |
| 5,674,533 | A | 10/1997 | Santus et al. |
| 5,733,566 | A | 3/1998 | Lewis |
| 5,855,913 | A | 1/1999 | Hanes et al. |
| 5,874,064 | A | 2/1999 | Edwards et al. |
| 5,934,272 | A | 8/1999 | Lloyd et al. |
| 5,985,309 | A | 11/1999 | Edwards et al. |
| 5,985,320 | A | 11/1999 | Edwards et al. |
| 6,019,968 | A | 2/2000 | Platz et al. |
| 6,103,489 | A | 8/2000 | Arakaki et al. |
| 6,207,195 | B1 | 3/2001 | Walsh et al. |
| 6,261,569 | B1 | 7/2001 | Comis et al. |

(Continued)

FOREIGN PATENT DOCUMENTS

| | | |
|---|---|---|
| EP | 2857033 A2 | 4/2015 |
| EP | 2629797 B1 | 5/2018 |

(Continued)

OTHER PUBLICATIONS

Adjei et al.: Pulmonary delivery of peptide drugs: effect of particle size on bioavailability of leuprolide acetate in healthy male volunteers. Pharm Res.7(6): 565-569 (1990).
Alturaihi et al.: Interaction of CD154 with different receptors and its role in bidirectional signals. Eur J Immunol. Feb. 2015;45(2):592-602.doi: 10.1002/eji.201444941. Epub Dec. 16, 2014.
Anderson et al.: Effect of cystic fibrosis on inhaled aerosol boluses. Am Rev Respir Dis.140(5): 1317-1324 (1989).
Arano et al.: A novel bifunctional metabolizable linker for the conjugation of antibodies with radionuclides. Bioconjug Chem. 2(2): 71-76 (1991).
Bajorath et al.: Analysis of gp39/CD40 Interactions Using Molecular Models and Site-Directed Mutagenesis. Biochemistry 34(31): 9884-9892 (1995).
Bajorath et al.: Identification of residues on CD40 and its ligand which are critical for the receptor-ligand interaction. Biochemistry. 34(6): 1833-1844 (1995).

(Continued)

*Primary Examiner* — Sergio Coffa
(74) *Attorney, Agent, or Firm* — Greenberg Traurig, LLP

(57) ABSTRACT

The present disclosure is related to compositions comprising peptides that bind CD40 and methods of use in inhibiting interaction of CD40 and CD154 and inducing immunosuppression. Provided herein are methods of transplantation and methods of inhibiting donor specific immune response. Also provided herein are methods of treatment for autoimmune diseases, inflammatory diseases and cancer.

19 Claims, 6 Drawing Sheets

Specification includes a Sequence Listing.

(56) References Cited

U.S. PATENT DOCUMENTS

| | | | |
|---|---|---|---|
| 6,326,193 | B1 | 12/2001 | Liu et al. |
| 6,339,069 | B1 | 1/2002 | Meers et al. |
| 6,365,185 | B1 | 4/2002 | Ritschel et al. |
| 7,741,280 | B2 | 6/2010 | Guichard et al. |
| 8,507,448 | B2 | 8/2013 | Camussi et al. |
| 8,734,786 | B2 | 5/2014 | Miller et al. |
| 9,289,381 | B2 | 3/2016 | Elliott et al. |
| 9,562,088 | B2 | 2/2017 | Wagner |
| 9,888,673 | B2 | 2/2018 | Hering et al. |
| 2007/0041971 | A1* | 2/2007 | Wagner ............ C07K 16/2878 424/144.1 |
| 2008/0305989 | A1 | 12/2008 | Wen et al. |
| 2008/0311214 | A1 | 12/2008 | Rao |
| 2008/0318837 | A1 | 12/2008 | Quay et al. |
| 2011/0229495 | A1 | 9/2011 | Wagner |
| 2012/0302505 | A1 | 11/2012 | Fetzer et al. |
| 2017/0355747 | A1 | 12/2017 | Wagner |
| 2018/0172683 | A1 | 6/2018 | Roberts et al. |

FOREIGN PATENT DOCUMENTS

| | | |
|---|---|---|
| WO | WO-9005785 A1 | 5/1990 |
| WO | WO-9219244 A2 | 11/1992 |
| WO | WO-9732572 A2 | 9/1997 |
| WO | WO-9744013 A1 | 11/1997 |
| WO | WO-9831346 A1 | 7/1998 |
| WO | WO-9966903 A2 | 12/1999 |
| WO | WO-0129058 A1 | 4/2001 |
| WO | WO-0196584 A2 | 12/2001 |
| WO | WO-2005006949 A2 | 1/2005 |
| WO | WO-2005044294 A2 | 5/2005 |
| WO | WO-2007129895 A2 | 11/2007 |
| WO | WO-2009071486 A1 | 6/2009 |
| WO | WO-2011123489 A2 | 10/2011 |
| WO | WO-2012054584 A2 | 4/2012 |
| WO | WO-2016069921 A1 | 5/2016 |
| WO | WO-2016196314 A1 | 12/2016 |
| WO | WO-2020102454 A1 | 5/2020 |

OTHER PUBLICATIONS

Baxendale et al.: Constitutive activation of the CD40 pathway promotes cell transformation and neoplastic growth. Oncogene. 24(53): 7913-7923 (2005).
Bensigner et al.: A phase 1 study of lucatumumab, a fully human anti-CD40 antagonist monoclonal antibody administered intravenously to patients with relapsed or refractory multiple myeloma. Br J Haematol.159(1): 58-66 (2012).
Biancone et al.: CD40-CD154 interaction in experimental and human disease (review). Int J Mol Med. 3(4): 343-353 (1999).
Bonelli et al.: Solid phase synthesis of retro-inverso peptide analogues: Synthesis and biological activity of the partially modified retro-inverso analogue of the bradykinin potentiating peptide BPP9a [gLys6, (RS)-mPhe7, Ala8] BPP9a.Int. J. of Peptide and Protein Research 24(6): 553-556(1984).
Byron, P.R.: Determinants of drug and polypeptide bioavailability from aerosols delivered to the lung. Advanced Drug Delivery Reviews 5(1-2): 107-132 (1990).
Carell et al. A Novel Procedure for the Synthesis of Libraries Containing Small Organic Molecules. Angew Them Int Ed Engl 33:2059 (1994).
Carell et al. A Solution-Phase Screening Procedure for the Isolation of Active Compounds From a Library of Molecules. Angew Chem Int Ed Engl 33:2061 (1994).
Carstensen Drug Stability: Principles & Practice, 2d. Ed., Marcel Dekker, NY, NY, (1995), pp. 379-380.
Cho et al. An Unnatural Biopolymer. Science 261:1303-1305 (1993).
Clark, et al. Long-acting growth hormones produced by conjugation with polyethylene glycol. J Biol Chem. 1996; 271(36):21969-77.
Clay et al.: Assays for monitoring cellular immune responses to active immunotherapy of cancer. Clin Cancer Res. 7(5): 1127-1135 (2001).
Cleland et al.: Formulation and Delivery of Proteins and Peptides: Design and Development Strategies. Chapter 1, pp. 1-19 (1994).
Cull et al. Screening for Receptor Ligands Using Large Libraries of Peptides Linked to the C Terminus of the lac Repressor. PNAS USA 89:1865-1869 (1992).
Cwirla, et al. Peptides on phage: a vast library of peptides for identifying ligands. Proc Natl Acad Sci U S A. Aug. 1990;87(16):6378-82.
Dai et al.: Characterization of physiochemical and biological properties of an insulin/lauryl sulfate complex formed by hydrophobic ion pairing. Int J Pharm. 336(1): 58-66 (2007).
Dawson et al.: Synthesis of native proteins by chemical ligation. Annu Rev Biochem. 69: 923-960 (2000).
Deambrosis et al.: Inhibition of CD40-CD154 costimulatory pathway by a cyclic peptide targeting CD154. J Mol Med (Berl).87(2): 181-197 (2009).
Devlin et al. Random peptide libraries: a source of specific protein binding molecules. Science 249(4967):404-406 (1990).
Dewitt, et al. "Diversomers": an approach to nonpeptide, nonoligomeric chemical diversity. Proc Natl Acad Sci U S A. Aug. 1, 1993;90(15):6909-13.
Dreborg et al.: Immunotherapy with monomethoxypolyethylene glycol modified allergens. Crit Rev Ther Drug Carrier Syst. 6(4): 315-365 (1990).
Duncan et al.: Soluble synthetic polymers as potential drug carriers. Polymers in Medicine 57: 51-101 (1984).
Erb et al. Recursive deconvolution of combinatorial chemical libraries. PNAS USA 91(24):11422-11426 (1994).
Felici et al. Selection of antibody ligands from a large library of oligopeptides expressed on a multivalent exposition vector. J Mol Biol 222:301-310 (1991).
Fodor, et al. Multiplexed biochemical assays with biological chips. Nature. Aug. 5, 1993;364(6437):555-6.
French et al.: Human induced pluripotent stem cell-derived B lymphocytes express sIgM and can be generated via a hemogenic endothelium intermediate. Stem Cells Dev. 24(9): 1082-1095 (2015).
French et al.: The influence of formulation on emission, deaggregation and deposition of dry powders for inhalation. Journal of Aerosol Science 27(5): 769-783 (1996).
French et al.: What is a conservative substitution? Journal of Molecular Evolution 19: 171-175 (1983).
Gallop et al. Applications of combinatorial technologies to drug discovery. 1. Background and peptide combinatorial libraries. J Med Chem 37(9):1233-1251 (1994).
Gonda. Aerosols for delivery of therapeutic and diagnostic agents to the respiratory tract. Critical Reviews in Therapeutic Drug Carrier Systems 6:273-313 (1990).
Grewal et al.: CD40 and CD154 in cell-mediated immunity. Annu Rev Immunol. 16:111-135 (1998).
Grewal et al.: The CD40-CD154 system in anti-infective host defense. Curr Opin Immunol. 9(4): 491-497 (1997).
Grewal et al.: The role of CD40 ligand in costimulation and T-cell activation. Immunol Rev. 153: 85-106 (1996).
Gruss et al.: CD40/CD40 ligand interactions in normal, reactive and malignant lympho-hematopoietic tissues. Leuk Lymphoma. 24(5-6): 393-422 (1997).
Hering BJ, Wijkstrom M, Graham ML, Hårdstedt M, Aasheim TC, Jie T, Ansite JD, Nakano M, Cheng J, Li W, Moran K, Christians U, Finnegan C, Mills CD, Sutherland DE, Bansal-Pakala P, Murtaugh MP, Kirchhof N, Schuurman HJ. Prolonged diabetes reversal after intraportal xenotransplantation of wild-type porcine islets in immunosuppressed nonhuman primates. Nat Med. Mar. 2006;12(3):301-3. PubMed PMID 16491083.
Hershfield, M.S.: Biochemistry and Immunology of Poly(ethylene glycol)-Modified Adenosine Deaminase (PED-ADA). Poly(ethylene glycol). Chapter 10, pp. 145-154 (1997).
Houghten et al. The use of synthetic peptide combinatorial libraries for the identification of bioactive peptides. Biotechniques 13(3):412-421 (1992).
"International Search Report and Written Opinion for corresponding PCT Application No. PCT/NL2019/050086 dated Jul. 8, 2019".
Kawabe et al.: CD40/CD40 ligand interactions in immune responses and pulmonary immunity. Nagoya J Med Sci. 73(3-4): 69-78 (2011).

(56) References Cited

OTHER PUBLICATIONS

Kobayashi et al.: Pulmonary delivery of salmon calcitonin dry powders containing absorption enhancers in rats. Pharm Res.13(1): 80-83 (1996).
Lam et al.: A new type of synthetic peptide library for identifying ligand-binding activity. Nature, 354:82-84 (1991).
Lam, K.S.: Application of Combinatorial Library Methods in Cancer Research and Drug Discovery. Anticancer Drug Des 12:145-167 (1997).
Laman et al.: CD40 in clinical inflammation: from multiple sclerosis to atherosclerosis. Dev Immunol. 6(3-4): 215-222 (1998).
Limbach, P A et al. "Summary: the modified nucleosides of RNA." Nucleic acids research vol. 22, No. 12, pp. 2183-2196, 1994.
Lowe et al.: A novel monoclonal antibody to CD40 prolongs islet allograft survival. Am J Transplant. 12(8): 2079-2087 (2012).
Mahajan et al.: Structural Modification of Proteins and Peptides. Indian Journal of Pharmaceutical Education and Research | vol. 48 | Issue 3 | pp. 34-47 | Jul.-Sep. 2014.
Mohiuddin et al.: Chimeric 2C10R4 anti-CD40 antibody therapy is critical for long-term survival of GTKO.hCD46.hTBM pig-to-primate cardiac xenograft. Nat Commun.7: 11138, 10 pages total (2016).
Mumtaz et al. Design of liposomes for circumventing the reticuloendothelial cells. Glycobiology 5:505-10 (1991).
Nakamura, et al., Codon usage tabulated from international DNA sequence databases: status for the year 2000. Nucleic Acids Res. Jan. 1, 2000; 28(1): 292.
Niven et al.: The pulmonary absorption of aerosolized and intratracheally instilled rhG-CSF and monoPEGylated rhG-CSF. Pharm Res. 12(9): 1343-1349 (1995).
Noelle et al.: CD40 and its ligand in autoimmunity. Ann N Y Acad Sci. 815: 384-391 (1997).
Noelle, R.J.: CD40 and its ligand in host defense. Immunity. 4(5): 415-419 (1996).
Olson et al.: Preparation and characterization of polyethylene glycosylated human growth hormone antagonist. In J. M. Harris and S. Zalipsky (Eds) Poly(ethylene glycol): Chemistry and Biological Applications. American Chemical Society, Washington, D.C., p. 170-181 (1997).
Pagni et al.: CD40-targeted peptide proposed for type 1 diabetes therapy lacks relevant binding affinity to its cognate receptor. Diabetologia. 62(9): 1727-1729 (2019).
Patton et al.: Bioavailability of pulmonary delivered peptides and proteins: α-interferon, calcitonins and parathyroid hormones. Journal of Controlled Release 28(1-3):79-85 (1994).
Patton et al.: (D) Routes of delivery: Case studies: (2) Pulmonary delivery of peptides and proteins for systemic action. Advanced Drug Delivery Reviews 8(2-3): 179-196 (1992).
Payne et al.: Peptide Formulation: Challenges and Strategies—The properties of peptides make them particularly difficult to formulate but, with the right approach, they can be developed into effective therapies. Innovations in Pharmaceutical Technology. pp. 64-68 (2009).
Plebanski et al.: Methods to measure T-cell responses. Expert Rev Vaccines. 9(6): 595-600 (2010).
Rudt et al.: In vitro phagocytosis assay of nano- and microparticles by chemiluminescence. I. Effect of analytical parameters, particle size and particle concentration. Journal of Controlled Release 22(3): 263-271 (1992).
Scott et al. Searching for Peptide Ligands With an Epitope Library. Science 249:386-390 (1990).
Senhaji et al.: The Contribution of CD40/CD40L Axis in Inflammatory Bowel Disease: An Update. Front Immunol.6: 529, pp. 1-6 (2015).
Su et al.: Efficient Culture of Human Naive and Memory B Cells for Use as APCs. J Immunol. 197(10): 4163-4176 (2016).
Sun et al.: Hydrophobic ion pairing of an insulin-sodium deoxycholate complex for oral delivery of insulin. Int J Nanomedicine. 6: 3049-3056 (2011).
Tabata et al.: Macrophage phagocytosis of biodegradable microspheres composed of L-lactic acid/glycolic acid homo- and copolymers. J Biomed Mater Res. 22(10): 837-858 (1988).
Taylor, W.R.: The classification of amino acid conservation. J Theor Biol. 119(2): 205-218 (1986).
Timsina et al.: Drug delivery to the respiratory tract using dry powder inhalers. International Journal of Pharmaceutics 101(1-2): 1-13 (1994).
Uhlig et al.: The emergence of peptides in the pharmaceutical business: From exploration to exploitation. EuPA Open Proteomics 4: 58-69 (2014).
Ui-Tei et al: Sensitive assay of RNA interference in *Drosophila* and Chinese hamster cultured cells using firefly luciferase gene as target;FEBS Lett, 479:79-82 (2000).
Ulysse et al. Photoregulation of cyclic peptide conformation. J Am Chem Soc 117:8466-8467 (1995).
Vaitaitis et al.: A CD40-targeted peptide controls and reverses type 1 diabetes in NOD mice. Diabetologia. 57(11): 2366-2373 (2014).
Van Kooten et al.: CD40-CD40 ligand. J Leukoc Biol.67(1): 2-17 (2000).
Van Kooten et al.: Functions of CD40 on B cells, dendritic cells and other cells. Curr Opin Immunol. 9(3): 330-337 (1997).
Verdini et al.: Synthesis, resolution, and assignment of configuration of potent hypotensive retro-inverso bradykinin potentiating peptide 5a(BPP5a) analogues. J. Chem. Soc. Perkin Trans. 1(0): 697-701 (1985).
Visser, J.: An Invited Review: Van der Waals and other cohesive forces affecting powder fluidization. Powder Technology 58(1): 1-10 (1989).
Waddell, et al. Towards resolving the interordinal relationships of placental mammals. Syst Biol. Mar. 1999;48(1):1-5.
Wall, D.A.: Pulmonary Absorption of Peptides and Proteins. Journal Drug Delivery 2(1): 1-20 (1995).
Xu et al.: Effects of combined treatment with CD25- and CD154-specific monoclonal antibodies in non-human primate allotransplantation. Am J Transplant. 3(11): 1350-1354 (2003).
Yoshimori et al.: Structure-based design of an agonistic peptide targeting Fas. Apoptosis.10(2): 323-329 (2005).
Zanen et al.: The optimal particle size for parasympathicolytic aerosols in mild asthmatics. International Journal of Pharmaceutics 114(1): 111-115 (1995).
Zuckermann et al. Discovery of nanomolar ligands for 7-transmembrane G-protein-coupled receptors from a DiverseN-(substituted)glycine peptoid library. J Med Chem 37(17):2678-2685 (1994).

* cited by examiner

CD40 TARGETED PEPTIDES AND USES THEREOF

CROSS REFERENCE

This application is a Continuation Application of International Patent Application PCT/US2019/061325, filed Nov. 13, 2019, which claims benefit to U.S. Provisional Patent Application No. 62/760,796, filed Nov. 13, 2018, each of which is incorporated herein by reference in its entirety.

BACKGROUND OF THE DISCLOSURE

CD40 ligand (CD40L), or CD154, binds to i) its classical receptor CD40 on B cells and other antigen presenting cells, ii) αMβ2, also known as Mac-1, on neutrophils, monocytes, and macrophages, iii) a5131 on monocytes, and αIIbβ3 on platelets. The interaction of CD154 with CD40 is implicated in the activation of CD40 expressing immune cells such as B-cell, T-cell, neutrophil, monocyte, macrophage, dendritic cell, and platelet.

INCORPORATION BY REFERENCE

All publications, patents, and patent applications mentioned in this specification are herein incorporated by reference to the same extent as if each individual publication, patent, or patent application was specifically and individually indicated to be incorporated by reference. Absent any indication otherwise, publications, patents, and patent applications mentioned in this specification are incorporated herein by reference in their entireties.

SUMMARY OF THE DISCLOSURE

In one aspect provided herein is a pharmaceutical composition comprising a peptide or a portion thereof, wherein the peptide comprises an amino acid sequence with at least 85%, or at least 90% sequence identity to an amino acid sequence selected from the group consisting of SEQ ID NOs: 1-6 and 8-17, and a pharmaceutically acceptable carrier, wherein said peptide binds a CD40 protein or portion thereof. In one aspect, provided herein is a pharmaceutical composition comprising a peptide, wherein the peptide comprises an amino acid sequence with at least 90% sequence identity to the sequences set forth in any one of SEQ ID NOs: 1-6 and 8-17, and a pharmaceutically acceptable carrier, wherein said peptide binds a CD40 protein or a portion thereof.

In some embodiments, the peptide comprises the amino acid sequence of SEQ ID NO: 1. In some embodiments, the peptide comprises the amino acid sequence of SEQ ID NO: 2. In some embodiments, the peptide comprises the amino acid sequence of SEQ ID NO: 3. In some embodiments, the peptide comprises the amino acid sequence of SEQ ID NO: 4. In some embodiments, the peptide comprises the amino acid sequence of SEQ ID NO: 5. In some embodiments, the peptide comprises the amino acid sequence of SEQ ID NO: 6. In some embodiments, the peptide comprises the amino acid sequence of SEQ ID NO: 8. In some embodiments, the peptide comprises the amino acid sequence of SEQ ID NO: 9. In some embodiments, the peptide comprises the amino acid sequence of SEQ ID NO: 10. In some embodiments, the peptide comprises the amino acid sequence of SEQ ID NO: 11. In some embodiments, the peptide comprises the amino acid sequence of SEQ ID NO: 12. In some embodiments, the peptide comprises the amino acid sequence of SEQ ID NO: 13. In some embodiments, the peptide comprises the amino acid sequence of SEQ ID NO: 14. In some embodiments, the peptide comprises the amino acid sequence of SEQ ID NO: 15. In some embodiments, the peptide comprises the amino acid sequence of SEQ ID NO: 16. In some embodiments, the peptide comprises the amino acid sequence of SEQ ID NO: 17.

In some embodiments, the peptide is from 4 to 20 amino acids in length. In some embodiments, the peptide comprises at least one non-naturally occurring amino acid. In some embodiments, the peptide comprises a carboxy terminus that is amidated. In some embodiments, the peptide is in a cyclic form. In some embodiments, the peptide further comprises PEG. In some embodiments, the peptide is comprises a lipophilic molecular group. In some embodiments, the peptide is recombinant or synthesized. In some embodiments, the peptide is fused to a carrier polypeptide. In some embodiments, the peptide is further conjugated to a detectable agent, a peptide tag, a magnetic particle, a diagnostic agent, a therapeutic agent, or a combination thereof. In some embodiments, the pharmaceutical composition disclosed herein, comprises a detectable agent that is an enzyme—substrate agent, a fluorescent agent, a chemiluminescent agent, or a radioisotope. In some embodiments, the pharmaceutical composition disclosed herein, comprises a therapeutic agent that is an anti-inflammatory, immunosuppressive, immunomodulatory, or an anti-tumor agent. In some embodiments, the peptide is in a soluble form.

In some embodiments, the peptide is formulated in a liposome or a nanoparticle delivery system. In some embodiments, the peptide is formulated with a biocompatible polymer. In some embodiments, the pharmaceutical composition of the aspects above further comprises a pharmaceutically acceptable diluent, additive or excipient. In some embodiments, the pharmaceutical composition of the aspects disclosed above is formulated for administration via a subcutaneous, intravenous, intradermal, intraperitoneal, oral, intramuscular, intracerebroventricular, intranasal, intracranial, intracelial, intracerebellar, intrathecal, transdermal, pulmonary, or topical administration route. In some embodiments, the pharmaceutical composition of the aspects disclosed above is formulated for administration via intravenous administration route. In some embodiments, the pharmaceutical composition further comprises a ganglioside and/or a phosphotidylserine.

In some embodiments, the pharmaceutical composition further comprises saccharides selected from the group consisting of cyclodextrins, disaccharides, polysaccharides, and a combination thereof. In some embodiments, the pharmaceutical composition of the aspects disclosed above is in a solution form or in a lyophilized form. In some embodiments, the pharmaceutical composition is contained in a delivery device selected from the group consisting of a syringe, a blunt tip syringe, a catheter, an inhaler, a nebulizer, a nasal spray pump, a nasal irrigation pump or nasal lavage pump, and an implantable pump. In some embodiments, the pharmaceutical composition has a shelf life of at least 2 days, 2 weeks, 1 month to 2 years at room temperature. In some embodiments, the pharmaceutical composition has a shelf life of at least 2 days, 2 weeks, 1 month to 2 years at 4° C. In some embodiments, the peptide or portion thereof binds a CD40 protein or a portion of the CD40 protein. In some embodiments, the peptide or portion thereof, wherein the peptide or the functional thereof is in an amount sufficient to inhibit binding of the CD40 protein to a CD154.

In one aspect, the technology herein relates to a complex comprising a peptide or a portion thereof non-covalently bound to a CD40 protein or a portion of the CD40 protein, wherein the peptide comprises an amino acid sequence with at least 85% or at least 90% sequence identity to an amino acid sequence selected from the group consisting of SEQ ID NOs: 1-6 and 8-17. In some embodiments, the CD40 protein is mammalian. In some embodiments, the CD40 protein is human. In some embodiments, the CD40 protein is recombinant. In one aspect provided herein is an isolated nucleic acid fragment encoding a peptide or a portion thereof, wherein the peptide comprises an amino acid sequence with at least 85% or at least 90% sequence identity to an amino acid sequence set forth in any one of SEQ ID NOs: 1-6 and 8-17. In some embodiments, the isolated nucleic acid fragment of the aspects disclosed above further comprising a nucleotide sequence encoding an agent, wherein the agent is a targeting agent, a detectable agent, a diagnostic agent, or a therapeutic agent. In one aspect provided herein is a vector comprising the isolated nucleic acid fragment of any one of aspects disclosed above. In some embodiments, the isolated nucleic acid fragment is operably linked to a regulatory control sequence. In one aspect provided herein is a host cell comprising the isolated nucleic acid fragment of aspects above or the vector of aspects above.

In one aspect, provided herein is a preparatory regimen for transplantation of a cell, tissue or organ from a recipient to a donor, comprising an anti-CD40 agent; wherein the anti-CD40 agent comprises a peptide containing an amino acid sequence with at least 85% or at least 90% sequence identity to the sequences set forth in any one of SEQ ID NOs. 1-6 and 8-17. In another aspect, provided herein is a preparatory regimen for transplantation of a cell, tissue or organ from a recipient to a donor, comprising an anti-CD40 agent; wherein the anti-CD40 agent comprises a peptide containing an amino acid sequence with at least 90% sequence identity to the sequences set forth in any one of SEQ ID NOs. 8-17. In one embodiment, the preparatory regimen can further comprise instructions for administration of said anti-CD40 agent to said recipient. In one embodiment, said anti-CD40 agent is administered to said recipient between about 10 days before and about 30 days after said transplantation. In another embodiment, said anti-CD40 agent is administered to said recipient at least 1, 2, 3, 4, 5, 6, 7, 8, 9, or 10 days before said transplantation. In another embodiment, said anti-CD40 agent is administered to said recipient at least 1, 2, 3, 4, 5, 6, 7, 8, 9, 10, 11, 12, 13, 14, 15, 15, 17, 18, 19, 20, 21, 22, 23, 24, or 25 days before said transplantation. In another embodiment, said anti-CD40 agent is administered to said recipient subcutaneously, intravenously, intradermally, intraperitoneally, orally, intramuscularly, intracerebroventricularly, intranasally, intracranially, intracelially, intracerebellarly, intrathecally, or transdermally, or topically. In another embodiment, said anti-CD40 agent is administered to said recipient at a dose of between about 1 mg/kg and 100 mg/kg. In one embodiment, the anti-CD40 agent is administered to said recipient at a dose of 50 mg/kg.

In one embodiment, the preparatory regimen provides long term tolerance to said transplant cell, tissue, or organ. In one embodiment, the preparatory regimen further comprises administering an effective amount of apoptotic donor leukocytes. In one embodiment, the donor leukocytes are fixed in a cross-linking agent. In one embodiment, the apoptotic leukocytes are mammalian leukocytes. In one embodiment, the apoptotic leukocytes are porcine leukocytes. In one embodiment, the apoptotic leukocytes are human leukocytes. In one embodiment, the apoptotic leukocytes are from a cadaveric donor, a brain dead donor, a non-heart beating donor, or a living donor. In one embodiment, the apoptotic leukocytes are ex vivo expanded leukocytes. In one embodiment, the apoptotic leukocytes are isolated from a spleen, or peripheral blood. In one embodiment, the apoptotic leukocytes comprise B-lymphocytes. In one embodiment, the apoptotic leukocytes comprise cells that have been differentiated from stem cells or induced pluripotent stem cells ex vivo. In some embodiments, the stem cells are derived from the donor of said transplant cell, tissue, or organ. In one embodiment, the apoptotic leukocytes and the recipient are matched for at least one of MHC class I A allele, MHC class I B allele, MHC class II DR allele, MHC class II DQ allele, or MHC class II DP allele. In one embodiment, the apoptotic leukocytes and the transplant are matched for at least one of MHC class I A allele, MHC class I B allele, MHC class II DR allele, MHC class II DQ allele, or MHC class II DP allele. In one embodiment, the apoptotic leucocytes and the transplant are haploidentical. the apoptotic leucocytes are from the donor of the transplant.

In one embodiment, transplant cell, tissue, or organ is a kidney, liver, heart, lung, pancreas, islet cell, small bowel, bone marrow, hematopoietic stem cell, embryonic stem cell-derived islet beta cell, induced pluripotent stem cell-derived islet beta cell, embryonic stem cell-derived islet, induced pluripotent stem cell-derived islet, a stem cell derived cell, tissue or organ, or a combination thereof. In one embodiment, recipient and the donor of said transplant cell, tissue, or organ are matched for at least one MHC class I A allele, MHC class I B allele, MHC class II DR allele, MHC class II DQ allele, or MHC class II DP allele.

In one aspect, provided herein is a preparatory regimen for transplanting a cell, tissue or organ transplant to a recipient, comprising: one or more anti-CD40 peptides conjugated to the surface of an apoptotic leukocyte, wherein the one or more anti-CD40 peptides, comprise an amino acid sequence with at least 85% or at least 90% sequence identity to a sequence selected from SEQ ID NOs: 1-6 and 8-17. In another aspect, provided herein is a preparatory regimen for transplanting a cell, tissue or organ transplant to a recipient, comprising: one or more anti-CD40 peptides conjugated to the surface of an apoptotic leukocyte, wherein the one or more anti-CD40 peptides, comprises an amino acid sequence with at least 90% sequence identity to a sequence selected from SEQ ID NOs: 8-17. the apoptotic leukocyte is further conjugated to one or more peptides derived from a MHC class II molecule of the recipient. In one embodiment, the apoptotic leukocyte is further conjugated to one or more peptides derived from a MHC class II molecule of the recipient. In one embodiment, the one or more peptides derived from the MHC class II molecule comprises peptides derived from a DR β-chain, a DQ β-chain, or a DP β-chain, or a combination thereof. In one embodiment, the one or more peptides derived from the MHC class II molecule comprise a sequence from a hypervariable region. In one embodiment, the one or more peptides conjugated to the surface of the leukocyte are synthesized in-vitro or recombinantly produced. In one embodiment, the apoptotic leukocyte is MHC class II matched to the donor and MHC class II mismatched to the recipient. In one embodiment, the apoptotic leukocyte is conjugated to one or more peptides derived from a MHC class I molecule of the donor of the cell, tissue or organ transplant. In one embodiment, the MHC class I molecule is expressed in the donor of the transplant. In one embodiment, the MHC class I molecule is HLA-A1, HLA-A3, HLA-B7, or HLAB8. In one embodiment, the MHC class I molecule is encoded by HLA-A*02, 24, 01 or HLA-B*35, 44, 51. In one embodiment, the apoptotic leukocyte is MHC class I matched to the recipient, or MHC class II matched to the recipient, or both.

In one embodiment, the preparatory regimen further comprises administering one or more agents for short-term immunosuppression of said recipient. In one embodiment, the one or more agents for short term immunosuppression is an anti-CD40 agent, wherein the anti-CD40 agent comprises a peptide containing an amino acid sequence with at least 85% or at least 90% sequence identity to an amino acid sequence set forth in any one of SEQ ID NOs: 1-6 and 8-17. In one embodiment, the one or more agents for short term immunosuppression is an anti-CD40 agent, wherein the anti-CD40 agent comprises a peptide containing an amino acid sequence with at least 90% sequence identity to an amino acid sequence set forth in any one of SEQ ID NOs: 8-17. In one embodiment, the one or more agents for short term immunosuppression comprise an mTOR inhibitor, an anti-tumor necrosis factor agent or an anti-tumor necrosis factor receptor agent, an anti-interleukin 6 agent or an anti-interleukin 6 receptor agent, an anti-CD40 agent, or a combination thereof. In one embodiment, the preparatory regimen further comprises instructions for administration of said one or more agents for short term immunosuppression to said transplant recipient. In one embodiment, the apoptotic leukocytes have further been contacted with an amount of one or more immunomodulatory molecules. In one embodiment, said amount of one or more immunomodulatory molecules is sufficient to modify a function of antigen-presenting cells in said recipient. In one embodiment, said one or more immunomodulatory molecules are selected from IFN-γ, an NF-kB inhibitor, vitamin D3, siCD40, cobalt protoporphyrin, insulin B9-23, all or a portion of a cluster of differentiation protein, or a combination thereof. In one embodiment, said NF-kB inhibitor is curcumin, triptolide, Bay-117085, or a combination thereof.

In one embodiment, the one or more peptides are conjugated to the surface of the apoptotic leukocytes by treatment with the crosslinking agent. In one embodiment, said crosslinking agent comprises a carbodiimide. In one embodiment, said carbodiimide comprises 1-ethyl-3-(3-dimethylaminopropyl)-carbodiimide (ECDI); N,N'-diisopropylcarbodiimide (DIC); N,N'-dicyclohexylcarbodiimide (DCC); or a combination thereof. In one embodiment, said crosslinking agent does not comprise a carbodiimide. In one embodiment, said crosslinking agent comprises genipin, acrylic aldehyde, diformyl, osmium tetroxide, a diimidoester, mercuric chloride, zinc sulphate, zinc chloride, trinitrophenol (picric acid), potassium dichromate, ethanol, methanol, acetone, acetic acid, or a combination thereof. IN one embodiment, said diimidoester is selected from cyanuric chloride, diisocyanate, diethylpyrocarbonate (DEPC), a maleimide, benzoquinone, or a combination thereof. In one embodiment, said apoptotic leukocytes are fixed for a pre-determined amount of time. In one embodiment, said pre-determined time is at least about 10 minutes, 20 minutes, 30 minutes, 40 minutes, 50 minutes, 60 minutes, 75, minutes, 90 minutes, 120 minutes, 150 minutes, 180 minutes, 210 minutes, or 240 minutes. In one embodiment, said apoptotic leukocytes are contacted with an amount of one or more immunomodulatory molecules, before fixation.

In one aspect, provided herein is a tolerizing regimen for post-transplant stabilization of a cell, tissue or organ transplant in a recipient, comprising administering to the recipient an effective amount of an anti-CD40 peptide, wherein the anti-CD40 peptide comprises an amino acid sequence with at least 85%. or at least 90% sequence identity to a sequence selected from SEQ ID NOs. 1-6 and 8-17. In another aspect, provided herein is a tolerizing regimen for post-transplant stabilization of cell, tissue or organ transplant in a recipient, comprising administering to the recipient an effective amount of an anti-CD40 peptide, wherein the anti-CD40 peptide comprises an amino acid sequence with at least 90% sequence identity to a sequence selected from SEQ ID NOs. 8-17. In one embodiment, the tolerizing regimen further comprises apoptotic leukocytes. In one embodiment, the apoptotic leukocytes are expanded at least about 3 fold, 5 fold, 10 fold, 50 fold, 100 fold, 150 fold, 200 fold or 250 fold relative to the starting population prior to contacting with said crosslinking agent. In one embodiment, the apoptotic leukocytes and the anti-CD40 peptide are administered separately. In one embodiment, the apoptotic leukocytes and the anti-CD40 peptide are administered simultaneously.

In one aspect, provided herein is a method of inhibiting an interaction between a CD40 protein and a CD154 protein, the method comprising contacting the CD40 protein with an anti-CD40 agent, wherein the anti-CD40 agent comprises a peptide containing an amino acid sequence with at least 85% or at least 90% sequence identity to an amino acid sequence selected from the group consisting of SEQ ID NOs: 1-6 and 8-17, thereby inhibiting the interaction between the CD40 protein and the CD154 protein. In another aspect, provided herein is a method of inhibiting an interaction between a CD40 protein and a CD154 protein, the method comprising contacting the CD40 protein with an anti-CD40 agent, wherein the anti-CD40 agent comprises a peptide containing an amino acid sequence with at least 90% sequence identity to an amino acid sequence selected from the group consisting of SEQ ID NOs: 8-17, thereby inhibiting the interaction between the CD40 protein and the CD154 protein. In one embodiment, the peptide or the functional fragment thereof binds the CD40 protein. In one embodiment, the CD40 protein is mammalian. In one embodiment, the inhibition is greater than that exhibited by contacting a peptide or a functional fragment thereof comprising a sequence set forth in SEQ ID NO: 7.

In one embodiment, the CD40 protein is human. In one embodiment, the CD154 protein is mammalian. In one embodiment, the CD154 protein is human. In one embodiment, the CD40 protein is expressed by an immune cell. In one embodiment, the immune cell is selected from the group consisting of B-cell, T-cell, neutrophil, monocyte, macrophage, dendritic cell, and platelet. In one embodiment, the contacting inhibits B-cell activation, T-cell proliferation, T-cell activation, B-cell proliferation, macrophage activation, cytokine production, or a combination thereof. In one embodiment, the CD40 protein is expressed by an endothelial cell, an epithelial cell, a fibroblast cell, a smooth muscle cell, a B lymphoma cell, a melanoma cell, or a carcinoma cell. In one embodiment, the contacting comprises administering the peptide or a functional fragment thereof to a subject. In one embodiment, the subject is a human.

In one aspect, provided herein is a method of transplantation of a cell or tissue transplant from a mammalian donor in a recipient, the method comprising administering an effective amount of the pharmaceutical composition of any one the aspects described above. In another aspect, provided herein is a method of transplantation of a cell, tissue or organ from a donor to a recipient, the method comprising administering an effective amount of an anti-CD40 agent; wherein the anti-CD40 agent comprises a peptide containing an amino acid sequence with at least 85% or at least 90% sequence identity to the sequences set forth in any one of SEQ ID NOs. 1-6 and 8-17 to the recipient. In another aspect, provided herein is a method of transplantation of a cell, tissue or organ from a donor to a recipient, the method comprising administering an effective amount of an anti-CD40 agent; wherein the anti-CD40 agent comprises a peptide containing an amino acid sequence with at least 90% sequence identity to the sequences set forth in any one of SEQ ID NOs. 8-17 to the recipient.

In one embodiment, the peptide is conjugated to apoptotic leukocytes. In one embodiment, the method further comprises administering apoptotic leukocytes. In one embodiment, the method further comprises administering apoptotic leukocytes fixed with a cross-linking agent. In one embodiment, the method further comprises administering the apoptotic leukocytes and the peptide separately. In one embodiment, the method further comprises administering the apoptotic leukocytes and the peptide simultaneously. In one embodiment, the method further comprises the method further comprises transplanting the cell, tissue or organ in the recipient. In one embodiment, the cell or tissue transplant is a kidney, liver, heart, lung, pancreas, islet cell, small bowel, bone marrow, hematopoietic stem cell, embryonic or induced pluripotent stem cell-derived islet beta cell, embryonic or induced pluripotent stem cell-derived islet, embryonic or pluripotent stem-cell derived hepatocyte or a combination thereof. In one embodiment, the cell or tissue transplant is a xenotransplant. In one embodiment, the cell or tissue transplant is an allotransplant. In one embodiment, the administering is subcutaneous, intravenous, intradermal, intraperitoneal, oral, intramuscular, intracerebroventricular, intranasal, intracranial, intracelial, intracerebellar, intrathecal, transdermal, pulmonary, or topical administration. In one embodiment, the administering is intravenous administration. In one embodiment, the administering is performed prior to, during, and after the transplantation. In one embodiment, the administering is performed at least 1, 2, 3, 4, 5, 6, 7, 8, 9, 10 or more days prior to the transplantation. In one embodiment, the administering is performed during the transplantation. In one embodiment, the administering is performed at least 1, 2, 3, 4, 5, 6, 7, 10, or more days after the transplantation. In one embodiment, administering a tolerizing agent to the recipient. In one embodiment, the tolerizing agent comprises mammalian leukocytes fixed with a crosslinking agent. In one embodiment, the mammalian leukocytes are from the mammalian donor or from a donor that is MHC matched to the mammalian donor. In one embodiment, the mammalian donor is genetically modified. In one embodiment, administering an immunomodulatory agent to the recipient. In one embodiment, the immunomodulatory agent is an anti-CD40 agent, anti-CD40L agent, a B-cell depleting or modulating agent, an mTOR inhibitor, a TNF-alpha inhibitor, a IL-6 inhibitor, alpha 1anti-trypsin inhibitor, dehydroxymethylepoxyquinomycin (DHMEQ), a nitrogen mustard alkylating agent, a complement C3 or C5 inhibitor, IFNγ, an NFκB inhibitor, vitamin D3, siCD40, cobalt protoporphyrin, insulin B9-23, a cluster of differentiation protein, or any combination thereof. In one embodiment, the cell or tissue transplant survives for at least 30 days, 50 days, 100 days, 1 year or more in the recipient. In one embodiment, the recipient is a mammal. In one embodiment, the recipient is a human.

In one aspect, provided herein is a method for inducing immunosuppression in a subject in need thereof, the method comprising administering to the subject an effective amount of the pharmaceutical composition in any one of the aspects described above. In one aspect, provided herein is a method of inducing immunosuppression in a subject in need thereof, the method comprising; administering to the recipient an effective amount of an anti-CD40 agent, wherein the agent is a peptide comprising an amino acid sequence with at least 85% or at least 90% sequence identity to the sequences set forth in any one of SEQ ID NOs. 1-6 and 8-17. In one aspect provided herein is a method of inducing immunosuppression in a subject in need thereof, the method comprising; administering to the recipient an effective amount of an anti-CD40 agent, wherein the agent is a peptide comprising an amino acid sequence with at least 90% sequence identity to the sequences set forth in any one of SEQ ID NOs. 8-17. In one embodiment, the method comprises further administering apoptotic leukocytes with the anti-CD40 agent. In one embodiment, the peptide is conjugated to apoptotic leukocytes. In one embodiment, the apoptotic leukocytes fixed with a cross-linking agent. In one embodiment, the apoptotic leukocytes and the peptides are administered separately. In one embodiment, the apoptotic leukocytes and the peptides are administered simultaneously. In one embodiment, the method further comprises transplanting a cell, tissue or organ in the subject. In one embodiment, the immune response comprises B-cell activation, T-cell proliferation, B-cell proliferation, macrophage activation, cytokine production, or a combination thereof. In one embodiment, the subject has undergone, is undergoing or will be undergoing an allotransplant. In one embodiment, the subject has undergone, is undergoing or will be undergoing a xenotransplant. In one embodiment, the subject is a human. In one embodiment, inhibits B-cell activation, T-cell proliferation, T-cell activation, B-cell proliferation, macrophage activation, cytokine production, or a combination thereof, thereby inducing immunosuppression. In one embodiment, the subject is suffering from or is at a risk of developing an inflammatory disease. In one embodiment, the inflammatory disease is an autoimmune disease.

In one aspect, provided herein is a method of inducing immune tolerance in a subject in need thereof, the method comprising administering to the subject an effective amount of the pharmaceutical composition of any one of the aspects described above. In another aspect, provided herein is a method of inducing tolerance to a cell, tissue or organ transplant in a recipient, the method comprising, administering to the recipient an effective amount of a composition comprising an anti-CD40 agent, wherein the agent comprises a peptide containing an amino acid sequence with at least 85% or at least 90% sequence identity to any one of the sequences set forth in SEQ ID NOs. 1-6 and 8-17. In another aspect, provided herein is a method of inducing tolerance to a cell, tissue or organ transplant in a recipient, the method comprising, administering to the recipient an effective amount of a composition comprising an anti-CD40 agent, wherein the anti-CD40 agent comprises a peptide containing an amino acid sequence with at least 90% sequence identity to the sequences set forth any one of SEQ ID NOs. 8-17.

In one embodiment, the anti-CD40 agent is conjugated to apoptotic leukocytes. In one embodiment, the method further comprises administering apoptotic leukocytes. In one embodiment, the method further comprises administering apoptotic leukocytes fixed with a cross-linking agent. In one embodiment, the method further comprises administering the apoptotic leukocytes and the anti-CD40 agent separately. In one embodiment, the method further comprises administering the apoptotic leukocytes and the anti-CD40 agent simultaneously. In one embodiment, the method further comprises apoptotic leukocytes conjugated to one or more peptides derived from a MHC class II molecule of the recipient. In one embodiment, the apoptotic leukocytes comprise cells that have been differentiated from stem cells ex vivo, wherein the stem cells are derived from a donor of the cell, tissue, or organ transplant. In one embodiment, the apoptotic leukocytes are MHC matched to the recipient. In one embodiment, the apoptotic leukocytes are conjugated to one or more peptides derived from a MHC class I molecule of a donor of the cell, tissue or organ transplant. In one embodiment, the method further comprises transplanting the cell, tissue or organ transplant. In one embodiment, the transplanting is performed at least 1, 2, 3, 4, 5, 6, 7, 8, 9, 10, 11, 12, 13, 14, 15, or more days after administering the composition. In one embodiment, the method further comprises administering at least one booster dose of the composition. In one embodiment, the booster dose is administered at least 1, 2, 3, 4, 5, 6, 7, 8, 9, 10, 12, 14, 15, 17, 20, 21, or 24 days after the transplanting. In one embodiment, said tolerance is for a period of at least one month. In one embodiment, said tolerance is for a period of at least 100 days. In one embodiment, said tolerance is for a period of at least one year.

In one aspect, provided herein is a method of post-transplant immune tolerizing a subject comprising administering to said subject: an anti-CD40 agent, wherein the agent comprises a peptide comprising an amino acid sequence with at least 85% or at least 90% sequence identity to the sequences set forth in any one of SEQ ID NOs: 1-6 and 8-17. In another aspect, provided herein is a method of post-transplant immune tolerizing a subject comprising administering to said subject: an anti-CD40 agent, wherein the agent comprises a peptide comprising an amino acid sequence with at least 90% sequence identity to the sequences set forth in any one of SEQ ID NOs: 8-17. In another embodiment, the anti-CD40 agent is conjugated to apoptotic leukocytes.

In one embodiment, the anti-CD40 agent is conjugated to apoptotic leukocytes. In one embodiment, the method further comprises administering apoptotic leukocytes. In one embodiment, the method further comprises administering apoptotic leukocytes fixed with a cross-linking agent. In one embodiment, the method further comprises administering the apoptotic leukocytes and the anti-CD40 agent separately. In one embodiment, the method further comprises administering the apoptotic leukocytes and the anti-CD40 agent simultaneously. In one embodiment, the apoptotic leukocytes are further conjugated to one or more peptides derived from a MHC class II molecule of the recipient. In one embodiment, the apoptotic leukocytes comprise cells that have been differentiated from stem cells ex vivo, wherein the stem cells are derived from a donor of the cell, tissue, or organ transplant. In one embodiment, the apoptotic leukocytes are MHC matched to the recipient. In one embodiment, the apoptotic leukocytes are conjugated to one or more peptides derived from a MHC class I molecule of a donor of the cell, tissue or organ transplant. In one embodiment, the method further comprises transplanting the cell, tissue or organ transplant. In one embodiment, the method further comprises apoptotic leukocytes isolated from peripheral blood. In one embodiment, the method further comprises apoptotic leukocytes enriched for B cells by positive or negative selection. In one embodiment, said apoptotic leukocytes are expanded at least 200 fold relative to a starting population prior to said modulating with said carbodiimide crosslinking agent.

In one aspect, provided herein is a method of treating a subject suffering from an inflammatory disease, the method comprising administering to the subject an effective amount of the pharmaceutical composition of any one of the aspects described above. In one aspect, provided herein is a method of treating a subject suffering from or is at a risk of developing a neoplastic disease characterized by a neoplastic cell that expresses CD40, the method comprising administering to the subject an effective amount of the pharmaceutical composition of any one of the aspects described above. In one embodiment, the inflammatory disease is an autoimmune disease. In one embodiment, the inflammatory disease is selected from the group consisting of type I diabetes, multiple sclerosis, rheumatoid arthritis, systemic lupus, erythematosa, chronic obstructive pulmonary disease, atherosclerosis, Crohn's colitis, ulcerative gastritis, primary biliary cirrhosis, Guillain-Barre syndrome, Psoriasis, Graves' disease, Hashimoto's Thyroiditis, Myasthenia Gravis, Vasculitis, acute lung injury, bronchial asthama and acute respiratory distress syndrome.

In one aspect, provided herein is a method of treating a subject suffering from or is at a risk of developing a neoplastic disease characterized by a neoplastic cell that expresses CD40, the method comprising administering to the subject an effective amount of the pharmaceutical composition of any of the aspects described above. In one embodiment, the neoplastic disease is a lymphoma, a myeloma or a carcinoma. In one embodiment, the lymphoma is a B cell lymphoma. In one embodiment, the subject is a mammal. In one embodiment, the subject is human.

In one aspect, provided herein is a method of reducing the number of donor cells required for a transplantation in a recipient, the method comprising administering an effective amount of the pharmaceutical composition of any one of the aspects described above. In one embodiment, the donor cells are islet cells, stem cell, induced pluripotent stem cell-derived islet cells or a combination thereof. In one embodiment, the donor cells are autologous, allogeneic, and xenogeneic.

In one aspect, provided herein is a kit for transplantation of a cell, tissue or organ transplant in a recipient comprising; (a) a first container comprising a first composition comprising apoptotic leukocytes fixed in a crosslinking agent, an optionally a container comprising a composition comprising an anti-CD40 agent, wherein the agent is a peptide comprising an amino acid sequence with at least 85% or at least 90% sequence identity to the sequences set forth in any one of SEQ ID NOs:1-6 and 8-17. In another aspect, provided herein is a kit for transplantation of a cell, tissue or organ transplant in a recipient comprising; (a) a first container comprising a first composition comprising apoptotic leukocytes fixed in a crosslinking agent, an optionally a container comprising a composition comprising an anti-CD40 agent, wherein the agent is a peptide comprising an amino acid sequence with at least 90% sequence identity to the sequences set forth in any one of SEQ ID NOs:8-17. In an embodiment, the anti-CD40 agent is conjugated to apoptotic leukocytes. In one embodiment, the apoptotic leukocytes is further conjugated to one or more peptides derived from a MHC class II molecule of the recipient. In one embodiment, the apoptotic leukocytes are MHC matched to the recipient. In one embodiment, the apoptotic leukocytes are further conjugated to one or more peptides derived from a MHC class I molecule of a donor of the cell, tissue or organ transplant. In one embodiment, the kit further comprises the cell, tissue or organ transplant. In one embodiment, the first container and the optional second container is a bottle, a vial, a syringe, or a test tube. In one embodiment, the first container and the optional second container is a multi-use container In one aspect, provided herein is a transplant kit comprising a preparatory regimen and a tolerizing regimen: said preparatory regimen comprising an anti-CD40 agent, wherein the agent comprises one or more peptides comprising an amino acid sequence with at least 85% or at least 90% sequence identity to the sequences set forth in any one of SEQ ID NOs: 8-17; said tolerizing regimen comprising: an anti-CD40 agent, wherein the agent comprises one or more peptides comprising an amino acid sequence with at least 85% or at least 90% sequence identity to the sequences set forth in any one of the sequences set forth in SEQ ID NOs: 8-17; wherein said preparatory regimen is administered to a subject prior to transplantation, and said tolerizing regimen is administered post-transplantation to said subject. In another aspect, provided herein is a transplant kit comprising a preparatory regimen and a tolerizing regimen: said preparatory regimen comprising an anti-CD40 agent, wherein the agent comprises one or more peptides comprising an amino acid sequence with at least 85% or at least 90% sequence identity to the sequences set forth in any one of SEQ ID NOs: 1-6; said tolerizing regimen comprising: an anti-CD40 agent, wherein the agent comprises one or more peptides comprising an amino acid sequence with at least 85% or at least 90% sequence identity to the sequences set forth in any one of the sequences set forth in SEQ ID NOs: 1-6; wherein said preparatory regimen is administered to a subject prior to transplantation, and said tolerizing regimen is administered post-transplantation to said subject In one embodiment, the transplant kit further comprises the transplant kit further comprises a cell, tissue or organ transplant. In one embodiment, the anti-CD40 agent is conjugated to apoptotic leukocytes. In one embodiment, the transplant kit further comprises apoptotic leukocytes. In one embodiment, the transplant kit further comprises apoptotic leukocytes fixed with a cross-linking agent. In one embodiment, the transplant kit further comprises apoptotic leukocytes conjugated with one or more peptides derived from a MHC class II molecule of the recipient. In one embodiment, the transplant kit further comprises apoptotic leukocytes conjugated one or more peptides derived from a MHC class I molecule of a donor of the cell, tissue or organ transplant. In one embodiment, the transplant kit further comprises apoptotic leukocytes that have been differentiated from stem cells ex vivo, wherein the stem cells are derived from a donor of the cell, tissue, or organ transplant. In one embodiment, the transplant kit further comprises apoptotic leukocytes that are MHC matched to the recipient. In one embodiment, the transplant kit further comprises instructions for transplanting the cell, tissue or organ transplant. In one embodiment, the transplant kit further comprises apoptotic leukocytes isolated from peripheral blood. In one embodiment, said apoptotic leukocytes of said tolerizing regimen are enriched for B cells by positive or negative selection. In one embodiment, said apoptotic leukocytes of said tolerizing regimen are expanded at least 200 fold relative to a starting population prior to contacting with said crosslinking agent.

In one aspect provided herein is a method of inhibiting immune response to a therapeutic agent in a subject, the method comprising administering to the subject the pharmaceutical composition of any one of aspects above.

In some embodiments, the therapeutic agent is a biologic. In some embodiments, the biologic is a protein, vaccine, antibody, aptamer, nucleic acids, DNA, RNA, antisense oligonucleotide, virus and bacteria.

In one aspect provided herein is a method of abrogating or reducing an undesired immune response to a therapy in a subject, the method comprising administering to the subject the pharmaceutical composition of any one of aspects above prior to, in conjugation with or after said therapy.

BRIEF DESCRIPTION OF THE DRAWINGS

The features of the present disclosure are set forth with particularity in the appended claims. A better understanding of the features and advantages of the present disclosure can be obtained by reference to the following detailed description that sets forth illustrative embodiments, in which the principles of the disclosure are utilized, and the accompanying drawings of which:

DETAILED DESCRIPTION OF THE DISCLOSURE

Figure 1:
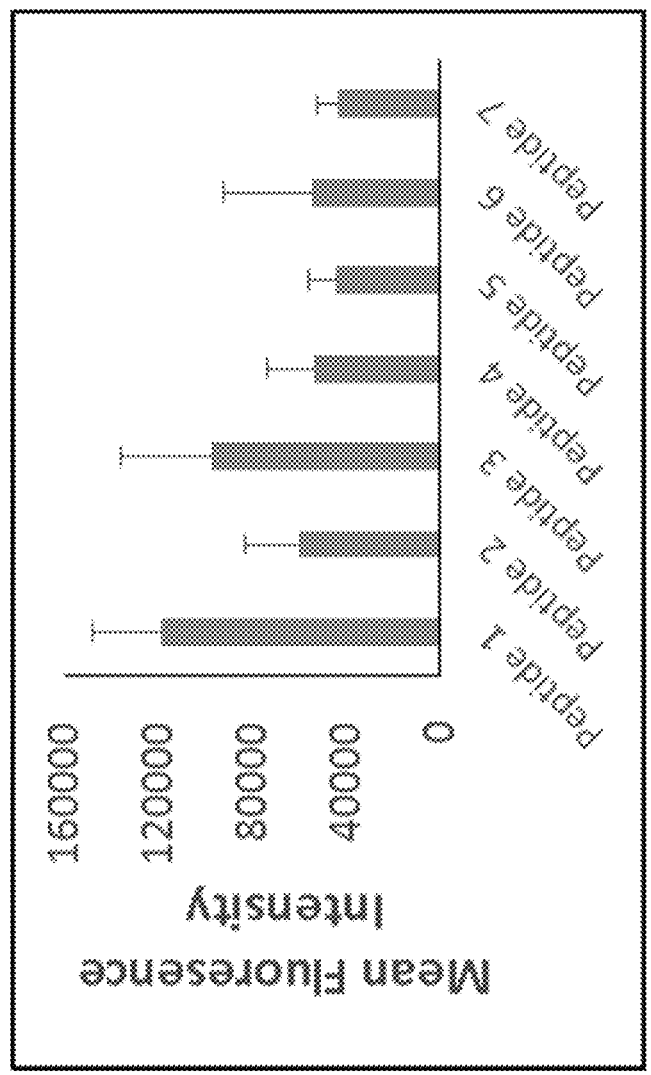
FIG. 1 shows binding of CD40 targeting peptides to PBMC. Binding of the CD40 targeting peptides was analyzed by incubating 5 µM of various fluorochrome tagged CD40 interacting peptides with PBMC from rhesus monkeys for 30 minutes at 4° C. and analyzed by flow cytometry. Peptides 1 and 3 showed high binding affinity.
Figure 2:
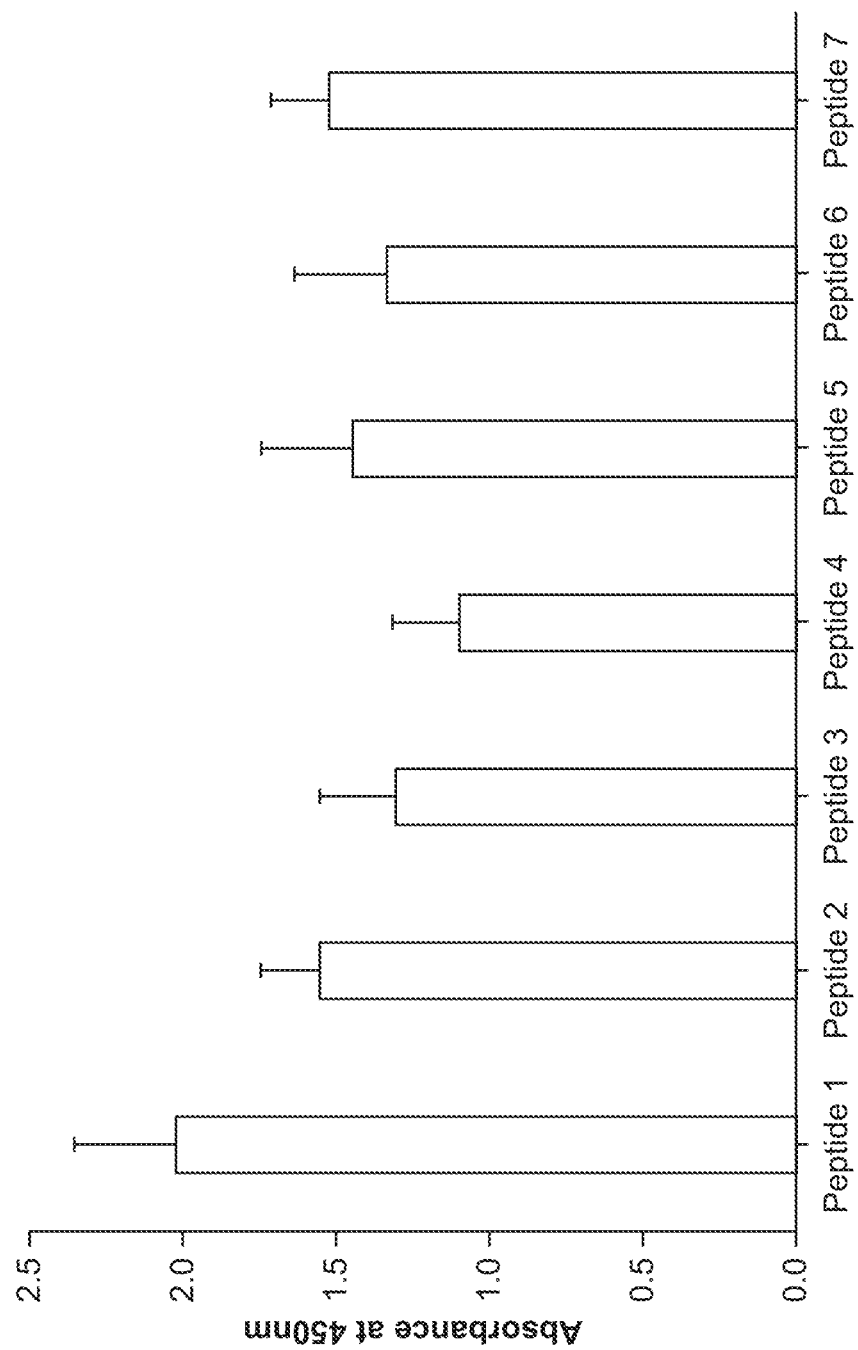
FIG. 2 demonstrates identified peptides bind specifically to CD40. Binding of the identified peptides to CD40 was analyzed by ELISA. Briefly, plates were coated with CD40 and then incubated with identified peptides and detected using Flag-tagged rhsCD40. Peptide #2, Peptide #5, and Peptide #7 showed similar binding affinity to Peptide #1.
Figure 3B:
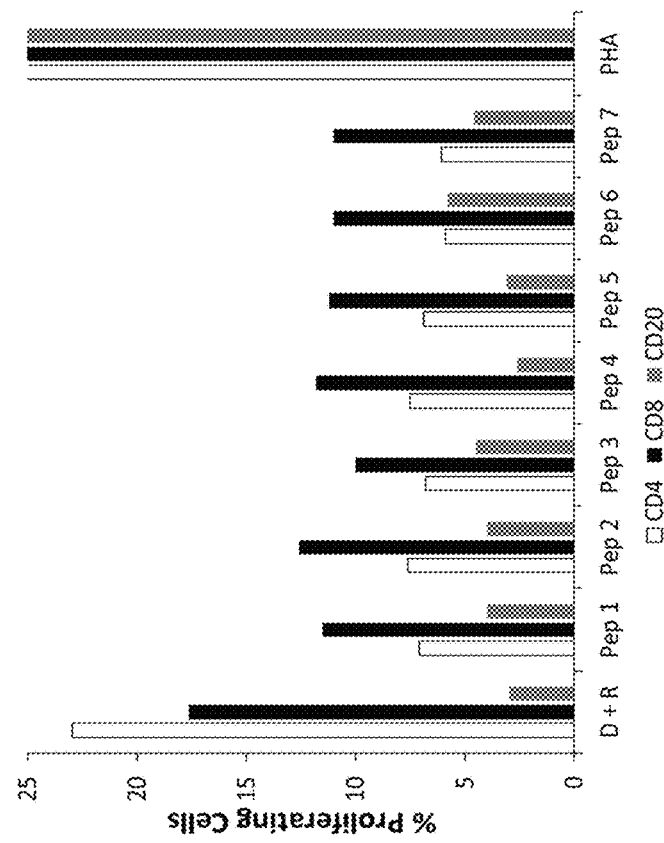
FIGS. 3A-3E shows newly identified peptides demonstrate robust inhibition of T and B cells proliferation. The ability of the CD40 targeting peptides to block CD40-CD40L signaling and inhibit T and B cell proliferation was assessed in a one-way CFSE-MLR. Each of the FIGS. 3A-3E show results of CFSE-MLR performed on PBMC obtained from a different Rhesus monkey. FACS analysis demonstrates that Peptide#2 and Peptide #3 inhibited T and B cell proliferation significantly better than the CD40 targeting peptide identified earlier. The levels of T cell and B cell proliferation was 35-46% in all the 5 animals and for sake clarity was capped at 25% in the figure for better visualization.
Figure 3A:
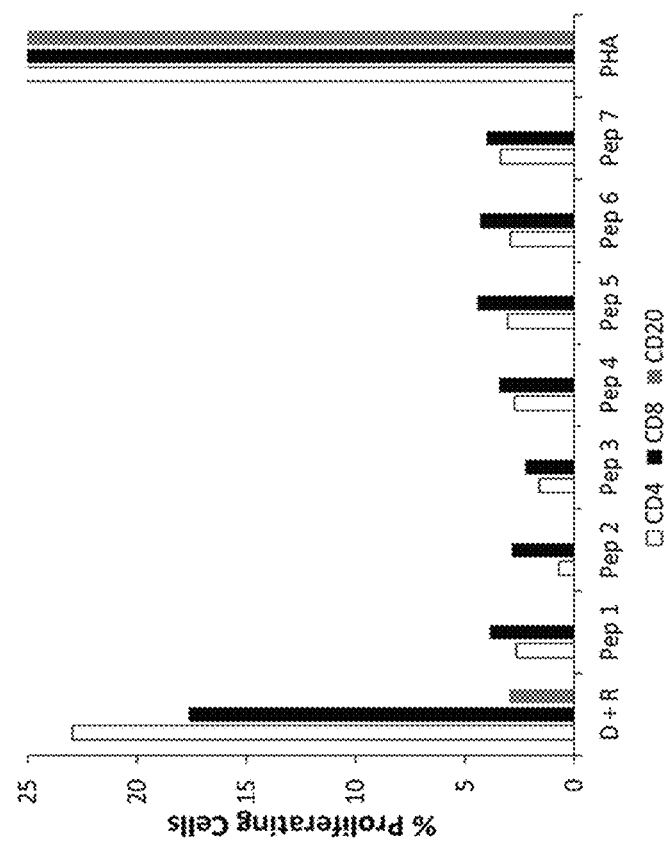
Figure 3D:
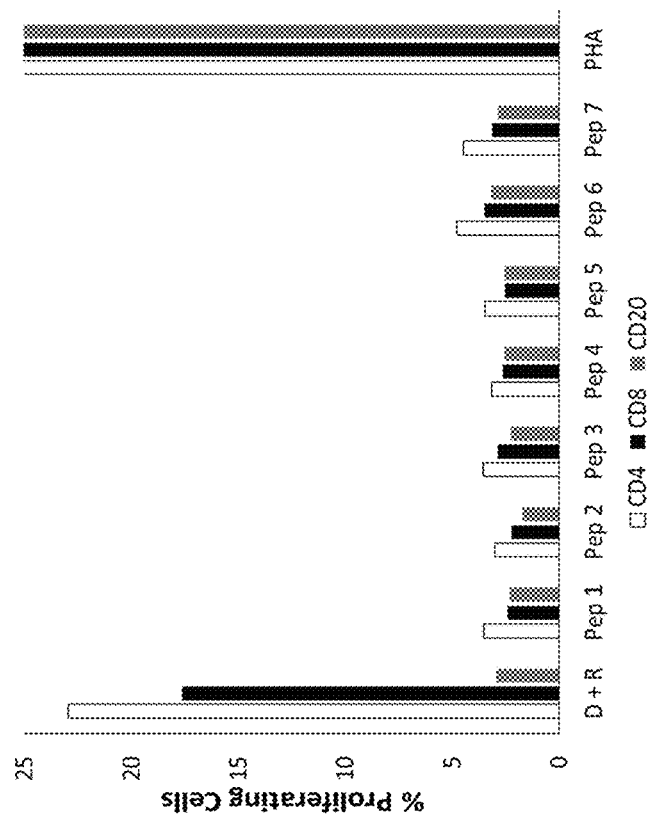
Figure 3C:
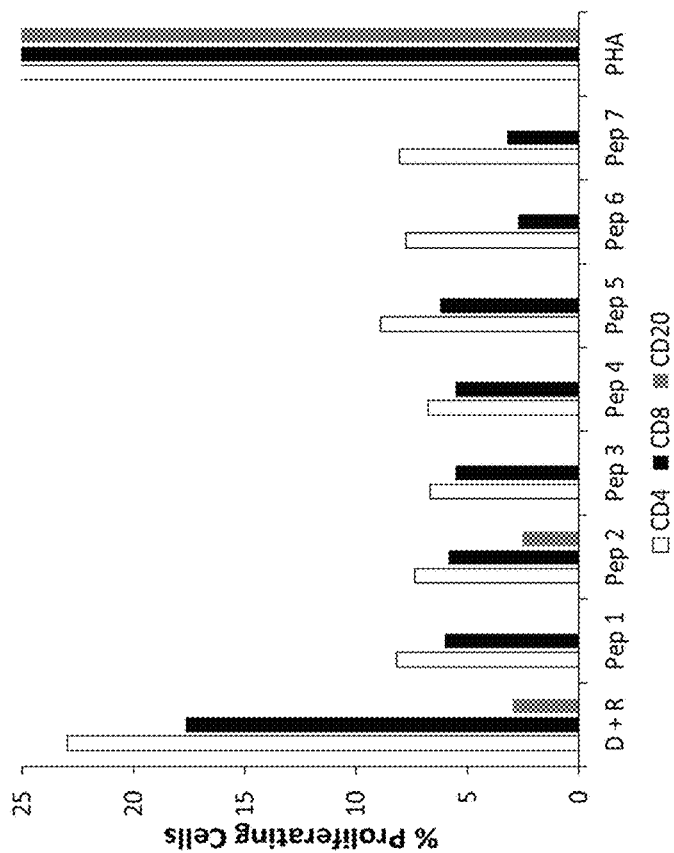
Figure 3E:
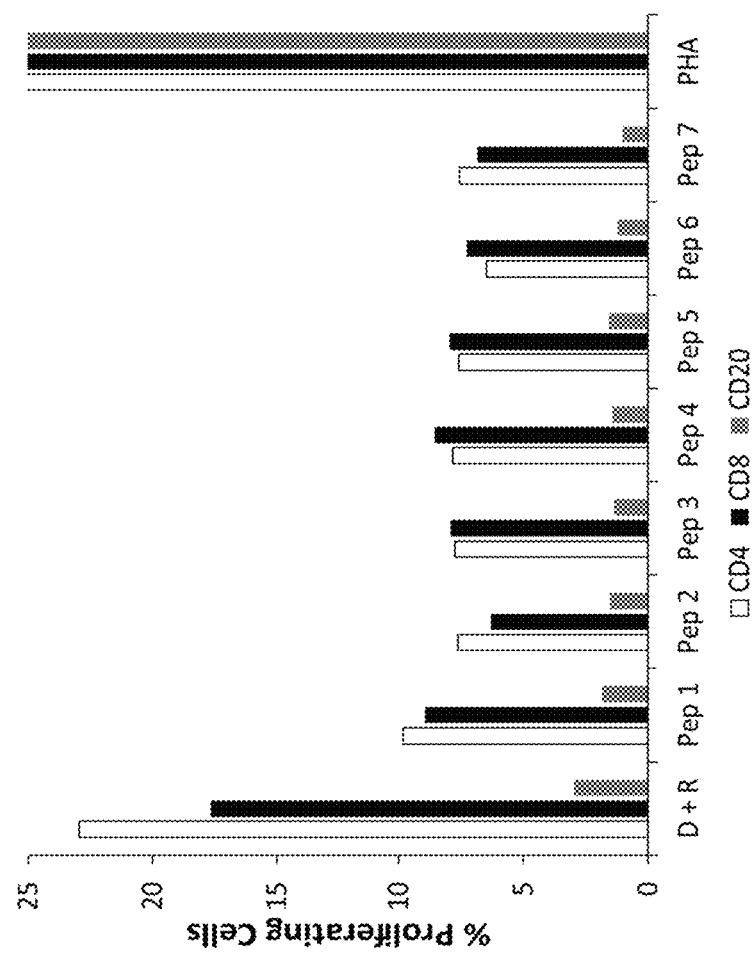
Figure 4:
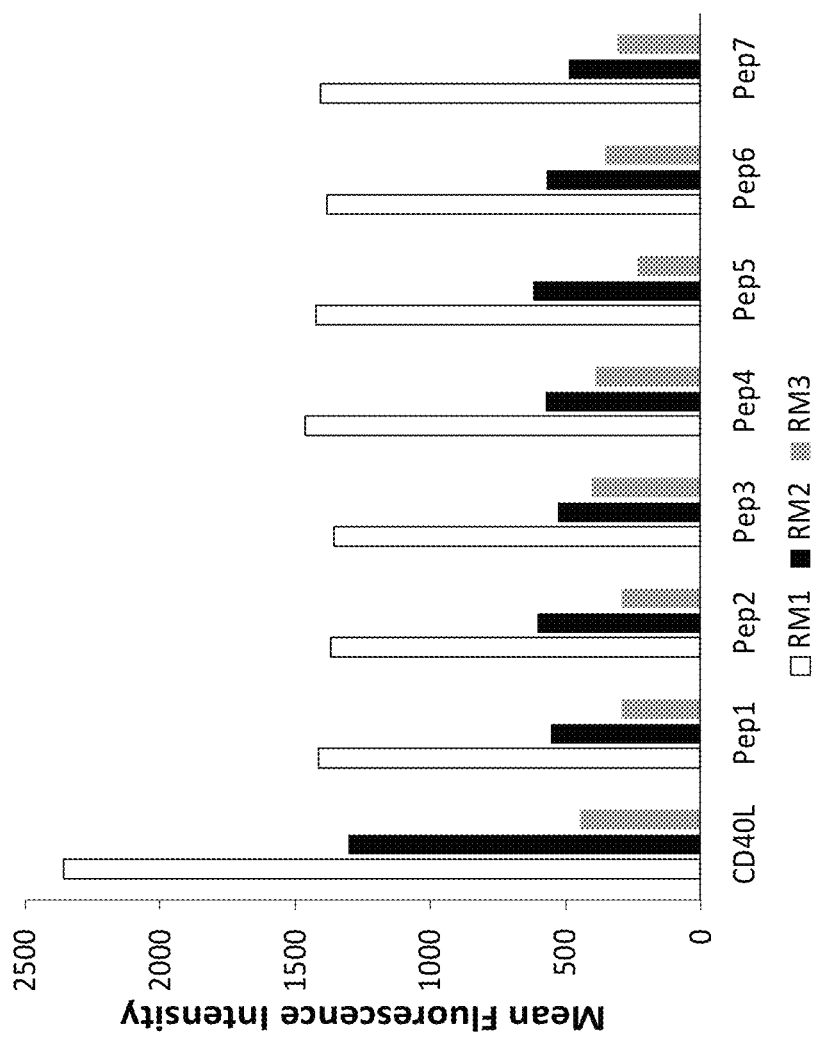
FIG. 4 shows CD40 targeting peptides block B cell activation. The ability of the newly identified peptides to block B cell activation by CD40L was analyzed in a peptide blocking study. Briefly, B cells were pre-incubated with newly identified peptides for 30 minutes before stimulation with rhCD40L. Activation of the B cells was analyzed by measuring the expression levels of MHC class II molecules on the cell surface by flow cytometry. FACS analysis demonstrates that Peptide #2, Peptide #4 and Peptide #5 have a similar or higher ability to block the B cell activation when compared to peptide listed in Peptide #1.

The following discussion of the present disclosure has been presented for purposes of illustration and description. The following is not intended to limit the invention to the form or forms disclosed herein. Although the description of the present disclosure has included description of one or more embodiments and certain variations and modifications, other variations and modifications are within the scope of the present disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

The section headings used herein are for organizational purposes only and are not to be construed as limiting the subject matter described.

Although various features of the disclosure may be described in the context of a single embodiment, the features can also be provided separately or in any suitable combination. Conversely, although the disclosure may be described herein in the context of separate embodiments for clarity, various aspects and embodiments can be implemented in a single embodiment.

The practice of some embodiments disclosed herein employ, unless otherwise indicated, conventional techniques of immunology, biochemistry, chemistry, molecular biology, microbiology, cell biology, genomics and recombinant DNA, which are within the skill of the art. See for example Sambrook and Green, Molecular Cloning: A Laboratory Manual, 4th Edition (2012); the series Current Protocols in Molecular Biology (F. M. Ausubel, et al. eds.); the series Methods In Enzymology (Academic Press, Inc.), PCR 2: A Practical Approach (M. J. MacPherson, B. D. Hames and G. R. Taylor eds. (1995)), Harlow and Lane, eds. (1988) Antibodies, A Laboratory Manual, and Culture of Animal Cells: A Manual of Basic Technique and Specialized Applications, 6th Edition (R. I. Freshney, ed. (2010)).

Definitions

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only, and is not intended to be limiting.

In this application, the use of the singular includes the plural unless specifically stated otherwise. It must be noted that, as used in the specification, the singular forms "a," "an" and "the" include plural referents unless the context clearly dictates otherwise. Furthermore, use of the term "including" as well as other forms, such as "include", "includes," and "included," is not limiting.

The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C."

The term "or" can be used conjunctively or disjunctively, unless the context specifically refers to a disjunctive use.

The term "about" or "approximately" means within an acceptable error range for the particular value as determined by one of ordinary skill in the art, which can depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the invention, and vice versa. Furthermore, compositions of the invention can be used to achieve methods of the invention.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the inventions.

As used herein, a "subject", "patient", "individual" and like terms are used interchangeably and refers to a vertebrate, preferably a mammal, more preferably a primate, still more preferably a human. Mammals include, without limitation, humans, primates, rodents, wild or domesticated animals, including feral animals, farm animals, sport animals, and pets. Primates include, for example, chimpanzees, cynomologous monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, buffalo, feline species, e.g., domestic cat, and canine species, e.g., dog, fox, wolf, avian species, e.g., chicken, emu, ostrich, and fish, e.g., trout, catfish and salmon. The terms, "individual," "patient" and "subject" are used interchangeably herein. A subject can be male or female.

Preferably, the subject is a mammal. The mammal can be a human, non-human primate, mouse, rat, dog, cat, horse, or cow, but is not limited to these examples. Mammals other than humans can be advantageously used as subjects that represent animal models of conditions or disorders associated with CD40 activity. In addition, the compositions and methods described herein can be used to treat domesticated animals and/or pets.

A subject can be one who has been previously diagnosed with or identified as suffering from or under medical supervision for a CD40 associated disorder, e.g., inflammatory disease, autoimmune disease, cancer. A subject can be one who is diagnosed and currently being treated for, or seeking treatment, monitoring, adjustment or modification of an existing therapeutic treatment, or is at a risk of developing a CD40 associated disorder. A subject can be a recipient of a transplant, for example, someone who has undergone, is undergoing, or will be undergoing transplantation.

As used herein, the term "in combination" refers to the use of more than one prophylactic and/or therapeutic agent simultaneously or sequentially and in a manner such that their respective effects are additive or synergistic.

The term "transplant" and its grammatical equivalents as used herein encompasses any procedure that involves transplantation, implantation, or infusion of cells, tissues, or organs from a donor into a recipient. Non-limiting exemplary types of transplant include autotransplant, autograft, allotransplant, allograft, isotransplant, isograft, xenotransplant, xenograft, and split graft, and domino transplant. In an embodiment, the term "split graft" encompasses any procedure that involves the transplantation of cells, organs, tissues, or even particular proteins from a donor is split into more than one recipient.

The term "autotransplantation", "autotransplant", "autograft", "autologous transplantation" or grammatical equivalents as used herein encompasses any procedure that involves the transplantation of organs, tissues, cells or even particular proteins, or expression products from one part of the body to another in the same subject. In an embodiment, the subject is a member of a Laurasiatheria super order. In an embodiment, the subject is an ungulate for instance a pig, giraffe, camel, deer or bovine. In an embodiment, the subject is a human or non-human primate. The autologous tissue (also called autogenous, autogeneic, or autogenic tissue) transplanted by such a procedure is called an autograft or autotransplant. Non limiting example can include autologous transplant of stem cell, induced pluripotent stem cell, cells derived from stem cells and induced pluripotent cells.

The term "allotransplantation", "allotransplant", "allograft" or their grammatical equivalents as used herein encompasses any procedure that involves transplantation, implantation, or infusion of cells, tissues, or organs into a recipient, where the recipient and donor are the same species. In an embodiment, the recipient and/or donor are a member of a Laurasiatheria super order. In an embodiment, the recipient and/or donor are ungulates for instance pig, giraffe, camel, deer or bovine. In an embodiment, the cells, tissues, or organs described herein are transplanted into humans or non-human primates. Allotransplantation includes but is not limited to vascularized allotransplant, partially vascularized allotransplant, unvascularized allotransplant, allodressings, allobandages, and allostructures. In some cases, an allotransplant is an isograft or isotransplant in which organs or tissues are transplanted from a donor to a genetically identical recipient (such as an identical twin).

The term "xenotransplantation", "xenotransplant", "xenograft" or its grammatical equivalents as used herein encompasses any procedure that involves transplantation, implantation, or infusion of cells, tissues, or organs into a recipient, where the recipient and donor are different species. In an embodiment, the recipient and/or donor are a member of a Laurasiatheria super order. In an embodiment, the recipient and/or donor is an ungulate, for instance a pig, giraffe, camel, deer or bovine. In an embodiment, the donor is a pig, and the recipient is a human or non-human primate. In an embodiment, the cells, tissues, or organs described herein are transplanted into humans or non-human primates. Xenotransplantation includes but is not limited to vascularized xenotransplant, partially vascularized xenotransplant, unvascularized xenotransplant, xenodressings, xenobandages, and nanostructures.

The term "transplant rejection" and its grammatical equivalents as used herein can refer to a process or processes by which an immune response of an organ transplant recipient mounts a reaction against the transplanted material (e.g., cells, tissues, and/or organs) sufficient to impair or destroy the function of the transplanted material.

The term "hyperacute rejection" and its grammatical equivalents as used herein can refer to rejection of a transplanted material or tissue occurring or beginning within the first 24 hours after transplantation. For example, hyperacute rejection can encompass but is not limited to "acute humoral rejection" and "antibody-mediated rejection".

"Improving," "enhancing," "bettering," and its grammatical equivalents as used herein can mean any improvement recognized by one of skill in the art. For example, improving transplantation can mean lessening hyperacute rejection, which can encompass a decrease, lessening, or diminishing of an undesirable effect or symptom.

The term "antibody" as used herein includes IgG (including IgG1, IgG2, IgG3, and IgG4), IgA (including IgA1 and IgA2), IgD, IgE, or IgM, and IgY, and is meant to include whole antibodies, including single-chain whole antibodies, and antigen-binding (Fab) fragments thereof. Antigen-binding antibody fragments include, but are not limited to, Fab, Fab' and F(ab')2, Fd (consisting of VH and CH1), single-chain variable fragment (scFv), single-chain antibodies, disulfide-linked variable fragment (dsFv) and fragments comprising either a VL or VH domain. The antibodies can be from any animal origin. Antigen-binding antibody fragments, including single-chain antibodies, can comprise the variable region(s) alone or in combination with the entire or partial of the following: hinge region, CH1, CH2, and CH3 domains. Also included are any combinations of variable region(s) and hinge region, CH1, CH2, and CH3 domains. Antibodies can be monoclonal, polyclonal, chimeric, humanized, and human monoclonal and polyclonal antibodies.

The term "islet", "islet cells", "islet equivalent", "islet-like cells", "pancreatic islets," "native islet cells," "non-native islet cells" and their grammatical equivalents as used herein refers to endocrine (e.g., hormone-producing) cells present in the pancreas of an organism, or cells that mimic one or more function of cells present in the pancreas of an organism. For example, islet cells can comprise different types of cells, including, but not limited to, pancreatic a cells, pancreatic f3 cells, pancreatic S cells, pancreatic F cells, and/or pancreatic c cells. Islet cells can also refer to a group of cells, cell clusters, or the like, including cells cultured in-vitro. In some embodiments, islet cells are extracted from an islet donor and implanted or transplanted at a predetermined site of an islet recipient for differentiation, expansion, and vascularization to form a therapeutic dose of n-cell mass by methods, systems, and/or reagents described herein. In an embodiment, the predetermined site is a renal subcapsular space of the islet recipient. The islets of Langerhans are the regions of the pancreas that contain the endocrine (e.g., hormone-producing) cells (e.g., beta cells). In some embodiments, provided herein are neonatal islet cluster (NICC) or neonatal porcine islet (NPI) comprising pancreas lineage cells (e.g., beta-like cells or a cell population comprising beta-like cells) isolated from a donor by methods, systems, and/or reagents described herein. In some embodiments, NICCs or NPIs are extracted from an islet donor and implanted or transplanted at a predetermined site of an islet recipient for differentiation, expansion, and vascularization to form a therapeutic dose of β-cell mass by methods, systems, and/or reagents described herein. In an embodiment, the predetermined site is a renal subcapsular space of the islet recipient. In some embodiments, NICCs or NPIs extracted from the donor are implanted or transplanted to the recipient under the cover of transient immunosuppression. In some embodiments, islet cells can be stem cell-derived islet cells, induced pluripotent stem cell-derived islet cells, transdifferentiated, or surrogate islet cells. A "donor" is meant to include any mammalian organism, human or non-human, that can serve as a source of donor tissue or cells for transplantation and/or for inducing donor cell tolerance. Non-human mammals include, but are not limited to, ungulates, such as an even-toed ungulate (e.g., pigs, peccaries, hippopotamuses, camels, llamas, chevrotains (mouse deer), deer, giraffes, pronghorn, antelopes, goat-antelopes (which include sheep, goats and others), or cattle) or an odd-toed ungulate (e.g., horse, tapirs, and rhinoceroses), a non-human primate (e.g., a monkey, or a chimpanzee), a Canidae (e.g., a dog) or a cat. A non-human animal can be a member of the Laurasiatheria superorder. The donor can be a living donor or a cadaveric donor. In some cases, the donor is a living donor. In some cases, the donor is a cadaveric donor. The cadaveric donor may be, for example, a brain dead, heart beating donor (BDD). The cadaveric donor may be, for example, a non-heart beating donor (NHBD). Whether the donor is a living donor or a cadaveric donor (e.g., a BDD or NHBD), the donor can be from any animal, for example, a human or non-human animal. The donor can be in any stage of development, including, but not limited to fetal, perinatal, neonatal, pre-weaning, post-weaning, juvenile, young adult, or adult. A donor of cells used in the preparation of a tolerizing vaccine or preparatory regimen can be fully or partially MHC (major histocompatibility complex) matched to a transplant donor (e.g., a donor of cells, tissues, or organs used for transplantation). In some cases, the partially matched donor is haploidentical to the transplant donor. In some cases, the partially matched donor shares one or more MHC alleles with a transplant donor. For example, the partially matched donor can share one or more of a MHC class I A allele, a MHC class I B allele, a MHC class II DR allele, a MHC class II DQ allele, or a combination thereof with a transplant donor. The partially matched donor can share one DR allele with the transplant donors.

A "recipient" can be a human or non-human animal that can receive, is receiving, or has received a transplant graft, a tolerizing vaccine, a preparatory regimen for transplantation, and/or other compositions provided in the present disclosure. A recipient can also be in need of a transplant graft, a tolerizing vaccine, a preparatory regimen for transplantation, and/or other compositions provided herein. In some cases, the recipient can be a human or non-human animal that can receive, is receiving, or has received a transplant graft. In some cases, the recipient can be a human or non-human animal that can receive, is receiving, or has received the presently described tolerizing vaccine or preparatory regimen for transplantation.

The term "non-human animal" and its grammatical equivalents as used herein includes all animal species other than humans, including non-human mammals, which can be a native animal or a genetically modified non-human animal. A non-human mammal includes, an ungulate, such as an even-toed ungulate (e.g., pigs, peccaries, hippopotamuses, camels, llamas, chevrotains (mouse deer), deer, giraffes, pronghorn, antelopes, goat-antelopes (which include sheep, goats and others), or cattle) or an odd-toed ungulate (e.g., horse, tapirs, and rhinoceroses), a non-human primate (e.g., a monkey, or a chimpanzee), a Canidae (e.g., a dog) or a cat. A non-human animal can be a member of the Laurasiatheria superorder. The Laurasiatheria superorder can include a group of mammals as described in Waddell et al., Towards Resolving the Interordinal Relationships of Placental Mammals. Systematic Biology 48 (1): 1-5 (1999). Members of the Laurasiatheria superorder can include Eulipotyphla (hedgehogs, shrews, and moles), Perissodactyla (rhinoceroses, horses, and tapirs), Carnivora (carnivores), Cetartiodactyla (artiodactyls and cetaceans), Chiroptera (bats), and Pholidota (pangolins). A member of Laurasiatheria superorder can be an ungulate described herein, e.g., an odd-toed ungulate or even-toed ungulate. An ungulate can be a pig. A member can be a member of Carnivora, such as a cat, or a dog. In some cases, a member of the Laurasiatheria superorder can be a pig.

The term "porcine", "porcine animal", "pig" and "swine" and its grammatical equivalents as used herein can refer to an animal in the genus Sus, within the Suidae family of even-toed ungulates. For example, a pig can be a wild pig, a domestic pig, mini pigs, a *Sus scrofa* pig, a *Sus scrofa domesticus* pig, or inbred pigs.

The term "fetal animal" and its grammatical equivalents can refer to any unborn offspring of an animal. In some cases, pancreatic cell or tissue are isolated from 6 weeks old embryonic pig for transplantation. The term "perinatal animal" and its grammatical equivalents can refer to an animal immediately before or after birth. For example, a perinatal period can start from 20th to 28th week of gestation and ends 1 to 4 weeks after birth. The term "neonatal animal" and its grammatical equivalents can refer to any new born animals. For example, a neonatal animal can be an animal born within a month. The term "pre-weaning non-human animal" and its grammatical equivalents can refer to any animal before being withdrawn from the mother's milk. The term "juvenile animal" and its grammatical equivalents can refer to any animal before becoming a young adult animal. For example, a juvenile stage of pigs can refer to any pigs of 2 years of age or younger.

The term "genetically modified", "genetically engineered", "transgenic", "genetic modification" and its grammatical equivalents as used herein refer to having one or more alterations of a nucleic acid, e.g., the nucleic acid within an organism's genome. For example, genetic modification can refer to alterations, additions, and/or deletion of genes. A genetically modified cell can also refer to a cell with an added, deleted and/or altered gene. A genetically modified cell can be from a genetically modified non-human animal. A genetically engineered cell from a genetically engineered non-human animal can be a cell isolated from such genetically engineered non-human animal. A genetically modified cell from a genetically modified non-human animal can be a cell originated from such genetically modified non-human animal. A genetically engineered cell or a genetically engineered animal can comprise a transgene, or other foreign DNA, added or incorporated, or an endogenous gene modified, including, targeted, recombined, interrupted, deleted, disrupted, replaced, suppressed, enhanced, or otherwise altered, to mediate a genotypic or phenotypic effect in at least one cell of the animal, and typically into at least one germ line cell of the animal.

The term "transgene" and its grammatical equivalents as used herein can refer to a gene or genetic material that can be transferred into an organism. For example, a transgene can be a stretch or segment of DNA containing a gene that is introduced into an organism. The gene or genetic material can be from a different species. The gene or genetic material can be synthetic. When a transgene is transferred into an organism, the organism can then be referred to as a transgenic organism. A transgene can retain its ability to produce RNA or polypeptides (e.g., proteins) in a transgenic organism. A transgene can comprise a polynucleotide encoding a protein or a fragment (e.g., a functional fragment) thereof. The polynucleotide of a transgene can be an exogenous polynucleotide. A fragment (e.g., a functional fragment) of a protein can comprise at least or at least about 5%, 10%, 20%, 30%, 40%, 50%, 60%, 70%, 80%, 90%, 95%, or 99% of the amino acid sequence of the protein. A fragment of a protein can be a functional fragment of the protein. A functional fragment of a protein can retain part or all of the function of the protein. An exogenous polypeptide can encode an exogenous protein or a functional fragment thereof.

The term "exogenous nucleic acid sequence", "exogenous polynucleotide" and its grammatical equivalents as used herein can refer to a gene or genetic material that was transferred into a cell or animal that originated outside of the cell or animal. An exogenous nucleic acid sequence can by synthetically produced. An exogenous nucleic acid sequence can be from a different species, or a different member of the same species. An exogenous nucleic acid sequence can be another copy of an endogenous nucleic acid sequence.

The term "gene knock-out" or "knock-out" can refer to any genetic modification that reduces the expression of the gene being "knocked out." Reduced expression can include no expression. The genetic modification can include a genomic disruption.

The term "disrupting" and its grammatical equivalents as used herein can refer to a process of altering a gene, e.g., by deletion, insertion, mutation, rearrangement, or any combination thereof. For example, a gene can be disrupted by knockout. Disrupting a gene can be partially reducing or completely suppressing expression (e.g., mRNA and/or protein expression) of the gene. Disrupting can also include inhibitory technology, such as shRNA, siRNA, microRNA, dominant negative, or any other means to inhibit functionality or expression of a gene or protein.

The term "gene editing" and its grammatical equivalents as used herein can refer to genetic engineering in which one or more nucleotides are inserted, replaced, or removed from a genome. For example, gene editing can be performed using a nuclease (e.g., a natural-existing nuclease or an artificially engineered nuclease).

The term "condition" and its grammatical equivalents as used herein can refer to a disease, event, or change in health status.

The term "diabetes" and its grammatical equivalents as used herein can refer to is a disease characterized by high blood sugar levels over a prolonged period. For example, the term "diabetes" and its grammatical equivalents as used herein can refer to all or any type of diabetes, including, but not limited to, type 1, type 2, type 3c (pancreatogenic diabetes including cystic fibrosis-related, and surgical, and hemochromatosis-related), gestational diabetes, and monogenic diabetes (HNF1A-MODY, GCK-MODY 2, etc.), and other forms of mitochondrial diabetes. In some cases, diabetes can be a form of hereditary diabetes.

As used herein, the term "susceptible to" refers to an individual who is "susceptible to" a disease, disorder, and/or condition has not been diagnosed with the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, condition, or event (for example, Muscular Dystrophy) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein associated with the disease, disorder, and/or condition; (4) habits and/or lifestyles associated with development of the disease, disorder, condition, and/or event (5) having undergone, planning to undergo, or requiring a transplant. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

The term "phenotype" and its grammatical equivalents as used herein can refer to a composite of an organism's observable characteristics or traits, such as its morphology, development, biochemical or physiological properties, phenology, behavior, and products of behavior. Depending on the context, the term "phenotype" can sometimes refer to a composite of a population's observable characteristics or traits.

"Inflammatory disorder" means an immune-mediated inflammatory condition that affects humans and is generally characterized by dysregulated expression of one or more cytokines. Examples of inflammatory disorders include skin inflammatory disorders, inflammatory disorders of the joints, inflammatory disorders of the cardiovascular system, certain autoimmune diseases, lung and airway inflammatory disorders, intestinal inflammatory disorders. Examples of skin inflammatory disorders include dermatitis, for example atopic dermatitis and contact dermatitis, acne vulgaris, and psoriasis. Examples of inflammatory disorders of the joints include rheumatoid arthritis. Examples of inflammatory disorders of the cardiovascular system are cardiovascular disease and atherosclerosis. Examples of autoimmune diseases include Type 1 diabetes, Graves disease, Guillain-Barre disease, Lupus, Psoriatic arthritis, and Ulcerative colitis. Examples of lung and airway inflammatory disorders include asthma, cystic fibrosis, COPD, emphysema, and acute respiratory distress syndrome. Examples of intestinal inflammatory disorders include colitis and inflammatory bowel disease. Other inflammatory disorders include cancer, hay fever, periodontitis, allergies, hypersensitivity, ischemia, depression, systemic diseases, post infection inflammation and bronchitis. The peptides and compositions of the invention may also be employed in the non-therapeutic treatment of inflammation. Examples of non-therapeutic treatment of inflammation include use to relieve normal, non-pathological, inflammation, for example inflammation in the muscles and joints following exercise As used herein, the terms "protein", "peptide" and "polypeptide" are used interchangeably to designate a series of amino acid residues connected to each other by peptide bonds between the alpha-amino and carboxy groups of adjacent residues. The terms "protein", "peptide" and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein", "peptide" and "polypeptide" are used interchangeably herein when referring to a gene product and fragments thereof.

The terms "increased"/'increase", "increasing" or "enhance" are all used herein to generally mean an increase by a statically significant amount; for the avoidance of doubt, the terms "increased", "increase", or "enhance", mean an increase of at least 10% as compared to a reference level, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. The increase can be, for example, at least 10%, at least 20%, at least 30%, at least 40% or more, and is preferably to a level accepted as within the range of normal for an individual without a given disease.

The terms, "decrease", "reduce", "reduction", "lower" or "lowering," or "inhibit" are all used herein generally to mean a decrease by a statistically significant amount. For example, "decrease", "reduce", "reduction", or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., absent level or non-detectable level as compared to a reference level), or any decrease between 10-100% as compared to a reference level. In the context of a marker or symptom, by these terms is meant a statistically significant decrease in such level. The decrease can be, for example, at least 10%, at least 20%, at least 30%, at least 40% or more, and is preferably down to a level accepted as within the range of normal for an individual without a given disease.

As used herein, substantially pure means sufficiently homogeneous to appear free of readily detectable impurities as determined by standard methods of analysis, such as thin layer chromatography [TLC], gel electrophoresis and high performance liquid chromatography [HPLC], used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound. In some embodiments, the compositions of the present disclosure are substantially pure.

By "detectable agent" is meant a compound that is linked to a diagnostic agent to facilitate detection. Such a "detectable agent" may be covalently or non-covalently linked to a diagnostic agent, hi addition, the linkage may be direct or indirect Examples of "detectable agents" include, protein purification tags, cytotoxins, enzymes, paramagnetic labels, enzyme substrates, co-factors, enzymatic inhibitors, dyes, radionuclides, chemiluminescent labels, fluorescent markers, growth inhibitors, cytokines, antibodies, and biotin.

As used herein, biological activity refers to the in vitro, ex vivo, or in vivo activities of a compound or physiological responses that result upon in vivo administration of a compound, composition or other mixture. Biological activity, thus, encompasses therapeutic effects and pharmaceutical activity of such compounds, compositions and mixtures.

Some numerical values disclosed throughout are referred to as, for example, "X is at least or at least about 100; or 200 [or any numerical number]." This numerical value includes the number itself and all of the following:
  i) X is at least 100;
  ii) X is at least 200;
  iii) X is at least about 100; and
  iv) X is at least about 200.

All these different combinations are contemplated by the numerical values disclosed throughout. All disclosed numerical values should be interpreted in this manner, whether it refers to an administration of a therapeutic agent or referring to days, months, years, weight, dosage amounts, etc., unless otherwise specifically indicated to the contrary.

The ranges disclosed throughout are sometimes referred to as, for example, "X is administered on or on about day 1 to 2; or 2 to 3 [or any numerical range]." This range includes the numbers themselves (e.g., the endpoints of the range) and all of the following:
  i) X being administered on between day 1 and day 2;
  ii) X being administered on between day 2 and day 3;
  iii) X being administered on between about day 1 and day 2;
  iv) X being administered on between about day 2 and day 3;
  v) X being administered on between day 1 and about day 2;
  vi) X being administered on between day 2 and about day 3;
  vii) X being administered on between about day 1 and about day 2; and
  viii) X being administered on between about day 2 and about day 3.

All these different combinations are contemplated by the ranges disclosed throughout. All disclosed ranges should be interpreted in this manner, whether it refers to an administration of a therapeutic agent or referring to days, months, years, weight, dosage amounts, etc., unless otherwise specifically indicated to the contrary.

Pharmaceutical Compositions

Provided herein are peptides capable of binding CD40 and thereby inhibit activity of CD40, i.e., interaction of CD40 with CD154. The terms "CD40 binding peptide" are used interchangeably with "anti-CD40 peptide". The present disclosure provides pharmaceutical compositions comprising a peptide which comprise an amino acid sequence selected from Table 1 or a portion thereof or a functional fragment thereof. As it relates to the composition and methods of the instant disclosure a peptide can be full length peptide selected from Table 1 or can be a portion thereof or a functional fragment thereof. In some embodiments, a peptide of the compositions and methods disclosed herein are less than 20 amino acids in length. In some embodiments, the peptide is 4, 6, 8, 10, 12, 14, or 15 amino acids in length. In some embodiments, the peptide comprises an amino acid sequence selected from group consisting of SEQ ID NOs: 1-6 and 8-17. The sequences of such peptides are shown in Table 1.

In some embodiments, the peptide of the compositions and methods disclosed herein have an amino acid sequence that is at least 80%, at least 85%, at least 90%, at least 95%, at least 97%, at least 99% or 100% identical to that of SEQ ID NO:1. In some embodiments, the peptide of the compositions and methods disclosed herein have an amino acid sequence that is at least 80%, at least 85%, at least 90%, at least 95%, at least 97%, at least 99% or 100% identical to that of SEQ ID NO: 2. In some embodiments, the peptide of the compositions and methods disclosed herein have an amino acid sequence that is at least 80%, at least 85%, at least 90%, at least 95%, at least 97%, at least 99% or 100% identical to that of SEQ ID NO:3. In some embodiments, the peptide of the compositions and methods disclosed herein have an amino acid sequence that is at least 80%, at least 85%, at least 90%, at least 95%, at least 97%, at least 99% or 100% identical to that of SEQ ID NO:4. In some embodiments, the peptide of the compositions and methods disclosed herein have an amino acid sequence that is at least 80%, at least 85%, at least 90%, at least 95%, at least 97%, at least 99% or 100% identical to that of SEQ ID NO:5. In some embodiments, the peptide of the compositions and methods disclosed herein have an amino acid sequence that is at least 80%, at least 85%, at least 90%, at least 95%, at least 97%, at least 99% or 100% identical to that of SEQ ID NO: 6.

In some embodiments, the peptide of the compositions and methods disclosed herein have an amino acid sequence that is at least 80%, at least 85%, at least 90%, at least 95%, at least 97%, at least 99% or 100% identical to that of SEQ ID NO:8.

In some embodiments, the peptide of the compositions and methods disclosed herein have an amino acid sequence that is at least 80%, at least 85%, at least 90%, at least 95%, at least 97%, at least 99% or 100% identical to that of SEQ ID NO:9.

In some embodiments, the peptide of the compositions and methods disclosed herein have an amino acid sequence that is at least 80%, at least 85%, at least 90%, at least 95%, at least 97%, at least 99% or 100% identical to that of SEQ ID NO:10.

In some embodiments, the peptide of the compositions and methods disclosed herein have an amino acid sequence that is at least 80%, at least 85%, at least 90%, at least 95%, at least 97%, at least 99% or 100% identical to that of SEQ ID NO:11.

In some embodiments, the peptide of the compositions and methods disclosed herein have an amino acid sequence that is at least 80%, at least 85%, at least 90%, at least 95%, at least 97%, at least 99% or 100% identical to that of SEQ ID NO:12.

In some embodiments, the peptide of the compositions and methods disclosed herein have an amino acid sequence that is at least 80%, at least 85%, at least 90%, at least 95%, at least 97%, at least 99% or 100% identical to that of SEQ ID NO:13.

In some embodiments, the peptide of the compositions and methods disclosed herein have an amino acid sequence that is at least 80%, at least 85%, at least 90%, at least 95%, at least 97%, at least 99% or 100% identical to that of SEQ ID NO:14.

In some embodiments, the peptide of the compositions and methods disclosed herein have an amino acid sequence that is at least 80%, at least 85%, at least 90%, at least 95%, at least 97%, at least 99% or 100% identical to that of SEQ ID NO:15.

In some embodiments, the peptide of the compositions and methods disclosed herein have an amino acid sequence that is at least 80%, at least 85%, at least 90%, at least 95%, at least 97%, at least 99% or 100% identical to that of SEQ ID NO:16.

In some embodiments, the peptide of the compositions and methods disclosed herein have an amino acid sequence that is at least 80%, at least 85%, at least 90%, at least 95%, at least 97%, at least 99% or 100% identical to that of SEQ ID NO:17.

In some embodiments, the peptide or functional fragment thereof of the present disclosure retain, the ability at a minimum, to bind a CD40 protein. In some embodiments, the peptide comprises a portion (e.g., a functional fragment of the peptide) of the wild type sequence selected from SEQ ID NOs 1-6 and 8-17.

Percent (%) amino acid sequence identity for a given peptide sequence relative to a reference sequence (e.g., unmodified, full length peptide selected from SEQ ID NOs: 1-6 and 8-17 is defined as the percentage of identical amino acid residues identified after aligning the two sequences and introducing gaps if necessary, to achieve the maximum percent sequence identity, and not considering any conservative substitutions as part of the sequence identity. Percent (%) amino acid sequence homology for a given polypeptide sequence relative to a reference sequence is defined as the percentage of identical or strongly similar amino acid residues identified after aligning the two sequences and introducing gaps if necessary, to achieve the maximum percent homology. Non identities of amino acid sequences include conservative substitutions, deletions or additions that do not affect the biological activity of the peptide. Strongly similar amino acids can include, for example, conservative substitutions known in the art. Percent identity and/or homology can be calculated using alignment methods known in the art, for instance alignment of the sequences can be conducted using publicly available software software such as BLAST, Align, ClustalW2. Those skilled in the art can determine the appropriate parameters for alignment, but the default parameters for BLAST are specifically contemplated.

As used herein, the term "wild type peptide" refers to the native, un-modified peptide comprising amino acid sequence selected from SEQ ID NOs 1-6 and 8-17.

As used herein, a "fragment" or "portion" is one that substantially retains at least one biological activity normally associated with that peptide. In particular embodiments, the "fragment" or "portion" substantially retains all of the activities possessed by the wild type peptide. By "substantially retains" biological activity, it is meant that the fragment or portion retains at least about 50%, 60%, 75%, 85%, 90%, 95%, 97%, 98%, 99%, or more, of the biological activity of the wild type peptide (and can even have a higher level of activity than the wild type peptide). In some embodiments, a fragment or portion of the protein or polypeptide described herein is at least 4, 5, 6, 7, 8, 9, 10, 11, 12, 13, or 14 or more contiguous amino acids and/or less than about 15, 14, 13, 12, 11, 10, 9, 8, 7, 6, 5, or 4 contiguous amino acids, including any combination of the foregoing as long as the lower limit is less than the upper limit and retains at least one biological activity associated with the wild type peptide.

By "retains" biological activity, it is meant that the peptide retains at least about 50%, 60%, 75%, 85%, 90%, 95%, 97%, 98%, 99%, or more, of the biological activity of the native peptide (and can even have a higher level of activity than the native polypeptide). A "non-functional" peptide is one that exhibits essentially no detectable biological activity normally associated with the peptide (e.g., at most, only an insignificant amount, e.g., less than about 10% or even 5%).

As used herein, a "functional" peptide or fragment is one that retains at least one biological, activity normally associated with wild type peptide. Preferably, a "functional" peptide or fragment thereof retains all of the activities possessed by the native, unmodified or full-length wild type peptide. A "non-functional" peptide is one that exhibits essentially no detectable biological activity normally associated with the wild type peptide (e.g., at most, only an insignificant amount, e.g., less than about 10% or even 5%). The functional activity can be tested by one of ordinary skill in the art by the assays described below and in the Examples herein.

The compositions and methods of the present disclosure contemplate a functional derivative, functional fragment, variant, analogue or chemical derivative of a peptide disclosed herein (e.g., a peptide selected from Table 1).

In one embodiment, a peptide useful in the methods and compositions described herein consists of, consists essentially of, or comprises an amino acid sequence, or is a fragment thereof derived from sequence selected from SEQ ID NOs: 1-15, provided that the peptide or functional fragment retains at least one biological activity of corresponding full length wild type peptide, the biological activity being selected from at a minimum, to bind CD40, inhibiting interaction of CD40 and CD154 or modulate immune response mediated by CD40.

The peptides or functional fragment thereof described herein can comprise conservative amino acid substitutions at one or more amino acid residues, e.g., at essential or non-essential amino acid residues but will retain a therapeutically or physiologically relevant activity of a peptide as that term is described herein. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, in a conservative substitution variant, a nonessential amino acid residue in the polypeptide is preferably replaced with another amino acid residue from the same side chain family.

In some embodiments, peptide can be a variant of wild type peptide. The term "variant" as used herein refers to a peptide or nucleic acid that is "substantially similar" to a wild-type peptide. A molecule is said to be "substantially similar" to another molecule if both molecules have substantially similar structures (i.e., they are at least 50% similar in amino acid sequence as determined by BLASTp alignment set at default parameters) and are substantially similar in at least one therapeutically or physiologically relevant biological activity. A variant differs from the naturally occurring polypeptide or nucleic acid by one or more amino acid or nucleic acid deletions, additions, substitutions or side-chain modifications, yet retains one or more therapeutically relevant, specific functions or desired biological activities of the wild type peptide (e.g., binding CD40).

Amino acid substitutions include alterations in which an amino acid is replaced with a different naturally-occurring or a non-conventional amino acid residue. Some substitutions can be classified as "conservative," in which case an amino acid residue contained in a polypeptide is replaced with another naturally occurring amino acid of similar character either in relation to polarity, side chain functionality or size. Substitutions encompassed by variants as described herein can also be "non-conservative," in which an amino acid residue which is present in a peptide is substituted with an amino acid having different properties (e.g., substituting a charged or hydrophobic amino acid with an uncharged or hydrophilic amino acid), or alternatively, in which a naturally-occurring amino acid is substituted with a non-conventional amino acid.

"Conservative amino acid substitutions" result from replacing one amino acid with another having similar structural and/or chemical properties, such as the replacement of a leucine with an isoleucine or valine, an aspartate with a glutamate, or a threonine with a serine. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not reduce the activity of the peptide, (i.e. the ability of the peptide to penetrate the blood brain barrier (BBB)). Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984), incorporated by reference in its entirety.) In some embodiments, individual substitutions, deletions or additions that alter, add or delete a single amino acid or a small percentage of amino acids can also be considered "conservative substitutions" if the change does not reduce the activity of the peptide. Insertions or deletions are typically in the range of about 1 to 5 amino acids. The choice of conservative amino acids may be selected based on the location of the amino acid to be substituted in the peptide, for example if the amino acid is on the exterior of the peptide and expose to solvents, or on the interior and not exposed to solvents.

The term "insertions" or "deletions" are typically in the range of about 1 to 5 amino acids. The variation allowed can be experimentally determined by producing the peptide synthetically while systematically making insertions, deletions, or substitutions of nucleotides in the sequence using recombinant DNA techniques.

The term "substitution" when referring to a peptide, refers to a change in an amino acid for a different entity, for example another amino acid or amino-acid moiety. Substitutions can be conservative or non-conservative substitutions.

In alternative embodiments, one can select the amino acid which will substitute an existing amino acid based on the location of the existing amino acid, i.e. its exposure to solvents (i.e. if the amino acid is exposed to solvents or is present on the outer surface of the peptide or polypeptide as compared to internally localized amino acids not exposed to solvents). Selection of such conservative amino acid substitutions are well known in the art, for example as disclosed in Dordo et al, J. Mol Biol, 1999, 217, 721-739 and Taylor et al, J. Theor. Biol. 119(1986); 205-218 and S. French and B. Robson, J. Mol. Evol. 19(1983)171. Accordingly, one can select conservative amino acid substitutions suitable for amino acids on the exterior of a protein or peptide (i.e. amino acids exposed to a solvent), for example, but not limited to, the following substitutions can be used: substitution of Y with F, T with S or K, P with A, E with D or Q, N with D or G, R with K, G with N or A, T with S or K, D with N or E, I with L or V, F with Y, S with T or A, R with K, G with N or A, K with R, A with S, K or P.

In alternative embodiments, one can also select conservative amino acid substitutions encompassed suitable for amino acids on the interior of a protein or peptide, for example one can use suitable conservative substitutions for amino acids is on the interior of a protein or peptide (i.e. the amino acids are not exposed to a solvent), for example but not limited to, one can use the following conservative substitutions: where Y is substituted with F, T with A or S, I with L or V, W with Y, M with L, N with D, G with A, T with A or S, D with N, I with L or V, F with Y or L, S with A or T and A with S, G, T or V. In some embodiments, non-conservative amino acid substitutions are also encompassed within the term of variants. The term "derivative" as used herein refers to peptides which have been chemically modified, for example but not limited to by techniques such as ubiquitination, labeling, pegylation (derivatization with polyethylene glycol), lipidation, glycosylation, or addition of other molecules. A molecule also a "derivative" of another molecule when it contains additional chemical moieties not normally a part of the molecule. Such moieties can improve the molecule's solubility, absorption, biological half-life, etc. The moieties can alternatively decrease the toxicity of the molecule, eliminate or attenuate any undesirable side effect of the molecule, etc. Moieties capable of mediating such effects are disclosed in Remington's Pharmaceutical Sciences, 18th edition, A. R. Gennaro, Ed., MackPubl., Easton, Pa. (1990), incorporated herein, by reference, in its entirety.

A "derivative" is defined as a molecule having the amino acid sequence of a wild-type peptide (e.g., peptide selected from Table 1) or analog thereof, but additionally having a chemical modification of one or more of its amino acid side groups, alpha-carbon atoms, terminal amino group, or terminal carboxylic acid group for example by ubiquitination, labeling, pegylation (derivatization with polyethylene glycol) or addition of other molecules. A chemical modification includes, but is not limited to, adding chemical moieties, creating new bonds, and removing chemical moieties. Furthermore, one or more side groups, or terminal groups, may be protected by protective groups known to the ordinarily-skilled synthetic chemist. The term "functional" when used in conjunction with "derivative" or "variant" refers to a peptide which possesses a biological activity that is substantially similar to a biological activity of the entity or molecule of which it is a derivative or variant. By "substantially similar" in this context is meant that at least 50% of the relevant or desired biological activity of a corresponding wild-type peptide is retained. In some embodiments, the derivatives retains at least 60%, at least 70%, at least 80%, at least 90%, at least 95%, or more, including 100% or even more (i.e., the derivative or variant has improved activity relative to wild-type) of the wild type peptide.

In some embodiments a peptide useful in the composition and methods of the present disclosure is an analog of a wild type peptide (e.g., selected from Table 1). An "analog" of a molecule such as a peptide refers to a molecule similar in function to either the entire molecule or to a fragment thereof. The term "analog" is also intended to include allelic species and induced variants. Analogs typically differ from wild type peptides at one or a few positions, often by virtue of conservative substitutions. Analogs typically exhibit at least 80 or 90% sequence identity with wild type peptides. Some analogs also include unnatural amino acids or modifications of N or C terminal amino acids. Examples of unnatural amino acids are, for example but not limited to; disubstituted amino acids, N-alkyl amino acids, lactic acid, 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine. Other examples of unnatural amino acids include, but are not limited to the D-amino acids, 2,4-diaminobutyric acid, a-amino isobutyric acid, 2-aminoisobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, naphthalene, L-1-naphthalene, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. By "covalently bonded" is meant joined either directly or indirectly (e.g., through a linker) by a covalent chemical bond.

The compositions and methods of the instant disclosure also contemplate a peptidomimetic. As used herein, a "peptidomimetic" is a compound containing non-peptidic structural elements that is capable of mimicking the biological action of a parent peptide. A peptidomimetic may or may not comprise peptide bonds.

A peptide useful for compositions and methods of the present disclosure should be of a size sufficient to interact with CD40 protein in such a manner as to inhibit interaction of CD40 with CD154. In some embodiments, a peptide of the present disclosure is less than 20 amino acids in length. A peptide can be, for example, 4, 6, 13 or 15 amino acids in length. In one embodiment, the peptide consists of an amino acid selected from the group consisting of SEQ ID NO:1-6 and 8-17. The sequences of such peptides are shown below in Table 1. In some embodiments, the peptide comprises at least a portion that is capable of binding CD40 and inhibiting interaction of CD40 with CD154. In some embodiments, the peptide comprises at least a portion of peptide comprising an amino acid sequence selected from SEQ ID NOs: 1-6 and 8-17. In some embodiments, the peptide of the present disclosure is as short as possible, yet at a minimum, retains the biological activity or functional activity of binding to CD40. In some embodiments, the peptide is a shortest region of contiguous sequence of SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, or SEQ ID NO: 17 which retain at a minimum the biological ability or functional activity of binding CD40. Useful peptides can also comprise additional regions of sequence from SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, SEQ ID NO: 13, SEQ ID NO: 14 or SEQ ID NO: 15, SEQ ID NO: 16, or SEQ ID NO: 17 which surround the shortest possible contiguous sequence capable of binding CD40. In some embodiments, the peptide or portion thereof bind to CD40 at a site which overlaps the binding site of CD154. In some embodiments, the peptide or portion thereof bind CD40 at a site which is the binding site of CD154. In some embodiments, the peptide or portion thereof bind the CD40 at a site which is not a site of CD154 binding. The peptides of the present disclosure can comprise additional sequences and modifications that do not bind a CD40 protein, so long as the additional sequence do not lower the biological activity of the peptide than that of unmodified peptide, for example, biological activity of binding CD40. Non-limiting examples of additional sequences include sequences coding for B-galactosidase, luciferase, glutathione-s-transferase, thioredoxin, HIS-tags, biotin tags, and fluorescent proteins.

In some embodiments, the composition comprises at least one peptide or portion thereof or functional fragment thereof is selected from Table 1. In some embodiments, the composition can comprise for example more than one peptides or portion thereof or functional fragment thereof disclosed herein (e.g., a peptide selected from Table 1). In some embodiments, the compositions disclosed herein can comprise at least 2 peptides, at least 3 peptides, at least 4 peptides, at least 5 peptides, at least 6 peptides, at least 7 peptides, at least 8 peptides, at least 9 peptides, at least 10 peptides, at least 11 peptides, at least 12 peptides, at least 13 peptides, at least 14 peptides, at least 15 peptides, or portion thereof (e.g., peptides selected from Table 1). In some embodiments, the composition can comprise all the peptides or portion thereof disclosed herein (e.g., peptides in Table 1).

Biological Activity of Peptides

The term "biological activity," as used herein, refers to one having structural, regulatory, or biochemical functions of an unmodified molecule or any function related to or associated with a metabolic or physiological process. The biological activity can include an improved desired activity, or a decreased undesirable activity. For example, an entity demonstrates biological activity when it participates in a molecular interaction with another molecule (e.g., binding CD40), when it has therapeutic value in alleviating a disease condition, when it has prophylactic value or therapeutic value in modulating an immune response, when it has diagnostic and/or prognostic value in determining the presence of a molecule (e.g., cell expressing CD40).

Binding CD40 Protein

The biological activity and/or biological effect of a peptide disclosed herein include at least in part binding to a CD40 protein. As such, the peptides or functional fragment thereof disclosed herein are CD40 binding peptides or functional fragment thereof. In such a binding, the peptide associates with CD40 to form a complex. An example of complex formation is association of an antigen with an antibody. The binding of the peptides disclosed herein to CD40 can be covalent binding interactions between proteins include, for example, disulfide bonds, ester bonds, amide bonds and the like or non-covalent bonding interactions between proteins include, for example, hydrophobic interactions, van der Waals interactions, ionic interactions, hydrogen bonding interactions and the like. The binding of peptides disclosed herein with CD40 can be reversible (e.g., non-covalent binding interactions) or non-reversible (e.g., covalent bonds). Moreover, a reversible interaction can be strong or weak, the strength of the interaction being determined by the forces (e.g., ionic charges, hydrogen binding, van der Walls interactions, etc.) exerted by each protein on the other protein in the complex. Factors affecting the strength of an interaction between two molecules are known to those skilled in the art. One useful measure of the strength of binding between two molecules, such as a peptide and a protein, is the dissociation constant (Kd). The term "dissociation constant," "kinetic off-rate", "off-rate", or "koff" as used interchangeably herein, refers to the value indicating the dissociation rate of a ligand (e.g., peptides disclosed herein) from its target protein (e.g., CD40) or separation of the ligand and protein complex (e.g., complex of peptide disclosed herein with a CD40 protein) over time into free ligand and free protein. In some embodiments, peptides of the present disclosure are those that bind to a CD40 protein with a Kd of no more than about $1 \times 10^{-6}$ M, about $1 \times 10^{-7}$ M, or about $1 \times 10^{-8}$ M. In some embodiments of the compositions disclosed herein, a peptide has a Kd of less than about $1 \times 10^{-9}$ M. In one embodiment, a peptide of the present disclosure binds to a CD40 protein with a Kd of less than 100 nM, less than 50 nM, less than 25 nM, less than 10 nM, less than 5 nM, less than 3 nM, less than 2 nM, or less than 1 nM. Methods of measuring and analyzing binding interactions between a peptide and a CD40 protein are known by those of skill in the art e.g., US20180172683A1. Kd can be determined by measurement of the kinetics of complex formation and dissociation, e.g. by the SPR method (Biacore). In one aspect provided herein is a complex comprising a peptide disclosed herein or a portion thereof non-covalently bound to a CD40 protein.

In some embodiments, peptide of the present disclosure selectively binds with a CD40 protein in solution, as determined using an assay such as an immunosorbent assay, or on the surface of a cell. As used herein, the terms selectively, selective, specific, and the like, indicate the peptide has a greater affinity for a CD40 protein than it does for proteins unrelated to the CD40 protein. More specifically, the terms selectively, selective, specific, and the like indicate that the affinity of the peptide for CD40 is statistically significantly higher than its affinity for a negative control (e.g., an unrelated protein such as albumin) as measured using a standard assay (e.g., ELISA). Suitable techniques for assaying the ability of a peptide to selectively interact with a CD40 protein are known to those skilled in the art. Such assays can be in vitro or in vivo assays. Methods of determining selective binding of peptides with CD40 are described in Examples herein. Other non-limiting assays to determine selective binding include, but are not limited to, an enzyme-linked immunoassay, a competitive enzyme-linked immunoassay, a radioimmunoassay, a fluorescence immunoassay, a chemiluminescent assay, a lateral flow assay, a flow-through assay, an agglutination assay, a particulate-based assay (e.g., using particulates such as, but not limited to, magnetic particles or plastic polymers, such as latex or polystyrene beads), an immunoprecipitation assay, an immunoblot assay (e.g., a western blot), a phosphorescence assay, a flow-through assay, a chromatography assay, a polyacrylamide gel electrophoresis (PAGE)-based assay, a surface plasmon resonance assay, a spectrophotometric assay, a particulate-based assay, an electronic sensory assay and a flow cytometric assay. Methods of performing such assays are well known to those skilled in the art. In one embodiment, an assay can be performed using isolated CD40 protein, of CD40 expressed on a surface of a cell in culture, or it can be performed in a whole animal. Assays can be designed to give qualitative, quantitative or semi-quantitative results, depending on how they are used and the type of result that is desired.

Human CD40 antigen (CD40) is a peptide of 277 amino acids having a molecular weight of 30,600, and a 19 amino acid secretory signal peptide comprising predominantly hydrophobic amino acids. CD40 is a member of the tumor necrosis factor (TNF)/nerve growth factor (NGF) receptor family, which is defined by the presence of cysteine-rich motifs in the extracellular region.

As used herein, "CD40" or "CD40 protein" refers to a cell surface glycoprotein that is a member of the tumor necrosis factor receptor family. Other names in the art for CD40 include: TNFRSF5, p50, CDW40, CD40 receptor and Bp50. As used herein, the term "CD40 protein", generally refers to an CD40 polypeptide that is similar or identical in sequence to a wild-type CD40. In some embodiments, the term "CD40 protein" refers to a CD40 polypeptide having an amino acid sequence that is at least 80%, at least 85%, at least 90%, at least 95%, at least 97%, at least 99%, or 100%, identical to that of a wild-type CD40 and that retains the ability, at a minimum, to bind CD154. Accordingly in some embodiments, "CD40" can be full length CD40. In some embodiments, "CD40" can be a functional fragment of a full length CD40, a species homologue and/or functional fragments thereof, an ortholog of CD40 and/or functional fragments thereof. The CD40 protein can be a mammalian CD40 protein. The CD40 polypeptide can also be a functional isoform of the full length CD40 or functional fragment thereof.

In some embodiments, "CD40" is a wild-type CD40 of human origin, having the following amino acid sequence (SEQ ID NO:18), or a functional fragment thereof.

(SEQ ID NO: 18)
MVRLPLQCVLWGCLLTAVHPEPPTACREKQYLINSQCCSLCQPGQKLVSDC

TEFTETECLPCGESEFLDTWNRETHCHQHKYCDPNLGLRVQQKGTSETDTI

CTCEEGWHCTSEACESCVLHRSCSPGFGVKQIATGVSDTICEPCPVGFFSN

VSSAFEKCHPWTSCETKDLVVQQAGTNKTDVVCGPQDRLRALVVIPIIFGI

LFAILLVLVFIKKVAKKPTNKAPHPKQEPQEINFPDDLPGSNTAAPVQETL

HGCQPVTQEDGKESRISVQERQ (See GenBank Accession No. AAH12419.1 (sequence includes signal peptide), which is encoded by nucleic acid sequence GENBANK® Accession no. BC012419.1. The sequences are incorporated herein by reference in their entirety).

A "functional fragment" or a "portion thereof" as it relates to CD40 refers to fragment of the full length CD40 (e.g. corresponding to SEQ ID NO: 18 of at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200 or more consecutive amino acids of full length wild-type CD40, that has at least about 70%, 80%, 90%, 100% or more than 100% of the function of wild-type CD40 of binding CD154 The functional activity can be tested by one of ordinary skill in the art by the assays described in the examples.

The polypeptide and coding nucleic acid sequences of CD40 protein of human origin and those of a number of animals are publicly available, e.g., from the NCBI website and are contemplated for use in the methods and compositions herein. Examples include, but are not limited to, Mouse (GenBank Accession No. AAB08705.1), Rat (GenBank Accession No. AAH97949.1), monkey (Genbank Accession No. AWU67715.1), Porcine (GenBank Accession No. AWU67715.1) Bovine (GenBank Accession No. AAI34766.1).

In some embodiments, the CD40 can be a mammalian homolog of human CD40 or a functional fragment thereof. In some embodiments, the CD40 polypeptide has an amino acid sequence at least 85%, at least 90%, at least 95%, at least 97% or at least 99% identical to the amino acid sequence of SEQ ID NO:18 and is capable of binding its cognate ligand CD154. In some embodiments, the CD40 is a functional fragment or a portion of SEQ ID NO: 18 of at least 10, at least 20, at least 30, at least 40, at least 50, at least 60, at least 70, at least 80, at least 90, at least 100, at least 110, at least 120, at least 130, at least 140 consecutive amino acids of SEQ ID NO: 18, that has at least about 50%, 60%, 70%, 80%, 90%, 100% or more than 100% of the function of wild type CD40 of binding its ligand CD154. The functional activity can be tested by one of ordinary skill in the art by the assays described above.

Percent (%) amino acid sequence identity for a given polypeptide sequence relative to a reference sequence is defined as the percentage of identical amino acid residues identified after aligning the two sequences and introducing gaps if necessary, to achieve the maximum percent sequence identity, and not considering any conservative substitutions as part of the sequence identity. Percent (%) amino acid sequence homology for a given polypeptide sequence relative to a reference sequence is defined as the percentage of identical or strongly similar amino acid residues identified after aligning the two sequences and introducing gaps if necessary, to achieve the maximum percent homology. Non identities of amino acid sequences include conservative substitutions, deletions or additions that do not affect the biological activity of CD40. Strongly similar amino acids can include, for example, conservative substitutions known in the art. Percent identity and/or homology can be calculated using alignment methods known in the art, for instance alignment of the sequences can be conducted using publicly available software software such as BLAST, Align, ClustalW2. Those skilled in the art can determine the appropriate parameters for alignment, but the default parameters for BLAST are specifically contemplated.

In one embodiment, "CD40 protein" useful in the methods and compositions described herein consists of, consists essentially of, or comprises an amino acid sequence, or is a portion thereof derived from SEQ ID NO: 18, provided that the polypeptide retains at least one biological activity of full length CD40 of SEQ ID NO: 18, the biological activity being selected from at a minimum, binding to CD154. The CD40 described herein can comprise conservative amino acid substitutions at one or more amino acid residues, e.g., at essential or non-essential amino acid residues but will retain a therapeutically or physiologically relevant activity of an inhibitory peptide as that term is described herein. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, in a conservative substitution variant, a nonessential amino acid residue in the polypeptide is preferably replaced with another amino acid residue from the same side chain family.

In some embodiments, CD40 can be a variant of wild type CD40. The term "variant" as used herein refers to a polypeptide or nucleic acid that is "substantially similar" to a wild-type CD40. A molecule is said to be "substantially similar" to another molecule if both molecules have substantially similar structures (i.e., they are at least 50% similar in amino acid sequence as determined by BLASTp alignment set at default parameters) and are substantially similar in at least one therapeutically or physiologically relevant biological activity. A variant differs from the naturally occurring polypeptide or nucleic acid by one or more amino acid or nucleic acid deletions, additions, substitutions or side-chain modifications, yet retains one or more therapeutically relevant, specific functions or desired biological activities of the naturally occurring molecule (e.g., maintains primitive HSCs in a quiescent state, enhances hematopoietic reconstitution in vivo).

Amino acid substitutions include alterations in which an amino acid is replaced with a different naturally-occurring or a non-conventional amino acid residue. Some substitutions can be classified as "conservative," in which case an amino acid residue contained in a polypeptide is replaced with another naturally occurring amino acid of similar character either in relation to polarity, side chain functionality or size.

Substitutions encompassed by variants as described herein can also be "non-conservative," in which an amino acid residue which is present in a peptide is substituted with an amino acid having different properties (e.g., substituting a charged or hydrophobic amino acid with an uncharged or hydrophilic amino acid), or alternatively, in which a naturally-occurring amino acid is substituted with a non-conventional amino acid. Also encompassed within the term "variant," when used with reference to a polynucleotide or polypeptide, are variations in primary, secondary, or tertiary structure, as compared to a reference polynucleotide or polypeptide, respectively (e.g., as compared to a wild-type polynucleotide or polypeptide). Polynucleotide changes can result in amino acid substitutions, additions, deletions, fusions and truncations in the polypeptide encoded by the reference sequence. Variants can also include insertions, deletions or substitutions of amino acids in the peptide sequence. To be therapeutically useful, such variants will retain a therapeutically or physiologically relevant activity as that term is used herein.

In some embodiments, CD40 can be an agonist of wild-type CD40, an analog or a derivative thereof. In some embodiments, the agonist of wild-type CD40, an analog or a derivative thereof, retains at least one biological activity of full length CD40 of SEQ ID NO: 18, the biological activity being selected from at a minimum, to bind CD154. In some embodiments, the agonist of wild-type CD40, an analog or a derivative thereof, retains at least 50%, at least 60%, at least 70%, at least 80%, at least 90%, at least 100% or more than 100% of the biological activity of full length CD40 of SEQ ID NO: 18.

The CD40 polypeptide can be recombinant, purified, isolated, naturally occurring or synthetically produced. The term "recombinant" when used in reference to a nucleic acid, protein, cell or a vector indicates that the nucleic acid, protein, vector or cell containing them have been modified by introduction of a heterologous nucleic acid or protein or the alteration of a native nucleic acid or a protein, or that the cell is derived from a cell so modified. The term "heterologous" (meaning 'derived from a different organism') refers to the fact that often the transferred protein was initially derived from a different cell type or a different species from the recipient. Typically the protein itself is not transferred, but instead the genetic material coding for the protein (often the complementary DNA or cDNA) is added to the recipient cell. Methods of generating and isolating recombinant polypeptides are known to those skilled in the art and can be performed using routine techniques in the field of recombinant genetics and protein expression. For standard recombinant methods, see Sambrook et al, Molecular Cloning: A Laboratory Manual, Cold Spring Harbor Laboratory Press, N Y (1989); Deutscher, Methods in Enzymology 182:83-9 (1990); Scopes, Protein Purification: Principles and Practice, Springer-Verlag, NY (1982). The CD40 polypeptide can be immobilized onto a solid surface, e.g., a bead or array plate.

In some embodiments, the CD40 protein or a portion thereof is expressed on the surface of a cell. Accordingly, the methods and compositions of the present disclosure contemplates a cell expressing CD40 on its surface. The disclosure is not limiting as it relates to the type of cell expressing CD40 on its surface. The cell can be an immune cell (e.g., B-cell, T-cell, neutrophil, monocyte, macrophage, dendritic cell, platelet), non-immune cell (e.g., an endothelial cell, epithelial cell, smooth muscle cell, fibroblast), or a cancer cell (e.g., B lymphoma cell, carcinoma cell, melanoma cell.).

In some embodiments, the CD40 expressing cell is in vitro under cell culture conditions. In other embodiments, the cell expressing CD40 protein is in vivo. CD40 may be detected on the surface of a cell by any one of several means known in the art. For example, an antibody specific for CD40 may be used in a fluorescence-activated cell sorting technique to determine whether cells express CD40 and isolate cells expressing CD40. Other methods of detecting cell surface molecules are also useful in detecting and isolating cell expressing CD40.

Inhibiting Interaction of CD40 and CD154

As used herein, "CD154" refers to a cell surface glycoprotein that is a member of the tumor necrosis factor ligand family. CD40 ligand is the cognate ligand for CD40. Other names in the art for CD40 ligand include: CD40L, CD40LG, CD 40 ligand, TNFSF5, TRAP, gp39, HIGM1, IGM, IMD3, and T-BAM. An exemplary protein sequence for human CD40L is NP 000065.1, which is encoded by nucleic acid sequence NM_000074.2.

A CD40 ligand "protein, polypeptide or peptide", or CD154 as used herein, refers to a proteinaceous CD40 ligand component that has sufficient biological activity to be biologically effective. Accordingly, "CD154" include full-length CD154 proteins and polypeptides and also CD154 that have been subject to non-native processing or biological modification. Such modifications include truncations, extensions, active domains or fragments, fusion proteins, mutants with substantial or sufficient biological activity, peptidomimetics and the like. Any form of CD154 can be used methods disclosed herein, including those isolated and purified from natural sources. CD154 prepared by recombinant expression can also be used, i.e., those obtained by expressing a CD40 ligand nucleic acid in a recombinant host cell and collecting the expressed CD40 ligand protein. CD40 ligands prepared by automated peptide synthesis are also included.

CD40 is well known in the art to interact with its cognate ligand CD154. One type of interaction is binding interaction and the said binding or interaction can result in activation of immune response at least, for example, by B-cell development, lymphocyte activation and proliferation; modulation of antigen presenting cells function; regulation of activity of dendritic cells, macrophages and B cells; induction of production of inflammatory cytokines in macrophages and dendritic cells; up-regulating antigen presentation; up-regulating T cell stimulation; and promoting immunoglobulin class switching in B cells. The binding can result, for example, in the inhibition of biological activity mediated by CD40. In one embodiment, peptides of the present disclosure bind to CD40 in such a manner as to inhibit the interaction of CD40 with CD154. Accordingly, in some embodiments, the biological activity of the peptides of the instant disclosure can be inhibiting the interaction of a CD40 protein with a CD154 protein. Therefore the peptides or functional fragment thereof disclosed herein are anti-CD40 peptides or functional fragments thereof. The peptide can interact with the CD40 protein in such a manner that the strength of the interaction between the CD40 protein and a CD154 protein is increased or decreased.

In some embodiments, the peptides disclosed herein can inhibit the interaction between CD40 and CD154. As used herein, the term "interact" or "interaction", and the like mean that two molecules come into sufficient physical proximity such that they cause a biological downstream effect e.g., activation of an immune cell. The interaction can be, for example, a binding interaction. The interaction can be covalent binding interactions between proteins include, for example, disulfide bonds, ester bonds, amide bonds and the like or non-covalent bonding interactions between proteins include, for example, hydrophobic interactions, van der Waals interactions, ionic interactions, hydrogen bonding interactions and the like. The interaction can be reversible (e.g., non-covalent binding interactions) or non-reversible (e.g., covalent bonds). Moreover, a reversible interaction can be strong or weak, the strength of the interaction being determined by the forces (e.g., ionic charges, hydrogen binding, van der Walls interactions, etc.) exerted by each protein on the other protein in the complex. Factors affecting the strength of an interaction between two molecules are known to those skilled in the art. One useful measure of the strength of binding between two molecules, such as a peptide and a protein, is the dissociation constant (Kd). KD can be determined by measurement of the kinetics of complex formation and dissociation, e.g. by the SPR method (Biacore). "Inhibit" or "inhibiting," as used herein, e.g., as in "inhibiting an interaction" between two binding partners such as proteins, refers to a process of lowering or reducing the ability of a first protein (e.g., CD40 protein) and a second protein (e.g., CD154 protein) to bind or associate, or disrupting an interaction between a first protein and a second protein. "Inhibiting an interaction" between two proteins may involve disrupting one or more covalent or non-covalent interactions between the first protein and the second protein. Covalent bonding interactions between proteins include, for example, disulfide bonds, ester bonds, amide bonds and the like. Non-covalent bonding interactions between proteins include, for example, hydrophobic interactions, van der Waals interactions, ionic interactions, hydrogen bonding interactions and the like. As it relates to the present disclosure, inhibiting an interaction binding of one molecule (e.g., CD40) with another molecule (e.g., CD154) or the inhibition of stimulation of one cell (e.g., cell expressing a CD40 protein on its surface) by another cell (e.g., cell expressing CD154 on its surface) can be through steric hindrance, conformational alterations or other biochemical mechanism (e.g., through binding of peptides of instant disclosure to CD40 protein or cell expressing CD40 protein on its surface).

In some embodiments, the peptides of the present disclosure can inhibit an interaction between a CD40 protein and a CD154 protein by at least 10%, at least 20%, at least 30%, at least 40%, at least 50%, at least 60%, at least 70%, at least 80%), at least 90%>, or at least 95%. In some embodiments, the peptides disclosed herein can completely inhibit binding of CD40 to CD154. Complete inhibition of binding between CD40 and CD154 means that when a CD40 protein is contacted (treated or brought into proximity with) a peptide disclosed herein in the presence of a CD154 protein under conditions that would normally allow the interaction of CD40 and CD154, no such interaction occurs and activation signals are not stimulated in the CD40-expressing cell. Consequently CD40/CD154 mediated modulation of immune response does not occur. Methods to measure strength of binding between two proteins, for example, CD40 and CD154, has been discussed above and are known to those skilled in the art.

The term "contacting" as used herein, refers to bringing a disclosed agent (e.g., peptides disclosed herein or a portion thereof) and a cell, a target receptor, or other biological entity (e.g., CD40 protein or cell expressing CD40 on its surface) together in such a manner that the compound can affect the activity of the target, either directly; i.e., by interacting with the target itself, or indirectly; i.e., by interacting with another molecule, co-factor, factor, or protein on which the activity of the target is dependent. "Contacting" as used herein, e.g., as in "contacting a CD40 protein" refers to contacting directly or indirectly in vitro, ex vivo, or in vivo (i.e. within a subject as defined herein). In some embodiments, the CD40 protein can be isolated, recombinant, synthesized, or immobilized on a solid surface. In some embodiments, the CD40 protein can be expressed on a surface of cell (e.g. an immune cell or a cancer cell). The cell expressing CD40 can be present in an in vitro cell culture condition or in vivo in a subject. Contacting a CD40 protein can include contacting a cell expressing said CD40 protein. Contacting a CD40 protein can include addition of a peptide or a portion thereof, disclosed herein to a sample comprising a cell expressing a CD40 protein, or administration to a subject. Contacting encompasses administration to a solution, cell, tissue, mammal, subject, patient, or human. Further, contacting a cell includes adding a peptide or portion thereof, disclosed herein to a cell culture.

In one aspect, provided herein is a method of inhibiting an interaction between a CD40 protein and a CD154 protein comprising contacting the CD40 protein with a peptide disclosed herein.

In some embodiments, peptides disclosed herein can interact with any site on the CD40 protein. In some embodiments, peptides disclosed herein bind with the CD40 protein at a site that overlaps with the CD154 binding site. In some embodiments, a peptide disclosed herein binds the CD40 protein at the CD154 binding site.

Modulation of Immune Response Mediated by CD40-CD154 Interaction

CD40 is well known to play an important role in activation of immune response. B cells are known to constitutively express the CD40 molecule on the cells membrane (van Kooten C. et al, J. Leukoc. Biol. 2000). Stimulation of CD40 by CD154-expressing activated T cells, results in B cells activation, proliferation and isotype switching. Recent studies have indicated that CD40-CD154 interaction can upregulate costimulatory molecules, activate antigen presenting cells (APCs) and influence T-cell priming and T-cell-mediated effector of CD40 activities include modulating cell survival (e.g., functions as cell survival signal), antibody production, antibody isotype switching, production of cytokines (e.g., IL-2, IL-6, IL-8, IL-12, TNF-α, IL-4, IL-5 and IL-10), metalloproteases (e.g., MMP-I/collagenase and MMP-9/gelatinase B) and establishment of immune memory. CD40 activities further include modulating production of proteins involved in cell-cell contact or adhesion (e.g., E-selectin, VCAM-1 and ICAM-1). This interaction can activate macrophages, natural killer (NK) cells, and endothelial cells. CD40 plays a significant role in immune cell function and signaling, including B-cell and T-cell activation by antigen presenting cells, such as macrophages and dendritic cells. CD40 activation stimulates antibody production, isotype switching, and establishment of memory. CD40 activation stimulates production of cytokines, such as IL-2, IL-6, IL-8, IL-12, TNF-α, IL-4, IL-S and IL-10; and metalloproteases, such as MMP-I/collagenase and MMP-9/gelatinase B. CD40 activation stimulates production of proteins involved in cell-cell contact or adhesion, such as E-selectin, VCAM-1 and ICAM-1. CD40 recognition on target cells provides an activation pathway for NK cell cytotoxic activity. Thus, increasing or decreasing cell survival, antibody production, isotype switching, establishment of memory, production of cytokines, metalloproteases or proteins involved in cell-cell contact or adhesion, NK cell cytotoxic activity, B-cell activation, B-cell proliferation, T-cell activation, T-cell proliferation, macrophage activation, migration of immune cell can all be effected or inhibited by contacting an appropriate cell expressing CD40 with a peptide of the present disclosure (e.g., peptide selected from Table 1 or a pharmaceutical composition disclosed herein The term "immune response" encompasses but is not limited to one or both of the following responses: antibody production (e.g., humoral immunity), and induction of cell-mediated immunity (e.g., cellular immunity including helper T cell and/or cytotoxic T cell responses). "Immune response" generally refers to innate and acquired immune responses including, but not limited to, both humoral immune responses (mediated by B lymphocytes) and cellular immune responses (mediated by T lymphocytes). An immune response may be beneficial and lead to immunity against infectious pathogens, or an immune response may be pathogenic and lead to autoimmune or hypersensitivity disease. Immune responses against foreign viruses, bacteria, fungi, parasites typically represent beneficial adaptive immune responses. Immune responses against self-tissues, innocuous foreign objects (e.g., dust mite or pollen allergens, etc.), or tissue transplants represent examples of adverse maladaptive immune responses. The term "modulate," "modulates" or "modulation" refers to enhancement (e.g., an increase) or inhibition (e.g., a reduction) in the specified activity or suppression of a specified activity. As it relates to the present disclosure, immunosuppression also refers to inhibition of an immune response mediated by CD40 activity or one that is mediated by interaction of CD40 with CD154

As used herein, "modulation of immune response" can be change in the level of an immune cell (e.g., B-cell, T-cell, antigen presenting cell, activated B-cell, activated T-cell, activated macrophage), a change in level of immunomodulatory molecules (e.g., inflammatory cytokines, chemokines), or a combination thereof. In some embodiments, modulation of immune response can be suppression of immune response or immunosuppression. As used herein, the terms level, number, count and concentration can be used interchangeably. The term "immunomodulatory molecule" as used herein refers to any molecule which is capable of effecting the proliferation or activation of the cells of a subject's immune system. Such molecules include, without limitation, prostaglandin E2 (PGE2), transforming growth factor-β (TGF-β), indoleamine 2,3-dioxygenase (IDO), nitric oxide, hepatocyte growth factor (HGF), interleukin 6 (IL-6) and interleukin 10 (IL-10).

Modulation of immune response can mean increase or decrease of in the level of an immune cell. In some embodiments, the peptides of the present disclosure inhibit or decrease the immune response by inhibiting the level of immune cell (e.g., T-cell, B-cell, antigen presenting cell, activated T-cell, activated B-cell, or activated macrophage), inhibiting the level of immunomodulatory molecules, or a combination thereof).

Accordingly, in some embodiments the biological activity of peptides disclosed herein can be inhibition of CD40 activity such as CD40 mediated immune response (e.g., B-cell activation, B-cell proliferation, T-cell activation, T-cell proliferation, macrophage activation, inhibition of inflammatory cytokine production, or a combination thereof).

It will be appreciated by those skilled in the art that both a cell culture system and the immune system of a subject comprise basal levels of immune cells and immunomodulatory molecules. The phrases basal level and normal level can be used interchangeably. As used herein, the basal level of a type of immune cell, or a immunomodulatory molecule, refers to the average number of that cell type, or immunomodulatory molecule, present in a population of individuals considered healthy (i.e., free of metabolic, autoimmune, or infectious disease) or the basal level of a type of immune cell, or an immunomodulatory molecule, refers to the average level of that cell type, or immunomodulatory molecule, present in a population of cells that is not-activated. Those skilled in the art are capable of determining if an immune cell, or a population of such cells, is activated. For example, the expression of CD69, CD25 and/or CD154 proteins by a T-cell indicates that the cell has been activated. For example, the expression of MHC-class II, B220 and CD3 proteins by B-cell indicates that the B-cell has been activated. For example, the expression of IL-12, iNOS, Arg-1, or IL-1 proteins by macrophage indicates the macrophage has been activated.

Methods to measure immune cells are well known in the art including methods based on identifying expression of specific surface marker proteins e.g., by flow cytometry. Level of immune cell can be measure, for example, by measuring proliferation by 3H-Thymidine Uptake, Bromodeoxyuridine Uptake (BrdU), ATP Luminescence, Fluorescent Dye Reduction (carboxyfluorescein succinimidyl ester (CFSE)-like dyes); cytokine measurement, for example, using Multi-Analyte ELISArray Kits, bead-based multiplex assay; measuring surface antigen expression, for example, by flow cytometry; measuring cell cytotoxicity, for example, by Two-Label Flow Cytometry, Calcein AM Dye Release, Luciferase Transduced Targets, or Annexin V. Methods to measure T-cell responses and B-cell responses are well known in the art, for example see Expert Rev. Vaccines 9(6), 595-600 (2010), mBio. 2015 July-August; 6(4).

The reference level or basal level of a cell or molecule can be a specific amount (e.g., a specific concentration) or it can encompass a range of amounts. Basal levels, or ranges, of immune cells and immunoregulatory molecules are known to those in the art. For example, in a healthy individual, the normal level of CD4+ T-cells present in human blood is 500-1500 cells/ml. Basal levels of cells can also be reported as a percentage of a total cell population.

Immune cell number and function, for example may be monitored by assays that detect immune cells by an activity such as cytokine production, proliferation, or cytotoxicity. For example, Lymphoproliferation Assay, which assays the ability of T cells to proliferate in response to an antigen can be used as an indicator of the presence of antigen-specific CD4+ helper T cells. Typically, the specimen of purified T cells or PBMCs is mixed with various dilutions of antigen or antigen in the presence of stimulator cells (irradiated autologous or HLA matched antigen-presenting cells). After 72-120 h, [3H] thymidine is added, and DNA synthesis (as a measure of proliferation) is quantified by using a gamma counter to measure the amount of radiolabeled thymidine incorporated into the DNA. A stimulation index can be calculated by dividing the number of cpm for the specimen by the number of counts per minute in a control. As it relates to a treatment of an inflammatory disease, the proliferation assay can be used to compare T-cell responses before and after treatment with peptides of the present disclosure or pharmaceutical compositions disclosed herein. Another example of assay that can be employed for detection of proliferation of immune cells (e.g., T-cell, B-cells) include use of intracellular fluorescent dye, 5,6-carboxyfluorescein diacetate succinimidyl ester (CFSE) in mixed lymphocyte reaction (CFSE-MLR) and determination of proliferating cells using flow cytometry. Another example of an assay that can be employed is detection of secreted cytokines by ELISA and ELISPOT Assays.

Cytokine secretion by immune cells in a subject suffering from inflammatory disease or in response to a transplant) may be detected by measuring either bulk cytokine production (by an ELISA) or enumerating individual cytokine producing immune cells (by an ELISPOT assay). Generally, in an ELISA assay, PBMC specimens are incubated with antigen (with or without antigen-presenting cells), and after a defined period of time, the supernatant from the culture is harvested and added to microtiter plates coated with antibody for cytokines of interest such as IFN-γ, TNF-α, or IL-2. Antibodies ultimately linked to a detectable label or reporter molecule are added, and the plates are washed and read. In a modification of the assay, cytokine secretions can be measured in samples (e.g., serum or other body fluids) obtained from a subject using ELISA or ELISPOT before and after treatment with the peptides disclosed herein or pharmaceutical compositions disclosed herein. Other useful assays include, measurement of detection of intracellular cytokine assay by flow cytometry, measurement of cytokine mRNA levels by RT-PCR and direct cytotoxicity assays of T-cell (See: Clay et al., 2001). Macrophage activation can be determined, for example, by measuring levels of chemokines such as IL-8/CXCL8, IP-10/CXCL10, MIP-1 alpha/CCL3, MIP-1 beta/CCL4, and RANTES/CCL5, which are released as chemoattractants for neutrophils, immature dendritic cells, natural killer cells, and activated T cells. Levels of pro-inflammatory cytokines are released including IL-1 beta/IL-1F2, IL-6, and TNF-alpha can also be measured by assays well known in the art. Levels of proteolytic enzymes, MMP-1, -2, -7, -9, and -12, which degrade Collagen, Elastin, Fibronectin, and other ECM components can also be measured to determine macrophage activation. Leukocytes are attracted by the macrophage via its release of chemokines including MDC/CCL22, PARC/CCL18, and TARC/CCL17. Levels of activated B-cell can be determined, for example, by measuring antigen specific antibody secretion or detecting activated B-cell specific surface markers such as CD27, CD19, CD20, CD25, CD30, CD69, CD80, CD86, CD135, by assays such as flow cytometry.

In some embodiments, the peptides disclosed herein can reduce the level of an immune cell to less than about 50%, less than about 45%, less than about 40%, less than about 35%, less than about 30%, less than about 27%, or equal to about 25% of the total immune cell population. Methods of measuring different types of T-cells in the T-cell population are known to those skilled in the art. In some embodiments, binding of a peptide disclosed herein with a CD40 protein decreases the number of immune cells by at least 5%, at least 10%, at least 20%, at least 30%, at least 40%, at least 50%, at least 60%, at least 70%, at least 80%, at least 90%, or at least 95%. In another embodiment, binding of a peptide disclosed herein with a CD40 protein decreases the number of immune cells by a factor of at least 10, at least 100, at least 1,000, at least 10,000. In some embodiments, the level of immune cells is reduced so that immune cells comprise no more than about 20%>, about 25%, about 30%>, about 35%, or about 40%> of the total immune cell population.

Methods of Preparation of Peptides

The peptides can generally be prepared following techniques known in the art. The peptides can also be prepared using standard genetic engineering techniques known to those skilled in the art. For example, the peptide can be produced enzymatically by inserting nucleic acid encoding the peptide into an expression vector, expressing the DNA, and translating the DNA into the peptide in the presence of the required amino acids. The peptide is then purified using chromatographic or electrophoretic techniques, or by means of a carrier protein which can be fused to, and subsequently cleaved from, the peptide. This can be done by inserting into the expression vector in phase with the peptide encoding sequence, a nucleic acid sequence encoding the carrier protein. The fusion protein-peptide may be isolated using chromatographic, electrophoretic or immunological techniques (such as binding to a resin via an antibody to the carrier protein). The peptide can be cleaved using chemical methodology or enzymatically, as by, for example, using hydrolases.

Peptides of the disclosure can also be prepared using solution methods, by either stepwise or fragment condensations. An appropriately alpha amino-protected amino acid is coupled to an appropriately alpha carboxyl protected amino acid (such protection may not be required depending on the coupling method chosen) using diimides, symmetrical or unsymmetrical anhydrides, BOP, or other coupling reagents or techniques known to those skilled in the art. These techniques may be either or enzymatic. The alpha amino and/or alpha carboxyl protecting groups are removed and the next suitably protected amino acid or block of amino acids are coupled to extend the growing peptide. Various combinations of protecting groups and of chemical and/or enzymatic techniques and assembly strategies can be used in each synthesis.

A peptide of the instant disclosure can be synthesized by conventional techniques. For example, the peptides can be synthesized by chemical synthesis using solid phase peptide synthesis. These methods employ either solid or solution phase synthesis methods (see for example, J. M. Stewart, and J. D. Young, Solid Phase Peptide Synthesis, 2nd Ed., Pierce Chemical Co., Rockford 111. (1984) and G. Barany and R. B. Merrifield, The Peptides: Analysis Synthesis, Biology editors E. Gross and J. Meienhofer Vol. 2 Academic Press, New York, 1980, pp. 3-254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, suprs, Vol 1, for classical solution synthesis.)

The peptides can be chemically synthesized by Merrifield-type solid phase peptide synthesis. This method may be routinely performed to yield peptides up to about 60-70 residues in length, and may, in some cases, be utilized to make peptides up to about 100 amino acids long. Larger peptides may also be generated synthetically via fragment condensation or native chemical ligation (Dawson et al., 2000, Ann. Rev. Biochem. 69:923-960). An advantage to the utilization of a synthetic peptide route is the ability to produce large amounts of peptides, even those that rarely occur naturally, with relatively high purities, i.e., purities sufficient for research, diagnostic or therapeutic purposes. Solid phase peptide synthesis is described by Stewart et al. in Solid Phase Peptide Synthesis, 2nd Edition, 1984, Pierce Chemical Company, Rockford, III; and Bodanszky and Bodanszky in The Practice of Peptide Synthesis, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the alpha-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and coupling thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group, such as formation into a carbodiimide, a symmetric acid anhydride, or an "active ester" group, such as hydroxybenzotriazole or pentafluorophenyl esters.

Appropriate protective groups usable in such syntheses and their abbreviations will be found in the above text, as well as in J. F. W. McOmie, Protective Groups in Organic Chemistry, (Plenum Press, New York, 1973). The common protective groups used herein are t-butyloxycarbonyl (Boc), fluorenylmethoxycarboyl (FMOC), benzyl (Bzl), tosyl (Tos), o-bromo-phenylmethoxycarbonyl (BrCBZ), phenylmethoxycarbonyl (CBZ), 2-chloro-phenylmethoxycarbonyl (2-Cl-CBZ), 4-methoxy-2,3,6-trimethylbenzenesulfonyl (Mtr), trityl (Trt), formyl (CHD), and tertiary butyl (t-Bu). N-terminal acetylation on the deprotected N.sup.α-amino group of peptides synthesized using the Boc strategy can be accomplished with 10% Ac2 O and 5% DIEA in NMP, followed by washing of the peptide resin with NMP and/or CH2 Cl2.

Examples of solid phase peptide synthesis methods include the BOC method which utilized tert-butyloxcarbonyl as the alpha-amino protecting group, and the FMOC method which utilizes 9-fluorenylmethyloxcarbonyl to protect the alpha-amino of the amino acid residues, both which methods are well-known by those of skill in the art. Incorporation of N- and/or C-blocking groups may also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin, so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function, e.g. with DCC, can then proceed by addition of the desired alcohol, followed by de-protection and isolation of the esterified peptide product.

In one embodiment, the peptides of the present disclosure are manufactured by solid phase peptide synthesis using Fmoc chemistry. In certain embodiments, after synthesis the Fmoc group is deprotected at the N-terminus, the side chain protection group is deprotected, and the peptide is cleaved from the resin. In one embodiment, the resin is a Cl-resin. In one embodiment, the condensation reaction reagent is DIC+ HOBT. In one embodiment deprotection is done using Pip. In certain embodiments, the synthesized peptides are purified by RP-HPLC using a solvent of acetonitrile+deionized with TFA as the buffer. In one embodiment, the peptides are purified by gradient elution.

The peptides of the disclosure may be prepared by standard chemical or biological means of peptide synthesis. Biological methods include, without limitation, expression of a nucleic acid encoding a peptide in a host cell or in an in vitro translation system.

Included in the disclosure are nucleic acid sequences that encode the peptide of the instant disclosure. In one embodiment, the methods and compositions herein contemplate use of a nucleic acid fragment encoding a peptide disclosed herein (e.g., peptide selected from Table 1). Accordingly, subclones of a nucleic acid sequence encoding a peptide of the disclosure can be produced using conventional molecular genetic manipulation for subcloning gene fragments, such as described by Sambrook et al, Molecular Cloning: A Laboratory Manual, Cold Springs Laboratory, Cold Springs Harbor, New York (2012), and Ausubel et al. (ed.), Current Protocols in Molecular Biology, John Wiley & Sons (New York, N.Y.) (1999 and preceding editions), each of which is hereby incorporated by reference in its entirety. The subclones then are expressed in vitro or in vivo in bacterial cells to yield a smaller protein or polypeptide that can be tested for a particular activity.

Accordingly, in one aspect provided herein is an isolated nucleic acid fragment encoding a peptide comprising an amino acid sequence selected from group consisting of SEQ ID NOs: 1-6 and 8-17 or a portion thereof. Further, the disclosure encompasses an isolated nucleic acid encoding a peptide having substantial homology to a peptide selected from group consisting of SEQ ID NOs: 1-6 and 8-17. In some embodiments, the isolated nucleic acid fragment encodes a peptide having a sequence that is at least 80%, at least 85%, at least 90%, at least 95%, at least 97%, at least 99% or 100% identical to that of SEQ ID NO: 1. In some embodiments, the isolated nucleic acid fragment encodes a peptide having an amino acid sequence that is at least 80%, at least 85%, at least 90%, at least 95%, at least 97%, at least 99% or 100% identical to that of SEQ ID NO: 2. In some embodiments, the nucleic acid fragment encodes a peptide having an amino acid sequence that is at least 80%, at least 85%, at least 90%, at least 95%, at least 97%, at least 99% or 100% identical to that of SEQ ID NO:3. In some embodiments, the nucleic acid fragment encodes a peptide having an amino acid sequence that is at least 80%, at least 85%, at least 90%, at least 95%, at least 97%, at least 99% or 100% identical to that of SEQ ID NO: 4. In some embodiments, the nucleic acid fragment encodes a peptide having an amino acid sequence that is at least 80%, at least 85%, at least 90%, at least 95%, at least 97%, at least 99% or 100% identical to that of SEQ ID NO: 5. In some embodiments, the isolated nucleic acid fragment encodes a peptide having an amino acid sequence that is at least 80%, at least 85%, at least 90%, at least 95%, at least 97%, at least 99% or 100% identical to that of SEQ ID NO: 6. In some embodiments, the isolated nucleic acid fragment encodes a peptide having an amino acid sequence that is at least 80%, at least 85%, at least 90%, at least 95%, at least 97%, at least 99% or 100% identical to that of SEQ ID NO: 8. In some embodiments, the isolated nucleic acid fragment encodes a peptide having an amino acid sequence that is at least 80%, at least 85%, at least 90%, at least 95%, at least 97%, at least 99% or 100% identical to that of SEQ ID NO: 9. In some embodiments, the isolated nucleic acid fragment encodes a peptide having an amino acid sequence that is at least 80%, at least 85%, at least 90%, at least 95%, at least 97%, at least 99% or 100% identical to that of SEQ ID NO: 10. In some embodiments, the isolated nucleic acid fragment encodes a peptide having an amino acid sequence that is at least 80%, at least 85%, at least 90%, at least 95%, at least 97%, at least 99% or 100% identical to that of SEQ ID NO: 11. In some embodiments, the isolated nucleic acid fragment encodes a peptide having an amino acid sequence that is at least 80%, at least 85%, at least 90%, at least 95%, at least 97%, at least 99% or 100% identical to that of SEQ ID NO: 12. In some embodiments, the isolated nucleic acid fragment encodes a peptide having an amino acid sequence that is at least 80%, at least 85%, at least 90%, at least 95%, at least 97%, at least 99% or 100% identical to that of SEQ ID NO: 13. In some embodiments, the isolated nucleic acid fragment encodes a peptide having an amino acid sequence that is at least 80%, at least 85%, at least 90%, at least 95%, at least 97%, at least 99% or 100% identical to that of SEQ ID NO: 14. In some embodiments, the isolated nucleic acid fragment encodes a peptide having an amino acid sequence that is at least 80%, at least 85%, at least 90%, at least 95%, at least 97%, at least 99% or 100% identical to that of SEQ ID NO: 15. In some embodiments, the isolated nucleic acid fragment encodes a peptide having an amino acid sequence that is at least 80%, at least 85%, at least 90%, at least 95%, at least 97%, at least 99% or 100% identical to that of SEQ ID NO: 16. In some embodiments, the isolated nucleic acid fragment encodes a peptide having an amino acid sequence that is at least 80%, at least 85%, at least 90%, at least 95%, at least 97%, at least 99% or 100% identical to that of SEQ ID NO: 17.

As used herein, an "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence. In the context of the present invention, the following abbreviations for the commonly occurring nucleic acid bases are used, "A" refers to adenosine, "C" refers to cytosine, "G" refers to guanosine, "T" refers to thymidine, and "U" refers to uridine.

The present disclosure also encompasses recombinant nucleic acid encoding the peptides described herein. A "recombinant" nucleic acid is one that has been created using genetic engineering techniques.

Biological preparation of a peptide disclosed herein involves expression of a nucleic acid encoding a desired peptide. An expression cassette comprising such a coding sequence may be used to produce a desired peptide for use in the method of the disclosure. In the context of an expression vector, the vector can be readily introduced into a host cell, e.g., mammalian, bacterial, yeast or insect cell by any method in the art. Coding sequences for a desired peptide of the disclosure can be codon optimized based on the codon usage of the intended host cell in order to improve expression efficiency as demonstrated herein. Codon usage patterns can be found in the literature (Nakamura et al, 2000, Nuc Acids Res. 28:292). Representative examples of appropriate hosts include bacterial cells, such as streptococci, staphylococci, E. coli, Streptomyces and Bacillus subtilis cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like. The expression vector can be transferred into a host cell by physical, biological or chemical means, discussed in detail elsewhere herein. To ensure that the peptide obtained from either chemical or biological synthetic techniques is the desired peptide, analysis of the peptide composition can be conducted. Such amino acid composition analysis may be conducted using high resolution mass spectrometry to determine the molecular weight of the peptide.

Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, can also be used to determine definitely the sequence of the peptide.

The isolated nucleic acid can comprise any type of nucleic acid, including, but not limited to DNA and RNA. For example, in one embodiment, the composition comprises an isolated DNA molecule, including for example, an isolated cDNA molecule, encoding a peptide of the disclosure, or functional fragment thereof. In one embodiment, the composition comprises an isolated RNA molecule encoding a peptide of the invention, or a functional fragment thereof. The isolated nucleic acids can be synthesized using any method known in the art.

The nucleic acid molecules of the present disclosure can be modified to improve stability in serum or in growth medium for cell cultures. Modifications can be added to enhance stability, functionality, and/or specificity and to minimize immunostimulatory properties of the nucleic acid molecule of the disclosure. For example, in order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect function of the molecule.

In one embodiment of the present disclosure the nucleic acid molecule can contain at least one modified nucleotide analogue. For example, the ends may be stabilized by incorporating modified nucleotide analogues. Non-limiting examples of nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone—modified ribonucleotides the phosphoester group connecting to adjacent ribonucleotides is replaced by a modified group, e.g., of phosphothioate group. In preferred sugar-modified ribonucleotides, the 2' OH-group is replaced by a group selected from H, OR, R, halo, SH, SR, NH2, NHR, NR2 or ON, wherein R is Ci-C6 alkyl, alkenyl or alkynyl and halo is F, Cl, Br or I.

Other examples of modifications are nucleobase-modified ribonucleotides, i.e., ribonucleotides, containing at least one non-naturally occurring nucleobase instead of a naturally occurring nucleobase. Bases can be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; 0- and N-alkylated nucleotides, e.g., N6-methyl adenosine are suitable. It should be noted that the above modifications may be combined.

In some instances, the nucleic acid molecule comprises at least one of the following chemical modifications: 2'-H, 2'-0-methyl, or 2'-OH modification of one or more nucleotides. In certain embodiments, a nucleic acid molecule of the invention can have enhanced resistance to nucleases. For increased nuclease resistance, a nucleic acid molecule, can include, for example, 2 '-modified ribose units and/or phosphorothioate linkages. For example, the 2' hydroxyl group (OH) can be modified or replaced with a number of different "oxy" or "deoxy" substituents. For increased nuclease resistance the nucleic acid molecules of the invention can include 2'-0-methyl, 2'-fluorine, 2'-0-methoxyethyl, 2'-0-aminopropyl, 2'-amino, and/or phosphorothioate linkages. Inclusion of locked nucleic acids (LNA), ethylene nucleic acids (ENA), e.g., 2 '-4'-ethylene-bridged nucleic acids, and certain nucleobase modifications such as 2-amino-A, 2-thio (e.g., 2-thio-U), G-clamp modifications, can also increase binding affinity to a target.

In one embodiment, the nucleic acid molecule includes a 2 '-modified nucleotide, e.g., a 2'-deoxy, 2'-deoxy-2'-fluoro, 2'-0-methyl, 2'-0-methoxyethyl (2'-0-MOE), 2'-0-aminopropyl (2'-0-AP), 2'-0-dimethylaminoethyl (2'-0-DMAOE), 2'-0-dimethylaminopropyl (2'-0-DMAP), 2'-0-dimethylaminoethyloxyethyl (2'-0-DMAEOE), or 2'-0-N-methylacetamido (2'-0-NMA). In one embodiment, the nucleic acid molecule includes at least one 2'-0-methyl-modified nucleotide, and in some embodiments, all of the nucleotides of the nucleic acid molecule include a 2'-0-methyl modification.

Nucleic acid fragments discussed herein include otherwise unmodified RNA and DNA as well as RNA and DNA that have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al. {Nucleic Acids Res., 1994, 22:2183-2196). Such rare or unusual RNAs, often termed modified RNAs, are typically the result of a post-transcriptional modification and are within the term unmodified RNA as used herein. Modified RNA, as used herein, refers to a molecule in which one or more of the components of the nucleic acid, namely sugars, bases, and phosphate moieties, are different from that which occur in nature, preferably different from that which occurs in the human body. While they are referred to as "modified RNAs" they will of course, because of the modification, include molecules that are not, strictly speaking, RNAs. Nucleoside surrogates are molecules in which the ribophosphate backbone is replaced with a non-ribophosphate construct that allows the bases to be presented in the correct spatial relationship such that hybridization is substantially similar to what is seen with a ribophosphate backbone, e.g., non-charged mimics of the ribophosphate backbone.

Modifications of the nucleic acid of the disclosure can be present at one or more of, a phosphate group, a sugar group, backbone, N-terminus, C-terminus, or nucleobase.

Also provided herein is a vector comprising the isolated nucleic acid fragment of the present disclosure inserted. As used herein, a "vector" or "delivery vector" can be a viral or non-viral vector that is used to deliver a nucleic acid to a cell, tissue or subject. Exemplary vectors include, but are not limited to, adeno-associated virus vectors, adenovirus vectors, lentivirus vectors, paramyxovirus vectors, alphavirus vectors and herpes virus vectors.

A "recombinant" vector or delivery vector refers to a viral or non-viral vector that comprises one or more heterologous nucleotide sequences (i.e., transgenes), e.g., two, three, four, five or more heterologous nucleotide sequences. In an embodiment of the disclosure, the recombinant vectors and delivery vectors of the invention encode a fusion polypeptide of NAg and a cytokine such as IFN-β, but can also include one or more additional heterologous nucleotide sequences, for example, sequences encoding C- or N-terminal modifications and linker moieties. As used herein, the term "viral vector" or "viral delivery vector" can refer to a virus particle that functions as a nucleic acid delivery vehicle, and which comprises the vector genome packaged within a virion. Alternatively, these terms can be used to refer to the vector genome when used as a nucleic acid delivery vehicle in the absence of the virion. The art is replete with suitable vectors that are useful in the present disclosure.

In brief summary, the expression of natural or synthetic nucleic acids encoding a peptide is typically achieved by operably linking a nucleic acid encoding the peptide or portions thereof to a promoter, and incorporating the construct into an expression vector. The vectors to be used are suitable for replication and, optionally, integration in eukaryotic cells. Typical vectors contain transcription and translation terminators, initiation sequences, and promoters useful for regulation of the expression of the desired nucleic acid sequence. The vectors of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the disclosure provides a gene therapy vector.

The isolated nucleic acid of the disclosure can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors. Further, the vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

For example, vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In one embodiment, the composition includes a vector derived from an adeno-associated virus (AAV). Adeno-associated viral (AAV) vectors have become powerful gene delivery tools for the treatment of various disorders. AAV vectors possess a number of features that render them ideally suited for gene therapy, including a lack of pathogenicity, minimal immunogenicity, and the ability to transduce postmitotic cells in a stable and efficient manner. Expression of a particular gene contained within an AAV vector can be specifically targeted to one or more types of cells by choosing the appropriate combination of AAV serotype, promoter, and delivery method In certain embodiments, the vector also includes conventional control elements which are operably linked to a regulatory control sequence in a manner which permits its transcription, translation and/or expression in a cell transfected with the plasmid vector or infected with the virus produced by the disclosure. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (poly A) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized. Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operative 1y linked thereto. Another example of a suitable promoter is Elongation Growth Factor-1 (EF-1a). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Enhancer sequences found on a vector also regulates expression of the gene contained therein. Typically, enhancers are bound with protein factors to enhance the transcription of a gene. Enhancers may be located upstream or downstream of the gene it regulates. Enhancers may also be tissue-specific to enhance transcription in a specific cell or tissue type. In one embodiment, the vector of the present invention comprises one or more enhancers to boost transcription of the gene present within the vector.

In order to assess the expression of the peptide, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al, 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means. Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). A preferred method for the introduction of a polynucleotide into a host cell is calcium phosphate transfection. Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al, 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the disclosure.

The present disclosure includes a composition comprising a host cell which comprises a peptide of the disclosure, a nucleic acid encoding a peptide of the disclosure, or a combination thereof. As used herein, the term "host cell" comprises prokaryotic cells and eukaryotic cells. Exemplary prokaryotic host cells include *E. coli, Bacillus subtilis*, etc. Exemplary eukaryotic cells include yeast cells, insect cells, mammal cells, etc. In one embodiment, the cell is genetically modified to comprise a peptide and/or nucleic acid of the disclosure. In certain embodiments, genetically modified cell is autologous to a subject being treated with the composition of the invention. Alternatively, the cells can be allogeneic, syngeneic, or xenogeneic with respect to the subject. In certain embodiment, the cell is able to secrete or release the expressed peptide of the invention into extracellular space in order to deliver the peptide to one or more other cells.

The genetically modified cell may be modified in vivo or ex vivo, using techniques standard in the art. Genetic modification of the cell may be carried out using an expression vector or using a naked isolated nucleic acid construct. In one embodiment, the cell is obtained and modified ex vivo, using an isolated nucleic acid encoding a peptide. In one embodiment, the cell is obtained from a subject, genetically modified to express the peptide and/or nucleic acid, and is re-administered to the subject. In certain embodiments, the cell is expanded ex vivo or in vitro to produce a population of cells, wherein at least a portion of the population is administered to a subject in need. In one embodiment, the cell is genetically modified to stably express the peptide. In another embodiment, the cell is genetically modified to transiently express the peptide.

The present disclosure provides a scaffold or substrate composition comprising a peptide of the disclosure, an isolated nucleic acid of the disclosure, a host cell comprising the peptide or isolated nucleic acid fragment of the disclosure, or a combination thereof. For example, in one embodiment, a peptide of the disclosure, an isolated nucleic acid of the disclosure, a host cell producing the peptide of the disclosure, or a combination thereof is incorporated within a scaffold. In another embodiment, a peptide of the disclosure, an isolated nucleic acid of the disclosure, a host cell producing the peptide of the disclosure, or a combination thereof is applied to the surface of a scaffold. The scaffold of the disclosure can be of any type known in the art. Non-limiting examples of such a scaffold includes a, hydrogel, electrospun scaffold, foam, mesh, sheet, patch, and sponge.

Peptide Modifications

The compositions and methods of the present disclosure contemplate use of modified peptides, so long as the modified peptide, retains, the biological activity of the wild type unmodified peptide e.g., binding CD40. In some aspects of the disclosure, the peptide is altered. The term "altered polypeptide" refers to a peptide that includes alterations, such as deletions, additions, and substitutions (generally conservative in nature as would be known to a person in the art, such as alanines), to the wild type sequence, as long as the peptide retains the desired biological activity, i.e., binding CD40, or inhibiting interaction of CD40 and CD154, and/or modulating immune responses directed by interaction of CD40 and CD154. These modifications can be deliberate, as through site-directed mutagenesis, or can be accidental, such as through mutations of artificial hosts, such as genetically engineered bacteria, yeast or mammalian cells, that produce the proteins, or errors due to PCR amplification or other recombinant DNA methods.

Analogue Formation

In some aspects, a peptide of the instant disclosure is a "modified peptide" comprising non-naturally occurring amino acids. In some aspects, the peptides comprise a combination of naturally occurring and non-naturally occurring amino acids, and in some embodiments, the peptides comprise only non-naturally occurring amino acids.

"Modified peptide" may include the incorporation of non-natural amino acids into the peptides of the disclosure, including synthetic non-native amino acids, substituted amino acids, or one or more D-amino acids into the peptides (or other components of the composition, with exception for protease recognition sequences) is desirable in certain situations. D-amino acid-containing peptides exhibit increased stability in vitro or in vivo compared to L-amino acid-containing forms. Thus, the construction of peptides incorporating D-amino acids can be particularly useful when greater in vivo or intracellular stability is desired or required. More specifically, D-peptides are resistant to endogenous peptidases and proteases, thereby providing better oral trans-epithelial and transdermal delivery of linked drugs and conjugates, improved bioavailability of membrane-permanent complexes (see below for further discussion), and prolonged intravascular and interstitial lifetimes when such properties are desirable. The use of D-isomer peptides can also enhance transdermal and oral trans-epithelial delivery of linked drugs and other cargo molecules. Additionally, D-peptides cannot be processed efficiently for major histocompatibility complex class Il-restricted presentation to T helper cells, and are therefore less likely to induce humoral immune responses in the whole organism. Peptide conjugates can therefore be constructed using, for example, D-isomer forms of cell penetrating peptide sequences, L-isomer forms of cleavage sites, and D-isomer forms of therapeutic peptides.

Therefore, in some embodiments the peptides as disclosed comprise L and D amino acids, wherein no more than 1, 2, 3, 4, 5, 6, 7, 8, 9, or 10 D-amino acids are included. In certain aspects, the peptides comprise more than 10 D-amino acids, and in certain aspects all the amino acids of the peptides are D-amino acids.

Also included are peptides which have been modified using ordinary molecular biological techniques so as to improve their resistance to proteolytic degradation or to optimize solubility properties or to render them more suitable as a therapeutic agent. Such variants include those containing residues other than naturally-occurring L-amino acids, e.g., D-amino acids or non-naturally-occurring synthetic amino acids. The peptides disclosed herein may include unnatural amino acids formed by post-translational modification or by introducing unnatural amino acids during translation. A variety of approaches are available for introducing unnatural amino acids during protein translation. By way of example, special tRNAs, such as tRNAs which have suppressor properties, suppressor tRNAs, have been used in the process of site-directed non-native amino acid replacement (SNAAR). In SNAAR, a unique codon is required on the mRNA and the suppressor tRNA, acting to target a non-native amino acid to a unique site during the protein synthesis (described in WO90/05785). However, the suppressor tRNA must not be recognizable by the aminoacyl tRNA synthetases present in the protein translation system. In certain cases, a non-native amino acid can be formed after the tRNA molecule is aminoacylated using chemical reactions which specifically modify the native amino acid and do not significantly alter the functional activity of the aminoacylated tRNA. These reactions are referred to as post-aminoacylation modifications. For example, the epsilon-amino group of the lysine linked to its cognate tRNA (tRNALYs), could be modified with an amine specific photoaffinity label.

Cyclization

In some embodiments, a peptide of the composition and methods disclosed herein is in a cyclic form. In some embodiments, the cyclic peptide comprises a linkage between amino acids. Cyclic derivatives of the peptides disclosed herein are also part of the present disclosure. Cyclization may allow the peptide to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al, J. Am. Chem. Soc. 1995, 117, 8466-8467. The components that form the bonds may be side chains of amino acids, non-amino acid components or a combination of the two. In an embodiment of the aspects of the disclosure, cyclic peptides may comprise a beta-turn in the right position. Beta-turns may be introduced into the peptides of the invention by adding the amino acids Pro-Gly at the right position.

It may be desirable to produce a cyclic peptide which is more flexible than the cyclic peptides containing peptide bond linkages as described above. A more flexible peptide may be prepared by introducing cysteines at the right and left position of the peptide and forming a disulphide bridge between the two cysteines. The two cysteines are arranged so as not to deform the beta-sheet and turn. The peptide is more flexible as a result of the length of the disulfide linkage and the smaller number of hydrogen bonds in the beta-sheet portion. The relative flexibility of a cyclic peptide can be determined by molecular dynamics simulations.

Pharmaceutical Salts:

The peptides of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

Retro-Inverso Peptide:

In yet a further aspect, the peptides or fragments or derivatives thereof can be "retro-inverso peptides." A "retro-inverso peptide" refers to a peptide with a reversal of the direction of the peptide bond on at least one position, i.e., a reversal of the amino- and carboxy-termini with respect to the side chain of the amino acid. Thus, a retro-inverso analogue has reversed termini and reversed direction of peptide bonds while approximately maintaining the topology of the side chains as in the native peptide sequence. The retro-inverso peptide can contain L-amino acids or D-amino acids, or a mixture of L-amino acids and D-amino acids, up to all of the amino acids being the D-isomer. Partial retro-inverso peptide analogues are polypeptides in which only part of the sequence is reversed and replaced with enantiomeric amino acid residues. Since the retro-inverted portion of such an analogue has reversed amino and carboxyl termini, the amino acid residues flanking the retro-inverted portion are replaced by side-chain-analogous a-substituted geminal-diaminomethanes and malonates, respectively. Retro-inverso forms of cell penetrating peptides have been found to work as efficiently in translocating across a membrane as the natural forms. Synthesis of retro-inverso peptide analogues are described in Bonelli, F. et al., Int J Pept Protein Res. 24(6):553-6 (1984); Verdini, A and Viscomi, G. C, J. Chem. Soc. Perkin Trans. 1:697-701 (1985); and U.S. Pat. No. 6,261,569, which are incorporated herein in their entirety by reference. Processes for the solid-phase synthesis of partial retro-inverso peptide analogues have been described (EP 97994-B) which is also incorporated herein in its entirety by reference.

Modification in the N- or C-Terminus of Peptide Chains:

By Conjugation with Polymers-PEGylation

In certain embodiments, the peptides of the disclosure comprise an N-terminal and/or C-terminal modifications. Such modification can that in certain instances improve activity. For example, in one embodiment, the peptide of the disclosure comprises a butyric acid at the N-terminus of the peptide. In one embodiment, the peptide is PEGylated at the C-terminus of the peptide. In one embodiment, the carboxy terminus of the peptide of the present disclosure is amidated. The present disclosure encompasses variants of the peptide analogs, including those with terminal modifications, without terminal modifications, or having different terminal modifications.

For example, in one embodiment, a peptide of the present disclosure can have, for example, a butyric acid at the N-terminus and is PEGylated and/or amidated at the C-terminus. However, the present disclosure also encompasses analogs and derivatives of peptides disclosed herein, including peptides having different terminal modifications or no terminal modifications. In some embodiments, a peptide or compositions disclosed herein can be PEGylated. PEGylation is considered as a gold standard for chemical modifications of peptides. It involves one or more polyethylene glycol (PEG) chains linked to a protein, peptide or non-peptide molecule. PEGylation is the term given to conjugation with monomethoxy poly (ethyleneglycol) or mPEG. PEG polymer, a polyether compound, or a polymer of ethylene oxide is highly soluble in water.

The peptides of the disclosure may further be conjugated to non-amino acid moieties that are useful in their therapeutic application. In particular, moieties that improve the stability, biological half-life, water solubility, and/or immunologic characteristics of the peptide are useful. A non-limiting example of such a moiety is polyethylene glycol (PEG).

For maximum benefits, a stable bond is formed between PEG and polypeptide. To prepare an active PEG derivative with a functional group—such as active ester, active carbonate, tresylate or aldehyde suitable for coupling to a given peptide. Preferred positions for PEGylation are the N-terminal amino group of the polypeptide backbone and the ε-amino group in the side chain of the amino acid residue lysine. Being highly labile, mild chemical reaction conditions are used by proteins and peptides for the conjugation at the hydrophobic sites.

Poly(Styrene-Co-Maleic Acid Anhydride) or SMA:

It is a synthetic polymer, made up of styrene and maleic anhydride polymer, with molecular weight of 1.5 kDa, which on conjugation with proteins and peptide increases systemic circulation time and elimination half life of the conjugated peptide to natural long-circulating blood plasma components such as serum albumin or lipoproteins.

Polysialation:

It involves the conjugation of peptides and proteins to the naturally occurring, biodegradable α-(2→8) linked polysialic acid3. Polysialic acid is highly hydrophilic in nature which increases the systemic circulation. It has the advantage of being biodegradable and its catabolic products are not toxic (e.g. NeuNAc). It markedly reduces proteolysis, prolongs the half life in systemic circulation (up to 40 h) and retains the activity of protein and peptide in-vivo. It also reduces immunogenicity and antigenicity. Polysialic acids are linear polymers of N-acetylneuraminic acid (sialic acid) abundantly present on the surface of cells and many proteins. Polysialylation has been tested and are used in therapeutics for the treatment of various diseases. It includes preservation of stability and function, optimal pharmacokinetics and pharmacodynamics, and Covalent attachment of biologically active compounds to water-soluble polymers is one method for alteration and control of biodistribution, pharmacokinetics, and often, toxicity for these compounds (Duncan et al, 1984, Adv. Polym. Sci. 57:53-101). Many water-soluble polymers have been used to achieve these effects, such as poly(sialic acid), dextran, poly(N-(2-hydroxypropyl)methacrylamide) (PHPMA), poly(N-vinylpyrrolidone) (PVP), poly(vinyl alcohol) (PVA), poly(ethylene glycol-co-propylene glycol), poly(N-acryloyl morpholine (PAcM), and poly(ethylene glycol) (PEG) (Powell, 1980, Polyethylene glycol. In R. L. Davidson (Ed.) Handbook of Water Soluble Gums and Resins. McGraw-Hill, New York, chapter 18). PEG possess an ideal set of properties: very low toxicity (Pang, 1993, J. Am. Coll. Toxicol. 12: 429-456) excellent solubility in aqueous solution (Powell, supra), low immunogenicity and antigenicity (Dreborg et al, 1990, Crit. Rev. Ther. Drug Carrier Syst. 6: 315-365). PEG-conjugated or "PEGylated" protein therapeutics, containing single or multiple chains of polyethylene glycol on the protein, have been described in the scientific literature (Clark et al., 1996, J. Biol. Chem. 271: 21969-21977; Hershfield, 1997, Biochemistry and immunology of poly(ethylene glycol)-modified adenosine deaminase (PEG-ADA). In J. M. Harris and S. Zalipsky (Eds) Poly(ethylene glycol): Chemistry and Biological Applications. American Chemical Society, Washington, D.C., p 145-154; Olson et al, 1997, Preparation and characterization of poly(ethylene glycosylated human growth hormone antagonist. In J. M. Harris and S. Zalipsky (Eds) Poly(ethylene glycol): Chemistry and Biological Applications. American Chemical Society, Washington, D.C., p 170-181).

Post Translation Modification

In some aspects of all the embodiments of the disclosure, the peptides or modified peptides further comprise co-translational and post-translational (C-terminal peptide cleavage) modifications, such as, for example, disulfide-bond formation, glycosylation, acetylation, phosphorylation, proteolytic cleavage (e.g., cleavage by furins or metalloproteases), and the like. The main post-translational modifications associated with peptides are: Acetylation, acylation, ADP-ribosylation, Amidation, γ-Carboxylation and β-hydroxylation, Disulfide bond formation, Glycosylation, Phosphorylation, Proteolytic processing, Sulfation, Methylation, Acyl Lipidation. A peptide modification includes phosphorylation (e.g., on a Tyr, Ser or Thr residue), N-terminal acetylation, C-terminal amidation, C-terminal hydrazide, C-terminal methyl ester, fatty acid attachment, sulfonation (tyrosine), N-terminal dansylation, N-terminal succinylation, tripalmitoyl-S-Glyceryl Cysteine (PAMb 3 Cys-OH) as well as farnesylation of a Cys residue. Systematic chemical modification of a peptide can, for example, be performed in the process of peptide optimalization. For example, post-translational modifications that fall within the scope of the present disclosure include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or *Xenopus* egg extracts (U.S. Pat. No. 6,103,489) to a standard translation reaction. Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Site Specific Modifications

The peptides of the disclosure can be conjugated with other molecules, such as peptide tags or proteins, to prepare fusion proteins. This may be accomplished, for example, by the synthesis of N-terminal or C-terminal fusion proteins provided that the resulting fusion protein retains the functionality of the peptide of the invention. The term "fusion protein" as used herein refers to a recombinant protein of two or more proteins. Fusion proteins can be produced, for example, by a nucleic acid sequence encoding one protein is joined to the nucleic acid encoding another protein such that they constitute a single open-reading frame that can be translated in the cells into a single polypeptide harboring all the intended proteins. The order of arrangement of the proteins can vary. Fusion proteins can include an epitope tag or a half-life extender. Epitope tags include biotin, FLAG tag, c-myc, hemaglutinin, His6, digoxigenin, FITC, Cy3, Cy5, green fluorescent protein, V5 epitope tags, GST, β-galactosidase, AU1, AU5, and avidin. Half-life extenders include Fc domain and serum albumin. Accordingly, in some embodiments, the peptides disclosed herein can be conjugated to a peptide tag. Other modifications can be made, for example, Fusion of a peptide to a solubilising protein fusion partner such a maltose-binding protein (MBP), glutathione S-transferase (GST), green fluorescent protein (GFP). In some embodiments, a peptide of the present disclosure further comprises a peptide tag. Addition of short solubility enhancement peptide tags containing 5-10 positively charged amino acids to N- or C-terminus of proteins and peptides. Such peptide tags are small relative to large proteins but are in significant fraction for smaller proteins. Tolbert et al used a betaine moiety, a small molecule, containing a positively charged quaternary ammonium group (MW-100) is introduced as a small solubility enhancement tag onto the N-terminus of polypeptides by chemical ligation or expressed protein ligation. The modified forms of polypeptides are more water soluble. Modification with small ubiquitin related modifier (SUMO) has the ability to enhance protein expression and solubility.

In some embodiments, a peptide of the present disclosure can be conjugated to a detectable agent. The term "detectable agent" as used herein that is conjugated directly or indirectly to a probe (e.g., peptide) to generate a "labeled" probe. The label may be detectable by itself (e.g. radioisotope labels, fluorescent agent or chemiluminescent agent) or, in the case of an enzymatic label, may catalyze chemical alteration of a substrate compound or composition that is detectable (e.g., avidin-biotin). In some instances, primers can be labeled to detect a PCR product.

In some embodiments, the peptides of the compositions and methods disclosed herein is modified by linkage to a carrier peptide. The term "conjugated" are used to refer to any method known in the art for functionally connecting moieties (such as detectable agent, carrier peptide), including, without limitation, recombinant fusion, covalent bonding, disulfide bonding, ionic bonding, hydrogen bonding, and electrostatic bonding. The term "carrier peptide" as used herein indicates peptides that transport a specific substance or group of substances (e.g., peptides of the present disclosure) through intracellular compartments or in extracellular fluids (e.g. in the blood) or else across the cell membrane. Exemplary carrier proteins comprise subunit B of cholera toxin, Avidin, BTG protein, Bovine G globulin, Bovine Immunoglobulin G, Bovine Thyroglobulin, Bovine Serum Albumin (BSA), Conalbumin, Edestein, Exoprotein A from *Pseudomonas aeruginosa*, HC (Hemocyanin from crab Paralithodes camtschatica), Helix Promatia Haemocyanin (HPH), Human Serum Albumin (HSA), KTI (Kunits trypsin inhibitor from soybeans), Keyhole Limpet Heamocyanin (KLH), LPH (Haemocyanin from Limulus *polyphemus*) Ovalbumin, Pam3Cys-Th, Polylysine, porcine Thyroglobulin (PTG), Purified Protein Derivative (PPD), Rabbit Serum Albumin (RSA), Soybeab Trypsin Inhibitor (STI) (Sunflower Globulin (SFG) and additional molecules identifiable by a skilled person. Additional carriers comprise molecule having immunogenic activities including cytokines such as IL-10, IL12, IL-4 IL-16 and Transforming Growth Factor Beta (TGFP).

Accordingly, in some embodiments a peptide of the compositions and methods disclosed herein is fused to a carrier peptide. In some embodiments, attachment of the carrier is performed at the C-terminus or N-terminus of the fragment. In an embodiment the fusion protein (i.e., peptides of the present disclosure and a carrier peptide) can be provided as a single polypeptide through recombinant DNA technology and related processes, such as cloning, chimeric constructs, Polymerase Chain Reaction and additional procedures identifiable by a skilled person. In some embodiments, attachment can be performed through chemical linkage of the fragment to the carrier using methods also identifiable by a skilled person.

Non-limiting examples of such transportable peptides, or vectors, suitable for coupling to the pharmaceutical agent include transferrin, insulin-like growth factors I and II, basic albumin and prolactin. The conjugation can be carried out using bifunctional reagents which are capable of reacting with each of the polypeptides and forming a bridge between the two. The preferred method of conjugation involves polypeptide thiolation, wherein the two polypeptides are treated with a reagent such as N-succinimidyl 3-(2-pyridyldithio)propionate (SPDP) to form a disulfide bridge between the two polypeptides. Other known conjugation agents can be used, so long as they provide linkage of the two polypeptides (i.e. therapeutic polypeptide drug and the transportable peptide) together without denaturing them. Preferably, the linkage can be easily broken once the chimeric polypeptide has entered the region of interest. In some embodiments, the peptides of the present disclosure can be linked to short cell penetrating peptides, which have the ability to cross cell membrane bilayers. Non limiting examples of such peptides include TAT (HIV-1 transactivating transcriptor) SynB3, Tat, transportan.

Variants of suitable peptides of the invention can also be expressed. Variants may be made by, for example, the deletion, addition, or alteration of amino acids that have either (i) minimal influence on certain properties, secondary structure, and hydropathic nature of the polypeptide or (ii) substantial effect on one or more properties of the peptide mimetics of the invention. Variants may also include, for example, a peptide conjugated to a linker or other sequence for ease of synthesis, purification, identification, or therapeutic use (i.e., delivery) of the peptide. The variants of the peptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the peptide is an alternative splice variant of the peptide of the present invention, (iv) fragments of the peptides and/or (v) one in which the peptide is fused with another peptide, such as a leader or secretory sequence or a sequence which is employed for purification (for example, His-tag) or for detection (for example, Sv5 epitope tag). The fragments include peptides generated via proteolytic cleavage (including multi-site proteolysis) of an original sequence. Variants may be post-translationally, or chemically modified. Such variants are deemed to be within the scope of those skilled in the art from the teaching herein.

Conjugation with Fatty Acids (Lipidization)

Delivery to and uptake of peptides is favored by low molecular weight, lack of ionization at physiological pH and lipophilicity. Therefore one possible strategy to improve targeting of the compositions of the present disclosure is to modify the peptides to increase its lipophilicity. Accordingly, in some embodiments, the peptides disclosed herein can comprise a lipophilic molecular group. As used herein the term "lipophilic molecular group" refers to a lipid moiety, such as a fatty acid, glyceride or phospholipid which when coupled to a therapeutic molecule, increases its lipophilicity. The lipophilic molecular group can be attached to the therapeutic molecule through an ester bond. Examples of such modifications include, among others, esterification, or amidation of the hydroxy-, amino-, or carboxylic acid-groups of the polypeptide. Lipophilic molecular groups can comprise lipid moieties such as fatty acid, glyceride or phospholipids.

Lipidization can involve acylation of the ε-amino group of lysine residues or acylation of N-terminal α-amino groups. The presence of a lipid group in peptides changes their secondary structures, hydrophobicity and self-assembling propensities but retains its ability to bind to target receptors.

Reversible Aqueous lipidization technology (REAL) This is a new method for developing fatty acids-peptide conjugates which is carried out in aqueous solution and can regenerate the original active peptides in tissues or the blood and thus called REAL Technology. Lipidization can be carried out at cysteine residues following cleavage of intra-disulfide bonds with a reducing agent. This type of lipidization is typically reversible. Methods of REAL are described in, for example, Shen et al. In some embodiments, a modification combining site specific modification and lipidization technique is carried out, e.g., Chang et. al. L Pharm Sci 2002.

Hydrophobic Ion Pairing

In some embodiments, modification of a peptide disclosed herein is a modification by adding an opposite charged surfactant that binds to peptide to obtain neutral hydrophobicity entity. Solubility of ionic compounds is high due to ease of solvation of the counter ions with ionic detergents. Positively charged peptides and negatively charged surfactants should be employed, since cationic surfactants might have toxic side effects. Replacement of counter ions decreases the aqueous solubility and increases the lipophilicity. Thus, it changes the partition coefficient by orders of magnitude. HIP method is inexpensive and reversible. The process involves replacement of counter ions (e.g. chloride, acetate, nitrate) with an ionic detergent of similar charge. For many proteins, dissolution in organic solvents occurs with retention of native-like structure and maintenance of enzymatic activity without any chemical modification. Thus, ion-pairing is a useful method for increasing the bioavailability of drugs and enhancing permeation of certain drugs. Dai et al., (Int. J. Pharm. 2007; 336: 58-66), Sun et al. (Int. J. Nanomed, 2011) prepared insulin hydrophobic ion paired complex using different anionic surfactants like sodium lauryl sulphate, surfoplex, sodium deoxycholate and sodium oleate respectively in 1:6 ratio.

In some embodiments, peptides disclosed herein can be modified by attaching one or more amphiphilic oligomers, for example, Nobex Technology. Creation of amphiphilic oligomers is accomplished by binding a lipophilic alkyl unit to a hydrophilic polyethylene glycol (PEG) unit. The resulting oligomer is then covalently bound to a specific site or sites on the target molecule to facilitate the desired changes in properties of the peptide. The two types of bonds are involved in this technology are hydrolyzable bond at the site of attachment, and non-hydrolyzable bond to create a 'micro-pegylated' peptide. Methods for this modification are described in, for example, Still J G. et al. Diabetes Metab. Res. Rev. 2002. In some embodiments, the peptide disclosed herein can be modified by contacting with small hydrophobic organic compounds non-covalently. In Emisphere's Eligen™ technology. See Singh B et al. Oral Delivery of Therapeutic Macromolecules: A Perspective Using the Eligen™ Technology; 2014.

Methods of Preparation of Pharmaceutical Compositions and Formulations

Disclosed herein are compositions comprising peptides or portion thereof capable of biding CD40 and methods of their use. In some embodiments, the compositions disclosed herein are formulated for administration via intracerebroventricular, intravenous, intradermal, intraperitoneal, oral, intramuscular, subcutaneous, intranasal, intracranial, intracelial, intracerebellar, intrathecal, transdermal, pulmonary, or topical administration route.

The compositions provided herein can be prepared in a variety of ways depending on the intended use of the compositions. For example, a composition useful in practicing the technology herein may be a liquid comprising a peptide disclosed herein in solution, in suspension, or both (solution/suspension). The term "solution/suspension" refers to a liquid composition where a first portion of the active agent is present in solution and a second portion of the active agent is present in particulate form, in suspension in a liquid matrix. A liquid composition also includes a gel. The liquid composition may be aqueous or in the form of an ointment, salve, cream, or the like. An aqueous suspension or solution/suspension useful for practicing the methods disclosed herein may contain one or more polymers as suspending agents. Useful polymers include water-soluble polymers such as cellulosic polymers and water-insoluble polymers such as cross-linked carboxyl-containing polymers. An aqueous suspension or solution/suspension of the present disclosure can be viscous or muco-adhesive, or both viscous and muco-adhesive.

In some embodiments, the pharmaceutical compositions herein comprise a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the stability, solubility, or activity of, active agents in the compositions. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) excipients, such as cocoa butter and suppository waxes; (8) oils, such as peanut oil, cottonseed oil, safflower oil, sesame oil, olive oil, corn oil and soybean oil; (9) glycols, such as propylene glycol; (10) polyols, such as glycerin, sorbitol, mannitol and polyethylene glycol (PEG); (11) esters, such as ethyl oleate and ethyl laurate; (12) agar; (13) buffering agents, such as magnesium hydroxide and aluminum hydroxide; (14) alginic acid; (15) pyrogen-free water; (16) isotonic saline; (17) Ringer's solution; (19) pH buffered solutions; (20) polyesters, polycarbonates and/or polyanhydrides; (21) bulking agents, such as polypeptides and amino acids (22) serum components, such as serum albumin, HDL and LDL; (23) C2-C12 alcohols, such as ethanol; and (24) other non-toxic compatible substances employed in pharmaceutical formulations. Release agents, coating agents, preservatives, and antioxidants can also be present in the formulation. The terms such as "excipient", "carrier", "pharmaceutically acceptable carrier" or the like are used interchangeably herein. Examples of suitable pharmaceutical carriers are described in "Remington's Pharmaceutical Sciences" by E. W. Martin, and still others are familiar to skilled artisans.

The compositions of the present disclosure can take the form of solutions, suspensions, emulsion, tablets, pills, capsules, powders, sustained-release formulations and the like, including those adapted for the following: (1) parenteral administration, for example, by subcutaneous, intramuscular, intravenous or epidural injection as, for example, a sterile solution or suspension, or sustained-release formulation; (2) topical application, for example, as a cream, ointment, or a controlled-release patch or spray applied to the skin; (3) intravaginally or intrarectally, for example, as a pessary, cream or foam; (4) ocularly; (5) transdermally; (6) transmucosally; or (7) nasally. The pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The compositions disclosed herein can comprise a preservative. A "preservative" is a compound which can be added to the diluent to essentially reduce bacterial action in the reconstituted formulation, thus facilitating the production of a multi-use reconstituted formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. The most preferred preservative herein is benzyl alcohol. One important purpose of the present formulation is to stabilize these peptide or analogue against spontaneous dimerization. This is preferably accomplished by formulating the peptides at low pH that will prevent disulfide bond formation between two Cys residues. Such acid buffers are preferably biocompatible. Examples include citrate, acetate, 2-(N-morpholino)ethanesulfonic acid (MES), or any similar buffer with a pK of about 5, wherein in the presence of the buffer, the pH of the solution is <7.5 but preferably not below 3.0. A preferred acidic formulation comprises citrate, preferably at about 25 mM. The buffer is preferably supplemented with glycine (Gly) as an excipient and bulking agent. A preferred concentration is about 50 mg/ml Gly. Another advantage of Gly is that it is an accepted excipient for intravenous infusion or injection in humans. Other amino acids or compounds can be used in place of Gly. Examples of desirable acids or combinations are citrate+acetate, acetate and Tris, and the like.

A pharmaceutical composition of the disclosure is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

If the compositions of the disclosure are to be administered topically, the compositions can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well known in the art.

If the compositions disclosed herein are to be formulated for intranasal administration of a composition, the composition can be formulated in an aerosol form, spray, mist or in the form of drops. In particular, prophylactic or therapeutic agents for use according to the present invention can be conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the compositions disclosed herein are to be formulated for oral administration, compositions can be formulated orally in the form of tablets, capsules, cachets, gel caps, solutions, suspensions, and the like. Tablets or capsules can be prepared by conventional means with pharmaceutically acceptable excipients such as binding agents (e.g., pregelatinized maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method of the disclosure may comprise pulmonary administration, e.g., by use of an inhaler or nebulizer, of a composition formulated with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entireties. In a specific embodiment, an antibody of the invention, combination therapy, and/or composition of the invention is administered using Alkermes AIR pulmonary drug delivery technology (Alkermes, Inc., Cambridge, Mass.).

The method of the disclosure may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use.

The methods of the disclosure may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the disclosure encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the disclosure also provides that one or more of the peptides or pharmaceutical compositions of the disclosure is packaged in a hermetically sealed container such as an ampoule or sachette indicating the quantity of the agent. In one embodiment, one or more of the peptides, or pharmaceutical compositions of the disclosure is supplied as a dry sterilized lyophilized powder or water free concentrate in a hermetically sealed container and can be reconstituted (e.g., with water or saline) to the appropriate concentration for administration to a subject. Preferably, one or more of the peptides or pharmaceutical compositions of the disclosure is supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, at least 75 mg, or at least 100 mg. The lyophilized peptides or pharmaceutical compositions of the invention should be stored at between 2° C. and 8° C. in its original container and the peptides, or pharmaceutical compositions of the disclosure should be administered within 1 week, preferably within 5 days, within 72 hours, within 48 hours, within 24 hours, within 12 hours, within 6 hours, within 5 hours, within 3 hours, or within 1 hour after being reconstituted. In an alternative embodiment, one or more of the peptides or pharmaceutical compositions of the disclosure is supplied in liquid form in a hermetically sealed container indicating the quantity and concentration of the agent. Preferably, the liquid form of the administered composition is supplied in a hermetically sealed container at least 0.25 mg/ml, more preferably at least 0.5 mg/ml, at least 1 mg/ml, at least 2.5 mg/ml, at least 5 mg/ml, at least 8 mg/ml, at least 10 mg/ml, at least 15 mg/ml, at least 25 mg/ml, at least 50 mg/ml, at least 75 mg/ml or at least 100 mg/ml. The liquid form should be stored at between 2° C. and 8° C. in its original container.

The pharmaceutical compositions can be administered in various ways, depending on the preference for local or systemic treatment, and on the area to be treated. Administration may be done topically (including opthalmically, vaginally, rectally, intranasally), orally, by inhalation, or parenterally, for example by intravenous drip or intraperitoneal, subcutaneous, subdural, intramuscular or intravenous injection, or via an implantable delivery device. Formulations for topical administration may include, but are not limited to, lotions, ointments, gels, creams, suppositories, drops, liquids, sprays and powders Conventional pharmaceutical carriers, aqueous, powder or oily bases, thickeners and the like may be necessary or desirable. Compositions for oral administration include powders or granules, suspensions or solutions in water or nonaqueous media, sachets, capsules or tablets. Thickeners, diluents, flavorings, dispersing aids, emulsifiers or binders may be desirable. Formulations for parenteral administration may include, but are not limited to, sterile solutions, which may also contain buffers, diluents and other suitable additives. Formulations for implantable delivery devices may similarly include, but are not limited to, sterile solutions, which may also contain buffers, diluents and other suitable additives.

In some embodiments, a composition as described above is in a pharmaceutically acceptable medium suitable for administration to a recipient subject. Pharmaceutically acceptable mediums suitable for administration to a subject are known in the art. In some embodiments, compositions disclosed herein can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection (e.g., intravenous injection). Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene, glycol, liquid polyethylene glycol, and the like) and suitable mixtures thereof.

Sterile injectable solutions can be prepared by incorporating the compositions disclosed herein in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "Remington's Pharmaceutical Science", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, may be added. Prevention of the action of microorganisms can be ensured by various antibacterial and antifungal agents, for example, parabens, chlorobutanol, phenol, sorbic acid, and the like. The compositions can be isotonic, i.e., they can have the same osmotic pressure as blood and lacrimal fluid. The desired isotonicity of the compositions herein may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Parenteral dosage forms of the compositions can also be administered to a subject by various routes, including, but not limited to subcutaneous, intravenous (including bolus injection), intramuscular, and intraarterial. Since administration of parenteral dosage forms typically bypasses the subject's natural defenses against contaminants, parenteral dosage forms are preferably sterile or capable of being sterilized prior to administration to a subject. Examples of parenteral dosage forms include, but are not limited to solutions ready for injection, dry products ready to be dissolved or suspended in a pharmaceutically acceptable vehicle for injection, suspensions ready for injection, controlled-release parenteral dosage forms, and emulsions. Suitable vehicles that can be used to provide parenteral dosage forms of the disclosure are well known to those skilled in the art. Examples include, without limitation: sterile water; water for injection USP; saline solution; glucose solution; aqueous vehicles such as but not limited to sodium chloride injection, Ringer's injection, dextrose Injection, dextrose and sodium chloride injection, and lactated Ringer's injection; water-miscible vehicles such as, but not limited to ethyl alcohol, polyethylene glycol, and propylene glycol; and non-aqueous vehicles such as, but not limited to corn oil, cottonseed oil, peanut oil, sesame oil, ethyl oleate, isopropyl myristate, and benzyl benzoate.

Compositions provided herein can be packaged in a pressurized aerosol container together with suitable propellants, for example, hydrocarbon propellants like propane, butane, or isobutane with conventional adjuvants. Compositions can also be administered in a non-pressurized form such as in a nebulizer or atomizer. Compositions can also be administered directly to the airways in the form of a dry powder, for example, by use of an inhaler. Suitable powder compositions include, by way of illustration, powdered preparations of a composition comprising a peptide disclosed herein thoroughly intermixed with lactose, or other inert powders acceptable for intrabronchial administration. The powder compositions can be administered via an aerosol dispenser or encased in a breakable capsule which can be inserted by the subject into a device that punctures the capsule and blows the powder out in a steady stream suitable for inhalation. The compositions can include propellants, surfactants, and co-solvents and can be filled into conventional aerosol containers that are closed by a suitable metering valve.

Aerosols for the delivery to the respiratory tract are known in the art. See for example, Adjei, A. and Garren, J. Pharm. Res., 1: 565-569 (1990); Zanen, P. and Lamm, J.-W. J. Int. J. Pharm., 114: 111-115 (1995); Gonda, I. "Aerosols for delivery of therapeutic and diagnostic agents to the respiratory tract," in Critical Reviews in Therapeutic Drug Carrier Systems, 6:273-313 (1990); Anderson et al, Am. Rev. Respir. Dis., 140: 1317-1324 (1989)) and have potential for the systemic delivery of peptides and proteins as well (Patton and Platz, Advanced Drug Delivery Reviews, 8: 179-196 (1992)); Timsina et. al, Int. J. Pharm., 101: 1-13 (1995); and Tansey, I. P., Spray Technol. Market, 4:26-29 (1994); French, D. L., Edwards, D. A. and Niven, R. W., Aerosol Sci., 27: 769-783 (1996); Visser, J., Powder Technology 58: 1-10 (1989)); Rudt, S, and R. H. Muller, J. Controlled Release, 22: 263-272 (1992); Tabata, Y, and Y. Ikada, Biomed. Mater. Res., 22: 837-858 (1988); Wall, D. A., Drug Delivery, 2: 10 1-20 1995); Patton, J. and Platz, R, Adv. Drug Del. Rev., 8: 179-196 (1992); Bryon, P., Adv. Drug. Del. Rev., 5: 107-132 (1990); Patton, J. S., et al, Controlled Release, 28: 15 79-85 (1994); Damms, B. and Bains, W., Nature Biotechnology (1996); Niven, R. W., et al., Pharm. Res., 12(9); 1343-1349 (1995); and Kobayashi S., et al., Pharm. Res., 13(1): 80-83 (1996), contents of all of which are herein incorporated by reference in their entirety.

The formulations of the compositions disclosed herein further encompass anhydrous pharmaceutical compositions and dosage forms comprising the disclosed compounds as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, NY, N.Y.: 1995). Anhydrous pharmaceutical compositions and dosage forms of the disclosure can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected. Anhydrous compositions are preferably packaged using materials known to prevent exposure to water such that they can be included in suitable formulary kits. Examples of suitable packaging include, but are not limited to hermetically sealed foils, plastics, unit dose containers (e.g., vials) with or without desiccants, blister packs, and strip packs.

In some embodiments of the aspects described herein, the compositions can be administered to a subject by controlled- or delayed-release means. Ideally, the use of an optimally designed controlled-release preparation in medical treatment is characterized by a minimum of drug substance being employed to cure or control the condition in a minimum amount of time. Advantages of controlled-release formulations include: 1) extended activity of the active agent; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Chemg-ju, Controlled Release Dosage Form Design, 2 (Technomic Publishing, Lancaster, Pa.: 2000)). Controlled-release formulations can be used to control a compound of formula (I)'s onset of action, duration of action, plasma levels within the therapeutic window, and peak blood levels. In particular, controlled- or extended-release dosage forms or formulations can be used to ensure that the maximum effectiveness of a compound of formula (I) is achieved while minimizing potential adverse effects and safety concerns, which can occur both from under-dosing a drug (i.e., going below the minimum therapeutic levels) as well as exceeding the toxicity level for the drug.

A variety of known controlled- or extended-release dosage forms, formulations, and devices can be adapted for use with the compositions described herein. Examples include, but are not limited to those described in U.S. Pat. Nos. 3,845,770; 3,916,899; 3,536,809; 3,598, 123; 4,008,719; 5674,533; 5,059,595; 5,591,767; 5, 120,548; 5,073,543; 5,639,476; 5,354,556; 5,733,566; and 6,365,185 B1, each of which is incorporated herein by reference in their entireties. These dosage forms can be used to provide slow or controlled-release of one or more active ingredients using, for example, hydroxypropylmethyl cellulose, other polymer matrices, gels, permeable membranes, osmotic systems (such as OROS). (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to Duolite. A568 and Duolite. AP143 (Rohm&Haas, Spring House, Pa. USA). In some embodiments, compositions described herein can be administered to a subject by sustained release or in pulses. Pulse therapy is not a form of discontinuous administration of the same amount of a composition over time, but comprises administration of the same dose of the composition at a reduced frequency or administration of reduced doses. Sustained release or pulse administrations are particularly preferred when the disorder occurs continuously in the subject, for example where the subject has continuous or chronic symptoms of an inflammatory disease. Each pulse dose can be reduced and the total amount of a peptide disclosed herein can be administered over the course of treatment to the subject is minimized.

The interval between pulses, when necessary, can be determined by one of ordinary skill in the art. Often, the interval between pulses can be calculated by administering another dose of the composition when the composition or the active component of the composition is no longer detectable in the subject prior to delivery of the next pulse. Intervals can also be calculated from the in vivo half-life of the composition. Intervals can be calculated as greater than the in vivo half-life, or 2, 3, 4, 5 and even 10 times greater the composition half-life. Various methods and apparatus for pulsing compositions by infusion or other forms of delivery to the patient are disclosed in U.S. Pat. Nos. 4,747,825; 4,723,958; 4,948,592; 4,965,251 and 5,403,590.

Formulations suitable for parenteral administration, such as, for example, by intraarticular (in the joints), intravenous, intramuscular, intradermal, intraperitoneal, and subcutaneous routes, and carriers include aqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, preservatives, liposomes, microspheres and emulsions. The compositions described herein include, but are not limited to therapeutic compositions useful for practicing the therapeutic methods described herein. Therapeutic compositions contain a physiologically tolerable carrier together with an active agent as described herein, dissolved or dispersed therein as an active ingredient. In one embodiment, the therapeutic composition is not immunogenic (e.g., allergenic) when administered to a mammal or human patient for therapeutic purposes. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The compositions described herein can include pharmaceutically acceptable salts of the components therein.

Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of a particular disorder or condition will depend on the nature of the disorder or condition, and can be determined by standard clinical techniques.

While any suitable carrier known to those of ordinary skill in the art can be employed in the pharmaceutical compositions provided herein, the type of carrier will vary depending on the mode of administration. Compositions can be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) can also be employed as carriers for the pharmaceutical compositions of this invention. Suitable biodegradable microspheres are disclosed, for example, in U.S. Pat. Nos. 4,897,268 and 5,075,109. Such compositions can also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions as described herein can be formulated as a lyophilizate. Compounds can also be encapsulated within liposomes using well known technology. The compositions described herein can be administered as part of a sustained release formulation (i.e., a formulation such as a capsule or sponge that effects a slow release of compound following administration). Such formulations can generally be prepared using well known technology and administered by, for example, oral, rectal or subcutaneous implantation, or by implantation at the desired target site. Sustained-release formulations can contain a polypeptide, polynucleotide dispersed in a carrier matrix and/or contained within a reservoir surrounded by a rate controlling membrane. Carriers for use within such formulations are biocompatible, and can also be biodegradable; preferably the formulation provides a relatively constant level of active component release. The amount of active compound contained within a sustained release formulation depends upon the site of implantation, the rate and expected duration of release and the nature of the condition to be treated or prevented.

In some embodiments, the pharmaceutical composition is contained in an implantable pump. The pump can be designed to deliver to the intended site of action, at the required rate of administration, and in the proper therapeutic dose. One example of such pump includes but is not limited to the commercially available, the Alzet osmotic mini pump to delivering drugs at a controlled rate and dose over extended periods.

In some embodiments, the peptides of the compositions disclosed herein can be contained in a continuous flow pump. The delivery mechanism of one such pump is based on the expansion of Freon gas at 37° C. that pushes a diaphragm "plunger/pusher" plate. Usually, the pump reservoir is implanted subcutaneously and is connected to a catheter to deliver the therapeutic molecules. In some embodiments, the peptides can be contained in a programmable pump. Programmable pumps include electromechanical pumps of the peristaltic type, powered by batteries. Their built-in electronics can be remotely controlled from an external programming unit. An example is the SynchroMed system (Medtronic Inc.). The infusion can be programmed in various modes: continuous hourly infusions, repeated bolus infusions with a specified delay, multiple doses over a programmed interval, or a single bolus infusion. In some embodiments, the pharmaceutical composition comprising peptides disclosed herein is contained in a syringe, including a blunt tip syringe for injection to the target site. Microspheres can be implanted stereotactically in the target site.

In certain embodiments, the compositions disclosed herein can be formulated in liposomes, for example to improve stability and promote delivery. As used herein, the term "liposome" refers to a vesicular structure having lipid-containing membranes enclosing an aqueous interior. In cell biology, a vesicular structure is a hollow, lamellar, spherical structure, and provides a small and enclosed compartment, separated from the cytosol by at least one lipid bilayer. Liposomes can have one or more lipid membranes. Oligolamellar large vesicles and multilamellar vesicles have multiple, usually concentric, membrane layers and are typically larger than 100 nm. Liposomes with several nonconcentric membranes, i.e., several smaller vesicles contained within a larger vesicle, are termed multivesicular vesicles. Liposomes can further comprise one or more additional lipids and/or other components such as sterols, e.g., cholesterol. Additional lipids can be included in the liposome compositions for a variety of purposes, such as to prevent lipid oxidation, to stabilize the bilayer, to reduce aggregation during formation or to attach ligands onto the liposome surface. Any of a number of additional lipids and/or other components can be present, including amphipathic, neutral, cationic, anionic lipids, and programmable fusion lipids. Such lipids and/or components can be used alone or in combination. One or more components of the liposome can comprise a ligand, e.g., a targeting ligand.

Liposome compositions can be prepared by a variety of methods that are known in the art. See e.g., U.S. Pat. No. 6,339,069B1. Niosomes are non-phospholipid based synthetic vesicles that have properties and function like liposomes. Liposomes are vesicular structures with an aqueous core surrounded by a hydrophobic lipid membrane created by extrusion of phospholipids and known in the art to be used for drug delivery purposes. In some embodiments of the compositions and methods described herein, the peptide is encapsulated in a liposome. Liposomes can vary in size from 15 nm to 100μπι and are contemplated to have either a single layer (uni-lamellar), or multiple phospholipid bilayer membranes (mutilamellar structure). In one aspect, the peptide can be encapsulated in a niosome, a non-phospholipid-based synthetic vesicle In some embodiments, the compositions disclosed herein are formulated using micelles formed from lipid-associated peptides disclosed herein, e.g., peptides of the present disclosure conjugated to at least one amphiphilic carrier, in which the micelles have an average diameter of less than about 100 nm, preferably. More preferred embodiments provide micelles having an average diameter less than about 50 nm, and even more preferred embodiments provide micelles having an average diameter less than about 100 nm, or even less than about 20 nm. As used herein, "micelles" are a particular type of molecular assembly in which amphipathic molecules are arranged in a spherical structure such that all hydrophobic portions on the molecules are directed inward, leaving the hydrophilic portions in contact with the surrounding aqueous phase. The converse arrangement exists if the environment is hydrophobic.

In one aspect, the peptides of the present disclosure are encapsulated in a micelle. Micelles are spherical aggregates of amphiphilic molecules dispersing in water with their hydrophilic head groups on the surface of the sphere, and their hydrophobic tails collected inside. An important property of micelles is their ability to increase the solubility and bioavailability of poorly soluble pharmaceuticals. The amphiphilic molecules in micelles are in constant exchange with those in the bulk solution. On the other hand, polymeric micelles, also known as polymersomes, are self-assembled polymer shells composed of block copolymer amphiphiles such as polyethylene glycol-polylactic acid (PEG-PLA) and PEG-polycaprolactone (PEG-PCL). Polymeric micelles differ from nanoparticles that are either more solid or monolithic (nanospheres) or contain an oily or aqueous core and are surrounded by a polymer shell (nanocapsules). However, in practice, polymeric micelles also be referred to as nanoparticle or nanocarriers because of their particle size.

Accordingly, in some embodiments the peptides of the compositions disclosed herein is encapsulated in a nanoparticle. In some embodiment, the peptide disclosed herein can be encapsulated in a microcapsule or a microsphere, which are free flowing powders consisting of spherical particles of 2 millimeters or less in diameter, usually 500 microns or less in diameter. As used herein, the term "nanoparticle" refers to a particle having a size between 1 and 1000 nm which can be manufactured from artificial or natural macromolecular substances. To such nanoparticles can be bound drugs or other biologically active materials by covalent, ionic or adsorptive linkage, or the latter can be incorporated into the material of the nanoparticles. Nanoparticles may or may not exhibit size-related properties that differ significantly from those observed in fine particles or bulk materials. Nanoparticles provide improved bioavailability by enhancing aqueous solubility, increasing resistance time in the body (increasing half-life for clearance/increasing specificity for its cognate receptors and targeting drug to specific location in the body (its site of action). This results in concomitant reduction in quantity of the drug required and dosage toxicity, enabling the safe delivery of toxic therapeutic drugs and protection of non-target tissues and cells from severe side effects. Non-limiting examples of nanoparticles include solid lipid nanoparticles (comprise lipids that are in solid phase at room temperature and surfactants for emulsification, the mean diameters of which range from 50 nm to 1000 nm for colloid drug delivery applications), liposomes, nanoemulsions (oil-in-water emulsions done on a nanoscale), albumin nanoparticles, and polymeric nanoparticles. Nanoparticles can be surface coated to modulate their stability, solubility, and targeting. A coating that is multivalent or polymeric confers high stability. A non-limiting example includes coating with hydrophilic polymer such as polyethylene glycol or ploysorbate-80.

Methods of making nanoparticles encompassing therapeutic molecules are known in the art. See for example, U.S. Pat. No. 6,207,195B1, US20080311214A1, US20080311214A1, Tan et al, 2010. Nanoparticles are solid matrix colloidal particles with diameters ranging from 1-100 nm formed using various polymers like degradable starch, dextran, chitosan, microcrystalline cellulose (MCC), hydroxypropyl cellulose (HPC), hydroxypropyl ethylcellulose (HPMC), carbomer, and wax-like starch, gelatin polymers. In these carrier systems, the drug can be loaded via either incorporation with the system or its adsorption on the particulate system. The encapsulating nanoparticle can be, for example, solid-lipid nanoparticles (SLNs), polymeric nanoparticles, or oil-in-water nanoemulsions. Solid-lipid nanoparticles are surfactant-stabilized aqueous colloidal dispersions of lipid nanoparticles that solidify upon cooling. They contain a lipid phase dispersed in an aqueous environment. Polymeric nanoparticles are solid colloidal particles created from polymeric systems. These nanoparticles are made from biocompatible polymers that encapsulate or adsorb drugs for prolonged release. Nanoemulsions are oil-in-water (OAV) or water-in-oil (W/O) formulations made with edible or otherwise pharmaceutically acceptable oils, surface-active agents (surfactants), and water, where the diameter of the inner phase is reduced to nanometer length scale. The versatility of nanoemulsions is based on the different types of oils and surface modifiers that can be used. For instance, oils that are rich in omega-3 polyunsaturated fatty acids (PUFA) can play a very important role in overcoming biological barriers, including the blood brain barrier.

For effective targeting, the liposomes and nanoparticles encapsulating the peptides disclosed herein can be further linked with and/or coated with other agents. One example of such an agent can be an antibody binding fragment such as Fab, F(ab')2, Fab' or a single antibody chain polypeptide which binds to a receptor molecule present on a target cell of interest, (e.g., immune cell expressing CD40 or a neoplastic cell expressing CD40 on its surface). In some embodiments, the nanoparticles encapsulating the peptides of the compositions and methods disclosed herein can be coated with poly(ethylene glycol) or polysorbate 80 or albumin or its functional groups. PEG-containing surfactants, poly(oxy-ethylene)-poly(oxy-propylene) can also be used for coating nanoparticles. Polysorbate 80-coated poly (n-butylcyanoacrilate) nanoparticles have been formulated by emulsion polymerization method to target selectively rivastigmine or tacrine. Nanoparticles and liposomes can also be linked to carrier peptides for examples TAT, to improve their lipophilicity.

In some embodiments, the peptides of the compositions and methods disclosed herein can be fused to a carrier peptide, for example for transdermal administration. See for example, US20080305989A1, EP2857033A2

In some embodiments, the compositions of the present disclosure are formulated for intranasal administration. Therefore, in order to enhance the absorption of a therapeutic drug or agent into the olfactory neurons, the drug or agent should be capable of at least partially dissolving in the fluids that are secreted by the mucous membrane that surround the cilia of the olfactory receptor cells of the olfactory epithelium. Therefore the therapeutic peptide can be linked to a carrier that increases its dissolution within nasal secretions. Non-limiting examples of such carriers include GM-1 ganglioside, phosphotidylserine (PS), and emulsifiers such as polysorbate 80. Linkage with lipophilic carriers such as gangliosides or phosphatidylserine can improve the adsorption of the therapeutic drug into the olfactory neurons and through the olfactory epithelium. In some embodiments, the compositions of the present disclosure comprises a ganglioside or a phosphatidylserine (e.g., composition comprising a peptide disclosed herein formulated for intranasal administration).

In some embodiments, the peptides of the present disclosure can be encapsulated in nanoparticles, liposomes, micelles, microspheres, niosomes, cyclodextrin-inclusion complexes, or nanoemulsions. The nanoparticles can be coated with polymers such as polyethylene glycol-polylactic acid (PEG-PLA) or Chitosan (CS). Methods for preparation of (PEG-PLA) nanoparticles are well known in the art. The chitosan nanoparticles can be complexed with cyclodextrins. In some embodiments, the compositions of the present disclosure further comprise cyclodextrin. Use of cyclodextrin for delivery of peptide compositions is known in the art (US20120302505A1) The term "cyclodextrins" refers to cyclic oligosaccharides, like α-, β- and γ-cyclodextrin and their derivatives, preferably β-cyclodextrin and its derivatives, preferably methylated β-cyclodextrin, with a degree of CH3-substitution between 0.5 and 3.0, more preferably between 1.7 and 2.1. The term "saccharides" refers to disaccharides, like lactose, maltose, saccharose and also refers to polysaccharides, like dextrans, with an average molecular weight between 10,000 and 100,000, preferably 40,000 and 70,000. The term "sugar alcohols" refers to mannitol and sorbitol. In some embodiments, the compositions of the present disclosure further comprises saccharides selected from the group consisting of cyclodextrins, disaccharides, polysaccharides and combinations thereof. Peptides can be encapsulated in carriers, like cyclodextrins inclusion complexes containing a hydrophobic core and a hydrophilic shell which can help improve upon the solubility problems.

The compositions can be dispensed intranasally as a powdered or liquid nasal spray, nose drops, a gel or ointment, injection or infusion contained in a tube or catheter, by syringe, by pledge, or by submucosal infusion. Also the composition can made viscous using vehicles such as natural gums, methylcellulose and derivatives, acrylic polymers (carbopol) and vinyl polymers (polyvinylpyrrolidone). Many other excipients, known in the pharmaceutical literature, can be added, such as preservatives, surfactants, co-solvents, adhesives, antioxidants, buffers, viscosity enhancing agents, and agents to adjust the pH or the osmolarity.

Nasal powder compositions can be made by mixing the active agent and the excipient, both possessing the desired particle size. Other methods to make a suitable powder formulation can be selected. Firstly, a solution of the active agent and the cyclodextrin and/or the other saccharide and/or sugar alcohol is made, followed by precipitation, filtration and pulverization. It is also possible to remove the solvent by freeze drying, followed by pulverization of the powder in the desired particle size by using conventional techniques, known from the pharmaceutical literature. The final step is size classification for instance by sieving, to get particles that are less than 100 microns in diameter, preferably between 50 and 100 microns in diameter. Powders can be administered using a nasal insufflator. Powders may also be administered in such a manner that they are placed in a capsule. The capsule is set in an inhalation or insufflation device. A needle is penetrated through the capsule to make pores at the top and the bottom of the capsule and air is sent to blow out the powder particles. Powder formulation can also be administered in a jet-spray of an inert gas or suspended in liquid organic fluids. In some embodiments, the composition for intranasal administration can be adapted for aerosolization and inhalation. The composition can be administered nasally via pressurized aerosol, aqueous pump spray or other standard methods known to those skilled in the art.

The compositions of present disclosure can be administered in the form of spray in a non-pressurized aerosol device, for example a Pfeiffer pump. In some embodiments, the compositions can be contained in a syringe, catheter, an inhaler, a nebulizer, a nasal spray pump, a nasal irrigation pump, or a nasal lavage pump. Non-limiting example for intranasal administration of liquid formulation can include (a) delivering drops with a drop pipette, (b) rhinyle catheter and squirt tube which involves inserting the tip of a fine catheter or micropipette to the desired area under visual control and squirt the liquid into the desired location, (c) squeeze bottles which involve squeezing a partly air-filled plastic bottle, to deliver the atomized drug from a jet outlet, (d) metered-dose spray pumps which deliver a unit dose of drug per use, (e) single- and duo-dose spray devices which is used for a single administration of a unit dose of drug, (f) nasal pressurized metered-dose inhalers delivers a nasal aerosol preparation, and (g) powered nebulizers and atomizers to administer drug in the form of a mist. Non-limiting examples for intranasal administration of liquid formulations can include nasal powder inhalers (e.g., Rhinocort Turbuhaler®; BiDose™/Prohaler™) from Pfeiffer/Aptar), nasal powder sprayers (e.g., Fit-lizer™ device, Unidose-DP™), and nasal powder insufflators (e.g., Bi-Directional™ nasal delivery, Optinose).

Lyophilized Composition:

The compositions of the present disclosure can be provided in a lyophilized form. The composition in a lyophilized form can further comprise a lyoprotectant. A "lyoprotectant" is a molecule which, when combined with a protein or peptide of interest, significantly prevents or reduces chemical and/or physical instability of the protein or peptide upon lyophilization and subsequent storage. Exemplary lyoprotectants include sugars such as sucrose or trehalose; an amino acid such as monosodium glutamate or histidine; a methylamine such as betaine; a lyotropic salt such as magnesium sulfate; a polyol such as trihydric or higher sugar alcohols, e.g., glycerin, erythritol, glycerol, arabitol, xylitol, sorbitol, and mannitol; propylene glycol; polyethylene glycol; pluronics; and combinations thereof. The preferred lyoprotectant is a non-reducing sugar, such as trehalose or sucrose. The lyoprotectant is added to the pre-lyophilized formulation in a "lyoprotecting amount" which means that, following lyophilization of the peptide in the presence of the lyoprotecting amount of the lyoprotectant, the peptide essentially retains its physical and chemical stability and integrity upon lyophilization and storage. The composition in a lyophilized form can comprise a bulking agent. A "bulking agent" is a compound which adds mass to the lyophilized mixture and contributes to the physical structure of the lyophilized cake (e.g., facilitates the production of an essentially uniform lyophilized cake which maintains an open pore structure). Exemplary bulking agents include mannitol, glycine, polyethylene glycol and xorbitol.

Reconstitution of the Lyophilized Formulation

At the desired stage, typically when it is time to administer the peptide to a subject, the lyophilized formulation may be reconstituted with a diluent such that the peptide concentration in the reconstituted formulation is at least 10 mg/mL, for example from about 10 mg/mL to about 1000 mg/mL, more preferably from about 50 mg/mL to about 500 mg/mL, and most preferably from about 100 mg/mL to about 500 mg/mL. Such high peptide concentrations in the reconstituted formulation are considered to be particularly useful where subcutaneous delivery of the reconstituted formulation is intended. However, for other routes of administration, such as intravenous (i.v.) administration, lower concentrations of the peptide in the reconstituted formulation may be desired (for example from about 1-100 mg/mL, or from about 5-50 mg/mL peptide in the reconstituted formulation). In certain embodiments, the peptide concentration in the reconstituted formulation is significantly higher than that in the pre-lyophilized formulation. For example, the peptide concentration in the reconstituted formulation may be about 2-40 times, preferably 3-10 times and most preferably 3-6 times (e.g., at least three fold or at least four fold) that of the pre-lyophilized formulation.

Reconstitution generally takes place at a temperature of about 25° C. to ensure complete hydration, although other temperatures may be employed as desired. The time required for reconstitution will depend, for example, on the type of diluent, amount of excipient(s) and peptide. The "diluent" of interest is one which is pharmaceutically acceptable (safe and non-toxic for administration to a human) and is useful for diluting a peptide in solution or the preparation of a reconstituted formulation. Exemplary diluents include sterile water, bacteriostatic water for injection (BWFI), a pH buffered solution (e.g. phosphate-buffered saline, PBS), sterile saline solution, Ringer's solution or dextrose solution. The diluent optionally contains a preservative. Exemplary preservatives have been described above, with aromatic alcohols such as benzyl or phenol alcohol being the preferred preservatives. The amount of preservative employed is determined by assessing different preservative concentrations for compatibility with the peptide and preservative efficacy testing. For example, if the preservative is an aromatic alcohol (such as benzyl alcohol), it can be present in an amount from about 0.1-2.0% and preferably from about 0.5-1.5%, but most preferably about 1.0-1.2%. Preferably, the reconstituted formulation has less than 6000 particles per vial which are >10 μm in size.

In general, the composition, comprising the peptides, may be packaged in sterile form in a sterile container such as a vial, syringe (for injection) etc. In some embodiments, the composition has a shelf life in packaged form of at least 2, 3 or 4 days, up to 1, 2 or 3 weeks or one month, or in some embodiments a shelf life in packaged form of at least one or two months up to 6 months or one to two years, or more, at a temperature of 37° C., or at room temperature. "Shelf life' has its conventional meaning in the art and refers to the time period during which the active agent retains sufficient activity for accurate and effective administration thereof, and the formulation retains sufficient stability (e.g., a single phase solution remains as a single phase solution) for accurate and effective administration thereof at the recited temperature conditions.

Methods of Use

Assays

The peptides of the present disclosure selectively bind CD40 protein. In some embodiments, the CD40 protein is expressed on a surface of a cell (e.g., an immune cell, a non-immune cell, a cancer cell). It will be well appreciated by those skilled in the art that the peptides or portion thereof disclosed herein can bind CD40 protein in vitro, (for example when used in a cell culture system), ex vivo, and in vivo. In some embodiments, peptides of the present disclosure can be used to detect CD40 expressing cells. In some embodiments, the peptide is conjugated to a detectable agent, for example, fluorescent agent, chemiluminescent agent, radioistope, or enzyme-substrate agent such as alkaline phosphatase. An assay for detecting a cell expressing CD40 in a sample comprises, for example, a) contacting the sample with a peptide of the present disclosure under condition suitable to allow binding of the peptide with CD40 on the cell surface; b) washing the unbound peptide; and c) detecting the peptide bound to cells. The peptide can be detected, for example, by screening for the detectable agent conjugated to the peptide. The presence of detectable agent indicates presence of CD40 expressing cell. In some embodiments, a secondary detection agent (e.g., an antibody binding the peptide disclosed herein) can be used to detect the peptide bound to CD40 expressing cell. In some embodiments, the peptide useful for such assays can be immobilized onto a solid surface. The solid surface can be in the form of tubes, beads, discs, silicon chips, microplates, polyvinylidene difluoride (PVDF) membrane, nitrocellulose membrane, nylon membrane, other porous membrane, non-porous membrane, e.g., plastic, polymer, perspex, silicon, amongst others, a plurality of polymeric pins, or a plurality of microtitre wells, or any other surface suitable for immobilizing polypeptide or polynucleotides.

Activated immune cells expressing CD40 are associated with risk of developing inflammatory diseases, autoimmune disease or cancer. Accordingly, in some embodiments, the peptides disclosed herein can be used to identify patients at risk of developing inflammatory diseases, autoimmune disease or a cancer. A sample obtained from candidate patients can be assayed for presence of CD40 expressing cells using, for example, an assay described above. In some embodiments, the sample can be screened for a specific type of cell expressing CD40 alone or in combination with other surface markers specific for that cell type. For example, a sample can be assayed for a population of activated T-cell by using the peptides disclosed herein to detect expression of CD40 alone or using the peptides disclosed herein in combination with molecules detecting activated T-cell specific surface proteins such as CD25, CD38, CD69 and the like. In another embodiment, a sample can be assayed to identify a CD40 expressing cancer cell using the peptides disclosed herein alone or by using the peptides disclosed herein to detect the CD40 in combination with molecules detecting cancer markers on cell surface. An increase in number of a specific type of cell (e.g., activated T-cell) relative to the total cell population in a sample can be indicative of a disease condition (e.g. inflammatory diseases, autoimmune disease or a cancer).

In some embodiments, the peptides disclosed herein can be used to screen for molecules (e.g., small molecule, proteins, peptides) that bind CD40 and modulate CD40 activity. The assay can be designed, for example, as a competitive binding assay. The assay can be designed, to test the ability of a test molecule to compete with the peptides disclosed herein for binding to a CD40 protein. The peptides disclosed herein useful for such an assay can be one that is fused to a detectable agent. In one embodiment, the method comprises: a) contacting a cell or biological sample with a peptide disclosed herein in the presence or absence of a test agent under conditions which allow for their binding to CD40; b) washing the sample to remove any unbound peptides; and c) screening the sample for presence of detectable agent. In one embodiment, absence of a detectable agent, indicates the test molecule is able to compete with the peptide for binding to a CD40 protein. The assay can be used, for example, to screen for molecules that partially inhibit binding of peptides to the CD40 protein.

Methods of competitive binding assay are well known in the art. The test agents can be obtained using any of the numerous approaches in combinatorial-library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam et al., 1997, Anticancer Drug Des. 12:45). Examples of methods for the synthesis of molecular libraries can be found in the art, for example, in: DeWitt et al, 1993, Proc. Natl. Acad. USA 90:6909; Erb et al, 1994, Proc. Natl. Acad. Sci. USA 91: 11422; Zuckermann et al, 1994, J. Med. Chem. 37:2678; Cho et al, 1993, Science 261: 1303; Carrell et al, 1994, Angew. Chem. Int. Ed. Engl. 33:2059; Carell et al, 1994, Angew. Chem. Int. Ed. Engl. 33:2061; and Gallop et al, 1994, J. Med. Chem. 37: 1233. Libraries of compounds may be presented in solution (e.g., Houghten, 1992, Biotechniques 13:412-421), or on beads (Lam, 1991, Nature 354:82-84), chips (Fodor, 1993, Nature 364:555-556), bacteria (Ladner U.S. Pat. No. 5,223,409), spores (Ladner U.S. Pat. No. '409), plasmids (Cull et al, 1992, Proc. Natl. Acad. Sci. USA 89: 1865-1869) or on phage (Scott and Smith, 1990, Science 249:386-390; Devlin, 1990, Science 249:404-406; Cwirla et al, 1990, Proc. Natl. Acad. Sci. USA 87:6378-6382; Felici, 1991, J. Mol. Biol. 222:301-310; and Ladner supra).

In situations where "high-throughput" modalities are preferred, it is typical that new chemical entities with useful properties are generated by identifying a chemical compound (called a "lead compound") with some desirable property or activity, creating variants of the lead compound, and evaluating the property and activity of those variant compounds. The current trend is to shorten the time scale for all aspects of drug discovery. In one embodiment, high throughput screening methods involve providing a library containing a large number of compounds (candidate compounds) potentially having the desired activity. Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics. Assays disclosed herein are meant as examples of useful assays and it is understood that other assays or modifications of assays described above using the peptides disclosed herein can be employed. Suitable assay techniques are known to those skilled in the art and are disclosed for example in Molecular Cloning: A Laboratory Manual, Sambrook, J., Fritsch, E. F., and Maniatis, T, Cold Spring Harbor Laboratory Press; 2nd Edition (December 1989). All referenced cited herein are incorporated herein in their entirety.

Methods of Immunosuppression and Treatment

The term "immunosuppression" as used herein relates to an inhibition in the activation and/or maintenance of an immune response (for example, immune response directed towards a transplant). As used herein, the term "immune response" refers to the alteration in the reactivity of an organism's immune system upon exposure to an antigen. The term "immune response" encompasses but is not limited to one or both of the following responses: antibody production (e.g., humoral immunity), and induction of cell-mediated immunity (e.g., cellular immunity including helper T cell and/or cytotoxic T cell responses). "Immune response" generally refers to innate and acquired immune responses including, but not limited to, both humoral immune responses (mediated by B lymphocytes) and cellular immune responses (mediated by T lymphocytes). An immune response may be beneficial and lead to immunity against infectious pathogens, or an immune response may be pathogenic and lead to autoimmune or hypersensitivity disease. Immune responses against foreign viruses, bacteria, fungi, parasites typically represent beneficial adaptive immune responses. Immune responses against self tissues, innocuous foreign objects (e.g., dust mite or pollen allergens, etc.), or tissue transplants represent examples of adverse maladaptive immune responses. The term "modulate," "modulates" or "modulation" refers to enhancement (e.g., an increase) or inhibition (e.g., a reduction) in the specified activity or suppression thereof. As it relates to the present disclosure, immunosuppression also refers to inhibition of an immune response mediated by CD40 activity or one that is mediated by interaction of CD40 with CD154.

CD40 is well known to play an important role in activation of immune response. B cells are known to constitutively express the CD40 molecule on the cells membrane (van Kooten C. et al, J. Leukoc. Biol. 2000). Stimulation of CD40 by CD154-expressing activated T cells, results in B cells activation, proliferation and isotype switching. Recent studies have indicated that CD40-CD154 interaction can upregulate costimulatory molecules, activate APCs, and influence T-cell priming and T-cell-mediated effector CD40 activities include modulating cell survival (e.g., functions as cell survival signal), antibody production, antibody isotype switching, production of cytokines (e.g., IL-2, IL-6, IL-8, IL-12, TNF-α, IL-4, IL-5 and IL-10), metalloproteases (e.g., MMP-I/collagenase and MMP-9/gelatinase B) and establishment of immune memory. CD40 activities further include modulating production of proteins involved in cell-cell contact or adhesion (e.g., E-selectin, VCAM-1 and ICAM-1). This interaction can activate macrophages, natural killer (NK) cells, and endothelial cells. CD40 plays a significant role in immune cell function and signaling, including B-cell and T-cell activation by antigen presenting cells, such as macrophages and dendritic cells. CD40 activity stimulates antibody production, isotype switching, and establishment of memory. CD40 activity stimulates production of cytokines, such as IL-2, IL-6, IL-8, IL-12, TNF-α, IL-4, IL-S and IL-10; and metalloproteases, such as MMP-I/collagenase and MMP-9/gelatinase B. CD40 activity stimulates production of proteins involved in cell-cell contact or adhesion, such as E-selectin, VCAM-1 and ICAM-1. CD40 recognition on target cells provides an activation pathway for NK cell cytotoxic activity. Thus, increasing or decreasing cell survival, antibody production, isotype switching, establishment of memory, production of cytokines, metalloproteases or proteins involved in cell-cell contact or adhesion, NK cell cytotoxic activity, B-cell activation, B-cell proliferation, T-cell activation, T-cell proliferation, macrophage activation, migration of immune cell can all be effected or inhibited by contacting an appropriate cell expressing CD40 with the peptide of the present disclosure or a pharmaceutical composition disclosed herein Thus, the disclosure further provides methods of modulating cell survival, antibody production, isotype switching, establishment of memory, production of cytokines, metalloproteases or proteins involved in cell-cell contact or adhesion, NK cell cytotoxic activity, B-cell activation, B-cell proliferation, T-cell activation, T-cell proliferation, macrophage activation, or migration of an immune cell, comprising contacting a cell expressing CD40 with an effective amount of a peptide disclosed herein. By "a cell expressing CD40" herein is intended any normal or malignant cells that express detectable levels of the CD40 antigen. The cell can be an immune cell, a nonimmune cell, or a cancer cell, for example, lymphoma cell. Methods for detecting CD40 expression in cells are well known in the art and include, but are not limited to, PCR techniques, immunohistochemistry, flow cytometry, Western blot, ELISA, and the like. These methods allow for the detection of CD40 mRNA, CD40 antigen and cell-surface CD40 antigen. Preferably, the CD40-expressing cells are cells that express detectable levels of cell-surface CD40 antigen. The cell to be contacted can be informed by the immune response to be modulated. For example, in embodiments related to B-cell mediated immune response, such as B-cell proliferation, B-cell activation, the cell contacted with the peptides or compositions disclosed herein can be a B-cell. For example, in embodiments related to inhibiting activation of macrophage activation or production of cytokines, the cell contacted with the peptides or compositions disclosed herein can be a macrophage. The cell to be contacted can be easily determined by one of skill in the art.

Assays for monitoring immune responses are well known in the art and are described above. Methods of immunosuppression can be practiced on a subject in order to achieve the effect in the subject. Accordingly, the disclosure provides for a method for inducing immunosuppression in a subject in need thereof, the method comprising administering to the subject an effective amount of a peptide of the present disclosure or a pharmaceutical composition disclosed herein.

Compositions, methods, kits, and systems provided herein can be utilized to prevent and/or treat an autoimmune disorder. The term "autoimmune disorder", "autoimmune disease", "autoimmune condition", and their grammatical equivalents as used herein can be used interchangeably. In some cases, the tolerance vaccine provided herein can be crosslinked to autoantigenic peptides, autoantigens, or other cellular carriers and used as a tolerance therapy for an autoimmune disorder. In some cases, the cellular carrier is an apoptotic cellular carrier. In some cases, the cellular carrier is a syngeneic apoptotic cellular carrier.

The tolerizing vaccine as described herein can be used with a cellular carrier (e.g., autoantigens, autoantigenic peptides, apoptotic cellular carriers) to induce antigen-specific T cell tolerance for treatment of an autoimmune condition. Without being bound by theory, the tolerizing vaccine with or without the carrier can be taken up, processed, and presented in a tolerogenic manner by host splenic antigen presenting cells, thereby inducing regulatory T cells, and the secretion of immune suppressive cytokines (e.g., IL-4, IL-10, IL-13, TGF-β).

Methods and composition of the present disclosure can be employed to treat a CD40 associated disorder. The disclosure therefore also provides methods of treating a CD40 associated disorder. As used herein, the term "CD40 associated disorder" means any undesirable physiological condition or pathological disorder in which modulating a CD40 activity (e.g., binding CD154 or activation of immune response mediated by CD40 may improve or reduce one or more undesirable symptoms of the condition or disorder.

Thus, where CD40 is associated with an undesirable immune response or process in vivo, such as autoimmunity, hypersensitivity, inflammation or transplant rejection, a peptide disclosed herein or a pharmaceutical composition disclosed herein can be administered to a subject having, or at risk of having autoimmunity, hypersensitivity, inflammation or transplant rejection in order to induce immunosuppression and inhibit or prevent autoimmunity, hypersensitivity, inflammation or transplant rejection in the subject.

Accordingly, in one embodiment, the method of inducing immunosuppression disclosed herein can be useful to a subject who is suffering from or is at a risk of developing an inflammatory disease. "Inflammatory disease" means an immune-mediated inflammatory condition, generally characterized by dysregulated expression of one or more cytokines. Examples of inflammatory disease include skin inflammatory disorders, inflammatory disorders of the joints, and inflammatory disorders of the cardiovascular system, autoimmune diseases, lung and airway inflammatory disorders, intestinal inflammatory disorders. Examples of skin inflammatory disorders include dermatitis, for example atopic dermatitis and contact dermatitis, acne vulgaris, and psoriasis. Examples of inflammatory disorders of the joints include rheumatoid arthritis. Examples of inflammatory disorders of the cardiovascular system are cardiovascular disease and atherosclerosis. Examples of autoimmune diseases include Type 1 diabetes, Graves' disease, Guillain-Barre disease, Lupus, Psoriatic arthritis, and Ulcerative colitis. Examples of lung and airway inflammatory disorders include asthma, cystic fibrosis, COPD, emphysema, and acute respiratory distress syndrome. Examples of intestinal inflammatory disorders include colitis and inflammatory bowel disease. Other inflammatory disorders include cancer, hay fever, periodontitis, allergies, hypersensitivity, ischemia, depression, systemic diseases, post infection inflammation, amyotrophic lateral sclerosis and bronchitis.

As used herein, the term "autoimmune disease" refers generally to those diseases characterized by the failure of one or more B- and/or T-cell populations, or gene products thereof, to distinguish between self and non-self antigenic determinants. Autoimmune diseases are often characterized by the infiltration of the target cells with inflammatory lymphoid cells, for example, mononuclear phagocytes, lymphocytes and plasma cells as well as secondary lymphoid follicles. Exemplary autoimmune diseases include, but are not limited to, organ specific disorders such as Hashimoto's thyroiditis, primary myxoedema thyrotoxicosis, pernicious anemia, Addison's disease, and insulin-dependent diabetes mellitus as well as non-organ specific disorders such as systemic lupus erythematosus (SLE), rheumatoid arthritis (RA), multiple sclerosis, dermatomyositis, scleroderma and psoriasis. Non-limiting examples of autoimmune disorders treatable with a peptide or pharmaceutical composition of the disclosure include rheumatoid arthritis, lupus (e.g., SLE, lupus nephritis), production of auto-antibodies which, in the case of antibodies against myelin basic protein contribute to multiple sclerosis and in the case of antibodies against insulin contribute to diabetes, and Crohn's disease. Non-limiting examples of hypersensitivity treatable with a peptide disclosed herein or pharmaceutical compositions of the disclosure include allergic reactions to antigens, antibiotics, etc.

Non-limiting examples of inflammation treatable with a peptide or pharmaceutical composition of the present disclosure include vascular inflammatory disease (e.g., artherosclerotic lesions, plaque disruption and thrombus formation), production of inflammatory cytokines (e.g., LIF, GM-CSF, and IL-6), lung fibrosis and inflammation associated with multiple sclerosis or a tissue or organ transplant. CD40 activity can be associated with inflammation caused by viral myocarditis and, as such, a peptide or pharmaceutical composition disclosed herein can be used to inhibit inflammation associated with viral infection.

Additional situations exist in which it may be desired to inhibit an immune response. For example, production of neutralizing antibodies against therapeutic agents, such as anti-insulin antibodies in diabetics administered insulin repeatedly, or in subjects that produce anti-virus antibodies (e.g., adenovirus or adeno-associated virus) being treated with a gene therapy virus vector, may be inhibited using a peptide or pharmaceutical composition herein. Accordingly, provided herein is a method of treating a subject suffering from an inflammatory disease, the method comprising, administering to the subject an effective amount of a pharmaceutical composition disclosed herein.

CD40 is also present in various other tissues and cells. For example, CD40 is present in epithelial cells, vascular endothelium and smooth muscle cells, and CD40 ligand (CD 154) was expressed by thrombin-activated platelets. These findings indicate a role for CD40 activity in vascular thrombotic-atheromatic pathophysiology. Therefore, a peptide disclosed herein or a pharmaceutical composition of the present disclosure that decreases a CD40 activity can be used to inhibit thrombus formation or artherosclerosis in a subject.

CD40 is also expressed in human renal tubules, thymic epithelia and neural cells. Interestingly, CD40 activity appears to induce apoptosis in neural cells, in contrast to its cell survival role in the immune system. Thus, a peptide or pharmaceutical composition herein can be used to inhibit apoptosis in neural cells. Accordingly, CD40 can be used to treat neural disorders characterized by cell degeneration or undesirable or excessive cell death, such as Parkinson's disease, Alzheimer's, Huntington disease, spinocerebellar ataxias/atrophies, etc.

CD40 is also expressed in carcinomas, such as melanoma, Kaposi's sarcoma, osteosarcoma and Ewing' sarcoma. CD40 in malignant melanoma appears to be predictive of a negative prognosis. CD40 in human bladder carcinoma cells inhibits fas-mediated apoptosis. CD40 has been detected in tumor vasculature in a renal carcinoma mass. Stimulation of CD40 in B-cell lymphomas stimulates growth. CD40 can therefore function as a cell survival or growth factor in some tumors, and may promote angiogenesis. Other data indicate that CD40 may induce cell death in transformed cells.

Thus, a peptide or compositions disclosed herein that decreases a CD40 activity associated with tumor survival will be useful in treating cell proliferative disorders (e.g., tumors) in which CD40 functions as a cell survival signal or growth promoter, either directly (e.g., in the tumor cell) or indirectly (i.e., through stimulation of angiogenesis within a tumor mass). Other biological pathways and physiological conditions that CD40 participates in are described in Biancone, et al. (Int. J. Mol. Med. 3:343 (1999)), Laman et al. (Dev. Immunol. 6:215 (1998)), Kooten and Bachereau (J. Leukoc. Biol. 67:2 (2000)), Noelle et al. (Ann. NY Acad. Sci. 815:384 (1997)), Noelle (Immunity 4:415 (1996)), Grewal et al. (Curr. Opin. Immunol. 9:491 (1997)); Grewal et al. (Ann. Rev. Immunol. 16:111 (1998); Grewal et al. (Immunol. Rev. 153:85 (1996)); Gruss et al. (Leuk. Lymphoma 24(5-6):393 (1997)); van Kooten et al. (Curr. Opin. Immunol. 9:330 (1997)). Such pathways as well as others known in the art are amenable to modulation using the peptides disclosed herein or compositions comprising said peptides disclosed herein, as are the physiological conditions associated with CD40 activity described therein or otherwise known in the art.

Prevention or Treatment of a Cancer

The peptides or compositions disclosed can find use in treatment of a neoplastic disease. In one aspect, provided herein is a method of treating a subject suffering from or is at risk of developing a neoplastic disease characterized by a neoplastic cell that expresses CD40, the method comprising administering to the subject an effective amount of peptides disclosed herein or a composition comprising the peptides disclosed herein. CD40 has been shown to be expressed not only on immune cells, but also on tumor cells, including B-cell malignancies and solid tumors.

As used herein, the term "neoplastic cells that expresses CD40," refers to a cell (e.g., an immune cell such as B-cell, T-cell, or an non-immune cell, such as epithelial cell, endothelial cell, smooth muscle cell) that expresses a CD40 protein on its cell surface and exhibits abnormal cell growth, cell division and proliferation not undergoing apoptosis, or both, under inappropriate conditions. For example, a "neoplastic cell" may undergo cell division when a corresponding non-neoplastic cell does not undergo cell division, or, alternatively, a "neoplastic cell" may not respond to normal cellcycle checkpoint controls. Accordingly a neoplastic cell is one that exhibits abnormal proliferation of cells. The growth of neoplastic cells exceeds that of normal tissue around it and it is not coordinated with that of the normal tissue around it resulting in neoplasms. Neoplasms may be benign (e.g., benign tumor and atypical hyperplasia), pre-malignant (e.g., carcinoma in situ and pre-cancer) or malignant (e.g., cancer). The term "cancer" refers to any of the various malignant neoplasms characterized by the proliferation of cells that have the capability to invade surrounding tissue and/or metastasize to new colonization sites, including but not limited to leukemias, lymphomas, carcinomas, melanomas, sarcomas, germ cell tumors and blastomas. Exemplary cancers include cancers of the brain, bladder, breast, cervix, colon, head and neck, kidney, lung, non-small cell lung, mesothelioma, ovary, prostate, stomach and uterus, leukemia and medulloblastoma.

Neoplastic tissues can originate from any cell type or tissue found in a mammal, including, but not limited to hepatic, skin, breast, prostate, neural, optic, intestinal, cardiac, vasculature, lymph, spleen, renal, bladder, lung, muscle, connective, tissue, pancreatic, pituitary, endocrine, reproductive organs, bone, and blood. The neoplastic tissue for analysis may include any type of solid tumor or hematological cancer. In some embodiments, the neoplastic tissue is a breast cancer tissue. In other embodiments, the neoplastic tissue is a breast tissue with atypical hyperplasia.

The term "leukemia" refers to broadly progressive, malignant diseases of the blood-forming organs and is generally characterized by a distorted proliferation and development of leukocytes and their precursors in the blood and bone marrow. Leukemia diseases include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micro-myeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "sarcoma" generally refers to a tumor which arises from transformed cells of mesenchymal origin. Sarcomas are malignant tumors of the connective tissue and are generally composed of closely packed cells embedded in a fibrillar or homogeneous substance. Sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphomas (e.g., Non-Hodgkin Lymphoma), immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

The Examples herein show that the CD40 binding peptides disclosed herein can bind CD40 expressed on B-cell and inhibit, for example, B-cell proliferation and B-cell activation. The peptides of the present disclosure can find use, for example, in the treatment of B-cell lymphomas, prevention of EBV-induced B-cell lymphoma that can occur after transplantation or in other instances of immunosuppression, such as AIDS, and which present a significant risk in such patient populations. The methods disclosed herein can be useful in prevention of immunoblastic B-cell lymphomas that frequently arise in immunocompromised individuals. In such preventative methods, a mammal at risk of developing an immunoblastic B-cell lymphoma is administered an effective amount of peptides disclosed herein. The peptides can be administered for as long as the state of immunocompromise that places the individual at risk exists.

The peptides of the present disclosure or compositions comprising the peptides can be useful for treatment of cancer characterized by "neoplastic B-cell growth" is intended any disease or condition (including pre-malignant conditions) involving uncontrolled growth of cells of B-cell lineage. Such diseases and conditions include, but are not limited to, acute lymphoblastic leukemia (ALL), acute myelogenous leukemia (AML), chronic myelogenous leukemia (CML), chronic lymphocytic leukemia (CLL), prolymphocytic leukemia (PLL), small lymphocytic leukemia (SLL), diffuse small lymphocytic leukemia (DSLL), diffuse large B-cell lymphoma (DLBCL), hairy cell leukemia, non-Hodgkin's lymphomas, Hodgkin's disease, Epstein-Barr Virus (EBV) induced lymphomas, myelomas such as multiple myeloma, Waldenstrom's macroglobulinemia, heavy chain disease, mucosal associated lymphoid tissue lymphoma, monocytoid B cell lymphoma, splenic lymphoma, lymphomatoid granulomatosis, intravascular lymphomatosis, immunoblastic lymphomas, AIDS-related lymphomas, and the like.

In another aspect, the compositions and methods used to prevent occurrence (or reoccurrence) or treatment of neoplastic disease characterized by other types of malignant cells that express CD40 in individuals at risk for such disease. Individuals that are considered at risk in these instances include those with family history or other genetic characteristics indicating predisposition to cancers in which the neoplastic cells express CD40, and individuals that develop drug-resistant neoplastic disease as a result of chemotherapy, in which the drug-resistant neoplastic cells express CD40.

Individuals afflicted with disease characterized by neoplastic cells that express CD40 may also be treated according to the methods disclosed herein. The term treatment, as it is generally understood in the art, refers to initiation of therapy after clinical symptoms or signs of disease have been observed. The methods may be used in conjunction with other therapies appropriate for afflicted individuals, including chemotherapy, radiation therapy, and immunotherapy.

The "effective amount" to be administered will be governed by such considerations, and refers to the minimum amount necessary to ameliorate, treat, or stabilize, the cancer; to increase the time until progression (duration of progression free survival) or to treat or prevent the occurrence or recurrence of a tumor, a dormant tumor, or a micrometastases. The peptides, disclosed herein, can be optionally formulated with one or more additional therapeutic agents currently used to prevent or treat cancer or a risk of developing a cancer. The effective amount of such other agents depends on the amount of peptides present in the formulation, the type of disorder or treatment, and other factors such age, weight etc. These are generally used in the same dosages and with administration routes as used herein before or about from 1 to 99% of the heretofore employed dosages.

The efficacy of the treatment methods for cancer, comprising administering the peptides disclosed herein or pharmaceutical compositions of the present disclosure can be measured by various endpoints commonly used in evaluating cancer treatments, including but not limited to, tumor regression, tumor weight or size shrinkage, time to progression, duration of survival, progression free survival, overall response rate, duration of response, and quality of life. The peptides disclosed herein can require unique measures and definitions of clinical responses to drugs. In the case of cancers, the therapeutically effective amount of the peptides disclosed herein or compositions comprising the same can reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the peptides disclosed herein, act to prevent growth and/or kill existing cancer cells; it can be cytostatic and/or cytotoxic. For cancer therapy, efficacy in vivo can, for example, be measured by assessing the duration of survival, duration of progression free survival (PFS), the response rates (RR), duration of response, and/or quality of life.

In other embodiments, described herein are methods for increasing progression free survival of a human subject susceptible to or diagnosed with a cancer, for example, skin cutaneous melanoma. Time to disease progression is defined as the time from administration of the drug until disease progression or death. In a preferred embodiment, the combination treatment of the disclosure using a peptide or compositions disclosed herein, and one or more chemotherapeutic agents may significantly increase progression free survival by at least about 1 month, 1.2 months, 2 months, 2.4 months, 2.9 months, 3.5 months, such as by about 1 to about 5 months, when compared to a treatment with chemotherapy alone. In another embodiment, the methods described herein may significantly increase response rates in a group of human subjects susceptible to or diagnosed with a cancer that are treated with various therapeutics. Response rate is defined as the percentage of treated subjects who responded to the treatment. In one embodiment, the combination treatment described herein using a peptide or compositions disclosed herein, and one or more chemotherapeutic agents significantly increases response rate in the treated subject group compared to the group treated with chemotherapy alone.

For example, in some embodiments, the methods described herein comprise administering an effective amount of the peptides of the instant disclosure or compositions comprising said peptides, to a subject in order to alleviate a symptom of a cancer. As used herein, "alleviating a symptom of a cancer" is ameliorating or reducing any condition or symptom associated with the cancer. As compared with an equivalent untreated control, such reduction or degree of prevention is at least 5%, 10%, 20%, 40%, 50%, 60%, 80%, 90%, 95%, or 100% as measured by any standard technique. Ideally, the cancer is completely cleared as detected by any standard method known in the art, in which case the cancer is considered to have been treated. A patient who is being treated for a cancer is one who a medical practitioner has diagnosed as having such a condition. Diagnosis can be by any suitable means. Diagnosis and monitoring can involve, for example, detecting the level of cancer cells in a biological sample (for example, a tissue or lymph node biopsy, blood test, or urine test), detecting the level of a surrogate marker of the cancer in a biological sample, detecting symptoms associated with the specific cancer, or detecting immune cells involved in the immune response typical of such a cancer.

The treatment and/or prevention of cancer includes, but is not limited to, alleviating symptoms associated with cancer, the inhibition of the progression of cancer, the promotion of the regression of cancer, the promotion of the immune response, inhibition of tumor growth, inhibition of tumor size, inhibition of metastasis, inhibition of cancer cell growth, inhibition of cancer cell proliferation, or cause cancer cell death.

Transplant Immunomudulation

Described herein are compositions, systems, and methods for inducing graft tolerance. In particular, the present disclosure relates to administering a tolerizing vaccine or a preparatory regimen before, during, and/or after administration of donor transplant cells, tissue(s), or organ(s). The tolerizing vaccine or preparatory regimen can induce tolerance to the allograft or xenograft in the graft recipient.

An organ, tissue, or cell can be differentiated from stem cells, grown de novo, or isolated from an animal (e.g., a human or non-human animal) and can be transplanted into a recipient in need of a transplant from the same species (an allotransplant) or a different species (a xenotransplant). The donor of the organ, tissue, or cell can be referred to herein as a transplant donor. The transplanted organ, tissue, or cell can be referred to herein as a transplant or a graft.

The donor of transplant or graft can be any animal, including human and non-human animals. In some cases the donor is a human. In some cases, the transplant donor is a non-human animal. The transplant donor (e.g., a non-human animal donor) can be genetically modified, for example, to reduce or eliminate the likelihood that the transplant or graft can be recognized by the recipient's immune system, or to reduce the immune response by the recipient's immune system upon recognizing the transplant or graft.

The donor of a transplant or graft can be a living donor or a cadaveric donor. In some cases, the transplant donor is a living donor. In some cases, the transplant donor is a cadaveric donor. The cadaveric donor may be a brain dead, heart beating donor (BDD). Alternatively, the cadaveric donor may be a non-heart beating donor (NHBD). Whether the transplant donor is a living donor or a cadaveric donor (e.g., a BDD or NHBD), the donor can be from any animal, for example, a human or non-human animal.

The donor of a transplant or graft can be at any age or stage of development. For example, the transplant donor can be a fetal, perinatal, neonatal, pre-weaning, post-weaning, juvenile, young adult, or adult human or animal.

Transplants or grafts can be used to treat diseases or disorders in recipients in need thereof. Suitable diseases that can be treated are any in which an organ, tissue, or cell of a recipient is defective or injured, and the recipient can be treated by transplantation of an organ, tissue, or cell (e.g., a kidney, heart, lung, liver, vein, skin, endocrine pancreas, pancreatic islet cell, or a combination thereof). In some cases, the transplant comprises a kidney, liver, heart, lung, pancreas, endocrine pancreas, islet cell, small bowel, bone marrow, hematopoietic stem cell, embryonic or induced pluripotent stem cell-derived cells such as islet beta cells or hepatocytes, embryonic or induced pluripotent stem cell-derived islet, embryonic or induced pluripotent stem cell-derived hepatocyte, or a combination thereof.

Inhibiting Immune Response to a Donor Cell or Tissue Transplant.

In some embodiments, methods for inducing immunosuppression can be useful to prevent graft rejection in a subject who has undergone, is undergoing or will be undergoing a cell, organ or tissue transplant.

The peptides and compositions disclosed herein can find use in preventing transplant rejection by inhibiting a CD40 mediated immune response in a recipient, towards an antigen on a transplanted material (e.g., cells, tissues, an/or organs). In one aspect provided herein is a method of inhibiting an immune response to a donor cell or tissue transplantation in a recipient, the method comprising administering to the recipient a peptide or compositions disclosed herein. Examples of transplant rejection (acute or chronic) treatable with a peptide disclosed herein include blood vessels, kidney, liver, heart, lung, pancreas and skin. Transplantation includes grafting of tissues or organ from the body of an individual to a different place within the same individual, or a different individual. Transplantation also involves grafting of tissues or organs from one area of the body to another. Transplantation of tissues or organs between genetically dissimilar animals of the same species is termed as allogeneic transplantation. Transplantation of animal organs into humans is termed xenotransplants.

Transplant/graft rejection can involve recognition of donor-specific antigens, for example, recognition of donor-specific antigens presented to T cells by host antigen presenting cells (indirect) or donor antigen presenting cells (direct). T cell activation in response to donor-specific antigens can lead to a pro-inflammatory response and transplant rejection. Transplant rejection (e.g., T cell-mediated transplant rejection) can be prevented by chronic immunosuppression with one or more immunomodulatory molecules. However, immunosuppression is costly and associated with the risk of serious side effects.

In some embodiments, a method described herein to prevent transplantation rejection or prolong the time to transplantation rejection without or with minimal immunosuppressive drug use (e.g., one or more immunomodulatory molecules) involves using a genetically modified animal as a cell, organ, or tissue donor. The cells, organs, and/or tissues of the altered donor animal, e.g., a donor non-human animal, can be harvested and used in allografts or xenografts. Alternatively, a cell, organ, or tissue can be extracted from an animal, and used to generate a genetically-altered cell, organ or tissue. In some cases, primary cells can be extracted from an animal, and used to make genetically altered cells. In some cases, a cell, organ, or tissue derived from an animal (e.g., a cell line) can be used to create a genetically altered cell, organ, or tissue.

Transplant rejection can also be reduced or eliminated by inducing tolerance to a transplant or graft using a tolerizing vaccine or preparatory regimen. A tolerizing vaccine or preparatory regimen of the disclosure can be used to prevent transplant rejection or delay rejection, for example, by reducing a pro-inflammatory immune response to the transplant, and/or enhancing a tolerance-promoting immune response. In some cases, a tolerizing vaccine or preparatory regimen of the disclosure can circumvent the need for long-term immunosuppression of the recipient.

An effective amount, which is determined by these considerations, is the minimum amount necessary to inhibit an immune response in a recipient that would result in rejection of the transplant, but as much as necessary to achieve a longer transplant survival time. Such amount is preferably below the amount that is toxic to the recipient or renders the recipient significantly more susceptible to infections. The amount of peptides or compositions disclosed herein used for inhibiting immune response directed to a transplant can be lower than the amount of an immunosuppressive agent normally required for transplanted grafts and depends on the individual circumstances surrounding the transplant. A treatment with the peptides or compositions disclosed herein can also lessen or prevent the side effects frequently observed in transplant recipients who undergo immune suppressive therapy.

The present disclosure therefore provides a method for inhibiting transplant rejection and a method to increase transplant survival. In one aspect, the peptides or compositions-disclosed herein can administered as a part of a transplantation protocol. Accordingly, provided herein is a method for transplantation of a cell, organ, or tissue from a mammalian donor in a recipient, the method comprising administering an effective amount of the peptides or pharmaceutical compositions disclosed herein. In some embodiments, the method of transplantation further comprises transplanting the donor cell tissue or organ in a recipient.

An organ, tissue, or cell isolated from an animal (e.g., a human or non-human animal) can be transplanted into a recipient in need of a transplant from the same species (an allotransplant) or a different species (a xenotransplant). Transplants or grafts can be used to treat diseases or disorders in a recipient in need thereof. Suitable diseases that can be treated are any in which an organ, tissue, or cell of a recipient is defective or injured, (e.g., a kidney, heart, lung, liver, vein, skin, pancreatic islet cell, or a combination thereof) and the recipient can be treated by transplantation of an organ, tissue, or cell. In some cases, the transplant comprises a kidney, liver, heart, lung, pancreas, islet cell, small bowel, bone marrow, hematopoietic stem cell, embryonic or induced pluripotent stem cell-derived cells, embryonic or induced pluripotent stem cell-derived islet, embryonic or induced pluripotent stem cell-derived hepatocyte, or a combination thereof.

The methods herein can comprise administering one or more dose of a peptide or compositions disclosed herein to a recipient before, after, and/or during transplant of donor cells, organs, and/or tissues to inhibit donor-specific immune response in a recipient. In some cases, a first dose of a peptide or compositions disclosed herein can be given on or on about day −100, day −90, day −80, day −70, day −60, day −50, day −40, day −30, day −20, day −15, day −14, day −13, day −12, day −11, day −10, day −9, day −8, day −7, day −6, day −5, day −4, day −3, day −2 or day −1, relative to transplant of donor cells, organs, and/or tissues on day 0. In some cases, a first dose of a peptide or compositions disclosed herein can be given on or on about day −100 to −50; −50 to −40; −40 to −30; −30 to −20; −20 to −10; −10 to −5; −7 to −1, relative to transplant of donor cells, organs, and/or tissues on day 0. For example, a first dose of a peptide or compositions disclosed herein can be given 8 days (e.g., day −8) before transplant of donor cells, organs, and/or tissues. In some embodiments, a peptide or compositions of the present disclosure can be administered on the same day (e.g., day 0) as transplant of donor cells, organs, and/or tissues. In some cases, a peptide or a composition disclosed herein can be administered on or on about day 300, day 200, day 100, day 90, day 80, day 70, day 60, day 50, day 40, day 30, day 20, day 15, day 14, day 13, day 12, day 11, day 10, day 9, day 8, day 7, day 6, day 5, day 4, day 3, day 2 or day 1, relative to transplant of donor cells, organs, and/or tissues on day 0. For example, a peptide or compositions disclosed herein can be administered on or on about day 400 to 350; 350 to 300; 300 to 250; 250 to 200; 200 to 150; 150 to 100; 100 to 50; 50 to 40; 40 to 30; 30 to 20; 20 to 10; 10 to 5; 7 to 1, relative to transplant of donor cells, organs, and/or tissues on day 0. For example, a peptide or compositions disclosed herein can be administered on 1 day after (e.g., day 1) transplant of donor cells, organs, and/or tissues. In some embodiments, a peptide or compositions disclosed herein can be administered of day 14 after transplant of donor cells, organs, and/or tissues. In some embodiments, a peptide or compositions disclosed herein can be administered for a lifetime of the recipient.

A recipient (e.g., a human or a non-human animal) can require administration with a peptide or composition disclosed herein for at least or at least about 1, 5, 10, 20, 30, 40, 50, 60, 70, 80, 90, 100, 200, 300, 400, 500, 600, 700, 900, or 1,000 days after transplantation, e.g., for at least or at least about 1 to 5; 5 to 10; 10 to 20; 20 to 30; 30 to 60; 60 to 100; 100 to 200; 200 to 300; 300 to 400; 400 to 500; 500 to 600; 600 to 700; 700 to 800; 800 to 900; 900 to 1,000 days. A recipient (e.g., a human or a non-human animal) can require administration of a peptide or composition disclosed herein for at least or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months after transplantation, e.g., for at least or at least about 1 to 2; 2 to 3; 3 to 6; 6 to 9; 9 to 12; 12 to 18; 18 to 24; 24 to 30; 30 to 36 months after transplantation. A recipient (e.g., a human or a non-human animal) can require administration of a peptide or a composition disclosed herein for at least or at least about 1, 2, 3, 4, 5, 6, 7, 8, 9, 10, 15, 20, 25, or 30 years after transplantation, e.g. for at least or at least about 1 to 2; 2 to 3; 3 to 4; 4 to 5; 1 to 5; 5 to 10; 10 to 15; 15 to 20; 20 to 25; 25 to 30 years after transplantation. In some cases, a recipient (e.g., a human or a non-human animal) can require administration of a peptide or a composition disclosed herein for up to the lifetime of the recipient.

A recipient (e.g., a human or a non-human animal) can require administration for at least or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months after transplantation e.g., for at least or at least about 1 to 2; 2 to 3; 3 to 6; 6 to 9; 9 to 12; 12 to 18; 18 to 24; 24 to 30; 30 to 36 months after transplantation. A recipient (e.g., a human or a non-human animal) can require administration of a peptide or a composition disclosed herein for at least or at least about 1, 2, 3, 4, 5, 6, 7, 8, 9, 10, 15, 20, 25, or 30 years after transplantation, e.g. for at least or at least about 1 to 2; 2 to 3; 3 to 4; 4 to 5; 1 to 5; 5 to 10; 10 to 15; 15 to 20; 20 to 25; 25 to 30 years after transplantation.

The transplantation method of the present disclosure can comprise multiple doses of a peptide or a composition disclosed herein before, and/or during and/or after transplantation of a graft cell, tissue, or organ. The multiple doses can be referred to as comprising an initial dose and one or more booster doses. Typically, the initial dose occurs prior to or concurrently with the transplant of the graft cell tissue or organ. The booster dose(s), when administered, occur after the initial dose. In some embodiments, a booster dose is administered to achieve and maintain a particular serum/blood trough level of the peptides disclosed herein.

Depending upon when the initial dose of the peptide or composition disclosed herein is administered, one or more booster doses can be administered before, and/or concurrently with, and/or after transplant of the graft cell, tissue, or organ.

Subsequent (e.g., booster) dose(s) of the peptide or compositions disclosed herein can be administered in any interval of time following a preceding dose (e.g., an initial dose). For example, the subsequent dose can be administered 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 90 days, 120 days, 150 days, or 180 days after the preceding dose. Depending upon when the initial dose is administered subsequent (booster) dose(s) can be administered before, concurrently with, or after transplantation of the graft cell, tissue, or organ. In some cases, the methods of the present disclosure comprise at least one dose of the peptide or compositions disclosed herein prior to transplantation. In some cases, the methods of the present disclosure comprises at least two doses of a peptide or compositions disclosed herein prior to transplantation (e.g., an initial dose and a booster dose). In some cases, the methods herein comprises at least three doses of the peptide or compositions disclosed herein prior to transplantation (e.g., an initial dose and two booster doses). In some cases, the preparatory regimen comprises an initial dose of the peptide or compositions disclosed herein prior to transplantation and at least one dose of booster concurrently with or after transplantation of the graft cell, tissue, or organ.

In some cases, two doses of a peptide or compositions thereof can be administered. For example, the first dose can be administered on day −8 relative to transplant of donor cells, organs, and/or tissues on day 0. For example, the second dose can be administered on day −1 relative to transplant of donor cells, organs, and/or tissues on day 0. For example, the first dose can be administered on day −8, −9, −10, −11, −12, −13, or −14 relative to transplant of donor cells, organs, and/or tissues on day 0. For example, the second dose can be administered on day −1, −2, −3, −4, −5, or −6 relative to transplant of donor cells, organs, and/or tissues on day 0. In some cases, a second dose (e.g., a booster dose) can be administered on day 100, day 90, day 80, day 70, day 60, day 50, day 40, day 30, day 29, day 28, day 27, day 26, day 25, day 24, day 23, day 22, day 21, day 20, day 19, day 18, day 17, day 16, day 15, day 14, day 13, day 12, day 11, day 10, day 9, day 8, day 7, day 6, day 5, day 4, day 3, day 2 or day 1, relative to transplant of donor cells, organs, and/or tissues on day 0. For example, the second dose (e.g., a booster dose) can be administered on 1 day after (e.g., day 1) transplant of donor cells, organs, and/or tissues.

In some cases, a third dose of a peptide or compositions disclosed herein (e.g., a booster dose) can be administered on day 300, day 200, day 100, day 90, day 80, day 70, day 60, day 50, day 40, day 30, day 29, day 28, day 27, day 26, day 25, day 24, day 23, day 22, day 21, day 20, day 19, day 18, day 17, day 16, day 15, day 14, day 13, day 12, day 11, day 10, day 9, day 8, day 7, day 6, day 5, day 4, day 3, day 2 or day 1, relative to transplant of donor cells, organs, and/or tissues on day 0. For example, the peptide or compositions disclosed herein can be administered on or on about day 300 to 200; 200 to 100; 100 to 50; 50 to 40; 40 to 30; 30 to 20; 20 to 10; 10 to 5; 7 to 1, relative to transplant of donor cells, organs, and/or tissues on day 0.

In some cases, a fourth dose of a peptide or compositions disclosed herein (e.g., a booster vaccine) can be administered on day 600, day 500, day 400, day 300, day 200, 100, day 90, day 80, day 70, day 60, day 50, day 40, day 30, day 29, day 28, day 27, day 26, day 25, day 24, day 23, day 22, day 21, day 20, day 19, day 18, day 17, day 16, day 15, day 14, day 13, day 12, day 11, day 10, day 9, day 8, day 7, day 6, day 5, day 4, day 3, day 2 or day 1, relative to transplant of donor cells, organs, and/or tissues on day 0. For example, the peptide or compositions disclosed herein can be administered on or on about day 600 to 500; 500 to 400; 400 to 300; 300 to 200; 200 to 100; 100 to 50; 50 to 40; 40 to 30; 30 to 20; 20 to 10; 10 to 5; 7 to 1, relative to transplant of donor cells, organs, and/or tissues on day 0.

In some cases, a fifth dose of a peptide or compositions disclosed herein (e.g., a booster dose) can be administered on day 1,000, day 900, day 800, day 700, day 600, day 500, day 400, day 300, day 200, 100, day 90, day 80, day 70, day 60, day 50, day 40, day 30, day 29, day 28, day 27, day 26, day 25, day 24, day 23, day 22, day 21, day 20, day 19, day 18, day 17, day 16, day 15, day 14, day 13, day 12, day 11, day 10, day 9, day 8, day 7, day 6, day 5, day 4, day 3, day 2 or day 1, relative to transplant of donor cells, organs, and/or tissues on day 0. For example, the peptide or compositions disclosed herein can be administered on or on about day 1,000 to 900; 900 to 800; 800 to 700; 700 to 600; 600 to 500; 500 to 400; 400 to 300; 300 to 200; 200 to 100; 100 to 50; 50 to 40; 40 to 30; 30 to 20; 20 to 10; 10 to 5; 7 to 1, relative to transplant of donor cells, organs, and/or tissues on day 0. In some cases, a second dose of a booster is not required. In some cases, a second dose of a booster is given concomitantly on day 0 with transplant donor cells, organs, and/or tissues.

Booster doses of a peptide or compositions disclosed herein can be lower dose than the initial or preceding dose of the peptide or compositions disclosed herein. For example, a booster or subsequent dose can be about: 1%, 2%, 3%, 4%, 5%, 7.5%, 10%, 15%, 20%, 25%, 30%, 40%, 50%, 60%, or 75% lower than the initial or preceding dose.

Preparatory Regimen/Tolerizing Agent

In some embodiments, the transplantation method comprises administering a tolerizing agent in the subject. The term "tolerizing agent" or a "toleragen" as used herein means any donor antigen (such as a protein, nucleic acid, carbohydrate, lipid, or combination of any thereof) that mediates host unresponsiveness. By way of example, a tolerizing agent works by inducing the tolerized host not to produce antibodies or cell-mediated immune responses specific for the toleragen. Additional discussion of tolerizing may be found, for instance, in PCT publication WO 2006/052668, which is incorporated herein in its entirety. In some embodiments, the tolerizing agent can be a tolerizing vaccine comprising inactivated or apoptotic donor cells that upon intravenous injection can result in tolerance to transplanted donor cells or tissues or compositions comprising said cells with similar marks. In some embodiments, the tolerizing agent can be an anti-CD40 agent (e.g., agent comprising one or more amino acid sequences listed in any one of SEQ ID 1-6 and 8-17). In some embodiments, the tolerizing agent can be mammalian leukocytes fixed with a crosslinking agent. In some cases, the tolerizing agent can be mammalian leukocytes fixed with a crosslinking agent, administered together with an anti-CD40 binding agent (e.g., agent comprising one or more amino acid sequences listed in any one of SEQ ID 1-6 and 8-17). In some cases, the tolerizing agent can be mammalian leukocytes fixed with a crosslinking agent, surface-conjugated with an anti-CD40 binding agent (e.g., agent comprising one or more amino acid sequences listed in any one of SEQ ID 1-6 and 8-17).

In some embodiments, the preparatory regimen can be inactivated or apoptotic donor cells that upon intravenous injection can result in tolerance to transplanted donor cells or tissues or compositions comprising said cells with similar marks. In some embodiments, the preparatory regimen can be an anti-CD40 agent (e.g., agent comprising one or more amino acid sequences listed in any one of SEQ ID 1-6 and 8-17). In some embodiments, the preparatory regimen can be mammalian leukocytes fixed with a crosslinking agent. In some cases, the preparatory regimen can be mammalian leukocytes fixed with a crosslinking agent, administered together with an anti-CD40 binding agent (e.g., agent comprising one or more amino acid sequences listed in any one of SEQ ID 1-6 and 8-17). In some cases, the preparatory regimen can be fixed mammalian leukocytes surface-conjugated with an anti-CD40 binding agent (e.g., agent comprising one or more amino acid sequences listed in any one of SEQ ID 1-6 and 8-17).

Robust tolerance to allografts can be achieved without requiring same donor bone marrow or hematopoietic stem cell transplantation with the associated intense conditioning therapy by employing a negative vaccine strategy. In an exemplary embodiment, a tolerizing vaccine or preparatory regimen of the disclosure can comprise administering an anti-CD40 agent or an anti-CD40 ligand agent, e.g., any one or more of the peptides comprising an amino acid sequence with at least 80%, at least 85%, at least 90% or at least 95% sequence identity to the sequences set forth in any one of SEQ ID NOs. 1-6 and 8-17. In addition, the tolerizing vaccine or preparatory regimen can further comprise immunosuppression agents such as (i) an mTOR inhibitor, (ii) an anti-tumor necrosis factor agent or an anti-tumor necrosis factor receptor agent, or (iii) an anti-interleukin 6 agent or an anti-interleukin 6 receptor agent.

In another embodiment, a tolerizing vaccine or preparatory regimen of the disclosure can comprise administering apoptotic cells (e.g., apoptotic donor leukocytes) to a recipient conjugated to an anti-CD40 agent or an anti-CD40 ligand agent, e.g., any one or more of the peptides comprising an amino acid sequence with at least 80%, at least 85%, at least 90% or at least 95% sequence identity to the sequences set forth in any one of SEQ ID NOs. 1-6 and 8-17. The short-term administration of these agents along with apoptotic donor leukocytes as disclosed herein can promote long-term tolerance to a transplanted cell, organ, or tissue despite not administering long term maintenance immunosuppression to the recipient.

Sources of Cells for a Tolerizing Vaccine/Regimen or Preparatory Regimen

Cells for the preparation of a tolerizing vaccine or preparatory regimen can be obtained from any source, including animals, cells lines, and/or lab-generated cells. For example, the cells can be obtained from a human or non-human animal. In another example, the cells can be from a cell line (e.g., a human or non-human cell line). In some cases, the cells are human cells. In other cases, the cells are non-human cells. In some cases, the cells are of a non-human primate. In some cases, the cells are of a member of the Laurasiatheria superorder. In some cases, the cells are of an ungulate, for instance a camelid or a pig. In some cases, the cells are of a pig. In some cases, the cells are from the same species as the transplant donor. In some cases, the cells are from the same species as the transplant recipient. In some cases, the cells are from the same species as the transplant donor and the transplant recipient. In some cases, the cells are from a different species than the transplant donor. In some cases, the cells are from a different species than the transplant recipient. In some cases, the cells are from a different species than the transplant donor and the transplant recipient.

Cells for the preparation of a tolerizing vaccine or preparatory regimen can be obtained from living donors or cadaveric donors. In some cases, the donor is a living donor. In some cases, the donor is a cadaveric donor. The cadaveric donor may be, for example, a brain dead, heart beating donor (BDD). The cadaveric donor may be, for example, a non-heart beating donor (NHBD). Whether the donor is a living donor or a cadaveric donor (e.g., a BDD or NHBD), the donor can be from any animal, for example, a human or non-human animal. In some cases, cells for the preparation of a tolerizing vaccine can be from the same donor as a graft or transplant. In some cases, cells for the preparation of a tolerizing vaccine can be from a different donor than the graft or transplant.

Cells for the preparation of a tolerizing vaccine or preparatory regimen can be obtained from a donor animal of any age or stage of development. For example, the donor animal can be a fetal, perinatal, neonatal, pre-weaning, post-weaning, juvenile, young adult, or adult animal. In some cases, non-human animals can be past weaning age. For example, donor animals can be at least or at least about six months old. In some cases, donor animals can be at least or at least about 18 months old. In some cases, cells for the preparation of a tolerizing vaccine or preparatory regimen can be obtained (for example, differentiated) from stem cells (e.g., embryonic stem cells, induced pluripotent stem cells, and/or mesenchymal stem cells).

The cells used to make a tolerizing vaccine or preparatory regimen can include one or more cells from tissues, organs, or bodily fluids. For example, the cells can be from tissues, organs, or bodily fluids including, but not limited to: brain, lung, liver, heart, spleen, pancreas, small intestine, large intestine, skeletal muscle, smooth muscle, skin, bones, adipose tissues, hairs, thyroid, trachea, gall bladder, kidney, ureter, bladder, aorta, vein, esophagus, diaphragm, stomach, rectum, adrenal glands, bronchi, ears, eyes, retina, genitals, hypothalamus, larynx, nose, tongue, spinal cord, or ureters, uterus, ovary, testis, blood, spinal fluid, lymph fluid, or a combination thereof.

The cells used to make a tolerizing vaccine or preparatory regimen can include one or more types of cells. For example, the cells can include, but are not limited to: trichocytes, keratinocytes, gonadotropes, corticotropes, thyrotropes, somatotropes, lactotrophs, chromaffin cells, parafollicular cells, glomus cells melanocytes, nevus cells, Merkel cells, odontoblasts, cementoblasts corneal keratocytes, retina Muller cells, retinal pigment epithelium cells, neurons, glias (e.g., oligodendrocyte astrocytes), ependymocytes, pinealocytes, pneumocytes (e.g., type I pneumocytes, and type II pneumocytes), clara cells, goblet cells, G cells, D cells, ECL cells, gastric chief cells, parietal cells, foveolar cells, K cells, D cells, I cells, goblet cells, paneth cells, enterocytes, microfold cells, hepatocytes, hepatic stellate cells (e.g., Kupffer cells from mesoderm), cholecystocytes, centroacinar cells, pancreatic stellate cells, pancreatic a cells, pancreatic f3 cells, pancreatic 5 cells, pancreatic F cells (e.g., PP cells), pancreatic c cells, thyroid (e.g., follicular cells), parathyroid (e.g., parathyroid chief cells), oxyphil cells, urothelial cells, osteoblasts, osteocytes, chondroblasts, chondrocytes, fibroblasts, fibrocytes, myoblasts, myocytes, myosatellite cells, tendon cells, cardiac muscle cells, lipoblasts, adipocytes, interstitial cells of cajal, angioblasts, endothelial cells, mesangial cells (e.g., intraglomerular mesangial cells and extraglomerular mesangial cells), juxtaglomerular cells, macula densa cells, stromal cells, interstitial cells, telocytes simple epithelial cells, podocytes, kidney proximal tubule brush border cells, sertoli cells, leydig cells, granulosa cells, peg cells, germ cells, spermatozoon ovums, lymphocytes, myeloid cells, endothelial progenitor cells, endothelial stem cells, angioblasts, mesoangioblasts, pericyte mural cells, mesenchymal stromal cells, or splenocytes (e.g., T lymphocytes, B lymphocytes, dendritic cells, microphages, leukocytes). In some cases, the cells used to make a tolerizing vaccine or preparatory regimen comprise a cell type that expresses MHC class II. In some cases, the cells used to make a tolerizing vaccine or preparatory regimen comprise a cell type that does not expresses MHC class II.

A tolerizing vaccine or preparatory regimen can comprise leukocytes. Leukocytes can include, for example, neutrophils, eosinophils, basophils, lymphocytes, monocytes, or a combination thereof. Lymphocytes can include, for example, B lymphocytes (B cells), T lymphocytes (T cells), natural killer (NK) cells, or a combination thereof.

Leukocytes in a tolerizing vaccine or preparatory regimen can be obtained from any source, including, for example, a donor, a cell line, or a differentiated stem cell. Leukocytes obtained from a donor can include leukocytes obtained from a spleen (e.g., splenocytes, splenic B cells); a liver; peripheral blood (including peripheral blood B cells); a lymph node; a thymus; bone marrow; or any other organ, tissue, or bodily fluid; or any combination thereof. In some cases, the tolerizing vaccine or preparatory regimen comprises splenic B cells, peripheral blood B cells, or a combination thereof. In some cases, the tolerizing vaccine or preparatory regimen comprises cells mobilized from the bone marrow to peripheral blood with a mobilization agent, e.g., cells mobilized with granulocyte colony-stimulating factor (G-CSF), granulocyte macrophage colony-stimulating factor (GM-CSF), mozobil, or a combination thereof. The leukocytes in the tolerizing vaccine or preparatory regimen that are obtained from a donor can comprise primary cells, cells expanded ex vivo, or a combination thereof.

Genetically Modified Cells for a Tolerizing Vaccine or Preparatory Regimen

A donor of cells used in the preparation of a tolerizing vaccine or preparatory regimen can be genetically modified. Alternatively, or additionally, cells obtained from a donor can be genetically modified ex vivo. In some cases, cell lines are genetically modified to produce cells for use in a tolerizing vaccine or preparatory regimen. The genetically modified donors and/or cells can be produced using any method known in the art, including those described herein. Regardless of whether the genetically modified cells are isolated from a genetically modified animal, produced in culture, or a combination thereof, the genetically modified cells can be of any animal species, including human and non-human animals.

Genetically modified cells used in a tolerizing vaccine or preparatory regimen can comprise one or more genetic modifications that reduce or eliminate expression or a gene or gene product (e.g., a protein). The genetic modification(s) can be modifications to the gene whose expression is reduced or eliminated. Such genes can be referred to as disrupted genes. The genetic modification(s) can also be to areas of the genome separate from the gene whose expression is reduced or eliminated (for example, modification to a promoter, enhancer, silencer, transcription factor, etc.). The genetically modified cells used in the tolerizing vaccine or preparatory regimen can comprise, for example, 1, 2, 3, 4, 5, 6, 7, 8, 9, 10, 11, 12, 13, 14, 15, 16, 17, 18, 19, or 20, or more genes whose expression is reduced or eliminated by genetic modification.

Non-limiting examples of genes whose expression can be reduced or eliminated by genetic modification in the cells used in a tolerizing vaccine or preparatory regimen include, but are not limited to: alpha 1,3 galactosyltransferase (GGTA1); putative cytidine monophosphatase-N-acetyl-neuraminic acid hydroxylase-like protein (CMAH); β1,4 N-acetylgalactosaminyltransferase (B4GALNT2); a component of a major histocompatibility complex (MHC) I-specific enhanceosome (e.g., a NOD-like receptor family CARD domain containing 5 (NLRC5)); a transporter of an MHC I-binding peptide (e.g., transporter associated with antigen processing 1 (TAPI)); complement component 3 (C3); a CXC chemokine receptor 3 ligand (CXCL3); a CXC motif chemokine ligand10 (CXCL10) gene; MHC II transactivator (MHCIITA); a MHC class I polypeptide-related sequence A (MICA) gene; a MHC class I polypeptide-related sequence B (MICB) gene; a natural killer (NK) group 2D ligand (NKG2DL); a tumor necrosis factor receptor (TNF-R); a pig endogenous retrovirus (PERV); B2M, PD-1, PD-L1 or any combination thereof.

In some cases, the genetically modified cells used in a tolerizing vaccine can comprise disruptions in one or more genes comprising GGTA1, CMAH, B4GALNT2, B2M, NLRC5 or any combination thereof. For example, the genetically modified cells used to make a tolerizing vaccine or preparatory regimen can have disrupted GGTA1 only, or disrupted CMAH only, or disrupted B4GALNT2, B2M or NLRC5 only. The genetically modified cells used to make a tolerizing vaccine or preparatory regimen can also have disrupted GGTA1 and CMAH, disrupted GGTA1 and B4GALNT2, or disrupted CMAH and B4GALNT2, or disrupted NLRC5 and B2M. The genetically modified cells used to make a tolerizing vaccine or preparatory regimen can have disrupted GGTA1, CMAH, and B4GALNT2. Without wishing to be bound by any particular theory, such disruptions can minimize or eliminate cell-mediated immunity, antibody-mediated immunity, antibody-dependent cell-mediated immunity, and/or cell-dependent antibody-mediated immunity to organ, tissue, cell, and cell line grafts (e.g., xenografts or allografts comprising the same genetic modification(s) as the cells used in the tolerizing vaccine).

Genetically modified cells used in a tolerizing vaccine or preparatory regimen can comprise, or further comprise, one or more genetic modifications that increase expression of one or more genes or gene products. The increased expression can be from zero expression, e.g., the increased expression can be of a gene or gene product that is not normally expressed in the cell without genetic modification. The increased expression can be compared to a threshold level, e.g., a level normally expressed in the cell without genetic modification. The genetic modification(s) can comprise one or more exogenous polynucleotides encoding a polypeptide (e.g., an endogenous or exogenous polypeptide).

Non-limiting examples of exogenous polynucleotides include, but are not limited to, polynucleotides encoding one or more of an MHC I formation suppressor (e.g., an infected cell protein 47 (ICP47)); a regulator of complement activation (e.g., CD46, CD55, or CD59); an inhibitory ligand for NK cells; a B7 family member (e.g., a programmed death ligand such as PD-L1 or PD-L2); a serine protease inhibitor (e.g., Spi9); a galectin; an interleukin (e.g., IL-37); a CD40:CD40L blocking agent (e.g., a CD40 antagonist polypeptide, an anti-CD40 ligand polypeptide); a Fas ligand (FasL); any functional fragment thereof; or any combination thereof. In some embodiments, an inhibitory ligand for NK cells is a human leukocyte antigen (HLA), such as human leukocyte antigen E (HLA-E), human leukocyte antigen G (HLA-G), β-2-microglobulin (B2M) or any combination thereof. In some embodiments, the HLA-G is HLA-G1, HLA-G2, HLA-G3, HLA-G4, HLA-G5, HLA-G6, HLA-G7, or any combination thereof. In some cases, galectins is galectin-1, galectin-2, galectin-3, galectin-4, galectin-5, galectin-6, galectin-7, galectin-8, galectin-9, galectin-10, galectin-11, galectin-12, galectin-13, galectin-14, or galectin-15. For example, a galectin can be galectin-9.

Ex Vivo Expansion of Leukocytes

Donor leukocytes can be retrieved from a living donor's spleen. In one embodiment, B lymphocytes can be taken from the donor in one or more blood draws and/or apheresis procedures and optionally expanded ex vivo, or a separate cell donor can be identified that is a suitable match or partial match to the transplant donor. In some cases, separate donors can be used for the tolerogenic leukocytes and the allograft. For example, splenocytes from a cadaveric donor who is fully matched or partially matched (e.g., haploidentical) with the prospective living transplant donor are a clinically viable source of tolerogenic leukocytes. Upon availability of a matched, partially matched, or haploidentical spleen, a tolerization protocol can be initiated with the infusion of splenocytes on e.g., day −7 followed by the living donor transplant (e.g., a kidney transplant) on e.g., day 0 and the infusion of ex vivo expanded splenic B cells on e.g., on day +1.

Cells (e.g., leukocytes) used in preparing a tolerizing vaccine/regimen or preparatory regimen can be expanded ex vivo. In some cases, leukocyte cells can be expanded in vitro in the presence of one or more reagents for a predetermined amount of time prior to use as a tolerizing vaccine. For instance, the cells can be contacted with at least one cytokine for about 5, 10, 15, 20, 25, 30, 35, 40, 45, 50, 55, 60, 65, 70, 75, 80, 85, 90, 95, 100, 105, 110, 115, 120, 125, 130, 135, 140, 145, 160, 165, 170, 175, 180, 190, 200, 210, 220, 230, 240, 250, 260, 270, 280, 390, or 300 hours. In some cases, the cells can be contacted with at least one cytokine for about 10, 11, 12, 13, 14, 15, 16, 17, 18, 19, 20, 21, 22, 23, 24, 25, 26, 27, 28, 29, 30, or more days. In some cases, the cells can be contacted with at least one cytokine for about 1 to 2, 2 to 3, 3 to 4, 1 to 4, 1 to 3, or 2 to 4 weeks. In some cases, the cytokine is one or more interleukin. In some cases, the interleukin (IL) is at least one of IL-2, IL-4, IL-21, BAFF, multimer CD40L, IL-10, IL-12, and IL-15. In some cases, the cells are contacted with IL-2, IL-4, IL-21, BAFF, and multimer CD40L.

Leukocytes used in a tolerizing vaccine/regimen or preparatory regimen can comprise at least or at least about 10%, e.g., 25%, CD19 positive, CD20 positive, or CD21 positive MHC Class II positive B cells. For example, donor splenocytes can comprise at least or at least about 10%, 15%, 20%, 25%, 30%, 35%, 40%, 45%, 50%, 55%, 60%, 65%, 70%, 75%, or 80% CD19, CD20, and/or CD21 positive MHC Class II positive B cells, e.g., about, at least, or at least about 10 to 20; 20 to 30; 30 to 40; 40 to 50; 50 to 60%, or 60 to 70%. In some cases, splenic B cells or leukocytes used in a tolerizing vaccine/regimen or preparatory regimen can comprise at least or at least about 60%, e.g., 90%, CD19, CD20, or CD21 positive MHC Class II positive B cells. For example, splenic B cells or leukocytes used in a tolerizing vaccine/regimen or preparatory regimen can comprise can comprise about, at least, or at least about 60%, 65%, 70%, 75%, 80%, 85%, 90% or 95% CD19, CD20, or CD21 positive MHC Class II positive B cells e.g., at least or at least about 60 to 70; 70 to 80; 80 to 90; or 90 to 95%. In some cases, donor splenocytes or leukocytes used in a tolerizing vaccine/regimen or preparatory regimen can comprise from or from about 50% to 100%, e.g., from or from about 60% to 100% or 80% to 100%, CD19, CD20, or CD21 positive MHC Class II positive B cells. In some embodiments the MHC class II is swine leukocyte antigen (SLA) Class II. In some embodiments the MHC class II is human leukocyte antigen (HLA) Class II.

Generating Cells for a Tolerizing Vaccine or Preparatory Regimen

A tolerizing agent of the methods herein can comprise apoptotic cells, non-apoptotic cells, or a combination thereof. Cells for a tolerizing vaccine or preparatory regimen can be made apoptotic a number of different ways. For example, the cells can be contacted with a chemical (e.g., a fixative or cross-linking agent, a cellular damaging agent, or a combination thereof), to make some or all of the cells apoptotic. In another example, the cells can be irradiated (e.g., with ultraviolet radiation, gamma radiation, etc.) to make some or all of the cells apoptotic.

Cells for a tolerizing vaccine or preparatory regimen can be contacted with a chemical, such as a fixative or cross-linking agent, a carbodiimide, or a carbodiimide deriviative, a diimidoester, a sulfhydryl-to-sulfhydryl crosslinker, an amine-to-sulfhydryl crosslinker, a sulfhydryl-to-carbohydrate crosslinker, a photoreactive crosslinker, an in vivo crosslinker, a cellular damaging agent or an apoptosis inducer. The contacting can make some or all of the cells apoptotic. Suitable fixatives or cross-linking agents include, but are not limited to: an amine-to-amine crosslinker, a sulfhydryl-to-sulfhydryl crosslinker, an amine-to-sulfhydryl crosslinker, an in vivo crosslinker, a sulfhydryl-to-carbohydrate crosslinker, a photoreactive crosslinker, a chemoselective ligation crosslinking agent, a carboxyl-to-amine crosslinker, a carbodiimide, genipin, acrylic aldehyde, diformyl, osmium tetroxide, a diimidoester, mercuric chloride, zinc sulphate, zinc chloride, trinitrophenol (picric acid), potassium dichromate, ethanol, methanol, acetone, acetic acid, or a combination thereof.

The carbodiimide can comprise ethylcarbodiimide; ethylene carbodiimide; N,N'-diisopropylcarbodiimide (DIC); N,N'-dicyclohexylcarbodiimide (DCC); 1-ethyl-3-(3-dimethylaminopropyl)-carbodiimide (EDCI, EDC, ECDI, or EDAC); or a combination thereof. In some cases, the carbodiimide comprises ethylcarbodiimide. In some cases, the carbodiimide comprises ethylene carbodiimide. In some cases, the carbodiimide comprises N,N'-diisopropylcarbodiimide (DIC). In some cases, the carbodiimide comprises N,N'-dicyclohexylcarbodiimide (DCC). In some cases, the carbodiimide comprises 1-ethyl-3-(3-dimethylaminopropyl)-carbodiimide (EDCI, EDC, ECDI, or EDAC). In some cases, the tolerizing vaccine comprises cells treated with EDCI derivatives and/or functionalized EDCI. Methods of preparation, administration and use of tolerizing agent e.g., a tolerizing vaccine is well known in the art, for example, see U.S. Pat. No. 8,734,786B2, U.S. Pat. No. 9,888,673B2.

Cells for a tolerizing vaccine or preparatory regimen can be contacted with a diimidoester. The contacting can be for a pre-determined time. The contacting can make some or all of the cells apoptotic. The diimidoester can comprise cyanuric chloride; diisocyanate; diethylpyrocarbonate (DEPC) or diethyl dicarbonate; a maleimide; benzoquinone; or a combination thereof.

Cells for a tolerizing vaccine or preparatory regimen can be contacted with an amine-to-amine crosslinker. The contacting can be for a pre-determined time. The contacting can make some or all of the cells apoptotic. In some cases, the amine-to-amine-crosslinker comprises disuccinimidyl glutarate (DSG); disuccinimidyl suberate (DSS); bis(sulfosuccinimidyl)suberate (BS3); tris-(succinimidyl) aminotriacetate (TSAT); BS(PEG)5; BS(PEG)9; dithiobis (succinimidyl propionate) (DSP); 3,3'-dithiobis (sulfosuccinimidyl propionate) (DTSSP); disuccinimidyl tartrate (DST); bis(2-(succinimidooxycarbonyloxy)ethyl) sulfone (BSOCOES); ethylene glycol bis(succinimidyl succinate) (EGS); sulfo-EGS; or any combination thereof. In some cases, the amine-to-amine crosslinker comprises an imidoester, such as dimethyl adipimidate (DMA); dimethyl pimelimidate (DMP); dimethyl suberimidate (DMS); dimethyl 3,3'-dithiobispropionimidate (DTBP); or any combination thereof. In some cases, the amine-to-amine crosslinker comprises a difluoro, such as 1,5-difluoro-2,4-dinitrobenzene (DFDNB).

Cells for a tolerizing vaccine or preparatory regimen can be contacted with a sulfhydryl-to-sulfhydryl crosslinker. The contacting can be for a pre-determined time. The contacting can make some or all of the cells apoptotic. In some cases, the sulfhydryl-to-sulfhydryl crosslinker comprises a maleimide, such as bismaleimidoethane (BMOE); 1,4-bismaleimidobutane (BMB); bismaleimidohexane (BMH); tris(2-maleimidoethyl)amine (TMEA); BM(PEG)2 (such as 1,8-bismaleimido-diethyleneglycol); BM(PEG)3 (such as 1,11-bismaleimido-triethyleneglycol), dithiobismaleimidoethane (DTME); or any combination thereof.

Cells for a tolerizing vaccine or preparatory regimen can be contacted with an amine-to-sulfhydryl crosslinker. The contacting can be for a pre-determined time. The contacting can make some or all of the cells apoptotic. In some cases, the amine-to-sulfhydryl crosslinker comprises a NHS-haloacetyl crosslinker, a NHS-maleimide, a NHS-pyridyldithiol crosslinker, a sulfosuccinimidyl 4-(N-maleimidomethyl)cyclohexane-1-carboxylate (SMCC) crosslinker, or any combination thereof. The NHS-haloacetyl crosslinkers can comprise succinimidyl iodoacetate (SIA); succinimidyl 3-(bromoacetamido)propionate (SBAP); succinimidyl (4-iodoacetyl)aminobenzoate (SIAB); sulfo-SIAB; or a combination thereof. The NHS-maleimide can comprise N-α-maleimidoacet-oxysuccinimide ester (AMAS); N-β-maleimidopropyl-oxysuccinimide ester (BMPS); N-γ-maleimidobutyryl-oxysuccinimide ester (GMBS); sulfo-GMBS; m-maleimidobenzoyl-N-hydrosuccinimide ester (MBS); sulfo-MBS; SMCC; sulfo-SMCC; N-ε-maleimidocaproyl-oxysuccinimide ester (EMCS); sulfo-EMCS; succinimidyl 4-κ-maleimidophenyl)butyrate (SMPB); sulfo-SMPB; succinimidyl 6-((beta-maleimidopropionamido) hexanoate) (SMPH); sulfosuccinimidyl 4-(N-maleimidomethyl)cyclohexane-1-carboxy-(6-amidocaproate) (LC-SMCC); N-κ-maleimidoundecanoyl-oxysulfosuccinimide ester (sulfo-KMUS); or a combination thereof. The NHS-pyridyldithiol crosslinker can comprise succinimidyl 3-(2-pyridyldithio)propionate (SPDP), succinimidyl 6-(3(2-pyridyldithio)propionamido)hexanoate (LC-SPDP), sulfo-LC-SPDP, or 4-succinimidyloxycarbonyl-alpha-methyl-α(2-pyridyldithio)tolune (SMPT).

Cells for a tolerizing vaccine or preparatory regimen can be contacted with a sulfhydryl-to-carbohydrate crosslinker. The contacting can be for a pre-determined time. The contacting can make some or all of the cells apoptotic. In some cases, the sulfhydryl-to-carbohydrate crosslinker comprises (N-β-maleimidopropionic acid hydrazide (BMPH), N-ε-maleimidocaproic acid hydrazide (EMCH), 4-(4-N-maleimidophenyl)butyric acid hydrazide (MPBH), N-κ-maleimidoundecanoic acid hydrazide (KMUH), 3-(2-pyridyldithio)propionyl hydrazide (PDPH), or any combination thereof.

In some cases, the carboxyl-to-amine crosslinker is dicyclohexylcarbodiimide (DCC), 1-ethyl-3-(3-dimethylaminopropyl)-carbodiimide (EDCI, EDC, or EDAC), N-hydroxysuccinimide (NHS), sulfo-NHS, or any combination thereof.

Cells for a tolerizing vaccine or preparatory regimen can be contacted with a photoreactive crosslinker. The contacting can be for a pre-determined time. The contacting can make some or all of the cells apoptotic. In some cases, the photoreactive crosslinker comprises a NHS ester/aryl azide, a NHS ester/diazirine, or a combination thereof. The NHS ester/aryl azide can comprise N-5-azido-2-nitrobenzoyloxysuccinimide (ANB-NOS), sulfo-SANPAH, or a combination thereof. The NHS ester/diazirine can comprise SDA (NHS-diazirine/succinimidyl 4,4'-azipentanoate), sulfo-SDA, LC-SDA (NHS-LC-diazirine/succinimidyl 6-(4,4'-azipentanamido)hexanoate), sulfo-LC-SDA, SDAD (NHS-SS-diazirine/succinimidyl 2-((4,4'-azipentanamido)ethyl)1, 3'-dithiopropionate), sulfo-SDAD, or a combination thereof.

Cells for a tolerizing vaccine or preparatory regimen can be contacted with an in vivo crosslinker. The contacting can be for a pre-determined time. The contacting can make some or all of the cells apoptotic. The in vivo crosslinker can comprise BS3, DTSSP, sulfo-EGS, DSG, DSP, DSS, EGS, sulfo-SDA, sulfo-LC-SDA, sulfo-SDAD, SDA, LC-SDA, SDAD, NHS-ester diazirine, or any combination thereof.

In some cases, the cells for use in a tolerizing vaccine or preparatory regimen are treated with a cellular damaging agent or an apoptosis inducer. In some cases, the cellular damaging agent induces apoptosis in some or all of the contacted cells. Non-limiting exemplary cellular damaging agents include doxorubicin, staurosporine, etoposide, comptothecin, paclitaxel, vinblastine, or any combination thereof. Non-limiting exemplary apoptosis inducers include marinopyrrole A, maritoclax, (E)-3,4,5,4'-tetramethoxystilbene, 17-(Allylamino)-17-demethoxygeldanamycin, 2,4,3',5'-tetramethoxystilbene, 2OHOA, 6,8-bis(benzylthio)-octanoic acid, AT101, apoptolidin, FU 40A, ara-G hydrate, arylquin 1, BAD, BAM7, BAX activator molecule 7, BH3I-1, BID, BMS-906024, BV02, bendamustine, borrelidin, borrelidine, cyclopentanecarboxylic acid, NSC 216128, treponemycin, brassinin, brassinine, brefeldin A, ascotoxin, BFA, cyanein, decumbin, bufalin, CCF642, CCT007093, CD437, CHM-1 hydrate, 2-(2-fluorophenyl)-6,7-methylenedioxy-2-4-quinolone hydrate, NSC 656158, CIL-102, CP-31398, dihydrochloride hydrate, camalexin, 3-(Thiazol-2-yl)-1H-indole, camalexine, carboxyatractyloside, cepharanthine, cepharanthine, cinnabarinic acid, cirsiliol, combretastatin A4, costunolide, DBeQ, DIM-C-pPhtBu, DMXAA, DPBQ, enniatin A1, enniatin A, enniatin B1, enniatin B, erastin, eupatorin, FADD, fluticasone propionate, fosbretabulin disodium, GO-201 trifluoroacetate, gambogic acid, HA 14-1, HMBA, hexaminolevulinate (HAL), IMB5046, IMS2186, ikarugamycin, imiquimod, iniparib, kurarinone, LLP-3, lipocalin-2, lometrexol, MI-4F, ML 210, ML291, mollugin, muristerone A, NA-17, NID-1, NPC26, NSC59984, Nap-FF, neocarzinostatin, nifetepimine, nitidine chloride, nutlin-3, nutlin-3a, PKF118-310, PRIMA-1, PRT4165, pemetrexed, penta-O-galloyl-β-D-glucose hydrate, phenoxodiol, prodigiosin (PG), psoralidin, pterostilbene, raltitrexed, raptinal, ridaifen-B, rifabutin, roslin 2, s-p-bromobenzylglutathione cyclopentyl diester, SJ-17255, SMBA1, STF-62247, suprafenacine, syrosingopine, talniflumate, taurolidine, temoporfin, temozolomide, tetrazanbigen, thaxtomin A, thiocolchicine, tirapazamine, UCD38B, UMI-77, undecylprodigiosin, VK3-OCH3, vacquinol-1, violacein, vosaroxin, zerumbone, gAcrp30, gAcrp30/adipolean, or any combination thereof. Cells contacted with a cellular damaging agent or an apoptosis inducer may subsequently be contacted with a fixative or cross-linking agent.

Cells for a tolerizing vaccine or preparatory regimen can be made apoptotic by contacting the cells with a chemical (e.g., a fixative or cross-linking agent, a cellular damaging agent, or a combination thereof) for a predetermined amount of time. In some embodiments, the cells in the tolerizing vaccine or the preparatory regimen are made apoptotic by fixing for a predetermined amount time with the crosslinking agent (e.g., ECDI). In some cases, the predetermined amount of time is about 30 minutes, about 1 hour, about 2 hours, about 3 hours, about 4 hours, about 5 hours, about 6 hours, about 12 hours, about 18 hours, about 24 hours, about 36 hours, about 48 hours, about 60 hours, or about 72 hours. In some cases, the predetermined amount of time is less than an hour. In some cases, the predetermined time is at least about 1 minute, 5 minutes, 10 minutes, 20 minutes, 30 minutes, 40 minutes, 50 minutes, 60 minutes, 75, minutes, 90 minutes, 120 minutes, 150 minutes, 180 minutes, 210 minutes or 240 minutes. In some cases, the predetermined time is at most about 30 minutes, 40 minutes, 50 minutes, 60 minutes, 75, minutes, 90 minutes, 120 minutes, 150 minutes, 180 minutes, 210 minutes or 240 minutes. In some cases, the predetermined amount of time is about 1 minute to about 240 minutes, 1 minute to about 10 minutes, 10 minutes to about 240 minutes, about 10 minutes to about 180 minutes, about 10 minutes to about 120 minutes, about 10 minutes to about 90 minutes, about 10 minutes to about 60 minutes, about 10 minutes to about 30 minutes, about 30 minutes to about 240 minutes, about 30 minutes to about 180 minutes, about 30 minutes to about 120 minutes, about 30 minutes to about 90 minutes, about 30 minutes to about 60 minutes, about 50 minutes to about 240 minutes, about 50 minutes to about 180 minutes, about 50 minutes to about 120 minutes, about 50 minutes to about 90 minutes, about 50 minutes to about 60 minutes, about 10 minutes to about 20 minutes, about 20 minutes to about 30 minutes, about 30 minutes to about 40 minutes, about 40 minutes to about 50 minutes, about 50 minutes to about 60 minutes, about 60 minutes to about 70 minutes, about 70 minutes to about 80 minutes, about 80 minutes to about 90 minutes, about 90 minutes to about 100 minutes, about 100 minutes to about 110 minutes, about 110 minutes to about 120 minutes, about 10 minutes to about 30 minutes, about 30 minutes to about 50 minutes, about 50 minutes to about 70 minutes, about 70 minutes to about 90 minutes, about 90 minutes to about 110 minutes, about 110 minutes to about 130 minutes, about 130 minutes to about 150 minutes, about 150 minutes to about 170 minutes, about 170 minutes to about 190 minutes, about 190 minutes to about 210 minutes, about 210 minutes to about 240 minutes, up to about 30 minutes, about 30 minutes to about 60 minutes, about 60 minutes to about 90 minutes, about 90 minutes to about 120 minutes, or about 120 minutes to about 150 minutes.

The contacting can be at any temperature. In some cases the contacting is performed on ice (e.g., at 4° C.). In other cases, the contacting is performed at room temperature. In some cases, the contacting is performed at a temperature of at least about 0° C., 2° C., 4° C., 8° C., 15° C., 20° C., 25, 30° C., 35° C., or 37° C. In some cases, the contacting is performed at a temperature of at most about 4° C., 8° C., 15° C., 20° C., 25, 30° C., 35° C., 37° C., or 40° C. In some cases, the contacting is performed at a temperature of about 0° C. to about 37° C., about 0° C. to about 25° C., about 0° C. to about 15° C., about 0° C. to about 10° C., about 0° C. to about 8° C., about 0° C. to about 6° C., about 0° C. to about 4° C., about 0° C. to about 2° C., about 2° C. to about 10° C., about 2° C. to about 8° C., about 2° C. to about 6° C., about 4° C. to about 25° C., about 4° C. to about 10° C., about 15° C. to about 37° C., about 15° C. to about 25° C., about 20° C. to about 40° C., about 20° C. to about 37° C., or about 20° C. to about 30° C.

Cells in a tolerizing vaccine or preparatory regimen can aggregate as a result of the method of making some or all of the cells apoptotic. For example, cells can aggregate after contacting with a chemical, such as a fixative or crosslinking agent. The predetermined amount of time that the cells are contacted with the chemical can be selected to minimize the amount of aggregation in the tolerizing vaccine or preparatory regimen. In some cases, aggregates can be removed, for example, by washing and/or filtration.

In some cases, a tolerizing vaccine or preparatory regimen can comprise from or from about 0.01 to 10 aggregates, per µl. For example, the tolerizing vaccine or preparatory regimen can comprise from or from about 0.01 to 1, 0.1 to 1, 0.25 to 1, 0.5 to 1, 1 to 5; or 1 to 10 aggregate per µL. The tolerizing vaccine or preparatory regimen can comprise less than about 0.1, 0.5, 0.75, 1, 5, or 10 aggregates per µL.

In some cases, the tolerizing vaccine or preparatory regimen can comprise less than 5 aggregates per µL. For example, the tolerizing vaccine or preparatory regimen can comprise less than about: 5, 4, 3, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, 0.1, 0.05, or 0.01 aggregates per µL.

In some case, the tolerizing vaccine or preparatory regimen comprises 1 or fewer aggregates per µL. For example, the tolerizing vaccine or preparatory regimen can comprise about 0.01, about 0.05, about 0.1, about 0.2, about 0.3, about 0.4, about 0.5 about 0.6, about 0.7, about 0.8, about 0.9, or about 1.0 aggregates per µL.

The tolerizing vaccine or preparatory regimen can include from or from about 0.01% to 10%, e.g., from or from about 0.01% to 2%, necrotic cells. For example, cells of a tolerizing vaccine or preparatory regimen can comprise from or from about 0.01% to 10%; 0.01% to 7.5%, 0.01% to 5%; 0.01% to 2.5%; or 0.01% to 1% necrotic cells. In some embodiments, the cells of a tolerizing vaccine or preparatory regimen of the disclosure can comprise at most about 0.01%, 0.1%, 1%, 2%, 3%, 4%, 5%, 6%, 7%, 8%, 9%, or 10% necrotic cells.

Molecules Conjugated on the Surface of Apoptotic Leukocytes

Immunomodulatory Molecules

As used herein, the term "conjugate" or "conjugated to," and the like refer to molecular entities (.e.g, peptides of the present disclosure and an apoptotic leucocyte) being linked together through covalent or non-covalent bonds. Conjugation may be accomplished by directly coupling the two molecular entities, e.g., creating an ester or amide from an hydroxyl group, amino group, and a carboxylic acid. Conjugation may be accomplished by indirectly coupling the two molecular entities, e.g., instituting a linking group such as a polyethylene glycol. Conjugation may be accomplished by modifying the molecular entities with chemical groups that react with one another, e.g., alkyne-functionalized entity with an azide-functionalized entity or the reduction of thiol groups on individual entities to form a disulfide bond. Conjugates such as ethylene carbodiimide (ECDI), hexamethylene diisocyanate, propyleneglycol di-glycidylether which contain 2 epoxy residues, and epichlorohydrin can be used for fixation of peptides or proteins to the apoptotic leucocyte surface. Reactive carboxyl groups on the surface of an apoptotic leukocyte can be joined to free amines (e.g., from Lys residues) on the peptide or protein, by reacting them with, for example, 1-ethyl-3-[3,9-dimethyl aminopropyl] carbodiimide hydrochloride (EDC) or N-hydroxysuccinimide ester (NHS). Similarly, the same chemistry may be used to conjugate free amines on the surface of an apoptotic leukocyte with free carboxyls (e.g., from the C-terminus, or from Asp or Glu residues) on the peptide or protein. Alternatively, free amine groups on the surface of an apoptotic leuckocyte may be covalently bound to peptides and proteins, or peptide or protein fusion proteins, using sulfo-SIAB chemistry, essentially as described by Arano et al. (1991) Chem. 2:71-6. A great variety of means, well known in the art, may be used to conjugate the peptides to surface of apoptotic leuckocytes. These methods include any standard chemistry which do not destroy or severely limit the biological activity of the peptides and that of the apoptotic leuckocytes, and which allow for a sufficient number of peptides to be conjugated to the surface in an orientation which allows for inducing tolerance. In some embodiments the C-terminal regions of a peptide are conjugated. In other embodiments, the N-terminus of a peptide can be conjugated onto the surface of the apoptotic leucocyte.

In one aspect, the present disclosure provides preparatory regimen and/or tolerizing vaccines and regimen comprising apoptotic cells such as leucocytes or mesenchymal stromal cells comprising one or more peptides conjugated to the surface of the apoptotic cell. In some cases, the one or more peptides can comprise an amino acid sequence set forth in any one of SEQ ID NOs. 1-6 and 8-17. In some cases, the peptide conjugated to the surface of an apoptotic cell such as a leukocyte can vary in length. In some cases, the one or more peptides can comprise a sequence set forth in any one of SEQ ID NOs. 1-6 and 8-17 and can be at least about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 125, 150, 275, 200, or 250 amino acids in length. In some cases, the one or more peptides can comprise a sequence from 80%, 85%, 90%, 91%, 92%, 93%, 94%, 95%, 96%, 97%, 97.5%, 98%, 98.5%, 99%, 99.5%, 99.9%, 99.95% or 100% identical to the sequences set forth in any of SEQ ID NOs. 1-6 and 8-17. For example, in some cases, the one or more peptides can comprise a sequence set forth in any one of SEQ ID NOs. 1-6 and 8-17 and can be about 9, about 10, about 1, about 20, about 25, about 30, about 35, about 40, about 45, about 50, about 55, about 60, about 75, about 80, about 90, about 100, about 120, about 140, about 150, about 160, about 170, about 180, about 200, about 220, about 250, about 270, about 300, about 330, about 350, about 400, about 440, about 500, about 600, about 700, about 800, about 900 or about 1000 amino acids in length. In some cases, the one or more peptides can comprise a sequence set forth in any one of SEQ ID NOs. 1-6 and 8-17 and be at most about 10, 11, 12, 13, 14, 15, 16, 17, 18, 19, 20, 21, 22, 23, 24, 25, 26, 27, 28, 29, 30, 40, 50, 60, 70, 80, 90, 100, 125, 150, 275, 200, or 250 amino acids in length. In some cases, the peptides be about 10, 11, 12, 13, 14, 15, 16, 17, 18, 19, 20, 21, 22, 23, 24, 25, 26, 27, 28, 29, 30, 40, 50, 60, 70, 80, 90, 100, 125, 150, 275, 200, or 250 amino acids in length. In some embodiments, the one or more peptides can comprise a sequence set forth in any one of SEQ ID NOs. 1-6 and 8-17 and can be about 5-250, 10-250, 20-250, 30-250, 50-250, 100-250, 5-100, 10-100, 20-100, 30-100, 50-100, 5-50, 10-50, 20-50, 30-50, 5-30, 10-30, 15-30, or 20-30 amino acids in length.

In some embodiments, the peptides conjugated on the surface of apoptotic leukocytes are derived from a MHC molecule. The term "MHC molecule" refers to a molecule comprising Major Histocompatibility Complex (MHC) glycoprotein protein sequences. The term "MHC" as used herein will be understood to refer to the Major Histocompatibility Complex, which is defined as a set of gene loci specifying major histocompatibility complex glycoprotein antigens including the human leukocyte antigen (HLA). The term "HLA" as used herein will be understood to refer to Human Leukocyte Antigens, which is defined as the major histocompatibility antigens found in humans. As used herein, "HLA" is the human form of "MHC" and therefore can be used interchangeably. Examples of HLA proteins that can be utilized in accordance with the presently disclosed and claimed inventive concept(s) include, but are not limited to, an HLA class I α chain, an HLA class II α chain and an HLA class II β chain. Specific examples of HLA class II α and/or β proteins that may be utilized in accordance with the presently disclosed and claimed inventive concept(s) include, but are not limited to, those encoded at the following gene loci: HLA-DRA; HLA-DRB1; HLA-DRB3,4,5; HLA-DQA; HLA-DQB; HLA-DPA; and HLA-DPB.

In some embodiments, the apoptotic cells further comprise one or more peptides derived from a MHC class I molecule. As such, the sequences of amino acid residues in the peptide can be substantially similar or functionally comparable to a polypeptide sequence in the MHC molecule. Thus, "a peptide derived from a MHC class II molecule" refers to a peptide that has a sequence "from a region in an MHC class II molecule" (e.g., the hypervariable region), and is a peptide that has a sequence 70%, 75%, 80%, 85%, 90%, 91%, 92%, 93%, 94%, 95%, 96%, 97%, 97.5%, 98%, 98.5%, 99%, 99.5%, 99.9%, 99.95% or 100% identical to the naturally occurring MHC amino acid sequence of the region. In some embodiments, the peptide derived from a MHC class II molecule can comprise a sequence from 70%, 75%, 80%, 85%, 90%, 91%, 92%, 93%, 94%, 95%, 96%, 97%, 97.5%, 98%, 98.5%, 99%, 99.5%, 99.9%, 99.95% or 100% identical to the hypervariable region of the MHC class II molecule. Thus, "a peptide derived from a MHC class I molecule" refers to a peptide that has a sequence "from a region in an MHC class I molecule" (e.g., the hypervariable region), and is a peptide that has a sequence 70%, 75%, 80%, 85%, 90%, 91%, 92%, 93%, 94%, 95%, 96%, 97%, 97.5%, 98%, 98.5%, 99%, 99.5%, 99.9%, 99.95% or 100% identical to the naturally occurring MHC amino acid sequence of the region. In some embodiments, the peptide derived from a MHC class I molecule will comprise a sequence from the hypervariable region of the MHC class I molecule.

The peptides derived from a recipient's MHC class II molecule may comprise an entire MHC class II molecule.

The peptides derived from a recipient's MHC class II molecule may comprise an entire α chain of DR, DQ or DP. The peptides derived from a recipient's MHC class II molecule may comprise entire β chain of DR, DQ, or DP. The peptides derived from a recipient's MHC class II molecule may comprise entire α1 and/or α2 domains of DR, DQ or DP. The peptides derived from a recipient's MHC class II molecule may comprise entire in and/or P2 domains of DR, DQ, or DP. The peptides derived from a recipient's MHC class II molecule may comprise MHC-DR1, MHC-DR2, MHC-DR3, MHC-DR4, and/or MHC-DR5.

The peptides derived from a recipient's MHC class II molecule may comprise a fragment of an α1 and/or α2 domain of DR, DQ or DP. The peptides derived from a recipient's MHC class II molecule may comprise a fragment of a β1 and/or β2 domain of DR, DQ, or DP. The peptides derived from a recipient's MHC class II molecule may comprise a fragment of MHC-DR1, MHC-DR2, MHC-DR3, MHC-DR4, and/or MHC-DR5. The peptides derived from a recipient's MHC class II molecule may comprise a sequence from a hypervariable region. The peptides derived from a recipient's MHC class II molecule can comprise an in silico-identified high, medium, or low affinity peptides from the hypervariable region of the DRB molecule (e.g., a 10, 11, 12, 13, 14, 15, 16, 17, 18, 19, or 20 amino acid peptide).

The peptides derived from a recipient's MHC class H molecule may be synthesized or recombinant. In some cases, the peptides derived from a recipient's MHC class II molecule may between about 10 and 30 amino acids in length. The peptides derived from a recipient's MHC class II molecule may be at least 10 to 30 amino acids in length. In some embodiments, the peptides derived from a recipient's MHC class II molecule can be at least about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 125, 150, 275, 200, or 250 amino acids in length. In some embodiments, the peptides derived from a recipient's MHC class II molecule can be at most about 10, 11, 12, 13, 14, 15, 16, 17, 18, 19, 20, 21, 22, 23, 24, 25, 26, 27, 28, 29, 30, 40, 50, 60, 70, 80, 90, 100, 125, 150, 275, 200, or 250 amino acids in length. In some embodiments, the peptides derived from a recipient's MHC class II molecule can be about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 125, 150, 275, 200, or 250 amino acids in length. In some embodiments, the peptides derived from a recipient's MHC class II molecule can be about 5-250, 10-250, 20-250, 30-250, 50-250, 100-250, 5-100, 10-100, 20-100, 30-100, 50-100, 5-50, 10-50, 20-50, 30-50, 5-30, 10-30, 15-30, or 20-30 amino acids in length.

Cells (e.g., leukocytes) for a tolerizing vaccine or preparatory regimen can be treated with a fixative or crosslinking agent (e.g., a carbodiimide such as ECDI) in the presence of one or more antigens and/or epitopes. In some cases, the epitopes can comprise a peptide containing an amino acid sequence set forth in any one of SEQ ID NOs. 1-6 and 8-17. In some cases, the antigens and/or epitopes can comprise antigens and/or epitopes from a transplant donor, a transplant recipient, a third party, or a combination thereof. In some cases, the cells in the tolerizing vaccine or preparatory regimen are coupled to recipient antigens and/or epitopes. In some cases, the cells in the tolerizing vaccine or preparatory regimen are coupled to third party antigens and/or epitopes. In some cases, the cells in the tolerizing vaccine or preparatory regimen are coupled to transplant donor antigens and/or epitopes.

In some embodiments, a "cocktail" of peptides can be conjugated on the surface of the apoptotic leucocytes. In some embodiments, the apoptotic cells such as leucocytes can comprise one or more peptides derived from MHC class II molecule. In some embodiments, the apoptotic cells such as leucocytes can comprise, for example, at least 2, 3, 5, 7, 10, 15, 20, 30, 40, 50, 100 or more peptides derived from a MHC class II molecule. In some embodiments, the apoptotic leucocytes can comprise one or more peptides derived from a MHC class I molecule. In some embodiments, the apoptotic cells such as leucocytes can comprise, for example, at least 2, 3, 5, 7, 10, 15, 20, 30, 40, 50, 100 or more peptides derived from a MHC class I molecule. A mixture of more than one peptide derived from a MHC class II molecule, has the advantage of inducing increased immune tolerance response in the recipient. The increased tolerance can be, for example, through a mechanism called linked supersession. The mechanism of linked suppression will be known to an artisan skilled in the art. For instance, peptides comprising sequences from hypervariable regions of α and β chains may be used in combination.

In certain embodiments, the size of a protein or a peptide that is conjugated to the surface of the apoptotic leukocyte may comprise, but is not limited to 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 amino molecules or greater, including any range or value derivable therein, or derivative thereof. It is contemplated that peptides might be altered by fusing or conjugating a heterologous peptide sequence with a particular function (e.g., for presentation as a protein complex, for enhanced immunogenicity, etc.).

Cells (e.g., leukocytes) for a tolerizing vaccine or preparatory regimen can be treated with a fixative or crosslinking agent (e.g., a carbodiimide such as ECDI) in the presence of one or more immunomodulatory molecules. In some cases, the one or more immunomodulatory molecules can comprise one or more peptides comprising an amino acid sequence set forth in any one of SEQ ID NOs. 1-6 and 8-17. In some cases, the one or more immunomodulatory molecules can comprise all or a portion of: IFN-γ, an NF-kB inhibitor, vitamin D3, siCD40, anti-CD40 antibody, cobalt protoporphyrin, insulin B9-23, α1-antitrypsin, a cluster of differentiation protein, a gp39 antagonist, α1-antitrypsin, CD47, PD-L1, PD-L2, CTLA-4, rapamycin, compstatin, abatacept, ipilimumab, or a combination thereof. The NF-kB inhibitor can comprise dehydroxymethylepoxyquinomicin (DH-MEQ), curcumin, triptolide, Bay-117085, or a combination thereof. The cluster of differentiation protein can comprise CD4, CD46, CD47, CD55, CD59, or a portion thereof, or a combination thereof.

In some embodiments, the one or more immunomodulatory molecules can comprise all or a portion of a calcineurin inhibitor (e.g., cyclosporine or tacrolimus), a costimulatory signal blockade, an IL-2 signaling inhibitor (e.g., daclizumab or basiliximab), a cell cycle blocker (e.g., mycophenolate mofetil (MMF) or azathioprine), a T cell recirculation inhibitor (e.g., FTY720 or another sphingosine 1-phosphate (SIP) receptor agonist), a nitrogen mustard alkylating agent (e.g., cyclophosphamide), a complement C3 or C5 inhibitor, or any combination thereof.

In some embodiments, the immunomodulatory molecules can target T cell receptor (TCR), CD3e, FK506-binding protein 12 (FKBP12), cytotoxic T lymphocyte associated protein 4 (CTLA-4), programmed cell death protein 1 (PD-1, e.g., pembrolizumab), programmed death ligand 1 (PD-L1, e.g., MPDL3280A), CD40L (CD154), CD40, inducible costimulatory (ICOS), IL-2, TNF-α (e.g., infliximab), IL-6 or IL-6R (e.g., tocilizumab, actemra, clazakizumab, ALD518, siltuximab, elsilimomab, sirukumab, sarilumab, olokizumab), IL-7, CD2, CD20, CD52, α-4 integrin, mTOR (e.g., rapamycin or everolimus), DNA synthesis, molecules in pro-inflammatory pathways (e.g., cytokines, α1-antitrypsin, NFkB), or any combination thereof.

Cells (e.g., leukocytes) for tolerizing vaccine or preparatory regimen can be treated with a fixative or crosslinking agent (e.g., a carbodiimide such as ECDI) in the presence of an agent that increases expression of anti-inflammatory cytokines in a recipient. In some cases, the agent can comprise one or more peptides comprising an amino acid sequence set forth in any one of SEQ ID NOs. 1-6 and 8-17. In some cases, the anti-inflammatory cytokines may include, for example, TGF-β, IL-10, IL-13, or a combination thereof. In some cases, the agent that increases expression of anti-inflammatory cytokines in the recipient comprises α1-antitrypsin.

In some cases where ADLs are administered to a transplant recipient multiple times, ADLs from all the doses can all be conjugated with the same immunomodulatory molecules, agents that increases expression of anti-inflammatory cytokines, and/or antigens or epitopes. In some cases where ADLs are administered to a transplant recipient multiple times, ADLs from one or more doses can be conjugated with a first set of immunomodulatory molecules, agents that increases expression of anti-inflammatory cytokines, and/or antigens or epitopes, and ADLs from other dose(s) can be conjugated with a different set of immunomodulatory molecules, agents that increases expression of anti-inflammatory cytokines, and/or antigens or epitopes.

Short Term Immunosuppression

In some cases, a preparatory regimen or tolerizing vaccine of the disclosure can comprise administering one or more immunosuppression agents and/or anti-inflammatory agents to a transplant recipient. For example, in some cases, the regimen may include administering one or more immunosuppression agents and/or anti-inflammatory agents in addition to apoptotic cells (such as apoptotic donor leukocytes or mesenchymal stromal cells). In other cases, the regimen may include administering one or more immunosuppression agents and/or anti-inflammatory agents in addition to an anti-CD40 agent, for e.g., a peptide comprising an amino acid sequence with at least 80%, at least 85%, at least 90% or at least 95% sequence identity to the sequences set forth in any one of SEQ ID NOs. 1-6 and 8-17.

In some embodiments, the short term immunosuppression comprises administering an antagonistic anti-CD40 agent. An anti-CD40 agent or an anti-CD40 ligand agent can be, for example, a peptide comprising an amino acid sequence with at least 80%, at least 85%, at least 90% or at least 95% sequence identity to the sequences set forth in any one of SEQ ID NOs. 1-6 and 8-17. In some cases, the anti-CD40 agent or an anti-CD40 ligand agent can be, for example, a peptide comprising an amino with at least 80%, 85%, 88%, 90%, 93%95% or 99% sequence identity to the sequences set forth in any one of SEQ ID NOs. 1-6 and 8-17.

In some cases, an anti-CD40 agent or an anti-CD40 ligand agent can be, for example, an antagonistic anti-CD40 antibody, and antagonistic anti-CD40 ligand antibody, or an antigen binding fragmented thereof. An anti-CD40 agent or an anti-CD40 ligand agent can be an antagonistic anti-CD40 antibody or antigen-binding fragment thereof. Non-limiting examples of antagonistic anti-CD40 antibodies include 2C10, 2C10R4, ASKP1240, 4D11, bleselumab, BI-655064, HCD122, CFZ533, ch5D12, CDP7657, and FFP104. In some cases, the anti-CD40 agent is ASKP1240. An anti-CD40 agent or an anti-CD40 ligand agent can be an antagonistic anti-CD40 ligand antibody or antigen-binding fragment thereof. Non-limiting examples of antagonistic anti-CD40 ligand antibodies include BG9588, ruplizumab, toralizumab, IDEC-131, dapirolizumab, letolizumab, BMS-986004, VIB4920, and MEDI4920.

In some cases, an immunosuppression agent used for short term immunosuppression can be any one or more of MMF (mycophenolate mofetil (Cellcept)), ATG (anti-thymocyte globulin), anti-CD154 (CD40L), alemtuzumab (Campath), CTLA4-Ig (Abatacept/Orencia), belatacept (LEA29Y), daclizumab (Ze-napax), basiliximab (Simulect), infliximab (Remicade), cyclosporin, deoxyspergualin, soluble complement receptor 1, cobra venom factor, compstatin, anti C5 antibody (eculizumab/Soliris), methylprednisolone, FTY720, everolimus, anti-CD154-Ab, leflunomide, anti-IL-2R-Ab, anti-CXCR3 antibody, anti-ICOS antibody, anti-OX40 antibody, and anti-CD122 antibody, human anti-CD154 monoclonal antibody, CD40 antagonist, and CD40L (CD154) antagonist.

In some cases, an immunosuppression agent used for short term immunosuppression can target T cell receptor (TCR), CD3e, FK506-binding protein 12 (FKBP12), cytotoxic T lymphocyte associated protein 4 (CTLA-4), programmed cell death protein 1 (PD-1), programmed death ligand 1 (PD-L1), CD40L (CD154), CD40, inducible costimulatory (ICOS), IL-2, TNF-α, IL-6, IL-7, CD2, CD20, CD52, α-4 integrin, mTOR (mechanistic target of rapamycin, everolimus, serolimus), DNA synthesis, or any combination thereof. In some cases, an immunosuppression agent used for short term immunosuppression can be a MHC/TCR interaction blockade, a nonselective depleting agent, calcineurin inhibitor, costimulatory signal blockade, cytokine blockade, lymphocyte depleting agent, cell adhesion inhibitor, IL-2 signaling inhibitor, cell cycle blocker, or any combination thereof. For example, the MHC/TCR interaction blockade can be anti-abTCR mAb T10B9. For example, the nonselective depleting agent can be anti-CD3 mAb (OKT3) or antithymocyte globulin (ATG). For example, the calcineurin inhibitor can be cyclosporine or tacrolimus. For example, the costimulatory signal blockade can be anti-CTLA-4 mAb, abatacept, ipilimumab, anti-PD-1 (such as pembrolizumab), anti-PD-L1 (such as MPDL3280A), anti-CD154 mAb, anti-CD40 mAb, or anti-ICOS mAb. For example, the cytokine blockade can be anti-CD25 mAb (such as daclizumab or basiliximab), anti-TNF (etanercept, infliximab, adalimumab, certolizumab pegol, and golimumab), anti-IL-6/IL-6R mAb (such as clazakizumab, ALD518, siltuximab, elsilimomab, sirukumab, olokizumab, sarilumab, tocilizumab, actemra), or anti-IL-7 mAb. For example, the lymphocyte depleting agent can be anti-CD2 mAb, fusion protein with IgG1 (such as alefacept), anti-CD20 mAb (such as rituximab), or anti-CD52 mAb (such as alemtuzumab). For example, the cell adhesion inhibitor can be anti-very large antigen 4 (VLA4) (such as natalizumab). For example, the IL-2 signaling inhibitor can be sirolimus (rapamycin) or everolimus. For example, the cell cycle blocker can be mycophenolate mofetil (MMF) or azathioprine.

Short term immunosuppression can comprise administering one or more immunosuppression agents and/or anti-inflammatory agents of the disclosure for at most about 100 days after a transplant. Short term immunosuppression can comprise administering one or more immunosuppression agents and/or anti-inflammatory agents of the disclosure, for example, for at most about 7, 8, 9, 10, 11, 12, 13, 14, 15, 16, 17, 18, 19, 20, 21, 22, 23, 24, 25, 26, 25, 28, 29, 30, 31, 32, 33, 34, 35, 40, 42, 49, 50, 55, 60, 70, 80, 90, or 100 days after a transplant. In some cases, short term immunosuppression can conclude within 28 days after a transplant. In some cases, short term immunosuppression can conclude about 21 days after a transplant.

In some embodiments, short term immunosuppression can begin prior to transplantation. For example, short term immunosuppression can commence about or at most about 1, 2, 3, 4, 5, 6, 7, 8, 9, 10, 11, 12, 13, 14, 15, 16, 17, 18, 19, 20, 21, 22, 23, 24, 25, 26, 25, 28, 29, 30, 35, or 50 days prior to a transplant. In some cases, short term immunosuppression can commence at most about 10 days prior to a transplant. In some cases, short term immunosuppression can commence about 7 days prior to a transplant.

The duration of short term immunosuppression (e.g., the length of time between administering a first dose and a final dose of an immunosuppression agents and/or anti-inflammatory agents can be about or at most about 7, 8, 9, 10, 11, 12, 13, 14, 15, 16, 17, 18, 19, 20, 21, 22, 23, 24, 25, 26, 25, 28, 29, 30, 31, 32, 33, 34, 35, 40, 42, 49, 50, 55, 60, 70, 80, 90, or 100 days. In some cases, the duration of short term immunosuppression can be about or at most about 30 days. In some cases, the duration of short term immunosuppression can be about 28 days.

Administration of Compositions in Combination with a Tolerizing Agent

In one aspect, a peptide or compositions disclosed herein can be administered as a tolerizing agent. In another embodiment, a peptide or compositions disclosed herein can be administered before, after, and/or during the administration of a tolerizing agent. In some cases, the peptide of compositions disclosed herein can be administered between day −100 and day 0, e.g., on day −90, day −80, day −70, day −60, day −50, day −40, day −30, day −20, day −15, day −14, day −13, day −12, day −11, day −10, day −9, day −8, day −7, day −6, day −5, day −4, day −3, day −2, day −1, or day 0 relative to the administration of a tolerizing agent. In some cases, the peptide or compositions disclosed herein can be administered concomitantly with the tolerizing agent. In some cases, the peptide or compositions disclosed herein can be administered on or on about day −100 to −50; −50 to −40; −40 to −30; −30 to −20; −20 to −10; −10 to −5; −7 to −1, relative to the administration of a tolerizing agent.

In some cases, the peptide or composition disclosed herein can be administered between day 0 and day 100, e.g., on day 100, day 90, day 80, day 70, day 60, day 50, day 40, day 30, day 20, day 15, day 14, day 13, day 12, day 11, day 10, day 9, day 8, day 7, day 6, day 5, day 4, day 3, day 2 or day 1 relative to the administration of a tolerizing agent. For example, the peptide or compositions disclosed herein can be administered on or on about day 100 to 50; 50 to 40; 40 to 30; 30 to 20; 20 to 10; 10 to 5; 7 to 1, relative to the administration of a tolerizing agent.

In some cases, the peptide or compositions disclosed herein can be administered between day 0 and day 300, e.g., on day 300, day 200, day 100, day 90, day 80, day 70, day 60, day 50, day 40, day 30, day 20, day 15, day 14, day 13, day 12, day 11, day 10, day 9, day 8, day 7, day 6, day 5, day 4, day 3, day 2 or day 1 relative to the administration of a tolerizing agent. For example, the peptide or compositions disclosed herein can be administered on or on about day 300 to 200; 200 to 100; 100 to 50; 50 to 40; 40 to 30; 30 to 20; 20 to 10; 10 to 5; 7 to 1, relative to the administration of a tolerizing agent.

In some cases, a peptide or compositions disclosed herein can be administered between day 0 and day 600, e.g., on day 600, day 500, day 400, day 300, day 200, day 100, day 90, day 80, day 70, day 60, day 50, day 40, day 30, day 20, day 15, day 14, day 13, day 12, day 11, day 10, day 9, day 8, day 7, day 6, day 5, day 4, day 3, day 2 or day 1 relative to the administration of a tolerizing agent. For example, a peptide or composition disclosed herein can be administered on or on about day 600 to 500; day 500 to 400; day 400 to 300; 300 to 200; 200 to 100; 100 to 50; 50 to 40; 40 to 30; 30 to 20; 20 to 10; 10 to 5; 7 to 1, relative to the administration of a tolerizing agent.

In some cases, a peptide or compositions disclosed herein can be administered between day 0 and day 1,000, e.g., on day 1,000, day 900, day 800, day 700, day 600, day 500, day 400, day 300, day 200, day 100, day 90, day 80, day 70, day 60, day 50, day 40, day 30, day 20, day 15, day 14, day 13, day 12, day 11, day 10, day 9, day 8, day 7, day 6, day 5, day 4, day 3, day 2 or day 1 relative to the administration of a tolerizing agent. For example, the a peptide or compositions disclosed herein can be administered on or on about day 1,000 to 900; 900 to 800; 800 to 700; 700 to 600; 600 to 500; day 500 to 400; day 400 to 300; 300 to 200; 200 to 100; 100 to 50; 50 to 40; 40 to 30; 30 to 20; 20 to 10; 10 to 5; 7 to 1, relative to the administration of a tolerizing agent.

In some cases, a peptide or compositions disclosed herein can be administered on the day when a tolerizing agent is administered. In other cases, a peptide or can be administered before and after the administration of the tolerizing vaccine or preparatory regimen.

A peptide or compositions disclosed herein can be administered before, after, and/or during the day of the transplantation of the graft cell, tissue, or organ. In some cases, the peptide of compositions disclosed herein can be administered between day −100 and day 0, e.g., on day −90, day −80, day −70, day −60, day −50, day −40, day −30, day −20, day −15, day −14, day −13, day −12, day −11, day −10, day −9, day −8, day −7, day −6, day −5, day −4, day −3, day −2, day −1, or day 0 relative to the day of the transplantation of the graft cell, tissue, or organ. In some cases, the peptide or compositions disclosed herein can be administered concomitantly with the day of the transplantation of the graft cell, tissue, or organ. In some cases, the peptide or compositions disclosed herein can be administered on or on about day −100 to −50; −50 to −40; −40 to −30; −30 to −20; −20 to −10; −10 to −5; −7 to −1, relative to the day of the transplantation of the graft cell, tissue, or organ.

In some cases, the peptide or composition disclosed herein can be administered between day 0 and day 100, e.g., on day 100, day 90, day 80, day 70, day 60, day 50, day 40, day 30, day 20, day 15, day 14, day 13, day 12, day 11, day 10, day 9, day 8, day 7, day 6, day 5, day 4, day 3, day 2 or day 1 relative to the day of the transplantation of the graft cell, tissue, or organ. For example, the peptide or compositions disclosed herein can be administered on or on about day 100 to 50; 50 to 40; 40 to 30; 30 to 20; 20 to 10; 10 to 5; 7 to 1, relative to the day of the transplantation of the graft cell, tissue, or organ.

In some cases, the peptide or compositions disclosed herein can be administered between day 0 and day 300, e.g., on day 300, day 200, day 100, day 90, day 80, day 70, day 60, day 50, day 40, day 30, day 20, day 15, day 14, day 13, day 12, day 11, day 10, day 9, day 8, day 7, day 6, day 5, day 4, day 3, day 2 or day 1 relative to the day of the transplantation of the graft cell, tissue, or organ. For example, the peptide or compositions disclosed herein can be administered on or on about day 300 to 200; 200 to 100; 100 to 50; 50 to 40; 40 to 30; 30 to 20; 20 to 10; 10 to 5; 7 to 1, relative to the day of the transplantation of the graft cell, tissue, or organ.

In some cases, a peptide or compositions disclosed herein can be administered between day 0 and day 600, e.g., on day 600, day 500, day 400, day 300, day 200, day 100, day 90, day 80, day 70, day 60, day 50, day 40, day 30, day 20, day 15, day 14, day 13, day 12, day 11, day 10, day 9, day 8, day 7, day 6, day 5, day 4, day 3, day 2 or day 1 relative to the day of the transplantation of the graft cell, tissue, or organ. For example, a peptide or composition disclosed herein can be administered on or on about day 600 to 500; day 500 to 400; day 400 to 300; 300 to 200; 200 to 100; 100 to 50; 50 to 40; 40 to 30; 30 to 20; 20 to 10; 10 to 5; 7 to 1, relative to the day of the transplantation of the graft cell, tissue, or organ.

In some cases, a peptide or compositions disclosed herein can be administered between day 0 and day 1,000, e.g., on day 1,000, day 900, day 800, day 700, day 600, day 500, day 400, day 300, day 200, day 100, day 90, day 80, day 70, day 60, day 50, day 40, day 30, day 20, day 15, day 14, day 13, day 12, day 11, day 10, day 9, day 8, day 7, day 6, day 5, day 4, day 3, day 2 or day 1 relative to the day of the transplantation of the graft cell, tissue, or organ. For example, the a peptide or compositions disclosed herein can be administered on or on about day 1,000 to 900; 900 to 800; 800 to 700; 700 to 600; 600 to 500; day 500 to 400; day 400 to 300; 300 to 200; 200 to 100; 100 to 50; 50 to 40; 40 to 30; 30 to 20; 20 to 10; 10 to 5; 7 to 1, relative to the day of the transplantation of the graft cell, tissue, or organ.

In some cases, a peptide or compositions disclosed herein can be administered on the day of the transplantation of the graft cell, tissue, or organ. In other cases, a peptide or can be administered before and after the day of the transplantation of the graft cell, tissue, or organ.

A preparatory regimen can comprise multiple doses of a peptide or composition described herein, before, and/or during and/or after transplantation of a graft cell, tissue, or organ. In some cases, a preparatory regimen can comprise multiple doses of a peptide comprising a sequence with at least 80%, 85% 90% or 95% sequence identity set forth in any one of SEQ ID NOs. 1-6 and 8-17, before, and/or during and/or after transplantation of a graft cell, tissue, or organ. A tolerizing regimen can comprise multiple doses of a peptide or composition described herein, before, and/or during and/or after transplantation of a graft cell, tissue, or organ. In some cases, a tolerizing regimen can comprise multiple doses of a peptide comprising a sequence with at least 80%, 85% 90% or 95% sequence identity set forth in any one of SEQ ID NOs. 1-6 and 8-17, before, and/or during and/or after transplantation of a graft cell, tissue, or organ. The multiple doses can be referred to as comprising an initial dose and one or more booster doses. The initial dose can occur prior to or concurrently with the transplant of the graft cell tissue or organ. The booster dose(s), when administered, occur after the initial dose. Depending upon when the initial dose of the tolerizing vaccine is administered, one or more booster doses can be administered before, and/or concurrently with, and/or after transplant of the graft cell, tissue, or organ.

Subsequent (e.g., booster) dose(s) of a preparatory regimen or tolerizing vaccine can be administered in any interval of time following a preceding dose (e.g., an initial dose). For example, the subsequent dose can be administered about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 90 days, 120 days, 150 days, or 180 days after the preceding dose.

Depending upon when the initial dose is administered subsequent (booster) dose(s) can be administered before, concurrently with, or after transplantation of the graft cell, tissue, or organ. In some cases, the preparatory regimen comprises at least one dose, at least two doses, at least three doses of a preparatory regimen or tolerizing vaccine prior to transplantation.

In some cases, two doses of the tolerizing vaccine or preparatory regimen can be administered. The first dose can be administered, for example, on day −14, −10, −9, −8, −7, −6, −5, −4, −3, −2, −1, 0, 1, 2, 3, 4, 5, 6, or 7 relative to transplant of donor cells, organs, and/or tissues on day 0. The second dose can be administered, for example, on day −3, −2, −1, 0, 1, 2, 3, 4, 5, 6, 7, 8, 9, 10, 11, 12, 13, 14, 15, 16, 17, 18, 19, 20, 21, 22, 23, 24, 25, 26, 27, or 28 relative to transplant of donor cells, organs, and/or tissues on day 0. In some embodiments, the first dose is administered on day −8 and the second dose is administered on day −1. In some embodiments, the first dose is administered on day −8 and the second dose is administered on day 0. In some embodiments, the first dose is administered on day −8 and the second dose is administered on day 1. In some embodiments, the first dose is administered on day −7 and the second dose is administered on day −1. In some embodiments, the first dose is administered on day −7 and the second dose is administered on day 0. In some embodiments, the first dose is administered on day −7 and the second dose is administered on day 1. In some embodiments, the first dose is administered on day −12 and the second dose is administered on day −4. In some embodiments, the first dose is administered on day −11, −12, −13, or −14 and the second dose is administered on day −3, −4, −5, or −6.

In some cases, a second dose of the tolerizing vaccine/preparatory regimen (e.g., a booster vaccine) can be administered on day 100, day 90, day 80, day 70, day 60, day 50, day 40, day 30, day 29, day 28, day 27, day 26, day 25, day 24, day 23, day 22, day 21, day 20, day 19, day 18, day 17, day 16, day 15, day 14, day 13, day 12, day 11, day 10, day 9, day 8, day 7, day 6, day 5, day 4, day 3, day 2 or day 1, relative to transplant of donor cells, organs, and/or tissues on day 0. For example, the second dose of the tolerizing vaccine (e.g., a booster vaccine) can be administered 1 day after transplant of donor cells, organs, and/or tissues. In some cases, a second dose of a tolerizing vaccine is given concomitantly on day 0 with transplant donor cells, organs, and/or tissues. In some cases, a second dose of a tolerizing vaccine is not required.

In some cases, three doses of the tolerizing vaccine/preparatory regimen or preparatory regimen can be administered. The first dose can be administered, for example, on day −14, −10, −9, −8, −7, −6, −5, −4, −3, −2, −1, 0, 1, 2, 3, 4, 5, 6, or 7 relative to transplant of donor cells, organs, and/or tissues on day 0. The second dose can be administered, for example, on day −3, −2, −1, 0, 1, 2, 3, 4, 5, 6, 7, 8, 9, 10, 11, 12, 13, 14, 15, 16, 17, 18, 19, 20, 21, 22, 23, 24, 25, 26, 27, or 28 relative to transplant of donor cells, organs, and/or tissues on day 0. The third dose can be administered, for example, on day 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 120, 150, 180, 200, 250, 300, 350, or 365 relative to transplant of donor cells, organs, and/or tissues on day 0. In some embodiments, the first dose is administered on day −8, the second dose is administered on day 1, and the third dose is administered on day 7. In some embodiments, the first dose is administered on day −8, the second dose is administered on day 1, and the third dose is administered on day 14. In some embodiments, the first dose is administered on day −8, the second dose is administered on day 1, and the third dose is administered on day 21. In some embodiments, the first dose is administered on day −7, the second dose is administered on day 1, and the third dose is administered on day 7. In some embodiments, the first dose is administered on day −7, the second dose is administered on day 1, and the third dose is administered on day 14. In some embodiments, the first dose is administered on day −7, the second dose is administered on day 1, and the third dose is administered on day 21.

In some cases, a third dose of the tolerizing vaccine/preparatory regimen (e.g., a booster vaccine) can be administered on day 300, day 200, day 100, day 90, day 80, day 70, day 60, day 50, day 40, day 30, day 29, day 28, day 27, day 26, day 25, day 24, day 23, day 22, day 21, day 20, day 19, day 18, day 17, day 16, day 15, day 14, day 13, day 12, day 11, day 10, day 9, day 8, day 7, day 6, day 5, day 4, day 3, day 2 or day 1, relative to transplant of donor cells, organs, and/or tissues on day 0. For example, the tolerizing vaccine can be administered on or on about day 300 to 200; 200 to 100; 100 to 50; 50 to 40; 40 to 30; 30 to 20; 20 to 10; 10 to 5; or 7 to 1, relative to transplant of donor cells, organs, and/or tissues on day 0.

In some cases, a fourth dose of the tolerizing vaccine/preparatory regimen (e.g., a booster vaccine) can be administered on day 600, day 500, day 400, day 300, day 200, 100, day 90, day 80, day 70, day 60, day 50, day 40, day 30, day 29, day 28, day 27, day 26, day 25, day 24, day 23, day 22, day 21, day 20, day 19, day 18, day 17, day 16, day 15, day 14, day 13, day 12, day 11, day 10, day 9, day 8, day 7, day 6, day 5, day 4, day 3, day 2 or day 1, relative to transplant of donor cells, organs, and/or tissues on day 0. For example, the tolerizing vaccine can be administered on or on about day 600 to 500; 500 to 400; 400 to 300; 300 to 200; 200 to 100; 100 to 50; 50 to 40; 40 to 30; 30 to 20; 20 to 10; 10 to 5; 7 to 1, relative to transplant of donor cells, organs, and/or tissues on day 0.

In some cases, a fifth dose of the tolerizing vaccine or preparatory regimen (e.g., a booster vaccine) can be administered on day 1,000, day 900, day 800, day 700, day 600, day 500, day 400, day 300, day 200, 100, day 90, day 80, day 70, day 60, day 50, day 40, day 30, day 29, day 28, day 27, day 26, day 25, day 24, day 23, day 22, day 21, day 20, day 19, day 18, day 17, day 16, day 15, day 14, day 13, day 12, day 11, day 10, day 9, day 8, day 7, day 6, day 5, day 4, day 3, day 2 or day 1, relative to transplant of donor cells, organs, and/or tissues on day 0. For example, the tolerizing vaccine can be administered on or on about day 1,000 to 900; 900 to 800; 800 to 700; 700 to 600; 600 to 500; 500 to 400; 400 to 300; 300 to 200; 200 to 100; 100 to 50; 50 to 40; 40 to 30; 30 to 20; 20 to 10; 10 to 5; 7 to 1, relative to transplant of donor cells, organs, and/or tissues on day 0.

Administration of the tolerizing vaccine or preparatory regimen can result in long term tolerance to the cell, tissue, or organ transplant in the transplant recipient. In some cases, the long term tolerance is for a period of at least one month, at least two months, at least three months, at least four months, at least five months, at least six months, at least seven months, at least eight months, at least nine months, at least ten months, at least eleven months, at least twelve months, at least thirteen months, at least fourteen months, at least fifteen months, at least sixteen months, at least seventeen months, at least eighteen months, at least nineteen months, at least twenty months, at least twenty-one months, at least twenty-two months, at least twenty-three months, or at least twenty-four months. In some cases, the long term tolerance is for a period of at least 1 year, at least 2 years, at least 3 years, at least 4 years, at least 5 years, at least 6 years, at least 7 years, at least 8 years, at least 9 years, or at least 10 years. In some cases, the long term tolerance is achieved in the absence of a booster vaccine or booster regimen. In some cases, the long term tolerance is achieved with an administration of a booster vaccine or booster regimen in one or multiple doses. In some cases, one or more booster vaccine doses are administered on the day of, or at least 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 65 days, 70 days, 75 days, 80 days, 85 days, 90 days, 95 days, 100 days, 105 days, 110 days, 115 days, 120 days, 125 days, 130 days, 135 days, 140 days, 145 days, 150 days, 155 days, 160 days, 165 days, 170 days 175 days, 180 days, 185 days, 190 days, 195 days, 200 days, 205 days, 210 days, 215 days, 220 days, 230 days or 240 days after the transplantation. In certain specific cases, one or more (for instance three) doses of a preparatory regimen is administered prior to transplantation, and one or more booster vaccine doses are provided 1, 7, 14, 21, 90, or up to 180 days after transplantation.

A tolerizing vaccine or preparatory regimen can be administered with or without an adjuvant (e.g., one or more immunomodulatory molecules). In some cases, the adjuvant enhances the tolerogenic properties of the tolerizing vaccine by inhibiting activation and maturation of antigen presenting cells.

A dose of a tolerizing vaccine or preparatory regimen can vary based upon the weight of a recipient of a tolerizing vaccine. For example, the dose of the tolerizing vaccine or preparatory regimen can comprise about: $1\times10^1$ cells/kg, $1\times10^2$ cells/kg, $1\times10^3$ cells/kg, $1\times10^4$ cells/kg, $1\times10^5$ cells/kg, $1\times10^6$ cells/kg, $1\times10^7$ cells/kg, $1\times10^8$ cells/kg, $1\times10^9$ cells/kg, $1\times10^{10}$ cells/kg, $1\times10^{11}$ cells/kg, $1\times10^{12}$ cells/kg, or more. In some cases, a dose of the tolerizing vaccine or preparatory regimen can comprises about: $1\times10^1$ to $1\times10^2$ cells/kg; $1\times10^2$ to $1\times10^3$ cells/kg; $1\times10^3$ to $1\times10^4$ cells/kg; $1\times10^4$ to $1\times10^5$ cells/kg; $1\times10^5$ to $1\times10^6$ cells/kg; $1\times10^6$ to $1\times10^7$ cells/kg; $1\times10^7$ to $1\times10^8$ cells/kg; $1\times10^8$ to $1\times10^9$ cells/kg; $1\times10^9$ to $1\times10^{10}$ cells/kg, $1\times10^{10}$ to $1\times10^{11}$ cells/kg, 1×1011 to 1×1012 cells/kg. For example, a dose of the tolerizing vaccine or preparatory regimen for administration can be about 0.01×10$^9$ cells/kg, 0.02×10$^9$ cells/kg, 0.03×10$^9$ cells/kg, 0.04×10$^9$ cells/kg, 0.05×10$^9$ cells/kg, 0.06×10$^9$ cells/kg, 0.07×10$^9$ cells/kg, 0.08×10$^9$ cells/kg, 0.09×10$^9$ cells/kg, 0.1×10$^9$ cells/kg, 0.2×10$^9$ cells/kg, 0.21× 10$^9$ cells/kg, 0.22×10$^9$ cells/kg, 0.23×10$^9$ cells/kg, 0.24× 10$^9$ cells/kg, 0.25×10$^9$ cells/kg, 0.26×10$^9$ cells/kg, 0.27× 10$^9$ cells/kg, 0.28×10$^9$ cells/kg, 0.29×10$^9$ cells/kg, 0.3×10$^9$ cells/kg, 0.4×10$^9$ cells/kg, 0.5×10$^9$ cells/kg, 0.6×10$^9$ cells/kg, 0.7×10$^9$ cells/kg, 0.8×10$^9$ cells/kg, 0.9×10$^9$ cells/kg, 1.0×10$^9$ cells/kg, 1.5×10$^9$ cells/kg, 2.0×10$^9$ cells/kg, 2.5× 10$^9$ cells/kg, 3.0×10$^9$ cells/kg, 3.5×10$^9$ cells/kg, 4.0×10$^9$ cells/kg, 4.5×10$^9$ cells/kg, 5.0×10$^9$ cells/kg, 5.5×10$^9$ cells/kg, 6.0×10$^9$ cells/kg, 6.5×10$^9$ cells/kg, 7.0×10$^9$ cells/kg, 7.5×10$^9$ cells/kg, 8.0×10$^9$ cells/kg, 8.5×10$^9$ cells/kg, 9.0× 10$^9$ cells/kg, 9.5×10$^9$ cells/kg, 10.0×10$^9$ cells/kg, or 25.0× 10$^9$ cells/kg.

In some cases, a dose of the tolerizing vaccine or preparatory regimen can comprise at least about: 1×10$^4$ cells/kg, 5×10$^4$ cells/kg, 1×10$^5$ cells/kg, 5×10$^5$ cells/kg, 1×10$^6$ cells/kg, 5×10$^6$ cells/kg, 1×10$^7$ cells/kg, 5×10$^7$ cells/kg, 1×10$^8$ cells/kg, 2×10$^8$ cells/kg, 3×10$^8$ cells/kg, 4×10$^8$ cells/kg, 5×10$^8$ cells/kg, 6×10$^8$ cells/kg, 7×10$^8$ cells/kg, 8×10$^8$ cells/kg, 9×10$^8$ cells/kg, 1×10$^9$ cells/kg, 1×10$^{10}$ cells/kg, or more.

The methods herein can comprise administering at least or at least about 0.25×10$^9$ cells (e.g., apoptotic donor leukocytes (ADLs), such as ECDI-treated cells, e.g., ECDI-treated leukocytes, or apoptotic mesenchymal stromal cells) per kg recipient body weight. For example, at least or at least about 1×10$^7$, 1×10$^8$, 0.25×10$^9$, 0.50×10$^9$, 0.75×10$^9$, 1.00× 10$^9$, 1.25×10$^9$, 1.50×10$^9$, 1.75×10$^9$ or 2×10$^9$ cells (e.g., ECDI-treated cells, e.g., ECDI-treated leukocytes) per kg recipient body weight ECDI-treated cells can be administered.

The cells can comprise leukocytes, e.g., splenocytes, peripheral blood mononuclear cells (PBMCs), stem-cell derived leukocytes, or a combination thereof. The splenocytes, PBMCs, stem-cell derived leukocytes, or the combination thereof can comprise B cells or B lymphocytes. The cells can comprise primary cells, cells expanded ex vivo, cells of a cell line, or a combination thereof. The cells can comprise mesenchymal stromal cells.

Cells of tolerizing vaccine/regimen or preparatory regimen for each dose of administration can be suspended in a volume suitable for transfusion. For example, the cells can be suspended in a volume of about: 0.1 ml, 0.2 ml, 0.3 ml, 0.4 ml, 0.5 ml, 0.6 ml, 0.7 ml, 0.8 ml, 0.9 ml, 1 ml, 2 ml, 3 ml, 4 ml, 5 ml, 6 ml, 7 ml, 8 ml, 9 ml, 10 ml, 11 ml, 12 ml, 13 ml, 14 ml, 15 ml, 16 ml, 17 ml, 18 ml, 19 ml, 20 ml, 21 ml, 22 ml, 23 ml, 24 ml, 25 ml, 26 ml, 27 ml, 28 ml, 29 ml, 30 ml, 31 ml, 32 ml, 33 ml, 34 ml, 35 ml, 36 ml, 37 ml, 38 ml, 39 ml, 40 ml, 41 ml, 42 ml, 43 ml, 44 ml, 45 ml, 46 ml, 47 ml, 48 ml, 49 ml, 50 ml, 60 ml, 70 ml, 80 ml, 90 ml, 100 ml, 200 ml, 300 ml, 400 ml, or 500 ml. For example, the cells of tolerizing vaccine or preparatory regimen for each dose of administration can be suspended in a volume of about: 0.1 ml to 1 ml; 1 ml to 10 ml; 10 ml to 50 ml; 50 ml to 100 ml; 100 ml to 200 ml; 200 ml to 300 ml; 300 ml to 400 ml; or 400 ml to 500 ml. For example, 75×10$^6$ cells of tolerizing vaccine or preparatory regimen can be suspended in a volume of 0.5 ml.

Tolerizing vaccines/regimen or preparatory regimens can be administered (e.g., by intravenous infusion) in a volume that varies depending upon the weight of the recipient. For example, the tolerizing vaccine or preparatory regimen can be given intravenously in a volume of at least or at least about 0.01 ml, 0.1 ml, 0.5 ml, 1 ml, 2 ml, 3 ml, 4 ml, 5 ml, 10 ml, 20 ml, 30 ml, 40 ml or 50 ml per kg recipient body weight, e.g., at least or at least about 0.01 to 0.1, 0.1 to 1, 1 to 2; 2 to 3; 3 to 4; 4 to 5; 1 to 5; 5 to 10; 10 to 20; 20 to 30; 30 to 40; or 40 to 50 ml per kg recipient body weight. In some cases, the tolerizing vaccine (e.g., comprising ECDI-treated cells) is given intravenously in a volume of about 7 ml per kg recipient body weight.

Booster doses of a tolerizing vaccine or preparatory regimen can comprise fewer cells than an initial dose of the tolerizing vaccine or preparatory regimen. For example, a booster or subsequent dose of the tolerizing vaccine or preparatory regimen can comprise about: 1%, 2%, 3%, 4%, 5%, 7.5%, 10%, 15%, 20%, 25%, 30%, 40%, 50%, 60%, or 75% fewer cells, or less than the initial or preceding dose of the tolerizing vaccine or preparatory regimen.

A cell of a tolerizing vaccine or a preparatory regimen can have a circulation half-life after it is administered to a subject. In some cases, a tolerizing vaccine or preparatory regimen described herein can have a circulation half-life of at least or at least about 0.1, 0.5, 1, 2, 3, 4, 5, 6, 7, 8, 9, 10, 12, 18, 24, 36, 48, 60, or 72 hours. For example, the circulation half-life of the tolerizing vaccine or preparatory regimen cells can be from or from about 0.1 to 0.5; 0.5 to 1.0; 1.0 to 2.0; 1.0 to 3.0; 1.0 to 4.0; 1.0 to 5.0; 5 to 10; 10 to 15; 15 to 24; 24 to 36; 36 to 48; 48 to 60; or 60 to 72 hours. In some cases, a tolerizing vaccine or preparatory regimen described herein can have a circulation half-life of at least or at least about 3 hours.

The cells of the tolerizing vaccine or preparatory regimen can be treated to enhance their circulation half-life. Such treatment can include coating the cell with a protein, e.g., CD47. The cell treated to enhance its circulation half-life can be a non-apoptotic cell. The cell treated to enhance its circulation half-life can be an apoptotic cell. Alternatively, the cell in a tolerizing vaccine or preparatory regimen can be genetically modified (e.g., insertion of a transgene such as CD47 in its genome) to enhance its circulation half-life. The cell genetically modified to enhance its circulation half-life can be a non-apoptotic cell. The cell genetically modified to enhance its circulation half-life can be an apoptotic cell.

The tolerizing vaccine or the preparatory regimen can be advantageous in transplantation, for example, in xenotransplantation or in allotransplantation, by tolerizing a graft recipient and preventing or delaying graft rejection. The tolerization or the preparatory regimen can be conferred to a graft recipient without the use of immunosuppressive therapies (e.g., one or more immunomodulatory molecules). However, in some cases, other immunosuppressive therapies can be used in combination with tolerizing vaccines to prevent, decrease, or delay transplantation rejection.

The dose of a peptide or composition thereof required in presence of a tolerizing agent can be lower than the dose of a peptide or composition disclosed herein required in its absence by at least or at least about 5%. For example, dose of a peptide or composition disclosed herein can be lower by at least or at least about 5%, 10%, 20%, 30%, 40%, 50%, or more. The term "lower" and its grammatical equivalents as used herein can refer to using less peptide or compositions thereof compared to a required dose when one or more wild-type cells, organs, and/or tissues is transplanted into a recipient (e.g., a human or a non-human animal).

Transplant Survival

In some embodiments, the methods disclosed herein can increase the duration of survival of a transplant (e.g., a xenograft or an allograft transplant) in a recipient for a period of at least one month, at least two months, at least three months, at least four months, at least five months, at least six months, at least 1 year, at least 2 years, at least 3 years, at least 4 years, at least 5 years, at least 6 years, at least 7 years, at least 8 years, at least 9 years, or at least 10 years.

In some cases, the transplant survives for a period of at least one month, at least two months, at least three months, at least four months, at least five months, at least six months, at least seven months, at least eight months, at least nine months, at least ten months, at least eleven months, at least twelve months, at least thirteen months, at least fourteen months, at least fifteen months, at least sixteen months, at least seventeen months, at least eighteen months, at least nineteen months, at least twenty months, at least twenty-one months, at least twenty-two months, at least twenty-three months, or at least twenty-four months. In some cases, the transplant survives for a period of at least 1 year, at least 2 years, at least 3 years, at least 4 years, at least 5 years, at least 6 years, at least 7 years, at least 8 years, at least 9 years, or at least 10 years. In some cases, the survival is achieved in the absence of a booster vaccine or booster regimen. In some cases, the transplant survival is achieved with an administration of a booster dose in one or multiple doses.

Different doses of a peptide or compositions disclosed herein can be given to a recipient before, after, and/or during transplant of donor cells, organs, and/or tissues to induce donor-specific tolerance in a recipient. In some cases, a first dose of a peptide or compositions disclosed herein can comprise at least or at least about 1 mg, 5 mg, 10 mg, 20 mg, 30 mg, 40 mg, 50 mg, 60 mg, 70 mg, 80 mg, 90 mg, 100 mg, or 200 mg of the a peptide or compositions disclosed herein per kg recipient body weight. In certain cases, a first dose of a peptide or compositions disclosed herein can comprise at least or at least about 30 mg, 40 mg, 50 mg, 60 mg, 70 mg of a peptide or compositions disclosed herein per kg recipient body weight. In some cases, a first dose of a peptide or compositions disclosed herein can comprise from or from about 1 mg to 200 mg, e.g., from or from about 20 mg to 100 mg; 30 mg to 80 mg; 30 mg to 70 mg; 40 mg to 70 mg; 40 mg to 60 mg; 50 mg to 70 mg; or 60 mg to 80 mg of the a peptide or compositions disclosed herein per kg recipient body weight.

Immunosuppressive Agents

Methods of the present disclosure further comprises administering an immunomodulatory agent to the recipient. The immunomodulatory agent can be for example, an immunosuppressive agent. The term "immunosuppressive agent" as used herein refers to substances that act to suppress or mask the immune system of the host into which the graft is being transplanted. This would include substances that suppress cytokine production, down-regulate or suppress self-antigen expression, or mask the MHC antigens.

Thus, peptides or compositions of the disclosure can be used alone or in some embodiments in combination with immunosuppressive agent that inhibits rejection of a transplant. The immunosuppressive agent can be administered simultaneously or at a separate time than the peptide or compositions herein. Non-limiting examples of immunosuppressive agents are azathioprine, corticosteroids, cyclosporine, 2-amino-6-aryl-5-substituted pyrimidines; azathioprine or cyclophosphamide; bromocriptine; glutaraldehyde; antiidiotypic antibodies for MHC antigens; cyclosporin A; one or more steroids, preferably corticosteroids and glucocorticosteroids such as prednisone, methyl prednisolone, and dexamethasone; anti-interferon-gamma antibodies; anti-tumor necrosis factor-alpha antibodies; anti-tumor necrosis factor-beta antibodies; anti-interleukin-2 antibodies; anticytokine receptor antibodies such as anti-IL-2 receptor antibodies; heterologous anti-lymphocyte globulin; pan-T antibodies, preferably OKT-3 monoclonal antibodies; antibodies to CD4; streptokinase; streptodomase; or RNA or DNA from the host.

In some cases, the immunosuppressive agent inhibits T cell activation. The immunosuppressive agent that inhibits T cell activation can be an anti-CD40 agent or anti-CD40L (CD154) agent. In some embodiment, the anti-CD40 agent can be an anti-CD40 antibody. The anti-CD40 antibody can be an antagonistic antibody. The anti-CD40 antibody can be a Fab' anti-CD40L monoclonal antibody fragment CDP7657. The anti-CD40 antibody can be a FcR-engineered, Fc silent anti-CD40L monoclonal domain antibody.

In some cases, the peptide or compositions disclosed herein is administered with one or more additional immunosuppression agent described herein, such as further comprising providing to the recipient one or more of an anti-CD40 agent or anti-CD40L (CD154) agent (e.g., an anti-CD40 antibody), a B-cell targeting agent (e.g., B cell depleting biologics, for example, a biologic targeting CD20, CD19, or CD22, and/or B cell modulating biologics, for example, a biologic targeting BAFF, BAFF/APRIL, CD40, IgG4, ICOS, IL-21, B7RP1), an mTOR inhibitor, a TNF-alpha inhibitor, a IL-6 inhibitor, a nitrogen mustard alkylating agent (e.g., cyclophosphamide), a complement C3 or C5 inhibitor, IFNγ, an NFκB inhibitor, α1-antitrypsin, vitamin D3, siCD40, cobalt protoporphyrin, insulin B9-23, a cluster of differentiation protein (e.g., CD46, CD55, or CD59), any combination thereof, or any fragment thereof. In some cases, the NFκB inhibitor is dehydroxymethylepoxyquinomicin (DHMEQ), curcumin, triptolide, Bay-117085, or a combination thereof. In some cases, B-cell targeting biologic can be Rituximab, anti-CD20 antibody.

In some cases, immunosuppressive agent can be MMF (mycophenolate mofetil (Cellcept)), ATG (anti-thymocyte globulin), anti-CD154 (CD40L), alemtuzumab (Campath), B-cell targeting agent (e.g., B cell depleting biologics, for example, a biologic targeting CD20, CD19, or CD22, and/or B cell modulating biologics, for example, a biologic targeting BAFF, BAFF/APRIL, CD40, IgG4, ICOS, IL-21, B7RP1), anti-IL-6R antibody (tocilizumab, Actemra), anti-IL-6 antibody (sarilumab, olokizumab), CTLA4-Ig (Abatacept/Orencia), belatacept (LEA29Y), mTOR inhibitor (sirolimus (e.g., Rapamune), rapamycin, everolimus), tacrolimus (Prograf), daclizumab (Zenapax), basiliximab (Simulect), infliximab (Remicade), cyclosporin, deoxyspergualin, soluble complement receptor 1, cobra venom factor, compstatin, anti C5 antibody (eculizumab/Soliris), methylprednisolone, FTY720, everolimus, anti-CD154-Ab, leflunomide, anti-IL-2R-Ab, anti-CXCR3 antibody, anti-ICOS antibody, anti-OX40 antibody, and anti-CD122 antibody, human anti-CD154 monoclonal antibody, CD40 antagonist, and CD40L (CD154) antagonist. Non-limiting examples of B-cell targeting biologics include antagonistic anti-CD40 mAb antibody, Fc-engineered anti-CD40L antibodies, Rituximab, anti-CD20 antibody. One or more than one immunosuppressive agents/drugs can be used together or sequentially. One or more than one immunosuppressive agents/drugs can be used for induction therapy or for maintenance therapy. The same or different drugs can be used during induction and maintenance stages. For example, daclizumab (Zenapax) is used for induction therapy and tacrolimus (Prograf) and sirolimus (Rapamune), or everolimus, or any other mTOR inhibitor is used for maintenance therapy. In another example, daclizumab (Zenapax) is used for induction therapy and low dose tacrolimus (Prograf) and low dose sirolimus (Rapamune) is used for maintenance therapy. Immunosuppression can also be achieved using non-drug regimens including, but not limited to, whole body irradiation, thymic irradiation, and full and/or partial splenectomy. These techniques can also be used in combination with one or more immuno-suppressive drug.

In some embodiments, one or more immunomodulatory molecules can target T cell receptor (TCR), CD3e, FK506-binding protein 12 (FKBP12), cytotoxic T lymphocyte associated protein 4 (CTLA-4), programmed cell death protein 1 (PD-1), programmed death ligand 1 (PD-L1), CD40L (CD154), CD40, inducible costimulatory (ICOS), IL-2, TNF-α, IL-6, IL-7, CD2, CD20, CD52, α-4 integrin, mTOR (mechanistic target of rapamycin, everolimus, serolimus), DNA synthesis, or any combination thereof. In some embodiments, the one or more immunomodulatory molecule can target B cell, (e.g., B cell depleting biologics, for example, a biologic targeting CD20, CD19, or CD22, and/or B cell modulating biologics, for example, a biologic targeting BAFF, BAFF/APRIL, CD40, IgG4, ICOS, IL-21, B7RP1). In some cases, the B cell targeting agent can be anti-CD20 mAb (such as rituximab) or other B-cell depleting antibody. In some embodiments, the immunosuppressive drugs can be a MHC/TCR interaction blockade, a nonselective depleting agent, calcineurin inhibitor, costimulatory signal blockade, cytokine blockade, lymphocyte depleting agent, cell adhesion inhibitor, IL-2 signaling inhibitor, cell cycle blocker, or any combination thereof. For example, the MHC/TCR interaction blockade can be anti-abTCR mAb T10B9. For example, the nonselective depleting agent can be anti-CD3 mAb (OKT3) or antithymocyte globulin (ATG). For example, the calcineurin inhibitor can be cyclosporine or tacrolimus. For example, the costimulatory signal blockade can be anti-CELA-4 mAb, abatacept, ipilimumab, anti-PD-1 (such as pembrolizumab), anti-PD-L1 (such as MPDL3280A), anti-CD154 mAb, anti-CD40 mAb, or anti-ICOS mAb. For example, the cytokine blockade can be anti-CD25 mAb (such as daclizumab or basiliximab), anti-TNF (infliximab), anti-IL-6 mAb (such as ALD518), or anti-IL-7 mAb. For example, the lymphocyte depleting agent can be anti-CD2 mAb, fusion protein with IgG1 (such as alefacept), anti-CD20 mAb (such as rituximab), or anti-CD52 mAb (such as alemtuzumab). For example, the cell adhesion inhibitor can be anti-very large antigen 4 (VLA4) (such as natalizumab). For example, the IL-2 signaling inhibitor can be sirolimus (rapamycin) or everolimus. For example, the cell cycle blocker can be mycophenolate mofetil (MMF) or azathioprine.

The doses, time and mode of administration of a peptide or compositions disclosed herein or an immunomodulatory agent can be easily determined by one of skill in the art. The key factor in selecting an appropriate dose and scheduling is the result obtained, i.e., graft survival long-term. For example, a relatively high dose may be needed either initially for the treatment of hyperacute graft rejection, which can be attributed to antibody-mediated graft destruction, or at a later stage characterized by a sudden decline in graft function.

When an immunosuppressive agent is used, it may be administered by any suitable means, including parenteral, and, if desired for local immunosuppressive treatment, intralesionally. Parenteral infusions include intramuscular, intravenous, intraarterial, intraperitoneal, and subcutaneous administration. In addition, when an immunosuppressive agent is used, it is suitably administered by pulse infusion, particularly with declining doses, or by continuous infusion.

In one aspect, provided herein is a compositions disclosed herein can further comprise an immunomodulatory agent, for example, an immunosuppressive agent. An "effective amount" of an immunosuppressive agent and peptides disclosed herein is an amount which achieves a degree of immunosuppression sufficient to delay, inhibit, suppress or moderate tissue transplant rejection and/or delay, inhibit, suppress or moderate one or more symptoms of an inflammatory disease e.g., autoimmune disease described herein. Preferably, the peptides of the present disclosure in combination with an immunomodulatory agent are used at dosages suitable for inducing transplant survival or, alternatively, at dosages at which the immunosuppressive activities of the two agents synergize. Accordingly, sub-therapeutic dosages can be used in the disclosed methods, i.e., dosages which are lower than the amounts that would be effective when the peptide or immunomodulatory agent is used alone. Suitable sub-therapeutic dosages of one or both agents of the disclosed combination therapy are those which are sufficient, when the two agents are used in combination, to delay, inhibit, suppress or moderate an undesired immune response to an antigen, or inhibit transplant rejection as a result as described above. The skilled artisan will be able to determine such dosages using ordinary experimentation, such as by using animal models. One advantage of the disclosed combined therapy, therefore, is that the subject being treated can in some instances be spared the side-effects of higher levels of immunosuppression resulting from, for example, corticosteroids and inhibitors of calcineurin.

Additional Therapeutic Agents

Of course, the peptides or compositions of the present disclosure can be used in combination with other therapies for treating autoimmune disorders, inflammation, cancer or for inhibiting transplant rejection. Accordingly, the compositions and methods of the present disclosure can comprise an additional therapeutic agent. The therapeutic agent can be, for example, anti-inflammatory agent, immunosuppressive agent, anti-tumor agent as relevant for the condition to be treated. Immunosuppressive agents have been described above.

Non-limiting example of anti-tumor agents include antibiotics and analogs (e.g., aclacinomycins, actinomycin f1, anthramycin, azaserine, bleomycins, cactinomycin, carubicin, carzinophilin, chromomycins, dactinomycin, daunorubicin, 6-diazo-5-oxo-L-norleucine, doxorubicin, epirubicin, idarubicin, menogaril, mitomycins, mycophenolic acid, nogalamycin, olivomycines, peplomycin, pirarubicin, plicamycin, porfiromycin, puromycin, streptonigrin, streptozocin, tubercidin, zinostatin, zorubicin), antimetabolites (e.g. folic acid analogs (e.g., denopterin, edatrexate, methotrexate, piritrexim, pteropterin, Tomudex®, trimetrexate), purine analogs (e.g., cladribine, fludarabine, 6-mercaptopurine, thiamiprine, thioguanine), pyrimidine analogs (e.g., ancitabine, azacitidine, 6-azauridine, carmofur, cytarabine, doxifluridine, emitefur, enocitabine, floxuridine, fluorouracil, gemcitabine, tagafur).

Anti-inflammatory agent can be Steroidal Anti-inflammatory Agents, such as 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide and the like. Anti-inflamatory agent can be Non-Steroidal antiinflammatory agents such as Aminoarylcarboxylic acid derivatives (e.g., enfenamic acid, etofenamate, flufenamic acid, isonixin, meclofenamic acid, mefenamic acid, niflumic acid, talniflumate, terofenamate, tolfenamic acid), arylacetic acid derivatives (e.g., aceclofenac, acemetacin, alclofenac, amfenac, amtolmetin guacil, bromfenac, bufexamac, cinmetacin, clopirac, diclofenac sodium, etodolac, felbinac, fenclozic acid, fentiazac, glucametacin, ibufenac, indomethacin, isofezolac, isoxepac, lonazolac, metiazinic acid, mofezolac, oxametacine, pirazolac, proglumetacin, sulindac, tiaramide, tolmetin, tropesin, zomepirac), arylbutyric acid derivatives (e.g., bumadizon, butibufen, fenbufen, xenbucin), arylcarboxylic acids (e.g., clidanac, ketorolac, tinoridine), arylpropionic acid derivatives (e.g., alminoprofen, benoxaprofen, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprolen, pirprofen, pranoprofen, protizinic acid, suprofen, tiaprofenic acid, ximoprofen, zaltoprofen), pyrazoles (e.g., difenamizole, epirizole), pyrazolones (e.g., apazone, benzpiperylon, feprazone, mofebutazone, morazone, oxyphenbutazone, phenylbutazone, pipebuzone, propyphenazone, ramifenazone, suxibuzone, thiazolinobutazone), salicylic acid derivatives (erg., acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide o-acetic acid, salicylsulfuric acid, salsalate, sulfasalazine), thiazinecarboxamides (e.g., ampiroxicam, droxicam, isoxicam, lornoxicam, piroxicam, tenoxicam), ε-acetamidocaproic acid, s-adenosylmethionine, 3-amino-4-hydroxybutyric acid, amixetrine, bendazac, benzydamine, α-bisabolol, bucolome, difenpiramide, ditazol, emorfazone, fepradinol, guaiazulene, nabumetone, nimesulide, oxaceprol, paranyline, perisoxal, proquazone, superoxide dismutase, tenidap, and zileuton and the like.

In some embodiments, the therapeutic agent can be a biologic. As used herein a biologic refers to any biological material suitable for a therapeutic or in vivo diagnostic purpose. Biologic therapeutics include peptides, proteins, vaccines, antibodies, aptamers, nucleic acids, DNA, RNA, antisense oligonucleotides, viruses and bacteria.

As used herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder associated with a CD40 activity, such as, but not limited to, a inflammation, autoimmune disease or a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

The methods of the disclosure, including treating a CD40 associated disorder of a subject, likely results in an improvement in the subjects' condition, a reduction of symptoms or decreasing the subject's risk for developing symptoms associated with a CD40 associated disorder. Improvements therefore include one or more decreased symptoms associated with autoimmunity, allergy, cancer, etc. An improvement may also be reducing the frequency or amount of a drug used for treating a subject having or at risk of having a CD40 associated disorder. For example, autoimmune patients treated with steroids may require less steroid when treated in combination with a peptide or compositions disclosed herein. An improvement therefore would include reducing the dosage frequency or amount of steroid that the subject was administered in comparison to the dosage frequency or amount administered prior to treatment with a peptide or compositions disclosed herein. An improvement may be, for example, longer transplant survival, or reduction of side effects associated with conventional immunosuppressive regiments for transplantation.

An improvement may be relatively short in duration, e.g., several hours, days or weeks, or extend over a longer period of time, e.g., months or years. The improvement need not be a complete ablation of any or all symptoms of the disorder. For example, reducing severe rheumatoid arthritis to a less severe form is an improvement. Thus, a satisfactory clinical endpoint is achieved when there is an incremental improvement or a partial reduction in the subject's condition or associated symptoms, over a short or long duration.

The term "effective amount" as used herein refers to the amount needed to alleviate at least one or more symptom of the disease or disorder, and relates to a sufficient amount of pharmacological composition to provide the desired effect (e.g., binding to CD40 and/or inhibition of the interaction of CD40 and CD154). The term "therapeutically effective amount" therefore refers to an amount that is sufficient to effect a particular effect when administered to a typical subject. An effective amount as used herein would also include an amount sufficient to delay the development of a symptom of the disease, alter the course of a symptom disease (for example but not limited to, slow the progression of a symptom of the disease), or reverse a symptom of the disease. Thus, it is not possible to specify the exact "effective amount". For any given case, however, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the antibody or antigen binding fragment thereof), which achieves a half-maximal inhibition of symptoms as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

The compositions of the disclosure are administered in effective amounts. An "effective amount" is that amount of a composition that alone, or together with further doses, produces the desired response. In the case of transplantation, a desired response is inhibition of transplant rejection or increasing transplant survival. In the case of treating a particular disease, such as arthritis, the desired response is inhibiting the progression of the disease. This may involve only slowing the progression of the disease temporarily, although more preferably, it involves halting the progression of the disease permanently. This can be monitored by routine methods.

Such amounts will depend, of course, on the particular condition being treated, the severity of the disorder, the activity of the specific compound, the route of administration, the rate of clearance of the composition, the duration of treatment, the drugs used in combination or coincident with the compositions, the age, body weight, sex, diet, and general health of the subject, and like factors well known in the medical arts and sciences. Various general considerations taken into account in determining the "therapeutically effective amount" are known to those of skill in the art and are described, e.g., in Gilman et al, eds., Goodman And Gilman's: The Pharmacological Bases of Therapeutics, 8th ed., Pergamon Press, 1990; and Remington's Pharmaceutical Sciences, 17th ed., Mack Publishing Co., Easton, Pa., 1990. These factors are well known to those of ordinary skill in the art and can be addressed with no more than routine experimentation. It is generally preferred that a maximum dose of the individual components or combinations thereof be used, that is, the highest safe dose according to sound medical judgment. The compositions used in the foregoing methods preferably are sterile and contain an effective amount of the active agents for producing the desired response in a unit of weight or volume suitable for administration to a patient.

Kits

In another embodiment of the disclosure, an article of manufacture which contains the pharmaceutical composition in a solution form or in a lyophilized form or a kit comprising an article of manufacture is provided. The kit can comprise instructions for diluting the composition or for its reconstitution and/or use. The article of manufacture comprises a container. Suitable containers include, for example, bottles, vials (e.g. dual chamber vials), syringes (such as dual chamber syringes) and test tubes. The container may be formed from a variety of materials such as glass or plastic. The container holds the lyophilized formulation and a label on, or associated with, the container may indicate directions for reconstitution and/or use. For example, the label may indicate that the lyophilized formulation is reconstituted to peptide concentrations as described above. The label may further indicate that the formulation is useful or intended for subcutaneous administration. The container holding the formulation may be a multi-use vial, which allows for repeat administrations (e.g., from 2-6 administrations) of the reconstituted formulation. The article of manufacture may further comprise a second container comprising a suitable diluent (e.g., BWFI). Upon mixing of the diluent and the lyophilized formulation, the final protein concentration in the reconstituted formulation will generally be at least 50 mg/mL. The article of manufacture may further include other materials desirable from a commercial and user standpoint, including other buffers, diluents, filters, needles, syringes, and package inserts with instructions for use.

Therapeutic kits may have a single container which contains the formulation of the peptide pharmaceutical compositions with or without other components (e.g., other compounds or pharmaceutical compositions of these other compounds) or may have distinct container for each component. In some embodiments, therapeutic kits of the disclosure include a formulation of peptide disclosed herein or compositions comprising said peptides or an acid addition salt thereof as disclosed herein packaged for use in combination with the co-administration of a second compound (such as an anti-inflammatory agent, immunomodulating agent, anti-tumor agent, a natural product, a hormone or antagonist, a anti-angiogenesis agent or inhibitor, a apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain apparatus (e.g., one or more needles, syringes, eye droppers, pipette, etc.), which enables administration of the peptides of the disclosure which are components of the present kit.

In another embodiment of the disclosure, an article of manufacture which contains compositions comprising apoptotic leukocytes and an anti-CD40 agent comprising one or more peptides with an amino sequence with at least 85%, at least 90% or at least 95% sequence identity to the sequences set forth in any one of SEQ ID NOs. 1-6 and 8-17, in a solution form or in a lyophilized form or a kit comprising an article of manufacture is provided. The kits of the instant disclosure can be for use in transplantation of a transplant in a recipient or reducing or inhibiting occurrence of GVHD in a recipient. In some embodiments, the kit is useful as a preparatory regimen prior to the transplantation. In some embodiments, the kit is useful as a tolerizing regimen post-transplantation. The kit can comprise instructions for diluting the composition or for its reconstitution and/or use. The article of manufacture comprises one or more containers. Suitable containers include, for example, bottles, vials (e.g. dual chamber vials), syringes (such as dual chamber syringes) and test tubes. The container may be formed from a variety of materials such as glass or plastic. The container holds the compositions e.g., in a lyophilized or solution form and a label on, or associated with, the container may indicate directions for reconstitution and/or use. For example, the label may indicate that the lyophilized composition is reconstituted to an effective amount as described above. The label may further indicate that the composition is useful or intended for subcutaneous administration or intravenous administration. The container holding the composition may be a multi-use vial, which allows for repeat administrations (e.g., from 2-6 administrations) of the composition. The article of manufacture may further comprise a container comprising a suitable diluent (e.g., BWFI). Upon mixing of the diluent and the composition, the final concentration in the composition can be, for example, an effective amount suitable for administration. The article of manufacture may further include other materials desirable from a commercial and user standpoint, including other buffers, diluents, filters, needles, syringes, and package inserts with instructions for use.

Kits may have a single container which contains, for example apoptotic leukocytes fixed in a crosslinking agent with or without other components (e.g., and an anti-CD40 agent or an anti-CD40 ligand agent). In some cases, the anti-CD40 agent conjugated to the apoptotic leukocytes may comprise a peptide comprising an amino acid sequence with at least 85%, at least 90% or at least 95% sequence identity to the sequences set forth in any one of SEQ ID NOs. 1-6 and 8-17. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container. In some embodiments, kits of the disclosure include the components disclosed herein packaged for use in combination with the co-administration of an additional component (such as an anti-inflammatory agent, immunomodulating agent, anti-tumor agent, a natural product, a hormone or antagonist, an anti-angiogenesis agent or inhibitor, a apoptosis-inducing agent, or a chelator). The container of a kit may be a vial, test tube, flask, bottle, syringe, or any other means of enclosing a solid or liquid. In some embodiments, the kit will contain a second vial or other container, which allows for separate dosing. The kit may also contain another container for a pharmaceutically acceptable liquid. Preferably, a kit will contain apparatus (e.g., one or more needles, syringes, eye droppers, pipette, etc.), which enables administration of the compositions of the disclosure which are components of the present kit.

In some embodiments, the kit disclosed herein further comprises the transplant. In some embodiments, the transplant is a kidney, liver, heart, lung, pancreas, islet cell, small bowel, bone marrow, hematopoietic stem cell, embryonic or induced pluripotent stem cell-derived islet beta cell, embryonic or induced pluripotent stem cell-derived islet, embryonic or induced pluripotent stem cell-derived hepatocyte or a combination thereof. In some embodiments, the transplant can be autologous, allograft, or a xenograft.

EXAMPLES

These examples are provided for illustrative purposes only and not to limit the scope of the claims provided herein.

Example 1. Identification of CD40 Binding Peptides that could Block CD40 Mediated Costimulation Table 1 lists the amino acid sequences of CD40 binding peptides. A control CD40-binding peptide, Peptide 1 was included in the studies described below for comparison. Peptide 1 has the amino acid sequence of VLQWAEKGYYTMSNN (SEQ ID NO: 7). In silico prediction using the Amino Acid Complement Wave method was used to identify peptides 2-7 that exhibited high affinity to the human CD40 epitope. Peptides that can bind CD40 and block the CD40-CD40L signaling cascade were identified. Sequences of the peptides are presented in the table below. The identified peptides were synthesized with and without fluorescent labeling to study the binding and functional properties of the peptides to interfere in the CD40-CD40L signaling. Peptides 8-17 are exemplary fragments of peptide 2-7 expected to exhibit high affinity to the human CD40 epitope.

Table 1 lists the amino acid sequences of the peptides identified to bind CD40.

| | | |
|---|---|---|
| SEQ ID NO: 1 | VLQWAERGFYTTSNN | Peptide 2 |
| SEQ ID NO: 2 | LLQWAERGYFMTSNN | Peptide 6 |
| SEQ ID NO: 3 | VVQWAEKGFFTMSNN | Peptide 3 |
| SEQ ID NO: 4 | VLNWADKAYFTMSQN | Peptide 4 |
| SEQ ID NO: 5 | LVNWADKAFYTTSNN | Peptide 5 |
| SEQ ID NO: 6 | VVQWAEKGYYTMSQN | Peptide 7 |
| SEQ ID NO: 8 | VLQWAERGFY | Peptide 8 |
| SEQ ID NO: 9 | LLQWAERGYF | Peptide 9 |
| SEQ ID NO: 10 | VVQWAEKGFF | Peptide 10 |
| SEQ ID NO: 11 | VLNWADKAYF | Peptide 11 |
| SEQ ID NO: 12 | LVNWADKAFY | Peptide 12 |
| SEQ ID NO: 13 | RGFYTTSNN | Peptide 13 |
| SEQ ID NO: 14 | RGYFMTSNN | Peptide 14 |
| SEQ ID NO: 15 | KGFFTMSNN | Peptide 15 |
| SEQ ID NO: 16 | KAYFTMSQN | Peptide 16 |
| SEQ ID NO: 17 | KAFYTTSNN | Peptide 17 |

Example 2. Screening of CD40-Binding Peptides for Binding to Mononuclear Cells

In order to screen the ability of the cyclic peptides to bind to CD40, peripheral blood mononuclear cells (PBMC) purified from 2 Rhesus macaques (RM) were incubated with 5 µM of fluorochrome tagged CD40 interacting peptides, Peptide 1-7 listed in Table 1 for 30 minutes at 4° C. The cells were washed 3× in PBS and analyzed by flow cytometry. Stained cells were acquired on a 3-laser BD Canto II instrument (BD Bioscience). A minimum of 200,000 events were acquired with FACSDIVA 6.1.3. Mean fluorescence intensity of the peptide binding to the cells were determined using FlowJo 10.1. software (Tree Star; Ashland, OR, USA). FACS analysis demonstrated that the synthetic peptides listed in SEQ ID NOs. 1-7 bind to the PBMC but at various intensities, confirming the ability of the synthetic peptides to bind to CD40 on mononuclear cells. Peptide 1 and Peptide 3 showed high affinity for binding to mononuclear cells whereas Peptide 7 has the least binding affinity to the mononuclear cells.

Example 3. Specificity of Peptide Binding to CD40

In order to confirm the specificity of the peptides to interfere with CD40:CD154 interaction, the specificity of peptides 1-7 as listed in table 1 to bind to human CD154 by ELISA was tested. Briefly, 96 well ELISA (Nunc Immunolon) plates were coated with the peptides in carbonate buffer. The wells are washed and probed with FLAG-tagged rhsCD40 (1 µg/ml; Alexis) and developed with HRP conjugated rabbit anti-FLAG antibody. The plates were washed and the enzymatic activity was determined using 3,3',5,5'-tetramethyl-benzidine substrate for 15 minutes and the reaction was stopped by the addition of 2 M H2SO4, and optical density was measured at 450 nm, with the correction wavelength set at 620 nm. Similar to the mononuclear cell binding studies, the Peptide #1 showed high binding affinity to recombinant human CD40, whereas Peptide 4 had the lowest binding affinity. These binding studies indicate Peptide 2, Peptide 3, and Peptide 7 showed specific binding to human CD40, and can therefore block CD40-CD154 interaction.

Example 4. Co-Stimulation Blockade with Peptides Abrogates Donor-Specific T and B Cell Proliferation In order to determine the functional effect of co-stimulation blockade with peptides targeting CD40, one-way mixed lymphocyte reactions (MLR) was performed. CFSE-labeled PBMC from 5 different RM were stimulated with irradiated PBMC for 6 days. Stimulation with PHA was used as positive control. Initial screening with various concentration of peptides 1-7 listed in table 1 (15, 30 and 45 µM). These studies demonstrated that peptides added at 30 µM showed the maximum potential for costimulation blockade and this concentration used in further assays. The cells were incubated in the presence of peptides at 30 µM. Following stimulation, PBMC were stained with antibodies specific for CD4, CD8 and CD20 and proliferating cells were quantitated by determining the frequency of CFSE-low CD4, CD8 and CD20 cells. Stained cells were acquired on a 3-laser BD Canto II instrument (BD Bioscience). A minimum of 200, 000 events were acquired with FACSDIVA 6.1.3. FACS analysis was performed with FlowJo Version 10 software. Analysis of the results demonstrated that all the peptides 1-7 showed significant suppression of CD4, CD8 and CD20 cell proliferation in 4/5 donor recipient combinations. More significantly, Peptide 2 and Peptide 3 suppressed the proliferation of CD4, CD8, and CD20 cells at a higher efficacy compared to the other peptides.

Example 5. Treatment of B Cells with Anti-CD40 Peptides Blocks B Cell Activation The ability of CD40-binding peptides 1-7 as listed in Table 1 to block B cell activation was assessed by analyzing the expression of MHC class II molecules on the B cell when subsequently incubated in the presence of recombinant hCD40L. Briefly, B cells were purified from 3 RM PBMC by magnetic sorting. B cells were incubated with peptides at 30 µM for 15 minutes at 37° C., then activated for 30 minutes with recombinant hCD40L, and then analyzed for expression of MHC class II by staining the cells with specific antibody. Stained cells were acquired on a 3-laser BD Canto II instrument (BD Bioscience). A minimum of 200,000 events were acquired with FACSDIVA 6.1.3. FACS analysis was performed with FlowJo Version 10 software. FACS analysis of the B cells demonstrated that pre-incubation with the peptides resulted in a 50% reduction in MHC class II expression on B cells following activation with CD40L.

This study identified new peptides that can bind to CD40 and inhibit CD40 activity (i.e., CD40 interaction with CD40L). The identified peptides bind specifically to CD40. Peptide 2, Peptide 3, and Peptide 5 listed in Table 1 exhibited a higher affinity to bind to CD40 when compared to the control Peptide 1. When compared with Peptide 1; Peptide 2, Peptide 3 and Peptide 5 show an enhanced ability to bind CD40 and inhibit CD40-CD40L interaction and downstream signaling as evidenced by complete abrogation of T and B cell proliferation as well as activation of B cells.

Example 6. Treating Diabetes by Transplanting Islets and Providing a Preparatory Regimen Using CD40 Binding Peptide This example examines effect of anti-CD40 peptides and the tolerogenic effect of ECDI-treated donor cells for islet transplantation in vivo. The effect of an exemplary CD40 binding peptide, peptide 3 is illustrated. ECDI-treated splenocytes from a xenogeneic or allogeneic source are administered to a human or a non-human primate transplanted with islets, thereby minimizing the possibility of graft rejection in the human or non-human primate. The preparatory regimen of this example can readily be adapted to allotransplantation or xenotransplantation in human recipients (for example, transplant of islets, kidneys, or other cells, tissues, or organs).

In an illustrative example, a streptozotocin-induced model of diabetes is utilized with non-human primate subjects. Diabetes is induced by intravenous treatment with streptozotocin. Recipient subjects are transplanted with islets from a MHC-I disparate, one MHC-II DRB-allele matched donor. Recipients are treated with a short term immunosuppressive regimen comprising: (i) an anti-CD40 peptide (Peptide 3), given intravenously at a dose of 50 mg/kg on day −8, −1, 7, and 14 relative to transplant; (ii) rapamycin, given orally from day −7 to day 21 relative to transplant with a target trough level of 5-12 ng/mL; (iii) soluble TNF receptor, given intravenously at a dose of 1 mg/kg on days −7 and 0 relative to transplant and subcutaneously at a dose of 0.5 mg/kg on days 3, 7, 10, 14, and 21 relative to transplant; and (iv) antagonistic anti-IL-6 receptor antibody, given intravenously at a dose of 10 mg/kg on days −7, 0, 7, 14, and 21 relative to transplant.

Transplant recipients in experimental groups receive an intravenous infusion of ECDI-treated apoptotic donor leukocytes (ADLs) together with anti-CD40 peptide, peptide 3 (or any one or more peptide selected from peptides 1-17) before and optionally after transplantation. In some cases, ADLs together with an anti-CD40 peptide, peptide 3 (or any one or more peptide selected from peptides 1-17) are administered about 8 days before transplantation. In some cases, ADLs are administered about 7 days before transplantation. In some cases, ADLs together with an anti-CD40 peptide, peptide 3 (or any one or more peptide selected from peptides 1-17) are administered about 1 day after transplantation. In some cases, ADLs together with an anti-CD40 peptide are administered about 7 days after transplantation. In some cases, ADLs together with an anti-CD40 peptide are administered about 14 days after transplantation. In some cases, ADLs together with an anti-CD40 peptide are administered about 7 or 8 days before transplantation, and about 1, 7, and/or 14 days after transplantation. ADLs can be from the same donor as the islets or a different donor as disclosed herein.

Transplant recipients in a control group do not receive ADLs. Small doses of exogenous insulin can be administered through day 21 after transplantation. Transplant recipients that receive ADLs together with an anti-CD40 peptide are expected to exhibit improved transplant survival compared to the group that do not receive ADLs. Transplant recipients that receive ADLs together with an anti-CD40 peptide are expected to exhibit improved rejection-free transplant survival compared to the group that do not receive ADLs. Transplant recipients that receive ADLs together with an anti-CD40 peptide are expected to exhibit long-term functional survival of islet allografts. For example, transplant recipients that receive ADLs together with an anti-CD40 peptide are expected to exhibit improved blood glucose control after transplant (e.g., become normoglycemic), including after they stop receiving exogenous insulin (e.g., past day 100 or day 365 post-transplant). Blood glucose control can be evaluated, for example, by intravenous glucose tolerance test (IVGTT), a mixed meal tolerance test (MMTT), or any other metabolic test established for monitoring pancreatic islet beta cell function. In IVGTT, exogenous glucose is injected intravenously, and the blood glucose level is measured over time after the injection. Transplant recipients that receive ADLs together with an anti-CD40 peptide are expected to exhibit rapid decreases in blood glucose levels and reduced area under the glucose concentration curve after IVGTT (e.g., comparable levels to those prior to streptozotocin treatment). Islet transplant recipients that receive ADLs together with an anti-CD40 peptide are expected to exhibit decreased hemoglobin A1C levels after transplant. Transplant recipients that receive ADLs together with an anti-CD40 peptide are expected to exhibit increased C-peptide levels after transplant that are maintained over time, indicating the transplanted islets are functional (e.g., fasted C-peptide levels, glucose-stimulated C-peptide levels, and/or increase in C-peptide levels upon glucose stimulation).

Example 7. Conjugation of Anti-CD40 Peptides to Mismatched Apoptotic Donor Leukocytes (ADLs) for Tolerance Induction This example demonstrates that conjugating anti-CD40 peptides (e.g., Peptides 1-17 listed in table 1) to apoptotic donor leukocytes (ADLs) can enhance the tolerance-inducing efficacy of a preparatory regimen. In addition, for donor-recipient pairs that are fully MHC class I and class II mismatched, additionally conjugating recipient-type MHC class II molecules to ADLs can enhance ADL efficacy in inducing tolerance to a transplanted cell, tissue, or organ.

Coupling one or more peptides that can abrogate CD40-CD154 binding (e.g., Peptides 1-17 listed in table 1) to the surface of ADLs can enhance tolerance to a transplanted cell, tissue or organ, after uptake of ADLs (for example, by recipient spleen marginal zone antigen presenting cells or liven sinusoidal endothelial cells). Additionally, coupling recipient-type MHC class II peptides for presentation after uptake of ADLs, derived from one (or more) of the transplant recipient's MHC class II molecules can promote tolerance in the recipient, for example, via regulatory T cell subsets.

Mixed Lymphocyte Reactions

To determine the ability of apoptotic donor leukocytes coupled via ECDI with anti-CD40 peptides (e.g. peptides listed in Table 1), and recipient-type DRB peptide to promote immune regulation and transplantation tolerance, the following fully mismatched monkey recipient/donor pair and experimental conditions are selected to test a mixed lymphocyte reaction (MLR) in vitro with MHC-defined stimulator (donor) and responder (recipient) peripheral blood mononuclear cells (PBMCs).

Recipient PBMCs are Mauritian Cynomolgus Monkey (Mafa M4A, M4A, M4B, M4B, M4DR, M1DR). Apoptotic donor leukocytes are Mauritian Cynomolgus Monkey (M3A, M3A, M3B, M3B, M3DR, M3DR), with 14 µg of synthetic peptides (e.g., Peptides 1-17 listed in table 1) conjugated to the cell surface via ECDI.

In the MLR assay, 3×106 apoptotic donor leukocytes with and without conjugated anti-CD40peptide are used to stimulate 3×106 recipient PBMCs at 37° C. in a CO2 incubator. Serial samples collected post stimulation on day 1 and day 3 are analyzed for the induction of DC-10 (CD141+CD163+ of CD14+CD16+), Treg cells (CD25hi CD127-FoxP3+ of CD4+) and Tr1 cells (CD49b+LAG-3+ of CD4+) by flow cytometry. Stimulated cells show that in comparison to PBLs stimulated with control apoptotic donor leukocytes alone, there is an increase in the frequency of Tregs on day 1 and further on day 3 following stimulation with anti-CD40 peptide-conjugated apoptotic donor leukocytes. Similarly, a gradual increase in the frequency of Tr1 cells (on day 1 and day 3), is observed following stimulation with anti-CD40 peptide-conjugated versus control apoptotic donor leukocytes. These results demonstrate that conjugating anti-CD40 peptides (e.g., Peptides 1-17 listed in table 1) to apoptotic donor leukocytes can promote expansion of tolerance-promoting immune regulatory cell subsets.

The preparatory regimen of this example can readily be adapted to allotransplantation or xenotransplantation in mammalian recipients (for example, transplant of islets, kidneys, or other cells, tissues, or organs, such as embryonic stem cell, induced pluripotent stem cell (iPS)-derived, or mesenchymal stem cell-derived cells, tissues and organs).

In an illustrative example, in addition to anti-CD40 peptides (e.g., Peptides 1-17 listed in table 1), recipient type MHC peptides are conjugated to ADLs, and the ADLs are used to induce tolerance to a human islet transplant recipient.

Splenocytes are obtained from a fully MHC-I and MHC-II mismatched xenogeneic or allogeneic source and are conjugated during ECDI treatment to anti-CD40 peptides (e.g., Peptides 1-17 listed in table 1). Following that, MHC class II chains, domains, and/or peptides are conjugated during ECDI treatment to generate ADLs conjugated to anti-CD40 peptides and peptides derived from MHC-II. The ADLs conjugated to anti-CD40 peptides and peptides derived from MHC-II are administered to human subjects that receive islet transplants, thereby reducing the possibility of graft rejection. Transplant recipients receive an intravenous infusion of ADLs conjugated to anti-CD40 peptides and peptides derived from MHC-II before and optionally after transplantation, for example, on day −7 and day +1 relative to transplantation. ADLs can be from the same donor as the islets or a different donor as disclosed herein.

Recipient subjects are transplanted with islets from the fully MHC class I and MHC class II mismatched donor. Recipients are treated with a short term immunosuppressive regimen comprising: (i) an antagonistic anti-CD40 peptide (e.g., Peptides 1-17 listed in table 1), given intravenously at a dose of 50 mg/kg on day −8, −1, 7, and 14 relative to transplant; (ii) rapamycin, given orally from day −7 to day 21 relative to transplant with a target trough level of 5-12 ng/mL; (iii) soluble TNF receptor, given intravenously at a dose of 1 mg/kg on days −7 and 0 relative to transplant and subcutaneously at a dose of 0.5 mg/kg on days 3, 7, 10, 14, and 21 relative to transplant; and (iv) antagonistic anti-IL-6 receptor antibody, given intravenously at a dose of 10 mg/kg on days −7, 0, 7, 14, and 21 relative to transplant.

Small doses of exogenous insulin can be administered through day 21 after transplantation. Transplant recipients in control groups do not receive ADLs, or receive ADLs without anti-CD40 peptide and MHC class II peptides conjugated. Transplant recipients that receive anti-CD40 peptide and MHC-II peptides conjugated ADLs are expected to exhibit improved survival compared to recipients that do not receive anti-CD40 peptide and MHC-II-conjugated ADLs. Transplant recipients that receive ADLs conjugated with anti-CD40 peptide and peptides derived from MHC-II are expected to exhibit improved rejection-free survival compared to recipients that do not receive anti-CD40 peptide and MHC-II-conjugated ADLs. Transplant recipients that receive ADLs conjugated to anti-CD40 peptides and peptides derived from MHC-II are expected to exhibit long-term functional survival of islet allografts compared to recipients that do not receive ADLs conjugated to anti-CD40 peptides and peptides derived from MHC-II. For example, transplant recipients that receive ADLs conjugated to anti-CD40 peptides and peptides derived from MHC-II are expected to exhibit improved blood glucose control after transplant (e.g., become normoglycemic), including after they stop receiving exogenous insulin (e.g., past day 100 or day 365 post-transplant). Blood glucose control can be evaluated, for example, by intravenous glucose tolerance test (IVGTT), a mixed meal tolerance test (MMTT), or any other metabolic test established for monitoring pancreatic islet beta cell function. In IVGTT, exogenous glucose is injected intravenously, and the blood glucose level is measured over time after the injection. Transplant recipients that receive ADLs conjugated to anti-CD40 peptides and peptides derived from MHC-II are expected to exhibit rapid decreases in blood glucose levels and reduced area under the glucose concentration curve after IVGTT (e.g., comparable levels to a healthy subject). Transplant recipients that receive ADLs conjugated to anti-CD40 peptides and peptides derived from MHC-II are expected to exhibit decreased hemoglobin AIC levels after transplant. Transplant recipients that receive anti-CD40L and MHC-II conjugated ADLs are expected to exhibit increased C-peptide levels after transplant that are maintained over time, indicating the transplanted islets are functional (e.g., fasted C-peptide levels, glucose-stimulated C-peptide levels, and/or increase in C-peptide levels upon glucose stimulation).

Example 8. Stem Cell-Derived B Cells Conjugated with Anti-CD40 Peptide for Tolerance Induction to Cells, Tissues, or Organs Derived from the Same Stem Cell Donor Stem cells from one donor can be differentiated into a first population of cells for use as apoptotic donor leukocytes (ADLs), and separately differentiated into a second population of cells for transplant. This technique can be used to induce tolerance to any universal cell-derived cell, tissue, or organ transplant.

The stem cells can be embryonic stems cells, induced pluripotent stem cells (iPSCs), and/or mesenchymal stem cells. The stem cells are differentiated into a first population of cells that express both MHC class I and MHC class II antigens. For example, iPSCs from a transplant donor are differentiated into B lymphocytes that express both MHC class I and II antigens. Methods of differentiating iPSCs into B cells are described, for example, in French A et al. (2015), Stem Cells and Development 24(9):1082-95. Preferably, for increased tolerogenic efficacy, the donor stem cell-derived B cells share one MHC class II antigen with the recipient (e.g., at least one MHC class II DR allele, MHC class II DQ allele, or MHC class II DP allele). Separately, the iPSCs are differentiated into a second population of cells to be transplanted. The stem-cell derived B cells are treated with ECDI in the presence of an anti-CD40 peptide (e.g., Peptides 1-17 listed in table 1) to generate anti-CD40 conjugated apoptotic donor leukocytes (anti-CD40 peptide conjugated ADLs).

The stem cell-derived, anti-CD40 peptide conjugated ADLs are administered to a subject that receives a transplant of cells, tissues, or organs derived from the same stem cell donor, thereby reducing the possibility of transplant rejection. The transplant recipient receives an intravenous infusion of stem cell-derived anti-CD40 peptide conjugated ADLs before and optionally after transplantation, for example, on day −7 and day +1 relative to transplantation.

The recipients can optionally be treated with a short term immunosuppressive regimen comprising: (i) an antagonistic anti-CD40 peptide (e.g., Peptides 1-17 listed in table 1), given intravenously at a dose of 50 mg/kg on day −8, −1, 7, and 14 relative to transplant; (ii) rapamycin, given orally from day −7 to day 21 relative to transplant with a target trough level of 5-12 ng/mL; (iii) soluble TNF receptor, given intravenously at a dose of 1 mg/kg on days −7 and 0 relative to transplant and subcutaneously at a dose of 0.5 mg/kg on days 3, 7, 10, 14, and 21 relative to transplant; and (iv) antagonistic anti-IL-6 receptor antibody, given intravenously at a dose of 10 mg/kg on days −7, 0, 7, 14, and 21 relative to transplant.

The recipient is expected to exhibit improved rejection-free survival compared to the recipients that do not receive the stem-cell derived, anti-CD40 peptide conjugated ADLs. This technique can be used to induce tolerance to any universal cell-derived cell, tissue, or organ transplant.

Example 9. Dendritic and T Cell Immunomodulatory Effects of B-Cell Products Conjugated with Anti-CD40 Peptide ECDI-fixed B cell products conjugated with CD40 binding peptide (e.g., Peptides 1-17 listed in table 1) generated under different experimental conditions are compared for their ability to induce maturation-arrest in dendritic cells (DC). Human monocyte-derived DC are generated with IL-4 and GCSF. These DC are incubated in the presence or absence of various ECDI-fixed B cell products coupled to inhibitors of DC maturation (e.g., rapamycin, curcumin, vitamin D3, Bay-117085, siCD40, cobalt protoporphyrin, and α1-antitrypsin). Readouts of DC maturation arrest include i) expression of DC phenotypic markers (CD83, CD80, CD86, MHC class II, CD40), ii) STAT-6 phosphorylation, iii) RELP nuclear translocation, iv) IL-12p70 production, v) allostimulatory capacity, and vi) priming of T cells with regulatory phenotypes (CD4+ CD25hiCD127lowFoxp3+Tregs and CD4+CD49b+Lag-3+ CD45RA-Tr1 cells). ECDI-treated B cell products are identified that induce maturation-arrest in DC.

The effects of ECDI-fixed donor B lymphocytes on immune profiles in responder peripheral blood lymphocytes (PBL) is evaluated. ECDI-fixed donor B cells are generated, including B cells with various anti-CD40 peptides conjugated to their surface by ECDI (e.g., Peptides 1-17 listed in table 1). One-way mixed lymphocyte reactions (MLRs) are performed using PBL from fully mismatched, one DRB-matched, or one-DQ matched donor-recipient pairs, with or without the addition of increasing doses of ECDI-fixed anti-CD40 peptide conjugated donor B cells.

Cells are phenotyped and proliferation evaluated at various time points by multi-parametric flow cytometry (e.g., including CFSE dilution and staining for markers that differentiate cell subsets of interest). Blocking antibodies are added and distinct cell subsets are depleted to dissect underlying mechanisms and to determine how the enhanced ECDI-fixed B cell products influence T cell immunity (e.g., B cell products with or without coupled anti-CD40 peptides). Readouts include i) fold-proliferation of CD4+ and CD8+ T cells with effector phenotypes as determined by surface markers, intracellular cytokines, and/or transcription factors; ii) fold-proliferation of CD4+ and CD8+ T cells with regulatory phenotypes as determined by surface markers, intracellular cytokines, and/or transcription factors; and iii) CD8+ T cell-mediated cytotoxicity against target cells in the MLR.

Example 10. Efficacy of Peri-Transplantation Infusions of Ex Vivo Expanded ADLs Coupled to Anti-CD40 Peptides, in Inducing Donor Specific Tolerance to Kidney Allograft The efficacy of peri-transplantation infusions of ADL products coupled to anti-CD40 peptides (e.g., Peptides 1-17 listed in table 1), for inducing stable renal allograft tolerance is evaluated in one DRB-matched, SI non-human primates. An experimental group receives ADL products comprising ex vivo expanded donor B cells coupled to anti-CD40 peptides (e.g., Peptides 1-17 listed in table 1), while a control group receives saline infusions. Group sizes of n=5 are studied; up to 2 additional non-human primates are added per group to replace non-informative recipients (e.g., recipients that contract unrelated diseases). SI mammalian recipients are identical in both groups and long-term maintenance drugs are not given to any recipient. Renal allograft failure is defined by serum creatinine >2.5 mg/dL and confirmed by graft histology.

Purpose-bred, qualified non-human primate donors and recipients (exam, labs, microbial screen, vaccination, etc.) are selected from qualified vendors. The donors and recipients have a defined MHC disparity (MHC class I-disparate and one MHC class II DRB allele-matched donor-recipient pairs, based on high-resolution MHC class I and II genotyping using Fluidigm Access Arrays to generate amplicons for deep sequencing).

Recipients with evidence of existing allo-reactive memory can be excluded from the study. Eligibility criteria for recipients can include ABO compatibility, low memory alloreactivity as defined by negative panel reactive antibodies (PRA; OneLambda Bead assay), negative donor-specific antibodies (DSA) by flow, and IFN-γ ELISPOT ≤12 SFC/106 PBMC (B cell ELISPOT) against donor non-human primate. Male or female non-human primate recipients are trained for cooperation and instrumented with indwelling central and intraportal vascular access.

Kidney transplantation in non-human primates follows established procedures. Briefly, following systemic heparinization of both donor and recipient, the donor organ is excised and the vessels are anastomosed to the recipient's infrarenal aorta and vena cava. Typically, this is performed in a left-to-right fashion owing to the longer length of the left renal vessels. The donor ureter is tunneled through the retroperitoneum and a primary ureteroneocystostomy is formed typically on the posterior wall of the bladder using a modified Leadbetter-Politano approach. Particular attention is paid to avoid urine leakage and ureteral stenosis. Bilateral native nephrectomy is completed prior to closure.

Ex vivo expanded and ECDI-fixed donor B cells coupled to anti-CD40 peptides (e.g., Peptides 1-17 listed in table 1) are infused IV into experimental recipients on days −7 and +1 at a dose of 0.25×10$^9$/kg recipient body weight. Approximately 60 ml of blood (corresponding to 1% of body weight) is drawn from donors on day −21 or −22 (±2 days) relative to planned renal transplant, and B cells are purified by magnetic sorting using non-human primate CD20 beads. Alternatively or additionally, B cells can be enriched from leukapheresis products. A B cell expansion protocol is adapted from the culture system reported by Su et al (J Immunol 2016, 197:4163-76). Purified B cells (approximately 24×10$^6$ B cells from 60 ml of blood) are expanded ex vivo in a GREX100M flask (Wilson Wolf) until day −7 in RPMI 1640 medium with added 5% rhesus macaque serum, 55 µM 2-ME, 2 mM L-glutamine, 100 U/ml penicillin, 100 µg/ml streptomycin, 10 mM HEPES, 1 mM sodium pyruvate, and 1% MEM nonessential amino acids. The culture medium is supplemented with anti-CD40 peptides (e.g., Peptides 1-17 listed in table 1), IL-2 (50 ng/ml), IL-4 (10 ng/ml), IL-21 (10 ng/ml), and BAFF (10 ng/ml). Input cell numbers, medium volume, and the concentration of CD40L-multimeric are optimized in feasibility studies. Cells are counted after 7 and 14 days, split after 14 days (day −7), and the cells not infused on day −7 are expanded for another 8 days for infusion on day +1. On the day of infusion, cells are agitated on ice for 1 hour with ECDI (30 mg/mL per 3.2×10$^8$ cells) in DPBS in the presence of the CD40 binding peptides (e.g., Peptides 1-17 listed in table 1), washed, cleaned to remove necrotic cells and microaggregates, and assessed for viability/necrosis by AO/PI fluorescent microscopy. ECDI-fixed B cells coupled to CD40 binding peptides, meeting all release criteria, are loaded into cold syringes for IV infusion with a maximum concentration of 20×10$^6$ cells/mL; the cells remain on ice until recipient administration. Induction of apoptosis is monitored in vitro by incubating an aliquot of ECDI-fixed cells coupled to CD40 binding peptides at 37° C. for 4-6 hours, labelling with Annexin V/PI, and analyzing via fluorescent microscopy or flow cytometry.

Identical short-term immunosuppression and anti-inflammatory therapies are administered to control and experimental subjects. The first dose of each drug is given on day −8 or −7 relative to transplantation on day 0. The antagonistic anti-CD40 peptides are given intravenously at 50 mg/kg on days −8, −1, 7, and 14. Rapamycin (Rapamune®) is given orally (PO) from day −7 through day 21 post-transplant; the target trough level is 5 to 12 ng/ml. Concomitant anti-inflammatory therapy is with i) α-IL-6R (tocilizumab, Actemra®) at 10 mg/kg IV on days −7, 0, 7, 14, and 21, and ii) sTNFR (etanercept, Enbrel®) at 1 mg/kg IV on days −7 and 0 and 0.5 mg/kg subcutaneously on days 3, 7, 10, 14, and 21.

The primary efficacy outcome is the proportion of transplanted non-human primate with rejection-free allograft survival (confirmed by histopathology) at day 365 post-transplant. Accordingly, follow-up is to day 365 or graft failure, whichever occurs first. The group experimental group that received ADLs coupled to CD40 binding peptides is expected to exhibit enhanced rejection-free allograft survival compared to the control group that received only the short-term immunosuppression and anti-inflammatory therapies.

What is claimed is:

1. A pharmaceutical composition comprising:
an isolated peptide comprising an amino acid sequence with at least 90% sequence identity to any one of SEQ ID NOs: 1-6 or SEQ ID NOs: 8-17, as determined by BLAST algorithm; and
a pharmaceutically acceptable excipient, carrier, or diluent,
wherein said isolated peptide binds a CD40 protein.

2. The pharmaceutical composition of claim 1, wherein said isolated peptide comprises the amino acid sequence set forth in any one of SEQ ID NOs: 1-6 or SEQ ID NOs: 8-17.

3. The pharmaceutical composition of claim 1, wherein said isolated peptide further comprises at least one modification, wherein said at least one modification is a chemical modification, or a post-translational modification.

4. The pharmaceutical composition of claim 3, wherein said chemical modification is selected from a group consisting of ubiquitination, pegylation, lipidation, glycosylation, alkylation, or thiolation.

5. The pharmaceutical composition of claim 3, wherein said post-translational modification is an acetylation, acylation, ADP-ribosylation, amidation, carboxylation, hydroxylation, disulfide bond formation, glycosylation, phosphorylation, proteolytic processing, sulfation, methylation, acyl lipidation, prenylation, methylation, or myristoylation.

6. The pharmaceutical composition of claim 1, wherein said isolated peptide is cyclized.

7. The pharmaceutical composition of claim 1, wherein said isolated peptide is further conjugated to a carrier polypeptide, a detectable agent, a peptide tag, a magnetic particle, a diagnostic agent, a therapeutic agent, a nanoparticle, or a combination thereof.

8. The pharmaceutical composition of claim 1, wherein said isolated peptide is formulated in a liposome or a nanoparticle delivery system.

9. The pharmaceutical composition of claim 1, wherein said isolated peptide inhibits binding of said CD40 protein to a CD154 protein.

10. The pharmaceutical composition of claim 1, wherein said pharmaceutical composition further comprises an apoptotic leukocyte.

11. The pharmaceutical composition of claim 10, wherein said apoptotic leukocyte is fixed with a cross-linking agent.

12. The pharmaceutical composition of claim 10, wherein said isolated peptide is conjugated to the surface of said apoptotic leukocyte.

13. A preparatory regimen for administration to a recipient of a transplant, comprising the pharmaceutical composition of claim 1 in an amount sufficient to induce tolerance in said recipient to said transplant.

14. The preparatory regimen of claim 13, wherein the preparatory regimen further comprises an immunomodulatory agent.

15. A method of inducing immunosuppression in a subject in need thereof, the method comprising;
administering to said subject an isolated peptide comprising an amino acid sequence with at least 90% sequence identity to any one of SEQ ID NOs: 1-6 or SEQ ID NOs: 8-17, as determined by BLAST algorithm,
wherein said isolated peptide binds a CD40 protein.

16. The method of claim 15, wherein said isolated peptide comprises the sequence set forth in any one of SEQ ID NOs 1-6 or SEQ ID NOs: 8-17.

17. The method of claim 15, wherein the subject has undergone, is undergoing, or will be undergoing an allotransplant or a xenotransplant.

18. A method of inducing tolerance to a transplant in a recipient, the method comprising administering to said recipient an isolated peptide comprising an amino acid sequence with at least 90% sequence identity to any one of SEQ ID NOs: 1-6 or SEQ ID NOs: 8-17, as determined by BLAST algorithm,
wherein said isolated peptide binds a CD40 protein, and
wherein said isolated peptide inhibits the binding of said CD40 protein to a CD154 protein.

19. The method of claim 18, wherein said isolated peptide comprises the amino acid sequence set forth in any one of SEQ ID NOs 1-6 or SEQ ID NOs: 8-17.

* * * * *

SEQUENCE LISTING

<160> NUMBER OF SEQ ID NOS: 19

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val Leu Gln Trp Ala Glu Arg Gly Phe Tyr Thr Thr Ser Asn Asn
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Leu Leu Gln Trp Ala Glu Arg Gly Tyr Phe Met Thr Ser Asn Asn
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Val Gln Trp Ala Glu Lys Gly Phe Phe Thr Met Ser Asn Asn
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Leu Asn Trp Ala Asp Lys Ala Tyr Phe Thr Met Ser Gln Asn
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Val Asn Trp Ala Asp Lys Ala Phe Tyr Thr Thr Ser Asn Asn
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Val Val Gln Trp Ala Glu Lys Gly Tyr Tyr Thr Met Ser Gln Asn
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Leu Gln Trp Ala Glu Lys Gly Tyr Tyr Thr Met Ser Asn Asn
1               5                   10                  15

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Leu Gln Trp Ala Glu Arg Gly Phe Tyr
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Leu Gln Trp Ala Glu Arg Gly Tyr Phe
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Val Val Gln Trp Ala Glu Lys Gly Phe Phe
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Leu Asn Trp Ala Asp Lys Ala Tyr Phe
1               5                   10

<210> SEQ ID NO 12

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Val Asn Trp Ala Asp Lys Ala Phe Tyr
1               5                   10

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Gly Phe Tyr Thr Thr Ser Asn Asn
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Gly Tyr Phe Met Thr Ser Asn Asn
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Gly Phe Phe Thr Met Ser Asn Asn
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Lys Ala Tyr Phe Thr Met Ser Gln Asn
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17
```

```
Lys Ala Phe Tyr Thr Thr Ser Asn Asn
1               5
```

<210> SEQ ID NO 18
<211> LENGTH: 277
<212> TYPE: PRT
<213> ORGANISM: Homo sapiens

<400> SEQUENCE: 18

```
Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
        275
```

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 19

```
His His His His His His
1               5
```